US008822530B2

(12) United States Patent
Yuan et al.

(10) Patent No.: US 8,822,530 B2
(45) Date of Patent: *Sep. 2, 2014

(54) SULFUR DERIVATIVES AS CHEMOKINE RECEPTOR MODULATORS

(71) Applicant: Allergan, Inc., Irvine, CA (US)

(72) Inventors: Haiqing Yuan, Irvine, CA (US); Richard L. Beard, Newport Beach, CA (US); Xiaoxia Liu, Lake Forest, CA (US); John E. Donello, Dana Point, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/794,494

(22) Filed: Mar. 11, 2013

(65) Prior Publication Data

US 2013/0190338 A1 Jul. 25, 2013

Related U.S. Application Data

(63) Continuation-in-part of application No. 13/315,615, filed on Dec. 9, 2011, now Pat. No. 8,450,367.

(60) Provisional application No. 61/423,940, filed on Dec. 16, 2010.

(51) Int. Cl.
*C07D 307/82* (2006.01)
*A61K 31/343* (2006.01)
*A61P 31/00* (2006.01)

(52) U.S. Cl.
USPC ............ 514/470; 514/602; 549/466; 549/467

(58) Field of Classification Search
CPC ........................... C07D 307/82; A61K 31/343
USPC .......................... 514/470, 602; 549/466, 467
See application file for complete search history.

(56) References Cited

U.S. PATENT DOCUMENTS

| | | | |
|---|---|---|---|
| 5,163,995 | A | 11/1992 | Van Heertum |
| 5,177,206 | A | 1/1993 | Johnson |
| 7,393,873 | B2 | 7/2008 | Anthony |
| 7,622,583 | B2 | 11/2009 | Ungashe |
| 7,884,110 | B2 | 2/2011 | Krasinski |
| 7,931,909 | B2 | 4/2011 | Hughes |
| 2007/0037794 | A1 | 2/2007 | Ungashe |
| 2008/0293720 | A1 | 11/2008 | Cleary |
| 2011/0118248 | A1 | 5/2011 | Ungashe |
| 2012/0014997 | A1 | 1/2012 | Ungashe |

FOREIGN PATENT DOCUMENTS

| | | |
|---|---|---|
| DE | 19629144 | 1/1998 |
| EP | 0142152 | 5/1985 |
| EP | 0244097 | 11/1987 |
| EP | 0244098 | 11/1987 |
| EP | 0246749 | 11/1987 |
| EP | 0947500 | 10/1999 |
| EP | 1325920 | 7/2003 |
| WO | 2003-099773 | 4/2003 |
| WO | 2005-004810 | 1/2005 |
| WO | 2007-067875 | 6/2007 |
| WO | 2008-008374 | 1/2008 |

OTHER PUBLICATIONS

Ambati, Jayakrishna et al, An Animal Model of Age-Related Macular Degeneration in Senescent Ccl-2- or Ccr-2Deficient Mice, Nature Medicine, 2003, 1390-1397, 9.
Beech, John et al, Neuroprotection in Ischemia—Reperfusion Injury: An Antiinflammatory Approach Using a Novel Broad-Spectrum Chemokine Inhibitor, Journal of Cerebral Blood Flow and Metabolism, 2001, 683-689, 21.
Database Caplus, 1998, Retrieved from STN accession No. 1999:104638 Database accession No. 130:248286, Compound with RN 98967-44-3.
Fang, I-Mo et al, Expression of chemokine and receptors in Lewis rats with experimental autoimmune anterior uveitis, Experimental Eye Research, 2004, 1043-1055, 78, US.
Feria, Manuel et al, The CCR2 Receptor as a Therapeutic Target, Expert Opin. Ther Patents, 2006, 49-57, 16.
Gerard, Craig et al, Chemokines and Disease, nature immunology, Chemokine Reviews, 2001, 108-115, 2, Nature Publishing Group.
Hidekazu Masaki, Structure-Activity Relationship of Benzo[b]thiophene-2-sulfonamide Derivatives as Novel Human Chymase Inhibitors, Bioorganic & Medicinal Chemistry Letters, 2003, 4085-4088, 13.
Keino, Kiroshi et al, Chemokine and Chemokine Receptor Expression During Experimental Autoimmune Uveoretinitis in Mice, Graefe's Arch Clin Exp Ophthalmol, 2003, 111-115, 241.
Klitgaard, Torben et al, Chemokine Receptors and Early Activation Markers in Acute Anterior Uveitis, Acta Ophthalmol. Scand., 2004, 179-183, 82.
Meleth, Annal et al, Serum Inflammatory Makers in Diabetic Retinopathy, Investigative Ophthalmology & Visual Science, Nov. 2005, 4295-4301, 46.
Reckless, Jill et al, Identification of Oligopeptide Sequences Which Inhibit Migration Induced by a Wide Range of Chemokines, Biochem. J., 1999, 803-811, 340.
Stahl, Heinrich et al, Handbook of Pharmaceutical Salts, Verlag Helvetica Chimica Acta—Zurich, 2002, 329-345.
Takeuchi, Aya et al, CCR5-Deficient Mice Develop Experimental Autoimmune Uveoretinitis in the Context of a Deviant Effector Response, Investigative Ophthalmology & Visual Science, Oct. 2005, 3753-3760, 46.

(Continued)

*Primary Examiner* — Sreeni Padmanabhan
*Assistant Examiner* — Irina Neagu
(74) *Attorney, Agent, or Firm* — Doina G. Ene

(57) ABSTRACT

The present invention relates to novel sulfur derivatives, processes for preparing them, pharmaceutical compositions containing them and their use as pharmaceuticals as modulators of chemokine receptors.

14 Claims, No Drawings

(56) References Cited

OTHER PUBLICATIONS

Tokuyama, Hirotake et al, The Simultaneous Blockage of Chemokine Receptors CCR2, CCR5 and CXCR3 by a Non-peptide Chemokine Receptor Antagonist Protects Mice From Dextran Sodium Sulfate-Mediated Colitis, International Immunology, 2005, 1023-1034, 17.

Tuaillon, Nadine et al, MCP-1 Expression in Endotoxin-Induced Uveitis, Investigative Ophthalmology & Visual Science, May 2002, 1493-1498, 43.

Wallace, Graham et al, The Role of Chemokines and Their Receptors in Ocular Disease, Progress in Retinal and Eye Research, 2004, 435-448, 23.

Weisberg, Stuart et al, CCR2 Modulates Inflammatory and Metabolic Effects of High-Fat Feeding, The Journal of Clinical Investigation, Jan. 2006, 115-124, 116.

Wells, Timothy et al, Chemokine blockers—therapeutics in the making?, Trends in Pharmacological Sciences, Jan. 2006, 41-47, 27.

Yamagami, Satoru et al, CCR5 Chemokine Receptor Mediates Recruitment of MHC Class II-Positive Langerhans Cells in the Mouse Corneal Epithelium, Investigative Ophthalmology & Visual Science, Apr. 2005, 1201-1207, 46.

Yang, Chang-Hao et al, Effects of the NF-kB Inhibitor Pyrrolidine Dithiocarbamate on Experimentally Induced Autoimmune Anterior Uveitis, Investigative Ophthalmology & Visual Science, 2005, 1339-1347, 46.

Patent Cooperation Treaty, Notification of Transmittal of the International Search Report and the Written Opinion of the International Searching Authority, or the Declaration, Form PCT/ISA/220, Int. App. No. PCT/US2011/064233, Feb. 17, 2012.

Cross, L.C. et al, Rules for the Nomenclature of Organic Chemistry, Section E: Stereochemistry, Pure & Appl. Chem., 1976, 11-30, 45.

Grainger, David et al, Broad-Spectrum Chemokine Inhibitors (BSCIs) and Their Anti-Inflammatory Effects in Vivo, Biochemical Pharmacology, 2003, 1027-1034, 65.

Stahl, Heinrich et al, Handbook of Pharmaceutical Salts: Properties, Selection, and Use, 2002, 324-325, International Union of Pure and Applied Chemistry.

SULFUR DERIVATIVES AS CHEMOKINE RECEPTOR MODULATORS

RELATED APPLICATION

This application is a continuation-in-part of U.S. patent application Ser. No. 13/315,615, filed Dec. 9, 2011, which claims the benefit of U.S. Provisional Application Ser. No. 61/423,940, filed Dec. 16, 2010, the disclosure of which is hereby incorporated in its entirety herein by reference.

FIELD OF THE INVENTION

The present invention relates to novel sulfur derivatives, processes for preparing them, pharmaceutical compositions containing them and their use as pharmaceuticals as modulators of chemokine receptors. The invention relates specifically to the use of these compounds and their pharmaceutical compositions to treat disorders associated with chemokine receptor modulation.

BACKGROUND OF THE INVENTION

Chemokines are a group of 7- to 14-kd peptides that play an important role in orchestrating leukocyte recruitment and migration during inflammation, and therefore represent an important target for anti-inflammatory therapies (Wells et al., 2006). They act by binding to seven-transmembrane, G protein-coupled receptors, the chemokine receptors. The chemokine system is complex, with about 50 chemokines and 20 chemokine receptors identified in humans, often acting with redundancy, making selection of specific antagonists difficult (Gerard and Rollins, 2001). Genetic knockout strategies have confirmed the importance of chemokines as regulators of immune function, but the deletion of specific chemokines has led to only specific and relatively mild defects in the inflammatory response further emphasizing the complex redundancy of the system. Selectivity is crucial for use of chemokine receptor antagonists in systemic diseases where a single chemokine-receptor system is implicated such as atherosclerorsis where the macrophage/monocyte system is the major player in order to allow a subtle and specific control over immune function (Weisberg et al., 2006; Feria and Diaz Gonzalez et al., 2006).

Many ocular conditions are characterized by inappropriate migration and infiltration of cells such as leukocytes and endothelial cells into the eye with deleterious effects to ocular structures (Wallace et al., 2004). Chemokines have been identified in such diseases and misregulation of the chemokine system is apparent in corneal graft rejection, diabetic retinopathy, age-related macular degeneration (ARMD), chronic inflammatory diseases such as uveitis, dry eye etc. Mice lacking CCR2 or MCP-1 develop features of ARMD with age, including drusen deposits, choroidal neovascularization and photoreceptor atrophy indicating a crucial role for this chemokine and its receptor signaling (Amabati et al., 2003). Thus CCR2 receptor-specific inhibitor might have potential therapeutic benefit in ocular diseases like ARMD. In contrast, various human and animal studies have identified several chemokines in different forms of uveitis, produced both by resident and infiltrating cells, that strongly suggests a prominent role for these molecules in its pathogenesis. Studies in rat and mice models of uveitis have demonstrated up-regulation of monocyte chemoattractant protein-1 (MCP-1), macrophage inflammatory protein-1 (MIP-1), RANTES, stromal derived factor-1 (SDF-1) which are powerful chemoattractants for monocytes and T-cells (Fang et al., 2004; Keino et al., 2003). Similar findings have been reported in peripheral blood mononuclear cells in patients with acute anterior uveitis (AAU), the most common form of human uveitis (Klitgaard et al., 2004). MCP-1 knockout mice and CCR5 knockout mice show reduced endotoxin-induced uveitis, which is the animal model for AAU (Takeuchi et al., 2005; Tuallion et al., 2002). It has also been demonstrated that blocking the chemokine system upstream with the use of NF-κB blockers significantly attenuates experimental AAU in rats (Yang et al., 2005). Blockage of NF-κB results in transcriptional inhibition of multiple chemokines. Given the complexity of pathogenesis in uveitis it is unlikely that a selective inhibition of a chemokine receptor in monotherapy will offer therapeutic benefit. A similar role of multiple chemokines have been shown to be correlated with clinical stage of disease in diabetic retinopathy and dry eye (Meleth et al., 2005; Yamagami et al., 2005). In these ocular diseases the use of broad spectrum chemokine receptor inhibitor which inhibits the function of a wide range of chemokines may be beneficial.

The first broad spectrum chemokine inhibitor (BSCI) to be reported was termed Peptide 3, which was derived from the sequence of human chemokine MCP-1 and was shown to block the migration of monocytes in response to MCP-1, MIP-1, RANTES and SDF-1 (Reckless and Grainger. 1999). A cyclic retro inverse analogue of Peptide 3, constructed of D-amino acids in the reverse sequence, called NR58-3.14.3 was observed to be a more potent chemokine inhibitor (Beech et al., 2001). NR58-3.14.3 has been used to test for anti-inflammatory activities in animal models of atherosclerosis, lung inflammation, irritable bowel syndrome etc (Beech et al., 2001; Grainger and Reckless. 2003; Tokuyama et al., 2005). However there are several disadvantages to using these BSCI as a long-term therapeutic strategy. The known BSCIs which are peptides which have relatively low potency, poor pharmacokinetics, and are unstable in vivo. In addition, systemic use of broad spectrum chemokine receptor inhibitors could potentially lead to deleterious side effects due to their systemic anti-inflammatory activity. However in ocular diseases, a local or topical application would prevent the broad spectrum inhibitor to be taken up systemically. Identification of a small molecule inhibitor of several chemokine receptors could be very useful for treatment of inflammatory ocular diseases. Given the evidence for the role of multiple chemokines in several ocular diseases and these results, we propose that the use of small and large molecule broad spectrum chemokine receptor inhibitors will have utility in the local treatment of ocular inflammatory diseases including, but not limited to, uveitis, dry eye, diabetic retinopathy, allergic eye disease and proliferative retinopathies. Manipulation of multiple chemokines therefore represents a novel therapeutic approach in treating ocular diseases.

WO2008008374 discloses CCR2 inhibitors and methods of use thereof.

WO03/099773 discloses CCR9 inhibitors and methods of use thereof.

U.S. Pat. No. 7,622,583 discloses heteroaryl sulfonamides as antagonists of the CCR2 receptor.

US 2008/0293720 discloses pyridinyl sulfonamide modulators of chemokine receptors.

U.S. Pat. No. 7,393,873 discloses arylsulfonamide derivatives.

SUMMARY OF THE INVENTION

We have now discovered a group of novel sulphur derivatives which are potent and selective chemokine receptor modulators. As such, the compounds described herein are useful in treating a wide variety of disorders associated with modulation of chemokine receptors. The term "modulator" as used herein, includes but is not limited to: receptor agonist, antagonist, inverse agonist, inverse antagonist, partial agonist, partial antagonist.

This invention describes compounds of Formula I, which have chemokine receptor biological activity. The compounds in accordance with the present invention are thus of use in medicine, for example in the treatment of humans with diseases and conditions that are alleviated by chemokine receptor modulation.

In one aspect, the invention provides a compound having Formula I or a pharmaceutically acceptable salt thereof or stereoisomeric forms thereof, or the individual geometrical isomers, enantiomers, diastereoisomers, tautomers, zwitterions and pharmaceutically acceptable salts thereof:

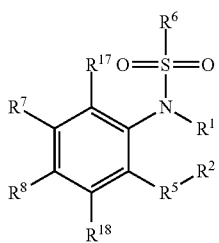

Formula I wherein:
$R^1$ is H or —C(O)(CH$_3$);
$R^2$ is substituted or unsubstituted C$_{1-6}$ alkyl, substituted or unsubstituted C$_{3-8}$ cycloalkyl or is substituted or unsubstituted C$_{3-8}$ cycloalkenyl;
$R^5$ is —S—, —S(O)—, or —S(O)$_2$—;
$R^6$ is optionally substituted 1-benzofuran;
$R^{17}$ is H, substituted or unsubstituted C$_{1-6}$ alkyl, halogen, substituted or unsubstituted —OC$_{1-6}$ alkyl, CN, C(O)R$^{19}$, NR$^{20}$R$^{21}$ or hydroxyl;
$R^{18}$ is H, substituted or unsubstituted C$_{1-6}$ alkyl, halogen, substituted or unsubstituted —OC$_{1-6}$ alkyl, CN, C(O)R$^{22}$, NR$^{23}$R$^{24}$ or hydroxyl;
$R^7$ is H, halogen, CN, substituted or unsubstituted —OC$_{1-6}$ alkyl, substituted or unsubstituted C$_{1-6}$ alkyl or is substituted or unsubstituted C$_{3-8}$ cycloalkyl;
$R^8$ is H, substituted or unsubstituted C$_{1-6}$ alkyl, halogen, substituted or unsubstituted —OC$_{1-6}$ alkyl, CN or hydroxyl;
$R^{19}$ is H, OH or substituted or unsubstituted C$_{1-6}$ alkyl
$R^{20}$ is H or substituted or unsubstituted C$_{1-6}$ alkyl;
$R^{21}$ is H or substituted or unsubstituted C$_{1-6}$ alkyl;
$R^{22}$ is H, OH or substituted or unsubstituted C$_{1-6}$ alkyl
$R^{23}$ is H or substituted or unsubstituted C$_{1-6}$ alkyl;
$R^{24}$ is H or substituted or unsubstituted C$_{1-6}$ alkyl;
and including compounds:
N-[6-(benzylsulfanyl)-1-oxo-2,3-dihydro-1H-inden-5-yl]-1-benzofuran-2-sulfonamide;
N-[6-(benzylsulfinyl)-1-oxo-2,3-dihydro-1H-inden-5-yl]-1-benzofuran-2-sulfonamide;
N-[6-(benzylsulfonyl)-1-oxo-2,3-dihydro-1H-inden-5-yl]-1-benzofuran-2-sulfonamide; and excluding compound:

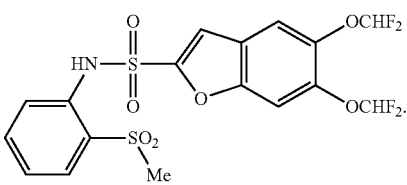 [SMILES: CS(=O)(=O)c1ccccc1NS(=O)(=O)c1cc2cc(OC(F)F)c(OC(F)F)cc2o1]

In another aspect, the invention provides a compound having Formula I wherein
$R^1$ is H;
$R^2$ is substituted or unsubstituted C$_{1-6}$ alkyl, substituted or unsubstituted C$_{3-8}$ cycloalkyl or substituted or unsubstituted C$_{3-8}$ cycloalkenyl;
$R^5$ is S;
$R^6$ is optionally substituted 1-benzofuran;
$R^{17}$ is H, substituted or unsubstituted C$_{1-6}$ alkyl, halogen, substituted or unsubstituted —OC$_{1-6}$ alkyl, CN, C(O)R$^{19}$, NR$^{20}$R$^{21}$ or hydroxyl;
$R^{18}$ is H, C$_{1-6}$ alkyl, halogen, substituted or unsubstituted —OC$_{1-6}$ alkyl, CN, C(O)R$^{22}$, NR$^{23}$R$^{24}$ or hydroxyl;
$R^7$ is H, halogen, CN, substituted or unsubstituted —OC$_{1-6}$ alkyl, substituted or unsubstituted C$_{1-6}$ alkyl or substituted or unsubstituted C$_{3-8}$ cycloalkyl;
$R^8$ is H, substituted or unsubstituted C$_{1-6}$ alkyl, halogen, substituted or unsubstituted —OC$_{1-6}$ alkyl, CN or hydroxyl;
$R^{19}$ is H, OH or substituted or unsubstituted C$_{1-6}$ alkyl;
$R^{20}$ is H or substituted or unsubstituted C$_{1-6}$ alkyl;
$R^{21}$ is H or substituted or unsubstituted C$_{1-6}$ alkyl;
$R^{22}$ is H, OH or substituted or unsubstituted C$_{1-6}$ alkyl;
$R^{23}$ is H or substituted or unsubstituted C$_{1-6}$ alkyl; and
$R^{24}$ is H or substituted or unsubstituted C$_{1-6}$ alkyl.
In another aspect, the invention provides a compound having Formula I wherein:
$R^1$ is H;
$R^2$ is substituted or unsubstituted C$_{1-6}$ alkyl, substituted or unsubstituted C$_{3-8}$ cycloalkyl or substituted or unsubstituted C$_{3-8}$ cycloalkenyl;
$R^5$ is —S(O)—;
$R^6$ is optionally substituted 1-benzofuran;
$R^{17}$ is H, substituted or unsubstituted C$_{1-6}$ alkyl, halogen, substituted or unsubstituted —OC$_{1-6}$ alkyl, CN, C(O)R$^{19}$, NR$^{20}$R$^{21}$ or hydroxyl;
$R^{18}$ is H, substituted or unsubstituted C$_{1-6}$ alkyl, halogen, substituted or unsubstituted —OC$_{1-6}$ alkyl, CN, C(O)R$^{22}$, NR$^{23}$R$^{24}$ or hydroxyl;
$R^7$ is H, halogen, CN, substituted or unsubstituted —OC$_{1-6}$ alkyl, substituted or unsubstituted C$_{1-6}$ alkyl or substituted or unsubstituted C$_{3-8}$ cycloalkyl;
$R^8$ is H, substituted or unsubstituted C$_{1-6}$ alkyl, halogen, substituted or unsubstituted —OC$_{1-6}$ alkyl, CN or hydroxyl;
$R^{19}$ is H, OH or substituted or unsubstituted C$_{1-6}$ alkyl;
$R^{20}$ is H or substituted or unsubstituted C$_{1-6}$ alkyl;
$R^{21}$ is H or substituted or unsubstituted C$_{1-6}$ alkyl;
$R^{22}$ is H, OH or substituted or unsubstituted C$_{1-6}$ alkyl;
$R^{23}$ is H or substituted or unsubstituted C$_{1-6}$ alkyl; and
$R^{24}$ is H or substituted or unsubstituted C$_{1-6}$ alkyl.
In another aspect, the invention provides a compound having Formula I wherein:
$R^1$ is H;
$R^2$ is substituted or unsubstituted C$_{1-6}$ alkyl, substituted or unsubstituted C$_{3-8}$ cycloalkyl or substituted or unsubstituted C$_{3-8}$ cycloalkenyl;
$R^5$ is —S(O)$_2$—;
$R^6$ is optionally substituted 1-benzofuran;

$R^{17}$ is H, substituted or unsubstituted $C_{1-6}$ alkyl, halogen, —$OC_{1-6}$ alkyl, CN, $C(O)R^{19}$, $NR^{20}R^{21}$ or hydroxyl;
$R^{18}$ is H, substituted or unsubstituted $C_{1-6}$ alkyl, halogen, substituted or unsubstituted —$OC_{1-6}$ alkyl, CN, $C(O)R^{22}$, $NR^{23}R^{24}$ or hydroxyl;
$R^7$ is H, halogen, CN, substituted or unsubstituted —$OC_{1-6}$ alkyl, substituted or unsubstituted $C_{1-6}$ alkyl or substituted or unsubstituted $C_{3-8}$ cycloalkyl;
$R^8$ is H, substituted or unsubstituted $C_{1-6}$ alkyl, halogen, —$OC_{1-6}$ alkyl, CN or hydroxyl;
$R^{19}$ is H, OH or substituted or unsubstituted $C_{1-6}$ alkyl;
$R^{20}$ is H or substituted or unsubstituted $C_{1-6}$ alkyl;
$R^{21}$ is H or substituted or unsubstituted $C_{1-6}$ alkyl;
$R^{22}$ is H, OH or substituted or unsubstituted $C_{1-6}$ alkyl;
$R^{23}$ is H or substituted or unsubstituted $C_{1-6}$ alkyl; and
$R^{24}$ is H or substituted or unsubstituted $C_{1-6}$ alkyl; and
and excluding compound:

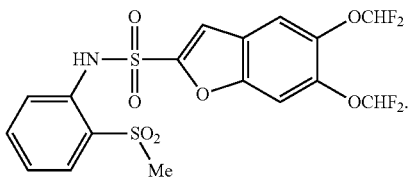 [SMILES: CS(=O)(=O)c1ccccc1NS(=O)(=O)c1cc2cc(OC(F)F)c(OC(F)F)cc2o1]

In another aspect, the invention provides a compound having Formula I wherein:
$R^1$ is H;
$R^2$ is substituted or unsubstituted $C_{1-6}$ alkyl, substituted or unsubstituted $C_{3-8}$ cycloalkyl or substituted or unsubstituted $C_{3-8}$ cycloalkenyl;
$R^5$ is —S—, —S(O)—, or —S(O)$_2$—;
$R^6$ is optionally substituted 1-benzofuran;
$R^{17}$ is H, substituted or unsubstituted $C_{1-6}$ alkyl or halogen;
$R^{18}$ is H, substituted or unsubstituted $C_{1-6}$ alkyl or halogen;
$R^7$ is H, halogen, CN, —$OC_{1-6}$ alkyl, substituted or unsubstituted $C_{1-6}$ alkyl or substituted or unsubstituted $C_{3-8}$ cycloalkyl;
$R^8$ is H, substituted or unsubstituted $C_{1-6}$ alkyl, CN or halogen; and excluding compound:

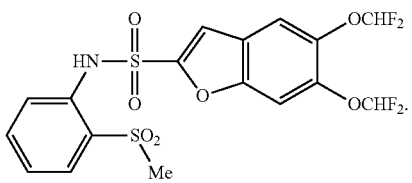 [SMILES: CS(=O)(=O)c1ccccc1NS(=O)(=O)c1cc2cc(OC(F)F)c(OC(F)F)cc2o1]

In another aspect, the invention provides a compound having Formula I wherein:
$R^1$ is H
$R^2$ is substituted or unsubstituted $C_{1-6}$ alkyl, substituted or unsubstituted $C_{3-8}$ cycloalkyl or substituted or unsubstituted $C_{3-8}$ cycloalkenyl;
$R^5$ is —S—;
$R^6$ is optionally substituted 1-benzofuran;
$R^{17}$ is H, substituted or unsubstituted $C_{1-6}$ alkyl or halogen;
$R^{18}$ is H, substituted or unsubstituted $C_{1-6}$ alkyl or halogen;
$R^7$ is H, halogen, CN, substituted or unsubstituted —$OC_{1-6}$ alkyl, substituted or unsubstituted $C_{1-6}$ alkyl or substituted or unsubstituted $C_{3-8}$ cycloalkyl; and
$R^8$ is H, substituted or unsubstituted $C_{1-6}$ alkyl, CN or halogen.

In another aspect, the invention provides a compound having Formula I wherein:
$R^1$ is H;
$R^2$ is substituted or unsubstituted $C_{1-6}$ alkyl, substituted or unsubstituted $C_{3-8}$ cycloalkyl or substituted or unsubstituted $C_{3-8}$ cycloalkenyl;
$R^5$ is —S(O)—;
$R^6$ is optionally substituted 1-benzofuran;
$R^{17}$ is H, substituted or unsubstituted $C_{1-6}$ alkyl or halogen;
$R^{18}$ is H, substituted or unsubstituted $C_{1-6}$ alkyl or halogen;
$R^7$ is H, halogen, CN, —$OC_{1-6}$ alkyl, substituted or unsubstituted $C_{1-6}$ alkyl or substituted or unsubstituted $C_{3-8}$ cycloalkyl;
$R^8$ is H, substituted or unsubstituted $C_{1-6}$ alkyl, CN or halogen.

In another aspect, the invention provides a compound having Formula I wherein:
$R^1$ is H;
$R^2$ is substituted or unsubstituted $C_{1-6}$ alkyl, substituted or unsubstituted $C_{3-8}$ cycloalkyl or substituted or unsubstituted $C_{3-8}$ cycloalkenyl;
$R^5$ is —S(O)$_2$—;
$R^6$ is optionally substituted 1-benzofuran;
$R^{17}$ is H, substituted or unsubstituted $C_{1-6}$ alkyl or halogen;
$R^{18}$ is H, substituted or unsubstituted $C_{1-6}$ alkyl or halogen;
$R^7$ is H, halogen, CN, substituted or unsubstituted —$OC_{1-6}$ alkyl, substituted or unsubstituted $C_{1-6}$ alkyl or substituted or unsubstituted $C_{3-8}$ cycloalkyl;
$R^8$ is H, substituted or unsubstituted $C_{1-6}$ alkyl, CN or halogen.

In another aspect, the invention provides a compound having Formula I wherein:
$R^1$ is H;
$R^2$ is substituted or unsubstituted $C_{1-6}$ alkyl;
$R^5$ is —S—, —S(O)—, or —S(O)$_2$—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is substituted $C_{1-6}$ alkyl with optionally substituted phenyl;
$R^5$ is —S—, —S(O)—, or —S(O)$_2$—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is substituted $C_{1-6}$ alkyl with optionally substituted phenyl;
$R^5$ is —S—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is substituted $C_{1-6}$ alkyl with optionally substituted phenyl;
$R^5$ is —S(O)—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is substituted $C_{1-6}$ alkyl with optionally substituted phenyl;
$R^5$ is —S(O)$_2$—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is $C_{1-6}$ alkyl;
$R^5$ is —S(O)$_2$;
$R^6$ is optionally substituted 1-benzofuran;
$R^{17}$ is H;
$R^{18}$ is H;
$R^7$ is H, halogen, or substituted or unsubstituted $C_{1-6}$ alkyl;
$R^8$ is H or CN.

In another aspect, the invention provides a compound having Formula I wherein:
$R^1$ is H;
$R^2$ is substituted or unsubstituted $C_{1-6}$ alkyl;
$R^5$ is —S(O);
$R^6$ is optionally substituted 1-benzofuran;
$R^{17}$ is H;
$R^{18}$ is H;
$R^7$ is H, halogen or $C_{1-6}$ alkyl;
$R^8$ is H or CN.

In another aspect, the invention provides a compound having Formula I wherein:
$R^1$ is H;
$R^2$ is substituted or unsubstituted $C_{1-6}$ alkyl;
$R^5$ is —S(O)$_2$—;
$R^6$ is optionally substituted 1-benzofuran;
$R^{17}$ is H;
$R^{18}$ is H;
$R^7$ is H, halogen or $C_{1-6}$ alkyl;
$R^8$ is H or CN.

In another aspect, the invention provides a compound selected from:
N-[6-(benzylsulfanyl)-1-oxo-2,3-dihydro-1H-inden-5-yl]-1-benzofuran-2-sulfonamide;
N-[6-(benzylsulfinyl)-1-oxo-2,3-dihydro-1H-inden-5-yl]-1-benzofuran-2-sulfonamide; and
N-[6-(benzylsulfonyl)-1-oxo-2,3-dihydro-1H-inden-5-yl]-1-benzofuran-2-sulfonamide.

In another aspect, the invention provides a compound having Formula I wherein:
$R^1$ is H;
$R^2$ is optionally substituted benzyl;
$R^5$ is —S—, —S(O)—, or —S(O)$_2$—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is optionally substituted benzyl;
$R^5$ is —S—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is optionally substituted benzyl;
$R^5$ is —S(O)—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is optionally substituted benzyl;
$R^5$ is —S(O)$_2$—;
$R^6$ is optionally substituted 1-benzofuran;
$R^{17}$ is H;
$R^{18}$ is H;
$R^7$ is H, halogen, substituted or unsubstituted $C_{1-6}$ alkyl;
$R^8$ is H or CN.

In another aspect, the invention provides a compound having Formula I wherein:
$R^1$ is H;
$R^2$ is methyl propionate, methyl-2-benzoic acid, methyl-2-methylbenzoate, methyl-3-methylphenylacetamide, methyl-3-methylphenylsulfonamide, methyl acetic acid, methyl-2-methylphenylcarboxylate or propionic acid;
$R^5$ is —S(O)$_2$—, —S— or —S(O)—;
$R^6$ is optionally substituted 1-benzofuran;
$R^7$ is H, chlorine, methyl or fluorine;
$R^{17}$ is H;
$R^{18}$ is H; and
$R^8$ is H or CN.

In another aspect, the invention provides a compound having Formula I wherein:
$R^1$ is H;
$R^2$ is methyl propionate, methyl-2-benzoic acid, methyl-2-methylbenzoate, methyl-3-methylphenylacetamide, methyl-3-methylphenylsulfonamide, methyl acetic acid, methyl-2-methylphenylcarboxylate or propionic acid;
$R^5$ is —S(O)$_2$—;
$R^6$ is optionally substituted 1-benzofuran;
$R^7$ is H, chlorine, methyl or fluorine;
$R^{17}$ is H;
$R^{18}$ is H; and
$R^8$ is H or CN.

In another aspect, the invention provides a compound having Formula I wherein:
$R^1$ is H;
$R^2$ is methyl propionate, methyl-2-benzoic acid, methyl-2-methylbenzoate, methyl-3-methylphenylacetamide, methyl-3-methylphenylsulfonamide, methyl acetic acid, methyl-2-methylphenylcarboxylate or propionic acid;
$R^5$ is —S—;

$R^6$ is optionally substituted 1-benzofuran;
$R^7$ is H, chlorine, methyl or fluorine;
$R^{17}$ is H;
$R^{18}$ is H; and
$R^8$ is H or CN.

In another aspect, the invention provides a compound having Formula I wherein:
$R^1$ is H;
$R^2$ is methyl propionate, methyl-2-benzoic acid, methyl-2-methylbenzoate, methyl-3-methylphenylacetamide, methyl-3-methylphenylsulfonamide, methyl acetic acid, methyl-2-methylphenylcarboxylate or propionic acid;
$R^5$ is —S(O)—;
$R^6$ is optionally substituted 1-benzofuran;
$R^7$ is H, chlorine, methyl or fluorine;
$R^{17}$ is H;
$R^{18}$ is H; and
$R^8$ is H or CN.

The term "alkyl", as used herein, refers to saturated, monovalent or divalent hydrocarbon moieties having linear or branched moieties or combinations thereof and containing 1 to 6 carbon atoms. One or more methylene (—CH$_2$—) groups, of the alkyl can be replaced by oxygen, sulfur, carbonyl, sulfoxide, nitrogen, sulfonyl, or by a divalent C$_{3-6}$ cycloalkyl. Hydrogen atoms on alkyl groups can be substituted by groups including, but not limited to: halogen, —OH, C$_{3-8}$ cycloalkyl, non-aromatic heterocycles, aromatic heterocycles, optionally substituted C$_{6-10}$ aryl, —O(C$_{1-6}$ alkyl), amine groups, amino groups, NO$_2$, amide groups, sulfonamide groups, ester groups, aldehyde groups, carboxylic acids, ketone groups.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by groups including, but not limited to: halogen, —OH, C$_{3-8}$ cycloalkyl, non-aromatic heterocycles, aromatic heterocycles, C$_{6-10}$ aryl, —O(C$_{1-6}$ alkyl), amine groups, amino groups, NO$_2$, amide groups, carboxylic acids, sulfonamide groups, ester groups, aldehyde groups, ketone groups.

The term "cycloalkenyl", as used herein, refers to a monovalent or divalent group of 3 to 8 carbon atoms, derived from a saturated cycloalkyl having one or more double bonds. Cycloalkenyl groups can be monocyclic or polycyclic. Cycloalkenyl groups can be substituted by groups including, but not limited to halogen, —OH, C$_{3-8}$ cycloalkyl, non-aromatic heterocycles, aromatic heterocycles, C$_{6-10}$ aryl, —O(C$_{1-6}$ alkyl), amine groups, amino groups, NO$_2$, amide groups, sulfonamide groups, carboxylic acids, ester groups, aldehyde groups, ketone groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. C$_{2-6}$ alkenyl can be in the E or Z configuration. Alkenyl groups can be substituted by C$_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted groups including, but not limited to: halogens, —OH, C$_{3-8}$ cycloalkyl, non-aromatic heterocycles, aromatic heterocycles, —OC$_{1-6}$ alkyl, —NH$_2$, —NO$_2$, amides, ethers, esters, ketones, carboxylic acids, aldehydes, sulfonamides groups.

Preferred substituted heterocycle groups are, but not limited to: pyridine, furan, azetidine, thiazol, thiophene, oxazol, pyrazol, isoxazole, 2-oxoindoline, 2-oxo-2,3-dihydro-1,3-benzoxazole, 2-oxo-2H-chromene, imidazole[2,1-b]thiazole, 1-H-pyrazole, indole, imidazole, quinoline, 2-thiophene, 2-benzofuran, 5-methyl-2-furan, 5-oxazolidine-2-one, pyrimidine-2,4(1H,3H)-dione, pyrimidine.

The term "aryl" as used herein, refers to an organic moiety derived from an aromatic hydrocarbon consisting of a ring containing 6 to 10 carbon atoms by removal of one hydrogen. Aryl can be substituted by groups including, but not limited to: halogens, —OH, C$_{3-8}$ cycloalkyl, non-aromatic heterocycles, aromatic heterocycles, —OC$_{1-6}$ alkyl, —NH$_2$, —NO$_2$, amides, ethers, esters, carboxylic acids, aldehydes, ketones, sulfonamides groups. Aryl can be monocyclic or bicyclic. Preferred substituted phenyl groups are, but not limited to: 4-chloro-3-trifluoromethyl-phenyl, 3,4-dichlorophenyl, 3-methoxyphenyl, 4-methyl-3-nitrophenyl, 4-chlorophenyl, 4-chloro-3-methylphenyl, nitro-3-trifluoromethylphenyl, 2,4-difluorophenyl, 4-chloro-2-fluorophenyl, 3-chloro-2-fluorophenyl, 4-isopropylphenyl, 4-bromophenyl, 4-iodophenyl, 3-chlorophenyl.

The term "amine" as used herein, represents a group of formula "—NR$^x$R$^y$", wherein R$^x$ and R$^y$ can be the same or independently H, alkyl, aryl, cycloalkyl, cycloalkenyl, heterocycle as defined above.

The term "amide" as used herein, represents a group of formula "—C(O)N(R$^x$)(R$^y$)" or "NR$^x$C(O)R$^y$" wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" or "NR$^x$R$^y$S(O)$_2$" or "—NR$^x$S(O)$_2$R$^y$" wherein R$^x$ and R$^y$ can be the same or independently H, alkyl, aryl, cycloalkyl, cycloalkenyl, heterocycle as defined above.

The term "ester" as used herein, represents a group of formula "—C(O)O(R$^x$)", wherein R$^x$ is alkyl, aryl, cycloalkyl, cycloalkenyl, heterocycle as defined above.

The term "aldehyde" as used herein, represents a group of formula "—C(O)H".

The term "ketone" as used herein, represents a group of formula "—C(O)R$^x$" wherein R$^x$ is C$_{1-6}$ alkyl.

The term "hydroxyl" as used herein, represents a group of formula "—OH".

The term "amino" as used herein, represents a group of formula "—NH$_2$".

The term "carbonyl" as used herein, represents a group of formula "—C(O)".

The term "carboxyl" as used herein, represents a group of formula "—C(O)O—".

The term "sulfonyl" as used herein, represents a group of formula "—SO$_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:

3-[({2-[(1-benzofuran-2-ylsulfonyl)amino]-4-fluorophenyl}sulfinyl)methyl]benzoic acid;
4-[({2-[(1-benzofuran-2-ylsulfonyl)amino]-4-fluorophenyl}sulfonyl)methyl]benzoic acid;
methyl 4-[({2-[(1-benzofuran-2-ylsulfonyl)amino]-4-fluorophenyl}sulfonyl)methyl]benzoate;
4-[({2-[(1-benzofuran-2-ylsulfonyl)amino]-4-fluorophenyl}sulfinyl)methyl]benzoic acid;
methyl 4-[({2-[(1-benzofuran-2-ylsulfonyl)amino]-4-fluorophenyl}sulfinyl)methyl]benzoate;
4-[({2-[(1-benzofuran-2-ylsulfonyl)amino]-4-fluorophenyl}sulfanyl)methyl]benzoic acid;
methyl 4-[({2-[(1-benzofuran-2-ylsulfonyl)amino]-4-fluorophenyl}sulfanyl)methyl]benzoate;
3-[({2-[(1-benzofuran-2-ylsulfonyl)amino]-4-fluorophenyl}sulfonyl)methyl]benzoic acid;
methyl 3-[({2-[(1-benzofuran-2-ylsulfonyl)amino]-4-fluorophenyl}sulfonyl)methyl]benzoate;
methyl 3-[({2-[(1-benzofuran-2-ylsulfonyl)amino]-4-fluorophenyl}sulfinyl)methyl]benzoate;
3-[({2-[(1-benzofuran-2-ylsulfonyl)amino]-4-fluorophenyl}sulfanyl)methyl]benzoic acid;
methyl 3-[({2-[(1-benzofuran-2-ylsulfonyl)amino]-4-fluorophenyl}sulfanyl)methyl]benzoate;
2-[({2-[(1-benzofuran-2-ylsulfonyl)amino]-5-chlorophenyl}sulfanyl)methyl]benzoic acid;
2-[({2-[(1-benzofuran-2-ylsulfonyl)amino]-4-methylphenyl}sulfonyl)methyl]benzoic acid;
2-[({2-[(1-benzofuran-2-ylsulfonyl)amino]-4-methylphenyl}sulfinyl)methyl]benzoic acid;
methyl 2-[({2-[(1-benzofuran-2-ylsulfonyl)amino]-4-methylphenyl}sulfonyl)methyl]benzoate;
methyl 2-[({2-[(1-benzofuran-2-ylsulfonyl)amino]-4-methylphenyl}sulfinyl)methyl]benzoate;
2-[({2-[(1-benzofuran-2-ylsulfonyl)amino]-4-methylphenyl}sulfanyl)methyl]benzoic acid;
methyl 2-[({2-[(1-benzofuran-2-ylsulfonyl)amino]-4-methylphenyl}sulfanyl)methyl]benzoate;
methyl 3-({2-[(1-benzofuran-2-ylsulfonyl)amino]-4-chlorophenyl}sulfonyl)propanoate;
methyl 3-({2-[(1-benzofuran-2-ylsulfonyl)amino]-4-chlorophenyl}sulfinyl)propanoate;
3-({2-[(1-benzofuran-2-ylsulfonyl)amino]-4-chlorophenyl}sulfanyl)propanoic acid;
methyl 3-({2-[(1-benzofuran-2-ylsulfonyl)amino]-4-chlorophenyl}sulfanyl)propanoate;
({2-[(1-benzofuran-2-ylsulfonyl)amino]-4-chlorophenyl}sulfonyl)acetic acid;
({2-[(1-benzofuran-2-ylsulfonyl)amino]-4-chlorophenyl}sulfinyl)acetic acid;
2-[({2-[(1-benzofuran-2-ylsulfonyl)amino]phenyl}sulfonyl)methyl]benzoic acid;
methyl 2-[({2-[(1-benzofuran-2-ylsulfonyl)amino]phenyl}sulfonyl)methyl]benzoate;
2-[({2-[(1-benzofuran-2-ylsulfonyl)amino]phenyl}sulfinyl)methyl]benzoic acid;
methyl 2-[({2-[(1-benzofuran-2-ylsulfonyl)amino]phenyl}sulfinyl)methyl]benzoate;
2-[({2-[(1-benzofuran-2-ylsulfonyl)amino]phenyl}sulfanyl)methyl]benzoic acid;
methyl 2-[({2-[(1-benzofuran-2-ylsulfonyl)amino]phenyl}sulfanyl)methyl]benzoate;
({2-[(1-benzofuran-2-ylsulfonyl)amino]-4-chlorophenyl}sulfanyl)acetic acid;
2-[({2-[(1-benzofuran-2-ylsulfonyl)amino]-4-fluorophenyl}sulfonyl)methyl]benzoic acid;
methyl 2-[({2-[(1-benzofuran-2-ylsulfonyl)amino]-4-fluorophenyl}sulfonyl)methyl]benzoate;
2-[({2-[(1-benzofuran-2-ylsulfonyl)amino]-4-fluorophenyl}sulfinyl)methyl]benzoic acid;
methyl 2-[({2-[(1-benzofuran-2-ylsulfonyl)amino]-4-fluorophenyl}sulfinyl)methyl]benzoate;
N-[5-chloro-2-({3-[(methylsulfonyl)amino]benzyl}sulfonyl)phenyl]-1-benzofuran-2-sulfonamide;
N-[5-chloro-2-({3-[(methylsulfonyl)amino]benzyl}sulfinyl)phenyl]-1-benzofuran-2-sulfonamide;
N-{3-[({2-[(1-benzofuran-2-ylsulfonyl)amino]-4-chlorophenyl}sulfonyl)methyl]phenyl}acetamide;
N-{3-[({2-[(1-benzofuran-2-ylsulfonyl)amino]-4-chlorophenyl}sulfinyl)methyl]phenyl}acetamide;
2-[({2-[(1-benzofuran-2-ylsulfonyl)amino]-4-fluorophenyl}sulfanyl)methyl]benzoic acid;
methyl 2-[({2-[(1-benzofuran-2-ylsulfonyl)amino]-4-fluorophenyl}sulfanyl)methyl]benzoate;
N-[5-chloro-2-({3-[(methylsulfonyl)amino]benzyl}sulfanyl)phenyl]-1-benzofuran-2-sulfonamide;
N-(2-{[3-(acetylamino)benzyl]sulfanyl}-5-chlorophenyl)-N-(1-benzofuran-2-ylsulfonyl)acetamide;
N-{3-[({2-[(1-benzofuran-2-ylsulfonyl)amino]-4-chlorophenyl}sulfanyl)methyl]phenyl}acetamide;
2-[({2-[(1-benzofuran-2-ylsulfonyl)amino]-4-chlorophenyl}sulfonyl)methyl]benzoic acid;
2-[({2-[(1-benzofuran-2-ylsulfonyl)amino]-4-chlorophenyl}sulfinyl)methyl]benzoic acid;
2-[({2-[(1-benzofuran-2-ylsulfonyl)amino]-4-chlorophenyl}sulfanyl)methyl]benzoic acid;
N-[6-(benzylsulfonyl)-1-oxo-2,3-dihydro-1H-inden-5-yl]-1-benzofuran-2-sulfonamide;
N-[6-(benzylsulfinyl)-1-oxo-2,3-dihydro-1H-inden-5-yl]-1-benzofuran-2-sulfonamide;
N-[6-(benzylsulfanyl)-1-oxo-2,3-dihydro-1H-inden-5-yl]-1-benzofuran-2-sulfonamide;
N-[2-(benzylsulfonyl)-4-cyanophenyl]-1-benzofuran-2-sulfonamide;
N-[2-(benzylsulfinyl)-4-cyanophenyl]-1-benzofuran-2-sulfonamide;
N-[2-(benzylsulfanyl)-4-cyanophenyl]-1-benzofuran-2-sulfonamide; and
methyl 2-(((2-(benzofuran-2-sulfonamido)-4-chlorophenyl)thio)methyl)benzoate
methyl 2-(((2-(benzofuran-2-sulfonamido)-5-chlorophenyl)thio)methyl)benzoate Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, a hydrohalic acid, such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta—Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the chemokine receptors.

In another embodiment, there are provided pharmaceutical compositions including at least one compound of the invention in a pharmaceutically acceptable carrier.

In a further embodiment of the invention, there are provided methods for treating disorders associated with modulation of chemokine receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by chemokine receptor modulation.

Therapeutic utilities of chemokine receptor modulators are skin inflammatory diseases and conditions, including, but are not limited to: rosacea (dilation of the blood vessels just under the skin), sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases, actinic keratoses, arsenic keratoses, inflammatory and non-inflammatory acne, ichthyoses and other keratinization and hyperproliferative disorders of the skin, eczema, wound healing.

Therapeutic utilities of chemokine receptor modulators are ocular inflammatory diseases including, but not limited to, uveitis, retinal degenerative conditions, angiogenesis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

In still another embodiment of the invention, there are provided methods for treating disorders associated with modulation of chemokine receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual nontoxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 7,931,909.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of chemokine receptors. Thus, in further embodiments of the invention, there are provided methods for treating a disorder associated with modulation of chemokine receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt Scheme 1 to synthesize any compounds of the invention covered by Formula I.

The described sulfur derivatives were prepared by general routes as shown in Scheme 1. In one route, an appropriately substituted 2-amino-benzenethiol such as Intermediate A can react with an electrophile such as a halide, tosylate, mesylate, enone, 2-enoate etc. in the presence of an acid or base to prepare sulfide Intermediate B. Alternatively, sulfide Intermediate B can be prepared by treatment of Intermediate A with an alcohol under Mitsunobu conditions. Reaction of Intermediate B with a sulfonyl chloride provides the sulfonamide of Formula I wherein $R^5$ is S. Further, upon treatment with an oxidant such as meta-chloroperoxybenzoic acid, the compound of Formula I wherein $R^5$ is S affords the compound wherein $R^5$ is S(O) or $R^5$ is $S(O)_2$.

In another route, di-sulfide Intermediate E type can be obtained through oxidation of an Intermediate A type. Reaction of Intermediate E with a, sulfonyl chloride provides sulfonamide Intermediate F. In situ or stepwise reduction of Intermediate F using polymer bound triphenylphosphine or sodium borohydride, respectively, followed by reaction of the resulting benzenethiol with an electrophile affords the sulfonamide of Formula I wherein $R^5$ is S.

Scheme 1

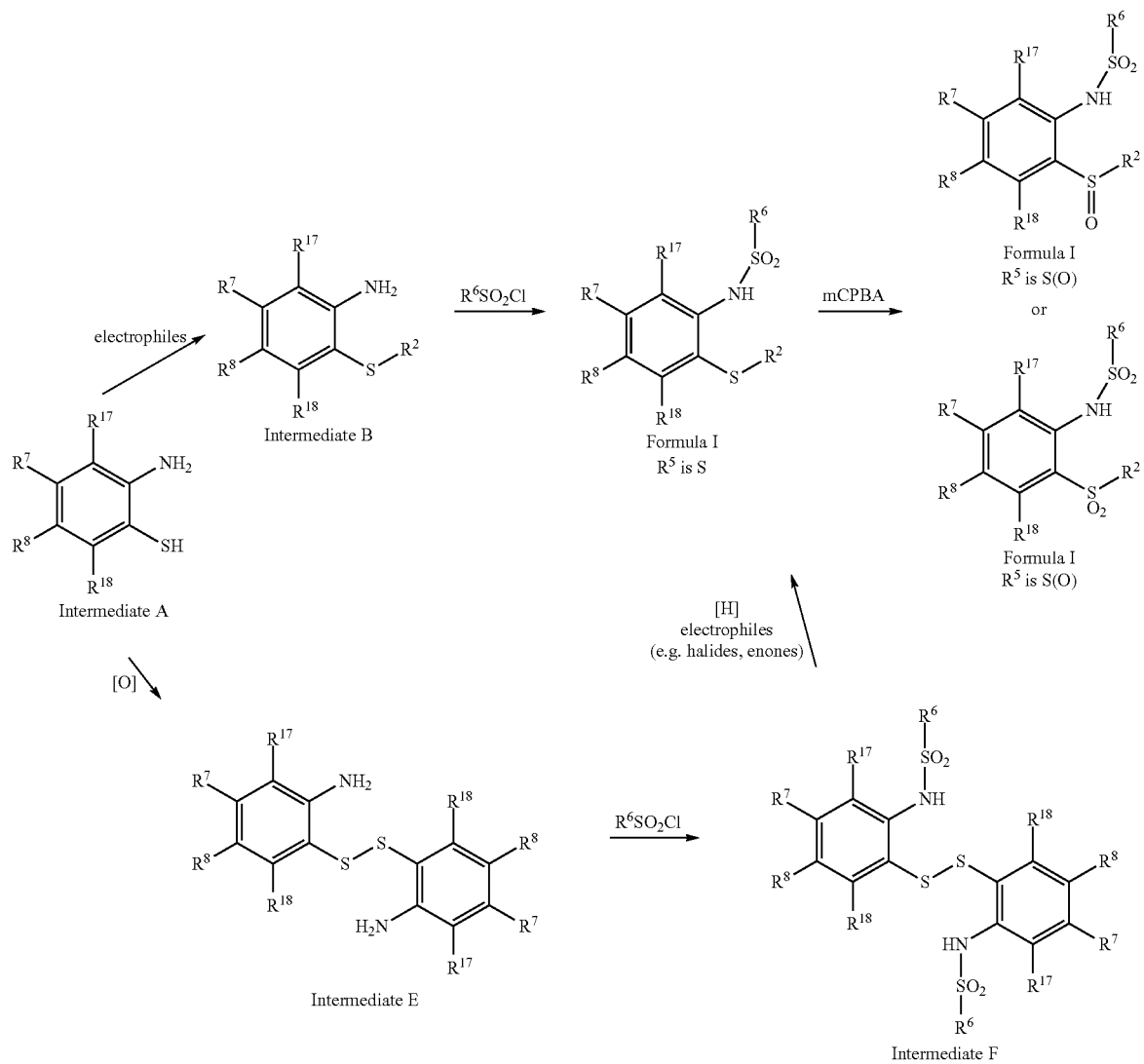

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 12.0 and some intermediates' and reagents' names used in the examples were generated with software such as Chem Bio Draw Ultra version 12.0 or Auto Nom 2000 from MDL ISIS Draw 2.5 SP1. In general, characterization of the compounds is performed according to the following methods:

NMR spectra are recorded on Varian 600 or Varian 300, in the indicated solvent at ambient temperature; chemical shifts in [ppm], coupling constants in [Hz].

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures. Solvents were purchased from commercial sources in appropriate quality and used as received. Air and/or moisture-sensitive reactions were run under an Ar- or $N_2$-atmosphere.

Usually the compounds of the invention were purified by chromatography: CombiFlash Companion and RediSep Rf silica gel 60 (0.04-0.063 mm); Preparative thin layer chromatography (PTLC): *Analtech* (silica gel 60 $F_{254}$, 500 or 1000 μm).

The following abbreviations are used in the examples:

$NH_3$ ammonia $CH_3CN$ acetonitrile $CH_2Cl_2$ dichloromethane

DMF N,N-dimethylformamide

NaOH sodium hydroxide

MeOH methanol $CD_3OD$ deuterated methanol

HCl hydrochloric acid $Na_2SO_4$ sodium sulfate

HBTU 2-(1H-Benzotriazole-1-yl)-1,1,3,3-tetramethyluronium hexafluorophosphate)

DIPEA N,N-Diisopropylethylamine

CuI copper iodide $Cs_2CO_3$ cesium carbonate

DMEDA N,N'-dimethylethylenediamine $MgSO_4$ magnesium sulfate

EtOAc ethyl acetate $CDCl_3$ deuterated chloroform

DMSO-$d_6$ deuterated dimethyl sulfoxide

TFA trifluoroacetic acid

THF tetrahydrofuran $K_2CO_3$ potassium carbonate mCPBA meta-Chloroperoxybenzoic acid $NaBH_4$ sodium borohydride $CaCl_2$ calcium chloride The following examples are for illustrative purposes only and are not intended, nor should they be construed as limiting the invention in any manner. Those skilled in the art will appreciate that variations and modifications of the following examples can be made without exceeding the spirit or scope of the invention.

SPECIFIC EXAMPLES

General Procedure A

Intermediate 1

5-chloro-2-[(1H-imidazol-4-ylmethyl)thio]aniline

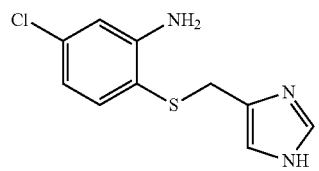 [SMILES: Nc1cc(Cl)ccc1SCc1c[nH]cn1]

A mixture of 2-amino-4-chlorobenzenethiol (CAS 1004-00-8) (1.1 g, 7.1 mmol), 4-(chloromethyl)-1H-imidazole hydrochloride (721 mg, 4.71 mmol) and $K_2CO_3$ (3.2 g, 23.6 mmol) in DMF (10 ml) was stirred at room temperature overnight. The reaction mixture was poured into water (50 ml) and extracted with ethyl acetate (2×50 ml). The organic layer was washed with brine, dried over $Na_2SO_4$, concentrated in vacuo. The crude product was purified by column chromatography on silica gel (0→100% ethyl acetate in hexane) to give Intermediate 1 as a solid (1.0 g, 60%).

$^1$H NMR (300 MHz, $CD_3OD$) δ 7.58 (s, 1H), 7.06 (d, J=8.20 Hz, 1H), 6.73 (d, J=2.34 Hz, 1H), 6.65 (s, 1H), 6.48 (dd, J=2.34, 8.20 Hz, 1H), 3.86 (s, 2H).

General Procedure B

Compound 1

N-{5-chloro-2-[(1H-imidazol-4-ylmethyl)thio]phenyl}-1-benzofuran-2-sulfonamide

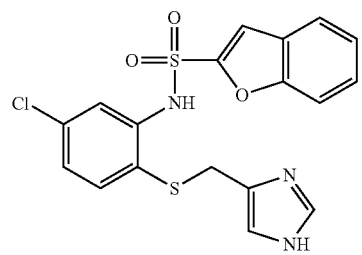 [SMILES: O=S(=O)(Nc1cc(Cl)ccc1SCc1c[nH]cn1)c1cc2ccccc2o1]

A mixture of Intermediate 1 (300 mg, 1.26 mmol) and 1-benzofuran-2-sulfonyl chloride (273 mg, 1.26 mmol) in pyridine (4 ml) was heated at 100° C. overnight. Pyridine was removed under reduced pressure and the residue was purified by column chromatography on silica gel (10% MeOH in $CH_2Cl_2$) to give Compound 1 (157 mg, 30%).

$^1$H NMR (600 MHz, acetone-$d_6$) δ 7.94 (s, 1H), 7.73 (d, J=7.92 Hz, 1H), 7.64 (d, J=2.35 Hz, 1H), 7.56 (d, J=8.51 Hz, 1H), 7.52 (d, J=8.22 Hz, 1H), 7.44-7.49 (m, 1H), 7.42 (s, 1H), 7.28-7.37 (m, 1H), 7.11 (dd, J=2.35, 8.22 Hz, 1H), 6.97 (s, 1H), 3.91 (s, 2H).

Compound 2

N-[5-chloro-2-(methylthio)phenyl]-1-benzofuran-2-sulfonamide

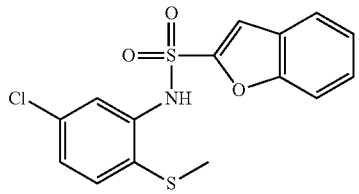 [SMILES: CSc1ccc(Cl)cc1NS(=O)(=O)c1cc2ccccc2o1]

Following General Procedure B, the title compound (243 mg, 60%) was prepared from 5-chloro-2-(methylthio)aniline (CAS 16423-54-4) (200 mg, 1.15 mmol) and 1-benzofuran-2-sulfonyl chloride (249 mg, 1.152 mmol).

$^1$H NMR (600 MHz, acetone-$d_6$) δ 7.75 (d, J=7.92 Hz, 1H), 7.60 (d, J=8.51 Hz, 1H), 7.48-7.54 (m, 2H), 7.47 (d, J=2.35 Hz, 1H), 7.29-7.38 (m, 2H), 7.22 (dd, J=2.35, 8.51 Hz, 1H), 2.22 (s, 3H).

General Procedure C

Compound 3

N-[5-chloro-2-(methylsulfinyl)phenyl]-1-benzofuran-2-sulfonamide

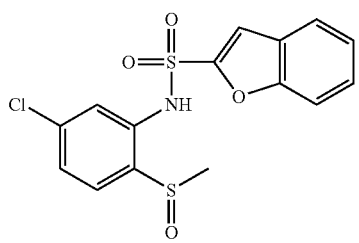 [SMILES: CS(=O)c1ccc(Cl)cc1NS(=O)(=O)c1cc2ccccc2o1]

To a solution of Compound 2 (194 mg, 0.554 mmol) in CH$_2$Cl$_2$ (6 ml) at 0° C. was added mCPBA (111 mg, ~0.554 mmol). After it was stirred for 30 min at 0° C., the mixture was separated into two portions. One portion (2 ml) was concentrated in vacuo and purified by column chromatography on silica gel (0→100% ethyl acetate in hexane followed by 0→10% MeOH in CH$_2$Cl$_2$) to give the title compound as a solid (35 mg, 52%).

Alternatively, the title compound can be prepared by treating Compound 2 with 1 equivalent of NaIO$_4$ in MeOH/CH$_3$CN and H$_2$O at 0° C. to room temperature.

In another alternative procedure, the title compound can be prepared by treating Compound 2 with 1-1.4 equivalent of Oxone® in MeOH/CH$_3$CN and H$_2$O at room temperature.

$^1$H NMR (600 MHz, CDCl$_3$) δ 7.74 (d, J=1.76 Hz, 1H), 7.71 (d, J=8.22 Hz, 1H), 7.52-7.59 (m, 2H), 7.49 (td, J=1.17, 7.78 Hz, 1H), 7.32-7.39 (m, 1H), 7.25 (d, J=8.22 Hz, 1H), 7.15 (dd, J=1.91, 8.36 Hz, 1H), 2.88 (s, 3H).

General Procedure D

Compound 4

N-[5-chloro-2-(methylsulfonyl)phenyl]-1-benzofuran-2-sulfonamide

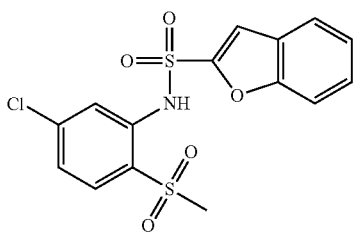 [SMILES: CS(=O)(=O)c1ccc(Cl)cc1NS(=O)(=O)c1cc2ccccc2o1]

To the other portion (4 ml) of solution from Compound 3 was added mCPBA (111 mg, 0.554 mmol) and the reaction was stirred at room temperature for 1 h. The mixture was concentrated in vacuo and the residue was purified by column chromatography on silica gel (0→100% ethyl acetate in hexane) to give the title compound as a solid (75 mg, 53%).

Alternatively, the title compound can be prepared by treating Compound 2 with 2-3 equivalents of mCPBA at room temperature.

In another alternative procedure, the title compound can be prepared by treating Compound 2 with 3 equivalents of Oxone® in MeOH/CH$_3$CN and H$_2$O at room temperature.

$^1$H NMR (600 MHz, CDCl$_3$) δ 9.43 (s, 1H), 7.88 (d, J=1.76 Hz, 1H), 7.81 (d, J=8.51 Hz, 1H), 7.72 (d, J=7.92 Hz, 1H), 7.61 (s, 1H), 7.47-7.57 (m, 2H), 7.34-7.40 (m, 1H), 7.26 (s, 1H), 7.23 (dd, J=2.05, 8.51 Hz, 1H), 3.05 (s, 3H).

Intermediate 2

5-chloro-2-(methylsulfinyl)aniline

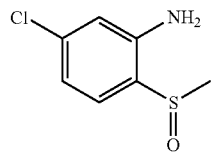

Following General Procedure C, the title compound (914 mg, 84%) was prepared from 5-chloro-2-(methylthio)aniline (1 g, 5.758 mmol).

$^1$H NMR (300 MHz, CD$_3$OD) δ 7.32 (d, J=8.20 Hz, 1H), 6.81 (d, J=2.05 Hz, 1H), 6.72 (dd, J=1.76, 8.20 Hz, 1H), 2.86 (s, 3H).

Compound 5

3,4-dichloro-N-[5-chloro-2-(methylthio)phenyl]benzenesulfonamide

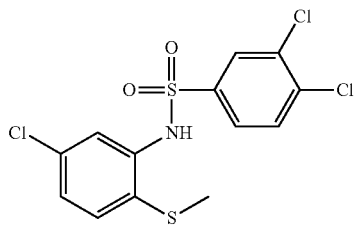 [SMILES: CSc1ccc(Cl)cc1NS(=O)(=O)c1ccc(Cl)c(Cl)c1]

Following General Procedure B, the title compound (52 mg, 21%) was prepared from 5-chloro-2-(methylsulfinyl)aniline (Intermediate 2) (120 mg, 0.635 mmol) and 3,4-dichlorobenzene-1-sulfonyl chloride (156 mg, 0.635 mmol).
$^1$H NMR (300 MHz, CD$_3$OD) δ 7.87 (d, J=1.76 Hz, 1H), 7.55-7.70 (m, 2H), 7.38 (s, 1H), 7.17-7.27 (m, 2H), 2.22 (s, 3H).

Compound 6

3,4-dichloro-N-[5-chloro-2-(methylsulfinyl)phenyl]benzenesulfonamide

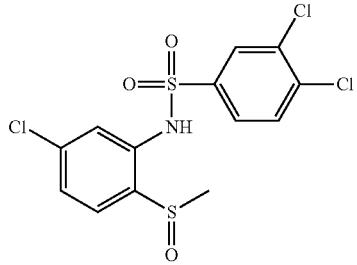 [SMILES: CS(=O)c1ccc(Cl)cc1NS(=O)(=O)c1ccc(Cl)c(Cl)c1]

Following General Procedure C, the title compound (28 mg, 52%) was prepared from 3,4-dichloro-N-[5-chloro-2-(methylthio)phenyl]benzenesulfonamide (52 mg, 0.136 mmol).
$^1$H NMR (300 MHz, acetone-d$_6$) δ 10.70 (br. s., 1H), 8.06 (s, 1H), 7.86 (s, 2H), 7.44-7.59 (m, 2H), 7.34 (dd, J=1.90, 8.35 Hz, 1H), 2.84 (s, 3H).

Compound 7

4-chloro-N-[5-chloro-2-(methylsulfinyl)phenyl]-3-methylbenzenesulfonamide

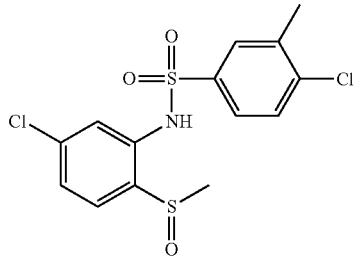 [SMILES: Cc1cc(S(=O)(=O)Nc2cc(Cl)ccc2S(C)=O)ccc1Cl]

Following General Procedure B and C, the title compound (90 mg) was prepared from 5-chloro-2-(methylthio)aniline and 4-chloro-3-methylbenzene-1-sulfonyl chloride.
$^1$H NMR (600 MHz, CDCl$_3$) δ 10.62 (s, 1H), 7.82 (d, J=2.05 Hz, 1H), 7.71 (dd, J=1.91, 8.36 Hz, 1H), 7.63 (d, J=2.05 Hz, 1H), 7.48 (d, J=8.51 Hz, 1H), 7.02-7.15 (m, 2H), 2.81 (s, 3H), 2.43 (s, 3H).

Compound 8

N-[5-chloro-2-(methylsulfinyl)phenyl]-3-nitro-4-(trifluoromethyl)benzenesulfonamide

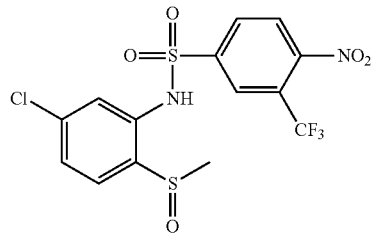 [SMILES: CS(=O)c1ccc(Cl)cc1NS(=O)(=O)c1ccc([N+](=O)[O-])c(C(F)(F)F)c1]

Following General Procedure B and C, the title compound (43 mg) was prepared from 5-chloro-2-(methylthio)aniline and 4-nitro-3-(trifluoromethyl)benzene-1-sulfonyl chloride.
$^1$H NMR (600 MHz, acetone-d$_6$) δ 8.25-8.35 (m, 2H), 8.11 (d, J=8.22 Hz, 1H), 7.39-7.48 (m, 2H), 6.75 (dd, J=2.05, 8.22 Hz, 1H), 2.70 (s, 3H).

Compound 9

4-chloro-N-[5-chloro-2-(methylthio)phenyl]-2-fluorobenzenesulfonamide

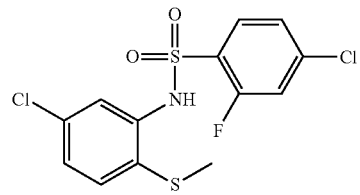 [SMILES: CSc1ccc(Cl)cc1NS(=O)(=O)c1ccc(Cl)cc1F]

Following General Procedure B, the title compound (380 mg, 66%) was prepared from 5-chloro-2-(methylthio)aniline (273 mg, 1.57 mmol) and 4-chloro-2-fluorobenzene-1-sulfonyl chloride (360 mg, 1.57 mmol).
$^1$H NMR (300 MHz, acetone-d$_6$) δ 8.77 (br. s., 1H), 7.84 (t, J=8.06 Hz, 1H), 7.53 (dd, J=1.90, 9.82 Hz, 1H), 7.35-7.48 (m, 3H), 7.25 (dd, J=2.20, 8.35 Hz, 1H), 2.34 (s, 3H).

Compound 10

4-chloro-N-{5-chloro-2-[(1H-imidazol-4-ylmethyl)sulfonyl]phenyl}-3-(trifluoromethyl)benzenesulfonamide

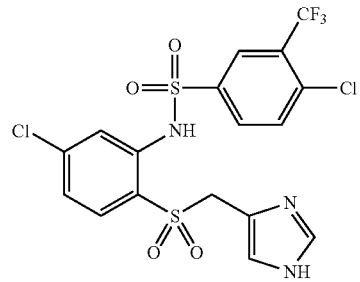 [SMILES: O=S(=O)(Cc1c[nH]cn1)c1ccc(Cl)cc1NS(=O)(=O)c1ccc(Cl)c(C(F)(F)F)c1]

Following General Procedure B and D, the title compound (95 mg, 36%) was prepared from 5-chloro-2-[(1H-imidazol-4-ylmethyl)thio]aniline (301 mg, 1.26 mmol) and 4-chloro-3-(trifluoromethyl)benzene-1-sulfonyl chloride (351 mg, 1.26 mmol).

¹H NMR (600 MHz, acetone-d₆) δ 8.27 (s, 1H), 8.15 (d, J=8.22 Hz, 1H), 7.81 (br. s., 1H), 7.73 (d, J=8.51 Hz, 1H), 7.68 (d, J=8.51 Hz, 1H), 7.30 (s, 1H), 6.91 (dd, J=1.47, 8.51 Hz, 1H), 4.56 (br. s., 2H).

Intermediate 3 tert-butyl [4-(chloromethyl)-1,3-thiazol-2-yl]carbamate

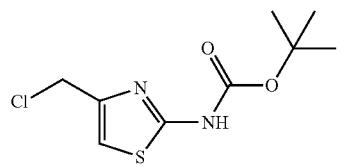

A solution of 4-(chloromethyl)-1,3-thiazol-2-amine hydrochloride (530 mg, 2.86 mmol), di-tert-butyl dicarbonate (750 mg, 3.44 mmol), triethylamine (0.6 ml, 4.30 mmol) and DMAP (cat. amount) in THF (10 ml) was stirred at room temperature overnight. The mixture was diluted with ethyl acetate. washed with water and brine, dried over Na₂SO₄, and concentrated in vacuo. The residue was purified by column chromatography (30% ethyl acetate in hexane) to give the title compound as a solid (391 mg, 45%).

¹H NMR (600 MHz, CD₃OD) δ 7.02 (s, 1H), 4.56 (s, 2H), 1.54 (s, 9H).

Intermediate 4 tert-butyl (4-{[(2-amino-4-chlorophenyl)thio]methyl}-1,3-thiazol-2-yl)carbamate

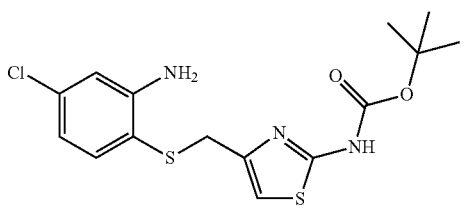 [SMILES: CC(C)(C)OC(=O)Nc1nc(CSc2ccc(Cl)cc2N)cs1]

Following General Procedure A, the title compound (588 mg, 67%) was prepared from 2-amino-4-chlorobenzenethiol (376 mg, 2.36 mmol), tert-butyl [4-(chloromethyl)-1,3-thiazol-2-yl]carbamate (391 mg, 1.57 mmol) and K₂CO₃ (1.08 g, 3.45 mmol) in DMF (10 ml).

¹H NMR (300 MHz, acetone-d₆) δ 10.18 (br. s., 1H), 7.17 (d, J=8.21 Hz, 1H), 6.79 (d, J=2.34 Hz, 1H), 6.62 (s, 1H), 6.51 (dd, J=2.05, 8.20 Hz, 1H), 5.30 (br. s., 1H), 3.88 (s, 2H), 1.53 (s, 9H).

Compound 11 tert-butyl {4-[({2-[(1-benzofuran-2-ylsulfonyl)amino]-4-chlorophenyl}thio)methyl]-1,3-thiazol-2-yl}carbamate

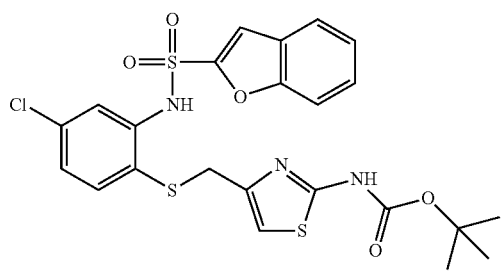 [SMILES: CC(C)(C)OC(=O)Nc1nc(CSc2ccc(Cl)cc2NS(=O)(=O)c2cc3ccccc3o2)cs1]

Following General Procedure B, the title compound (380 mg, 54%) was prepared from tert-butyl (4-{[(2-amino-4-chlorophenyl)thio]methyl}-1,3-thiazol-2-yl)carbamate (640 mg, 1.72 mmol) and 1-benzofuran-2-sulfonyl chloride (372 mg, 1.72 mmol) in pyridine (5 ml).

¹H NMR (300 MHz, acetone-d₆) δ 11.20 (br. s., 1H), 9.82 (br. s., 1H), 7.78 (d, J=7.91 Hz, 2H), 7.67 (d, J=2.34 Hz, 1H), 7.62 (s, 1H), 7.45-7.60 (m, 3H), 7.31-7.43 (m, 1H), 7.07-7.22 (m, 1H), 6.77 (s, 1H), 3.93 (s, 2H), 1.55 (s, 9H).

General Procedure E

Compound 12

N-(2-{[(2-amino-1,3-thiazol-4-yl)methyl]thio}-5-chlorophenyl)-1-benzofuran-2-sulfonamide

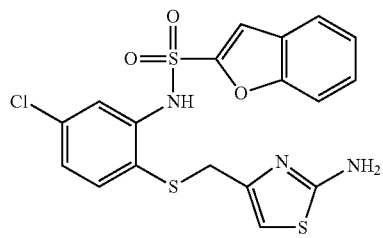 [SMILES: Nc1nc(CSc2ccc(Cl)cc2NS(=O)(=O)c2cc3ccccc3o2)cs1]

A solution of tert-butyl {4-[({2-[(1-benzofuran-2-ylsulfonyl)amino]-4-chlorophenyl}thio)methyl]-1,3-thiazol-2-yl}carbamate Compound 11 (62 mg, 0.11 mmol), TFA (0.2 ml) in CH₂Cl₂ (1 ml) was stirred overnight. The solvent was removed in vacuo and the crude product was purified by column chromatography on silica gel (50% ethyl acetate in hexane) to afford the title compound (45 mg, 88%).

$^1$H NMR (600 MHz, acetone-d$_6$) δ 8.78 (br. s., 1H), 7.77 (d, J=7.92 Hz, OH), 7.55-7.66 (m, 3H), 7.45-7.55 (m, 2H), 7.29-7.41 (m, 1H), 7.17 (dd, J=2.20, 8.36 Hz, 1H), 6.33 (s, 1H), 3.90 (s, 2H).

Compound 13

4-chloro-N-[5-chloro-2-(methylsulfinyl)phenyl]-3-(trifluoromethyl)benzenesulfonamide

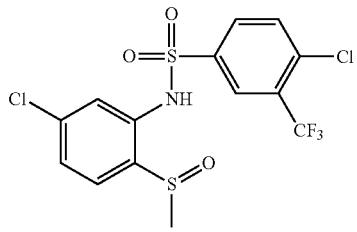 [SMILES: CS(=O)c1ccc(Cl)cc1NS(=O)(=O)c1ccc(Cl)c(C(F)(F)F)c1]

Following General Procedure B and C, the title compound was prepared from 5-chloro-2-(methylthio)aniline and 4-chloro-3-(trifluoromethyl)benzene-1-sulfonyl chloride.

$^1$H NMR (300 MHz, CD$_3$OD) δ 8.07 (s, 1H), 7.96 (d, J=8.50 Hz, 1H), 7.82 (d, J=8.21 Hz, 1H), 7.76 (d, J=8.50 Hz, 1H), 7.41 (d, J=7.91 Hz, 1H), 7.07 (s, 1H), 2.83 (s, 3H).

General Procedure F

Intermediate 5

N,N'-[dithiobis(5-chloro-2,1-phenylene)]bis[4-chloro-3-(trifluoromethyl)benzenesulfonamide]

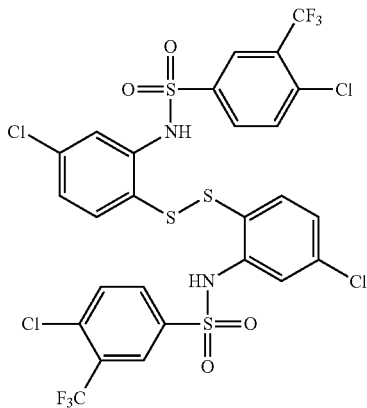 [SMILES: O=S(=O)(Nc1cc(Cl)ccc1SSc1ccc(Cl)cc1NS(=O)(=O)c1ccc(Cl)c(C(F)(F)F)c1)c1ccc(Cl)c(C(F)(F)F)c1]

To a solution of 2,2'-dithiobis(5-chloroaniline) (CAS 29124-55-8)(1.59 g, 5.0 mmol) in pyridine (20 ml) was added 4-chloro-3-(trifluoromethyl)benzene-1-sulfonyl chloride (2.76 g, 10.0 mmol) and the reaction was stirred at room temperature for 16 h. Additional 4-chloro-3-(trifluoromethyl)benzene-1-sulfonyl chloride (2.76 g, 10.0 mmol) and pyridine (20 ml) was added, and the reaction was stirred for 20 h. The mixture was concentrated in vacuo and H$_2$O was added. A gum-like semi-solid was formed. After decanting H$_2$O, the semi-solid was rinsed with H$_2$O (×2), taken in EtOAc, extracted with 1M HCl (×2), washed with H$_2$O, brine, dried over Na$_2$SO$_4$, and concentrated in vacuo to give a brown thick syrup (6.5 g). To a solution of the crude syrup in methanol (100 ml) was added 4M NaOH (12 ml), and the mixture was heated at 100° C. for 15 min, cooled to room temperature, quenched slowly with 1M HCl (~50 ml) with stirring and cooling to pH 4-5. The volume of the resulting suspension was reduced in vacuo, followed by extraction with EtOAc. The organic layer was washed with brine, dried over Na$_2$SO$_4$, and concentrated in vacuo. The crude solid containing sulfonic acid was pulverized in saturated NaHCO$_3$, and filtered, rinsed with minimal amount of diethyl ether to yield the title compound as an off-white solid (3.11 g).

$^1$H NMR (600 MHz, CD$_3$OD) δ 8.08 (d, J=2.05 Hz, 2H), 7.93 (dd, J=2.20, 8.36 Hz, 2H), 7.81 (d, J=8.51 Hz, 2H), 7.22 (d, J=2.05 Hz, 2H), 7.18-7.20 (m, 2H), 7.10 (d, J=8.51 Hz, 2H).

Compound 14

4-chloro-N-[5-chloro-2-(ethylthio)phenyl]-3-(trifluoromethyl)benzenesulfonamide

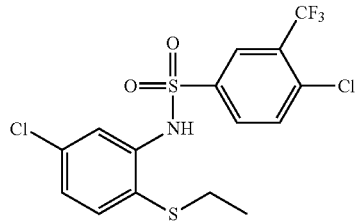 [SMILES: CCSc1ccc(Cl)cc1NS(=O)(=O)c1ccc(Cl)c(C(F)(F)F)c1]

To a solution of N,N'-[dithiobis(5-chloro-2,1-phenylene)]bis[4-chloro-3-(trifluoromethyl)benzenesulfonamide] Intermediate 5 (0.32 g, 0.40 mmol) in CH$_2$Cl$_2$ (10 ml) was added saturated aqueous NaHCO$_3$ (1.0 ml), polymer-bound triphenylphosphine (~3 mmol/g triphenylphosphine loading, 0.27 g, 0.80 mmol), and ethyl iodide (64 μl, 0.80 mmol). The reaction was stirred at room temperature for 2 h and was diluted with EtOAc, filtered, and washed with brine, dried over Na$_2$SO$_4$, and concentrated. The residue was purified by column chromatography on silica gel (0→25% ethyl acetate in hexane) to yield the title compound as a yellow syrup (204 mg, 59%).

$^1$H NMR (600 MHz, CDCl$_3$) δ 8.12 (d, J=2.35 Hz, 1H), 7.88 (dd, J=2.35, 8.22 Hz, 1H), 7.82 (br. s., 1H), 7.64 (d, J=2.35 Hz, 1H), 7.59 (d, J=8.51 Hz, 1H), 7.32 (d, J=8.22 Hz, 1H), 7.06 (dd, J=2.20, 8.36 Hz, 1H), 2.60 (q, J=7.34 Hz, 2H), 1.10 (t, J=7.34 Hz, 3H).

Compound 15

4-chloro-N-[5-chloro-2-(ethylsulfinyl)phenyl]-3-(trifluoromethyl)benzenesulfonamide

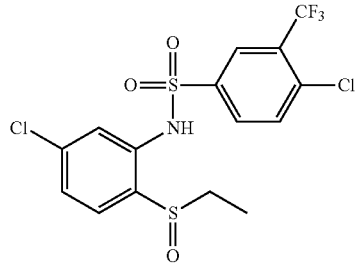 [SMILES: CCS(=O)c1ccc(Cl)cc1NS(=O)(=O)c1ccc(Cl)c(C(F)(F)F)c1]

Following General Procedure C, the title compound was prepared from 4-chloro-N-[5-chloro-2-(ethylthio)phenyl]-3-(trifluoromethyl)benzenesulfonamide.

$^1$H NMR (600 MHz, CD$_3$OD) δ 8.15 (d, J=2.35 Hz, 1H), 8.00 (dd, J=2.20, 8.36 Hz, 1H), 7.72 (d, J=8.51 Hz, 1H), 7.44

(d, J=8.51 Hz, 1H), 7.27 (d, J=2.05 Hz, 1H), 7.01 (dd, J=2.05, 8.51 Hz, 1H), 3.10-3.18 (m, 1H), 2.89-2.97 (m, 1H), 1.11 (t, J=7.34 Hz, 3H).

Intermediate 6 ethyl 6-[(tert-butoxycarbonyl)amino]pyridine-2-carboxylate

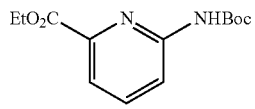

A mixture of ethyl 6-aminopyridine-2-carboxylate (1.57 g, 9.43 mmol), DMAP (1.12 g, 9.18 mmol), and di-tert-butyl dicarbonate (2.46 g, 11.3 mmol) in THF (45 ml) was heated at 60° C. for 16 h. The solvent was removed and the residue was purified by chromatography on silica gel (10→15% ethyl acetate in hexane) to yield the title compound as a white solid (2.50 g, 100%).

Intermediate 7 tert-butyl [6-(chloromethyl)pyridin-2-yl]carbamate

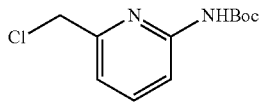 [SMILES: CC(C)(C)OC(=O)Nc1cccc(CCl)n1]

To a solution of ethyl 6-[(tert-butoxycarbonyl)amino]pyridine-2-carboxylate (456 mg, 1.71 mmol) in anhydrous ethanol (20 ml) was added pulverized $CaCl_2$ (395 mg, 3.42 mmol). The suspension was stirred and cooled to 0° C. and $NaBH_4$ (325 mg, 8.55 mmol) was added slowly. The reaction was stirred at 0° C. for 2 h, quenched with water, and extracted with $CHCl_3$ (×3). The combined organic layer was dried over $Na_2SO_4$ and concentrated. The residue was purified by column chromatography on silica gel (30→50% ethyl acetate in hexane) to yield a colorless syrup (308 mg) as a mixture containing tert-butyl [6-(hydroxymethyl)pyridin-2-yl]carbamate as the major component (~4:1 ratio). To a solution of the above mixture in $CH_2Cl_2$ (10 ml) was added pyridine (144 µl, 1.79 mmol) and $SOCl_2$ (120 µl, 1.65 mmol). The reaction was stirred at room temperature for 4 h, quenched with water and saturated $Na_2CO_3$, and extracted with $CHCl_3$. The combined organic layer was dried over $Na_2SO_4$ and concentrated. The residue was purified by column chromatography on silica gel (10% ethyl acetate in hexane) to yield the title compound as a colorless syrup (208 mg, 50% over 2 steps).

Intermediate 8

N,N'-[dithiobis(5-chloro-2,1-phenylene)]bis(1-benzofuran-2-sulfonamide)

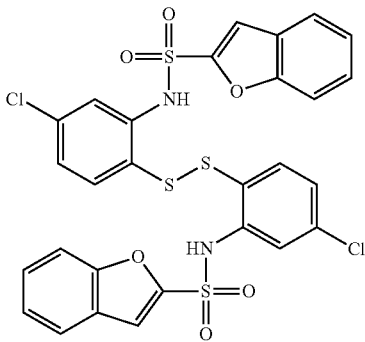 [SMILES: O=S(=O)(Nc1cc(Cl)ccc1SSc1ccc(Cl)cc1NS(=O)(=O)c1cc2ccccc2o1)c1cc2ccccc2o1]

Following General Procedure F, the title compound was prepared from 2,2'-dithiobis(5-chloroaniline) and 1-benzofuran-2-sulfonyl chloride.

$^1$H NMR (600 MHz, $CD_3OD$) δ 7.72 (d, J=7.92 Hz, 2H), 7.55 (dd, J=0.59, 8.51 Hz, 2H), 7.48 (s, 2H), 7.32-7.37 (m, 4H), 7.22 (d, J=2.05 Hz, 2H), 6.99-7.02 (m, 2H), 6.96-6.99 (m, 2H).

General Procedure G

Compound 16 tert-Butyl {6-[({2-[(1-benzofuran-2-ylsulfonyl)amino]-4-chlorophenyl}thio)methyl]pyridin-2-yl}carbamate

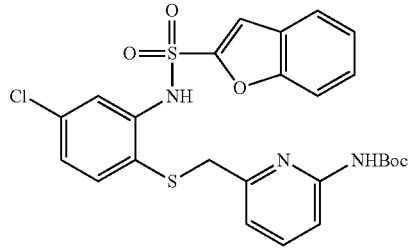 [SMILES: CC(C)(C)OC(=O)Nc1cccc(CSc2ccc(Cl)cc2NS(=O)(=O)c2cc3ccccc3o2)n1]

To a solution of N,N'-[dithiobis(5-chloro-2,1-phenylene)]bis(1-benzofuran-2-sulfonamide) (271 mg, 0.40 mmol) in $CH_2Cl_2$ (4 ml) and dioxane (4 ml) was added saturated aqueous $NaHCO_3$ (4 ml), polymer-bound triphenylphosphine (~3 mmol/g triphenylphosphine loading, 0.40 g, 1.20 mmol), tert-butyl [6-(chloromethyl)pyridin-2-yl]carbamate (195 mg, 0.80 mmol), and tetrabutylammonium iodide (30 mg, 0.08 mmol). The reaction was stirred at room temperature for 4 h and was diluted with EtOAc, filtered, and washed with brine, dried over $Na_2SO_4$, and concentrated. The residue was purified by column chromatography on silica gel (10→15% ethyl acetate in hexane) to yield the title compound as a yellow solid (260 mg, 59%).

¹H NMR (600 MHz, CD₃OD) δ 7.74 (d, J=8.22 Hz, 1H), 7.70 (d, J=7.63 Hz, 1H), 7.50-7.57 (m, 2H), 7.44-7.50 (m, 2H), 7.41 (s, 1H), 7.31-7.36 (m, 2H), 7.09 (d, J=8.22 Hz, 1H), 6.65 (d, J=7.34 Hz, 1H), 3.88 (s, 2H), 1.54 (s, 9H).

Compound 17

N-(2-{[(6-aminopyridin-2-yl)methyl]thio}-5-chlorophenyl)-1-benzofuran-2-sulfonamide

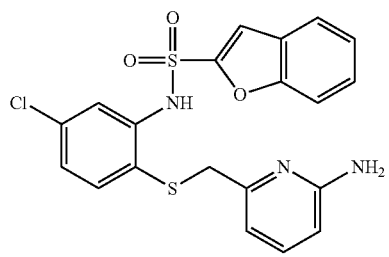 [SMILES: Nc1cccc(CSc2ccc(Cl)cc2NS(=O)(=O)c2cc3ccccc3o2)n1]

Following General Procedure E, the title compound (33 mg, 78%) was prepared from tert-butyl {6-[({2-[(1-benzofuran-2-ylsulfonyl)amino]-4-chlorophenyl}thio)methyl]pyridin-2-yl}carbamate.

¹H NMR (600 MHz, CD₃OD) δ 7.63 (d, J=7.92 Hz, 1H), 7.58 (d, J=2.35 Hz, 1H), 7.40-7.44 (m, 1H), 7.35-7.40 (m, 2H), 7.31-7.35 (m, 2H), 7.26 (ddd, J=0.88, 7.04, 7.92 Hz, 1H), 6.95 (dd, J=2.35, 8.22 Hz, 1H), 6.55 (d, J=8.51 Hz, 1H), 6.31 (d, J=7.04 Hz, 1H), 3.78 (s, 2H).

Compound 18 tert-butyl {6-[({2-[(1-benzofuran-2-ylsulfonyl)amino]-4-chlorophenyl}sulfinyl)methyl]pyridin-2-yl}carbamate

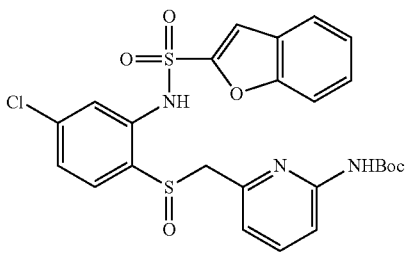 [SMILES: CC(C)(C)OC(=O)Nc1cccc(CS(=O)c2ccc(Cl)cc2NS(=O)(=O)c2cc3ccccc3o2)n1]

Following General Procedure C, the title compound (98 mg, 91%) was prepared from tert-butyl {6-[({2-[(1-benzofuran-2-ylsulfonyl)amino]-4-chlorophenyl}thio)methyl]pyridin-2-yl}carbamate.

¹H NMR (600 MHz, CD₃OD) δ 7.67 (d, J=8.22 Hz, 1H), 7.64 (d, J=7.04 Hz, 1H), 7.47 (d, J=2.05 Hz, 1H), 7.42-7.46 (m, 1H), 7.36-7.39 (m, 1H), 7.29-7.33 (m, 1H), 7.22-7.26 (m, 2H), 7.09 (d, J=8.22 Hz, 1H), 6.77 (dd, J=1.91, 8.36 Hz, 1H), 6.68 (d, J=7.34 Hz, 1H), 4.59 (d, J=12.62 Hz, 1H), 4.16 (d, J=12.62 Hz, 1H), 1.52 (s, 9H).

Compound 19

N-(2-{[(6-aminopyridin-2-yl)methyl]sulfinyl}-5-chlorophenyl)-1-benzofuran-2-sulfonamide

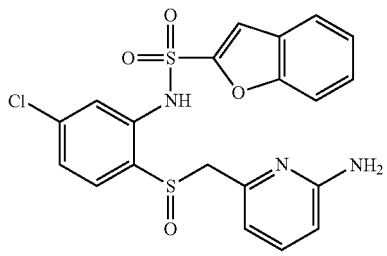 [SMILES: Nc1cccc(CS(=O)c2ccc(Cl)cc2NS(=O)(=O)c2cc3ccccc3o2)n1]

Following General Procedure E, the title compound (71 mg, 91%) was prepared from tert-butyl {6-[({2-[(1-benzofuran-2-ylsulfonyl)amino]-4-chlorophenyl}sulfinyl)methyl]pyridin-2-yl}carbamate.

¹H NMR (300 MHz, CD₃OD) δ 7.65 (d, J=7.91 Hz, 1H), 7.52-7.62 (m, 1H), 7.50 (d, J=1.47 Hz, 1H), 7.39-7.46 (m, 1H), 7.29-7.38 (m, 2H), 7.20-7.29 (m, 2H), 6.89 (dd, J=1.47, 8.50 Hz, 1H), 6.79 (d, J=8.79 Hz, 1H), 6.44 (d, J=7.03 Hz, 1H), 4.60 (d, J=13.48 Hz, 1H), 4.25 (d, J=13.19 Hz, 1H).

Compound 20 tert-butyl {6-[({2-[(1-benzofuran-2-ylsulfonyl)amino]-4-chlorophenyl}sulfonyl)methyl]pyridin-2-yl}carbamate

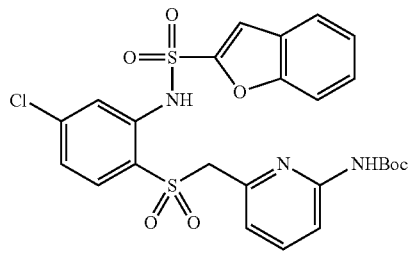 [SMILES: CC(C)(C)OC(=O)Nc1cccc(CS(=O)(=O)c2ccc(Cl)cc2NS(=O)(=O)c2cc3ccccc3o2)n1]

Following General Procedure D, the title compound (60 mg, 56%) was prepared from tert-butyl {6-[({2-[(1-benzofuran-2-ylsulfonyl)amino]-4-chlorophenyl}thio)methyl]pyridin-2-yl}carbamate.

¹H NMR (300 MHz, CD₃OD) δ 7.79 (d, J=1.76 Hz, 1H), 7.65 (d, J=7.62 Hz, 1H), 7.55 (d, J=8.50 Hz, 1H), 7.44 (s, 1H), 7.18-7.40 (m, 5H), 6.72 (dd, J=1.76, 8.50 Hz, 1H), 6.60 (d, J=7.33 Hz, 1H), 4.97 (s, 2H), 1.51 (s, 9H).

Compound 21

N-(2-{[(6-aminopyridin-2-yl)methyl]sulfonyl}-5-chlorophenyl)-1-benzofuran-2-sulfonamide

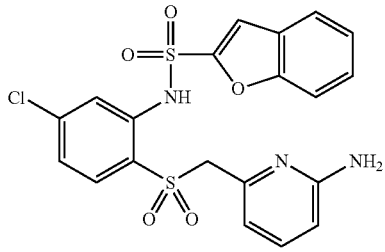 [SMILES: Nc1cccc(CS(=O)(=O)c2ccc(Cl)cc2NS(=O)(=O)c2cc3ccccc3o2)n1]

Following General Procedure E, the title compound (47 mg, 94%) was prepared from tert-butyl {6-[({2-[(1-benzofuran-2-ylsulfonyl)amino]-4-chlorophenyl}sulfonyl)methyl]pyridin-2-yl}carbamate.

$^1$H NMR (300 MHz, CD$_3$OD) δ 7.73 (d, J=2.05 Hz, 1H), 7.66 (d, J=7.62 Hz, 1H), 7.52 (d, J=8.79 Hz, 1H), 7.20-7.44 (m, 4H), 7.14 (t, J=7.77 Hz, 1H), 6.73 (dd, J=1.76, 8.50 Hz, 1H), 6.48 (d, J=8.20 Hz, 1H), 6.28 (d, J=7.33 Hz, 1H), 4.91 (s, 2H).

Compound 22 tert-butyl 3-[({2-[(1-benzofuran-2-ylsulfonyl)amino]-4-chlorophenyl}thio)methyl]-1H-pyrazole-1-carboxylate

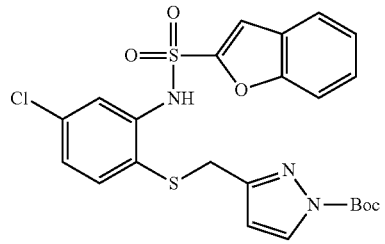 [SMILES: CC(C)(C)OC(=O)n1ccc(CSc2ccc(Cl)cc2NS(=O)(=O)c2cc3ccccc3o2)n1]

Following General Procedure G, the title compound (206 mg, 36%) was prepared from N,N'-[dithiobis(5-chloro-2,1-phenylene)]bis(1-benzofuran-2-sulfonamide) and tert-butyl 3-(bromomethyl)-1H-pyrazole-1-carboxylate.

$^1$H NMR (600 MHz, CDCl$_3$) δ 8.30 (br. s., 1H), 7.93 (d, J=2.64 Hz, 1H), 7.62-7.67 (m, 2H), 7.47-7.52 (m, 1H), 7.42-7.45 (m, 1H), 7.41 (s, 1H), 7.34 (d, J=8.22 Hz, 1H), 7.28-7.32 (m, 1H), 7.00 (dd, J=2.20, 8.36 Hz, 1H), 6.03 (d, J=2.64 Hz, 1H), 3.88 (s, 2H), 1.64 (s, 9H).

Compound 23

N-{5-chloro-2-[(1H-pyrazol-3-ylmethyl)thio]phenyl}-1-benzofuran-2-sulfonamide

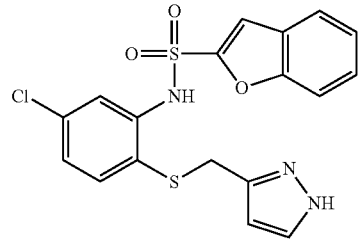 [SMILES: O=S(=O)(Nc1cc(Cl)ccc1SCc1cc[nH]n1)c1cc2ccccc2o1]

Following General Procedure E, the title compound (15 mg, 66%) was prepared from tert-butyl 3-[({2-[(1-benzofuran-2-ylsulfonyl)amino]-4-chlorophenyl}thio)methyl]-1H-pyrazole-1-carboxylate.

$^1$H NMR (600 MHz, CD$_3$OD) δ 7.70 (d, J=7.92 Hz, 1H), 7.51-7.55 (m, 1H), 7.45-7.50 (m, 2H), 7.37-7.44 (m, 2H), 7.34 (t, J=7.19 Hz, 1H), 7.25-7.31 (m, 1H), 7.11 (dd, J=1.76, 8.22 Hz, 1H), 5.88 (br. s., 1H), 3.89 (s, 2H).

General Procedure H

Intermediate 9

3-[(2-amino-4-chlorophenyl)thio]-N,N-dimethylpropanamide

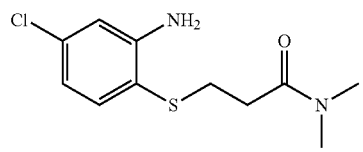 [SMILES: CN(C)C(=O)CCSc1ccc(Cl)cc1N]

A mixture of 2-amino-4-chlorobenzenethiol (327 mg, 2.05 mmol), N,N-dimethylacrylamide (203 mg, 2.05 mmol) and HOAc (0.5 ml) in CH$_2$Cl$_2$ (5 ml) was stirred at room temperature for 3 days. The reaction was quenched with NaHCO$_3$ (aq.) and then extracted with CH$_2$Cl$_2$ (2×10 ml). The organic layer was washed with water and brine and concentrated in vacuo. The crude product was purified by chromatography on silica gel (50% ethyl acetate in hexane) to yield the title compound (284 mg, 54%).

$^1$H NMR (300 MHz, CD$_3$OD) δ 7.26 (d, J=8.21 Hz, 1H), 6.76 (d, J=2.05 Hz, 1H), 6.56 (dd, J=2.34, 8.20 Hz, 1H), 2.85-3.02 (m, 8H), 2.57 (t, J=7.03 Hz, 2H).

Compound 24

3-{[4-Chloro-2-({[4-chloro-3-(trifluoromethyl)phenyl]sulfonyl}amino)phenyl]sulfinyl}-N,N-dimethylpropanamide

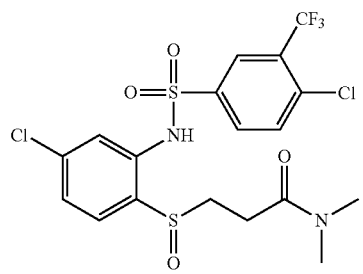 [SMILES: CN(C)C(=O)CCS(=O)c1ccc(Cl)cc1NS(=O)(=O)c1ccc(Cl)c(C(F)(F)F)c1]

Following General Procedure B and C, the title compound (280 mg) was prepared from 3-[(2-amino-4-chlorophenyl)thio]-N,N-dimethylpropanamide (284 mg, 1.11 mmo).

¹H NMR (600 MHz, CD₃OD) δ 8.16 (d, J=1.76 Hz, 1H), 8.00 (dd, J=2.05, 8.22 Hz, 1H), 7.75 (d, J=8.51 Hz, 1H), 7.57 (d, J=8.51 Hz, 1H), 7.32 (s, 1H), 7.21 (d, J=7.92 Hz, 1H), 3.26 (br. s., 1H), 3.18 (br. s., 1H), 3.02 (s, 3H), 2.95 (s, 3H), 2.83-2.91 (m, 1H), 2.62-2.76 (m, 1H).

Compound 25 tert-Butyl {4-[({2-[(1-benzofuran-2-ylsulfonyl)amino]-4-chlorophenyl}sulfinyl)methyl]-1,3-thiazol-2-yl}carbamate

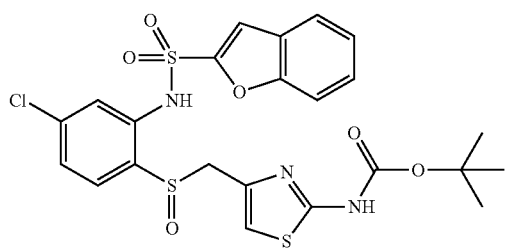 [SMILES: CC(C)(C)OC(=O)Nc1nc(CS(=O)c2ccc(Cl)cc2NS(=O)(=O)c2cc3ccccc3o2)cs1]

Following General Procedure C, tert-Butyl (4-(((2-(benzofuran-2-sulfonamido)-4-chlorophenyl)thio)methyl)thiazol-2-yl)carbamate (138 mg, 0.25 mmol) was oxidized to the title compound (97 mg, 68%).

1H NMR (600 MHz, acetone-d6) δ 10.43 (br. s., 1H), 7.75-7.84 (m, 2H), 7.66 (d, J=2.05 Hz, 1H), 7.62 (dd, J=0.88, 8.51 Hz, 1H), 7.50 (ddd, J=1.32, 7.26, 8.44 Hz, 1H), 7.32-7.41 (m, 1H), 7.11-7.24 (m, 2H), 6.74 (s, 1H), 4.47 (d, J=12.91 Hz, 1H), 4.37 (d, J=12.91 Hz, 1H), 1.50 (s, 9H).

Compound 26

N-(2-{[(2-amino-1,3-thiazol-4-yl)methyl]sulfinyl}-5-chlorophenyl)-1-benzofuran-2-sulfonamide

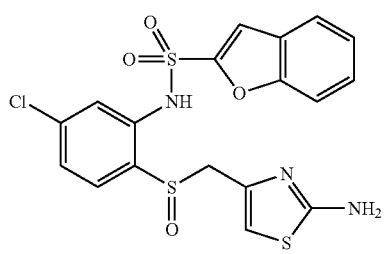 [SMILES: Nc1nc(CS(=O)c2ccc(Cl)cc2NS(=O)(=O)c2cc3ccccc3o2)cs1]

Following General Procedure E, tert-butyl {4-[({2-[(1-benzofuran-2-ylsulfonyl)amino]-4-chlorophenyl}sulfinyl)methyl]-1,3-thiazol-2-yl}carbamate (87 mg, 0.153 mmol) was de-Boc to give the title compound (58 mg, 82%).

1H NMR (600 MHz, acetone-d6) δ 10.43 (br. s., 1H), 7.75-7.84 (m, 2H), 7.66 (d, J=2.05 Hz, 1H), 7.62 (dd, J=0.88, 8.51 Hz, 1H), 7.50 (ddd, J=1.32, 7.26, 8.44 Hz, 1H), 7.32-7.41 (m, 1H), 7.11-7.24 (m, 2H), 6.74 (s, 1H), 4.47 (d, J=12.91 Hz, 1H), 4.37 (d, J=12.91 Hz, 1H), 1.50 (s, 9H).

Compound 27 tert-Butyl {4-[({2-[(1-benzofuran-2-ylsulfonyl)amino]-4-chlorophenyl}sulfonyl)methyl]-1,3-thiazol-2-yl}carbamate

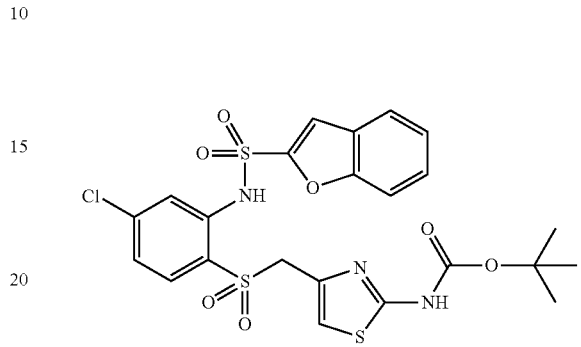

Following General Procedure D, the title compound (112 mg, 90%) was prepared from tert-Butyl (4-(((2-(benzofuran-2-sulfonamido)-4-chlorophenyl)thio)methyl)thiazol-2-yl)carbamate (117 mg, 0.212 mmol).

1H NMR (600 MHz, acetone-d6) δ 7.80 (d, J=7.92 Hz, 2H), 7.78 (d, J=1.76 Hz, 1H), 7.67 (d, J=8.51 Hz, 1H), 7.59 (d, J=7.92 Hz, 1H), 7.50 (t, J=7.63 Hz, 1H), 7.37 (t, J=7.48 Hz, 1H), 6.99 (s., 1H), 4.70 (s., 2H), 1.53 (s, 9H)

1H NMR (600 MHz, acetone-d6) δ 7.80 (d, J=7.92 Hz, 2H), 7.67 (d, J=8.51 Hz, 1H), 7.60 (br. s., 1H), 7.50 (t, J=7.63 Hz, 1H), 7.33-7.41 (m, 1H), 6.99 (br. s., 1H), 4.70 (br. s., 2H), 1.53 (s, 9H).

Compound 28

N-(2-{[(2-amino-1,3-thiazol-4-yl)methyl]sulfonyl}-5-chlorophenyl)-1-benzofuran-2-sulfonamide

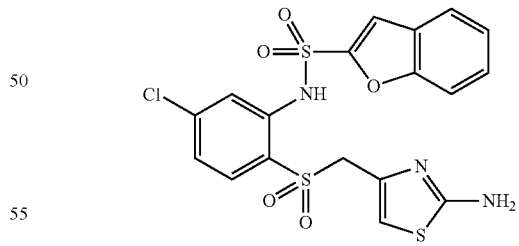

Following General Procedure E, the title compound (54 mg, 86%) was prepared from tert-butyl {4-[({2-[(1-benzofuran-2-ylsulfonyl)amino]-4-chlorophenyl}sulfinyl)methyl]-1,3-thiazol-2-yl}carbamate (77 mg, 0.153 mmol).

1H NMR (600 MHz, acetone-d6) δ 7.74-7.85 (m, 2H), 7.68 (d, J=2.35 Hz, 1H), 7.64 (dd, J=0.88, 8.51 Hz, 1H), 7.53 (ddd, J=1.32, 7.19, 8.51 Hz, 1H), 7.39 (ddd, J=0.88, 7.26, 8.00 Hz, 1H), 7.16-7.24 (m, 2H), 6.74 (s, 1H), 4.32-4.46 (m, 2H), 1.47-1.55 (m, 9H).

Intermediate 10

5-chloro-2-(((5-nitro-1H-pyrazol-3-yl)methyl)thio)aniline

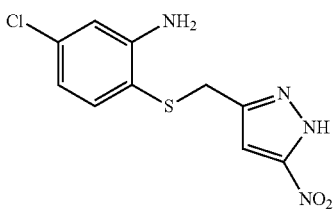 [SMILES: Nc1cc(Cl)ccc1SCc1cc([N+](=O)[O-])[nH]n1]

(5-Nitro-1H-pyrazol-3-yl)methanol (524 mg, 3.66 mmol) was first treated with SOCl$_2$ (3 ml) in CH$_2$Cl$_2$ (5 ml) at 35° C. for 2 hrs. The solvent was removed to get a crude 3-(chloromethyl)-5-nitro-1H-pyrazole. Then following General Procedure A, the title compound (515 mg, 49%) was prepared from 2-amino-4-chlorobenzenethiol (161 mg, 1.01 mmol), crude 3-(chloromethyl)-5-nitro-1H-pyrazole, K$_2$CO$_3$ (468 mg, 3.39 mmol) in DMF (3 ml).

1H NMR (600 MHz, CD$_3$OD) δ 7.05 (d, J=8.22 Hz, 1H), 6.77 (d, J=2.35 Hz, 1H), 6.60 (s, 1H), 6.49 (dd, J=2.05, 8.22 Hz, 1H), 3.95 (s, 2H).

Compound 29

N-(5-chloro-2-{[(5-nitro-1H-pyrazol-3-yl)methyl]thio}phenyl)-1-benzofuran-2-sulfonamide

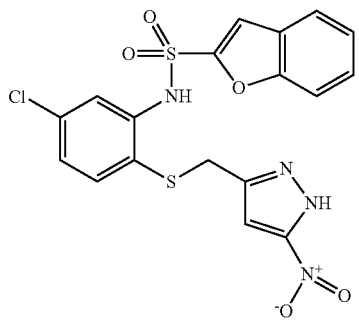

Following General Procedure B, the title compound (580 mg, 71%) was prepared from 5-chloro-2-(((5-nitro-1H-pyrazol-3-yl)methyl)thio)aniline (503 mg, 1.77 mmol) and benzofuran-2-sulfonyl chloride (384 mg, 1.77 mmol) in pyridine (5 ml).

1H NMR (600 MHz, CD$_3$OD) δ 7.70-7.73 (m, 1H), 7.53-7.56 (m, 1H), 7.49 (d, J=1.47 Hz, 1H), 7.47-7.49 (m, 1H), 7.47 (d, J=1.17 Hz, 1H), 7.45 (d, J=2.35 Hz, 1H), 7.44 (d, J=0.88 Hz, 1H), 7.35 (ddd, J=0.88, 7.26, 8.00 Hz, 1H), 7.15 (dd, J=2.35, 8.22 Hz, 1H), 6.42 (s, 1H), 3.97 (s, 2H).

Compound 30

N-(5-chloro-2-{[(5-nitro-1H-pyrazol-3-yl)methyl]sulfinyl}phenyl)-1-benzofuran-2-sulfonamide

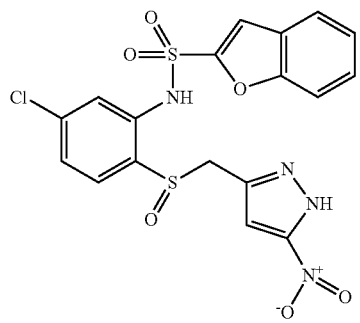

Following General Procedure C, the title compound (155 mg, 61%) was prepared from N-(5-chloro-2-{[(5-nitro-1H-pyrazol-3-yl)methyl]thio}phenyl)-1-benzofuran-2-sulfonamide (245 mg, 0.528 mmol).

1H NMR (600 MHz, CD$_3$OD) δ 7.67 (dt, J=0.77, 7.56 Hz, 1H), 7.42-7.45 (m, 2H), 7.35 (td, J=1.32, 7.85 Hz, 1H), 7.24-7.29 (m, 2H), 7.09 (d, J=8.22 Hz, 1H), 6.85 (d, J=8.22 Hz, 1H), 6.33 (s, 1H), 4.61 (d, J=14.09 Hz, 1H), 4.48 (d, J=14.09 Hz, 1H).

General Procedure I

Compound 31

N-(2-{[(5-amino-1H-pyrazol-3-yl)methyl]thio}-5-chlorophenyl)-1-benzofuran-2-sulfonamide

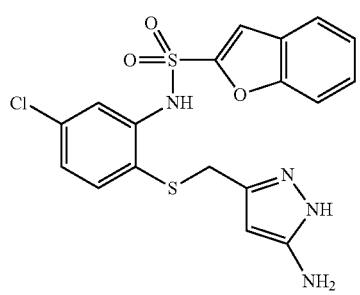 [SMILES: Nc1cc(CSc2ccc(Cl)cc2NS(=O)(=O)c2cc3ccccc3o2)n[nH]1]

N-(5-chloro-2-{[(5-nitro-1H-pyrazol-3-yl)methyl]thio}phenyl)-1-benzofuran-2-sulfonamide (77 mg, 0.166 mmol) was reduced to the title compound under H$_2$ balloon in the present of Pd/C (10% wt, 18 mg) in MeOH (3 ml).

1H NMR (600 MHz, CD$_3$OD) δ 7.70 (d, J=7.92 Hz, 1H), 7.52-7.56 (m, 2H), 7.48 (ddd, J=1.17, 7.12, 8.44 Hz, 1H), 7.44 (s, 1H), 7.40 (s, 1H), 7.34 (t, J=7.48 Hz, 1H), 7.28 (d, J=8.51 Hz, 1H), 7.11 (dd, J=2.20, 8.36 Hz, 1H), 3.74 (s, 2H).

Compound 32

N-(2-{[(5-amino-1H-pyrazol-3-yl)methyl]sulfinyl}-5-chlorophenyl)-1-benzofuran-2-sulfonamide

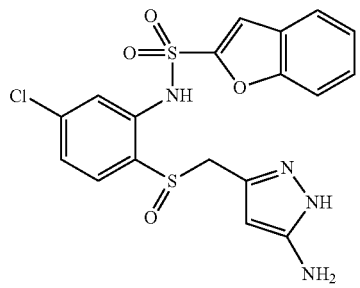 [SMILES: Nc1cc(CS(=O)c2ccc(Cl)cc2NS(=O)(=O)c2cc3ccccc3o2)n[nH]1]

Following the General Procedure I, the title compound (39 mg, 91%) was reduced from N-(5-chloro-2-{[(5-nitro-1H-pyrazol-3-yl)methyl]sulfinyl}phenyl)-1-benzofuran-2-sulfonamide (46 mg, 0.096 mmol).

1H NMR (600 MHz, CD$_3$OD) δ 7.91-7.99 (m, 1H), 7.67-7.72 (m, 1H), 7.56-7.62 (m, 1H), 7.50-7.55 (m, 1H), 7.41-7.48 (m, 2H), 7.29-7.40 (m, 2H), 7.13 (dd, J=1.91, 8.36 Hz, 1H), 4.55 (d, J=13.79 Hz, 1H), 4.05 (d, J=13.79 Hz, 1H)

Compound 33

N-(2-{[(5-amino-1H-pyrazol-3-yl)methyl]sulfonyl}-5-chlorophenyl)-1-benzofuran-2-sulfonamide

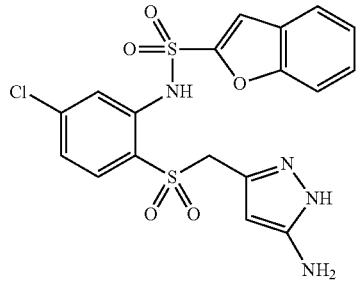 [SMILES: Nc1cc(CS(=O)(=O)c2ccc(Cl)cc2NS(=O)(=O)c2cc3ccccc3o2)n[nH]1]

Following General Procedure D and H, the title compound (27 mg) was prepared from N-(5-chloro-2-{[(5-nitro-1H-pyrazol-3-yl)methyl]thio}phenyl)-1-benzofuran-2-sulfonamide.

1H NMR (600 MHz, CD$_3$OD) δ 7.69-7.74 (m, 2H), 7.62-7.58 (m, 3H), 7.51 (dd, J=0.59, 8.51 Hz, 1H), 7.44 (ddd, J=1.17, 7.12, 8.44 Hz, 1H), 7.26-7.35 (m, 1H), 7.09 (dd, J=1.91, 8.66 Hz, 1H), 4.59 (s, 2H).

Intermediate 11

1-propyl-1H-imidazole-4-carbaldehyde

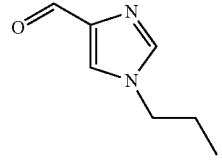

To a suspension of NaH (95%, 231 mg, 9.18 mmol) in THF (20 ml) was added 4-imidazole carboxaldehyde (588 mg, 6.12 mmol) under ice cooling. The mixture was refluxed for 2 hours under nitrogen atmosphere. The mixture was cooled to room temperature and 1-iodopropane (5 ml) was added to the mixture and then refluxed for another 2 hours. The mixture was cooled down to rt and quenched with water. The solution was extracted with EtOAc (2×50 ml), washed with brine, dried over Na$_2$SO$_4$, concentrated in vacuo. The crude product was purified by column chromatography on silica gel (0-10% MeOH in CH$_2$Cl$_2$) to give the title compound (487 mg, 58%).

1H NMR (600 MHz, CD$_3$OD) δ 9.73 (s, 1H), 7.97 (s, 1H), 7.84 (s, 1H), 4.07 (t, J=7.04 Hz, 2H), 1.73-1.92 (m, 2H), 0.93 (t, J=7.34 Hz, 3H).

Intermediate 12

(1-propyl-1H-imidazol-4-yl)methanol

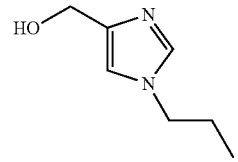

To a solution of LAH (2.0 M in THF, 1.9 ml, 3.882 mmol) in THF (10 ml) was added dropwise a solution of 1-propyl-1H-imidazole-4-carbaldehyde (487 mg, 3.529 mmol) in THF (4 ml) at 0° C. After stirred at 0° C. for 5 min, water (0.2 ml), 15% NaOH (0.2 ml) was added dropwise to the reaction mixture under 0° C. The mixture was further stirred at room temperature for 2 hours. MgSO$_4$ was added to the mixture and the solid was filtered away and the filtrate was concentrated in vacuo to get a yellow oil and used without further purification.

1H NMR (600 MHz, CD$_3$Cl$_3$) δ 7.42 (s, 1H), 6.86 (s, 1H), 4.59 (s, 2H), 3.87 (t, J=7.04 Hz, 2H), 1.73-1.82 (m, 2H), 0.93 (t, J=7.34 Hz, 3H).

Intermediate 13

5-chloro-2-(((1-propyl-1H-imidazol-4-yl)methyl)thio)aniline

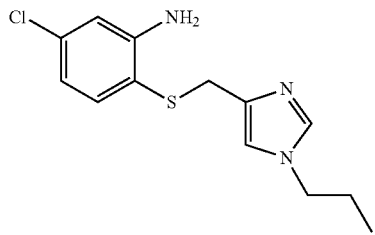 [SMILES: CCCn1cnc(CSc2ccc(Cl)cc2N)c1]

(1-propyl-1H-imidazol-4-yl)methanol (535 mg, 3.11 mmol) was first treated with SOCl$_2$ (3 ml) in CH$_2$Cl$_2$ (5 ml) at 35° C. for 2 hrs. The solvent was removed to get a crude 4-(chloromethyl)-1-propyl-1H-imidazole. Then following General Procedure A, the title compound (587 mg, 67%) was prepared from 2-amino-4-chlorobenzenethiol (744 mg, 4.66 mmol), 4-(chloromethyl)-1-propyl-1H-imidazole, K$_2$CO$_3$ (2.1 g, 15.54 mmol) in DMF (10 ml).

1H NMR (600 MHz, CDCL$_3$) δ 7.38 (s, 1H), 7.17 (d, J=8.22 Hz, 1H), 6.67 (d, J=2.05 Hz, 1H), 6.57 (dd, J=2.20, 8.07 Hz, 1H), 6.51 (s, 1H), 3.85 (s, 2H), 3.79 (t, J=7.04 Hz, 2H), 1.67-1.76 (m, 2H), 0.88 (t, J=7.34 Hz, 3H).

Compound 34

N-(5-chloro-2-{[(1-propyl-1H-imidazol-4-yl)methyl]thio}phenyl)-1-benzofuran-2-sulfonamide

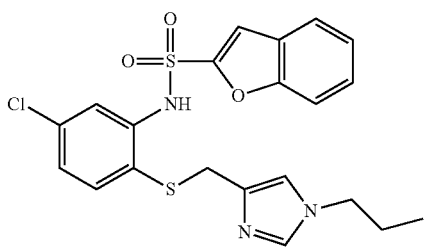 [SMILES: CCCn1cnc(CSc2ccc(Cl)cc2NS(=O)(=O)c2cc3ccccc3o2)c1]

Following General Procedure B, the title compound (463 mg, 48%) was prepared from 5-chloro-2-(((1-propyl-1H-imidazol-4-yl)methyl)thio)aniline (587 mg, 2.082 mmol) and benzofuran-2-sulfonyl chloride (451 mg, 2.082 mmol) in pyridine (10 ml).

1H NMR (600 MHz, CD$_3$OD) δ 7.71 (dt, J=1.03, 7.92 Hz, 1H), 7.57 (d, J=1.17 Hz, 1H), 7.52-7.55 (m, 1H), 7.44-7.51 (m, 2H), 7.42 (d, J=0.88 Hz, 1H), 7.34 (td, J=1.03, 7.56 Hz, 1H), 7.27 (d, J=8.22 Hz, 1H), 7.07 (dd, J=2.35, 8.51 Hz, 1H), 6.44-6.51 (m, 1H), 3.75-3.81 (m, 4H), 1.63 (dquin, J=7.19, 7.34 Hz, 2H), 0.74-0.82 (m, 3H).

Compound 35

N-(5-chloro-2-{[(1-propyl-1H-imidazol-4-yl)methyl]sulfinyl}phenyl)-1-benzofuran-2-sulfonamide

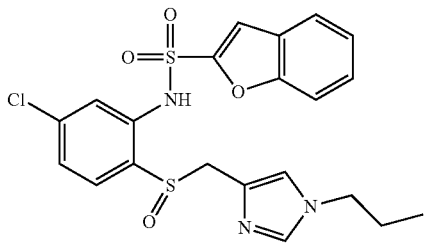 [SMILES: CCCn1cnc(CS(=O)c2ccc(Cl)cc2NS(=O)(=O)c2cc3ccccc3o2)c1]

Following General Procedure C, the title compound (148 mg, 75%) was prepared from N-(5-chloro-2-{[(1-propyl-1H-imidazol-4-yl)methyl]thio}phenyl)-1-benzofuran-2-sulfonamide.

1H NMR (600 MHz, CD$_3$OD) δ 8.46 (s, 1H), 7.70 (dd, J=1.47, 8.22 Hz, 1H), 7.49 (dd, J=0.88, 8.51 Hz, 1H), 7.38-7.43 (m, 2H), 7.35 (d, J=0.88 Hz, 1H), 7.30 (ddd, J=1.03, 7.19, 7.92 Hz, 1H), 7.12 (d, J=8.51 Hz, 1H), 6.91 (dd, J=1.91, 8.36 Hz, 1H), 6.80 (s, 1H), 4.57 (d, J=14.38 Hz, 1H), 4.43 (d, J=14.09 Hz, 1H), 3.84-3.99 (m, 2H), 1.57-1.71 (m, 2H), 0.81 (t, J=7.34 Hz, 3H).

Compound 36

N-(5-chloro-2-{[(1-propyl-1H-imidazol-4-yl)methyl]sulfonyl}phenyl)-1-benzofuran-2-sulfonamide

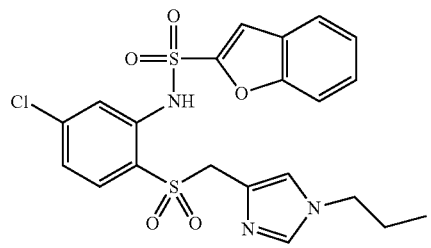 [SMILES: CCCn1cnc(CS(=O)(=O)c2ccc(Cl)cc2NS(=O)(=O)c2cc3ccccc3o2)c1]

Following General Procedure D, the title compound (115 mg, 60%) was prepared from N-(5-chloro-2-{[(1-propyl-1H-imidazol-4-yl)methyl]thio}phenyl)-1-benzofuran-2-sulfonamide.

1H NMR (300 MHz, CD$_3$OD) δ 7.82 (s, 1H), 7.71 (dd, J=1.32, 7.77 Hz, 1H), 7.67 (d, J=2.05 Hz, 1H), 7.55 (d, J=8.50 Hz, 1H), 7.44-7.50 (m, 2H), 7.41 (td, J=1.32, 7.69 Hz, 1H), 7.25-7.35 (m, 1H), 6.85 (dd, J=2.05, 8.79 Hz, 1H), 6.76 (s, 1H), 4.57 (s, 2H), 3.74 (t, J=7.03 Hz, 2H), 1.54 (quind, J=6.89, 7.07 Hz, 2H), 0.69 (t, J=7.47 Hz, 3H).

Intermediate 14 tert-butyl (4-(hydroxymethyl)pyridin-2-yl)carbamate

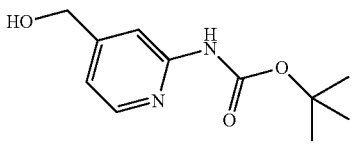 [SMILES: CC(C)(C)OC(=O)Nc1cc(CO)ccn1]

A solution of (2-aminopyridin-4-yl)methanol (547 mg, 4.408 mmol), di-tert-butyl dicarbonate (1.25 g, 5.730 mmol), in t-BuOH (20 ml) was stirred at room temperature overnight. The solvent was removed and added ethyl acetate, filtered away the solid and the filtrate was concentrated in vacuo. The residue was purified by column chromatography (10% MeOH in CH$_2$Cl$_2$) to give the title compound as a white solid (703 mg, 71%).

1H NMR (600 MHz, CDCl$_3$) δ 8.18 (d, J=5.28 Hz, 1H), 8.00 (s, 1H), 6.92-7.10 (m, 1H), 4.75 (s, 2H), 1.32-1.66 (m, 9H).

Intermediate 15 tert-butyl (4-(((2-amino-4-chlorophenyl)thio)methyl)pyridin-2-yl)carbamate

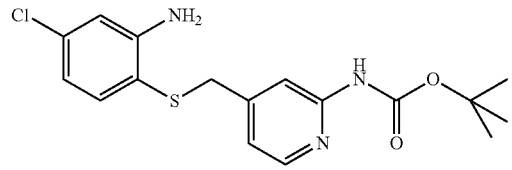 [SMILES: CC(C)(C)OC(=O)Nc1cc(CSc2ccc(Cl)cc2N)ccn1]

tert-butyl (4-(hydroxymethyl)pyridin-2-yl)carbamate (600 mg, 2.679 mmol) was first treated with SOCl₂ (3 ml) in CH₂Cl₂ (5 ml) at rt for 2 hrs. The solvent was removed to get a crude tert-butyl (4-(chloromethyl)pyridin-2-yl)carbamate. Then following General Procedure A, the title compound (667 mg, 68%) was prepared from 2-amino-4-chlorobenzenethiol (641 mg, 4.019 mmol), K₂CO₃ (1.8 g, 13.39 mmol) in DMF (20 ml).

1H NMR (600 MHz, CDCl₃) δ 9.83 (br. s., 1H), 8.20 (d, J=4.70 Hz, 1H), 7.85 (s, 1H), 6.92-7.18 (m, 1H), 6.60-6.75 (m, 2H), 6.55 (dd, J=2.05, 8.22 Hz, 1H), 4.42 (br. s., 2H), 3.78 (s, 2H), 1.54 (s, 9H).

Compound 37 tert-butyl {4-[({2-[(1-benzofuran-2-ylsulfonyl)amino]-4-chlorophenyl}thio)methyl]pyridin-2-yl}carbamate

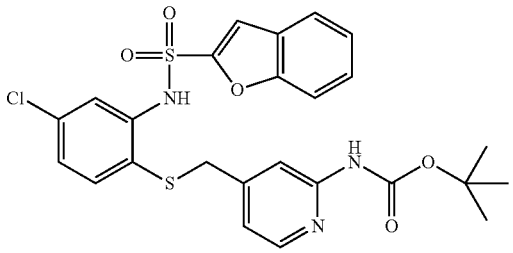 [SMILES: CC(C)(C)OC(=O)Nc1cc(CSc2ccc(Cl)cc2NS(=O)(=O)c2cc3ccccc3o2)ccn1]

Following General Procedure B, the title compound (555 mg, 56%) was prepared from tert-butyl (4-(((2-amino-4-chlorophenyl)thio)methyl)pyridin-2-yl)carbamate (667 mg, 1.827 mmol) and benzofuran-2-sulfonyl chloride (396 mg, 1.827 mmol) in pyridine (10 ml).

1H NMR (600 MHz, CD₃OD) δ 7.99 (d, J=4.99 Hz, 1H), 7.64-7.73 (m, 2H), 7.59 (d, J=1.17 Hz, 1H), 7.50-7.55 (m, 1H), 7.42-7.50 (m, 2H), 7.30-7.39 (m, 1H), 7.15 (dd, J=1.03, 8.36 Hz, 1H), 6.96-7.05 (m, 1H), 6.56 (d, J=5.28 Hz, 1H), 3.77 (s, 2H), 1.48-1.61 (m, 9H).

Compound 38

N-(2-{[(2-aminopyridin-4-yl)methyl]thio}-5-chlorophenyl)-1-benzofuran-2-sulfonamide

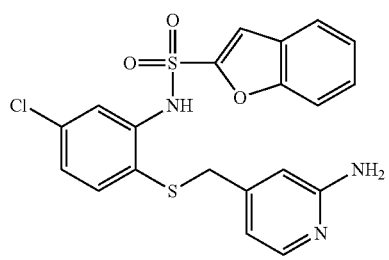 [SMILES: Nc1cc(CSc2ccc(Cl)cc2NS(=O)(=O)c2cc3ccccc3o2)ccn1]

Following General Procedure E, the title compound (76 mg, 100%) was prepared from tert-butyl {4-[({2-[(1-benzofuran-2-ylsulfonyl)amino]-4-chlorophenyl}thio)methyl]pyridin-2-yl}carbamate (96 mg, 0.176 mmol).

1H NMR (600 MHz, CD₃OD) δ 7.72-7.76 (m, 2H), 7.65 (d, J=6.46 Hz, 2H), 7.58 (dd, J=0.73, 8.36 Hz, 1H), 7.46-7.53 (m, 2H), 7.42 (d, J=2.05 Hz, 1H), 7.37 (td, J=1.03, 7.56 Hz, 1H), 7.31 (d, J=8.51 Hz, 1H), 7.16 (dd, J=2.35, 8.51 Hz, 1H), 6.64 (dd, J=1.61, 6.60 Hz, 1H), 6.50 (s, 1H), 3.90 (s, 2H).

Compound 39 tert-butyl {4-[({2-[(1-benzofuran-2-ylsulfonyl)amino]-4-chlorophenyl}sulfonyl)methyl]pyridin-2-yl}carbamate

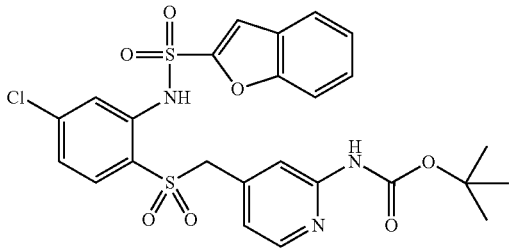 [SMILES: CC(C)(C)OC(=O)Nc1cc(CS(=O)(=O)c2ccc(Cl)cc2NS(=O)(=O)c2cc3ccccc3o2)ccn1]

Following General Procedure D, the title compound (49 mg) was prepared from tert-butyl {4-[({2-[(1-benzofuran-2-ylsulfonyl)amino]-4-chlorophenyl}thio)methyl]pyridin-2-yl}carbamate.

1H NMR (600 MHz, CD₃OD) δ 7.93 (d, J=6.75 Hz, 1H), 7.78 (s, 1H), 7.73 (d, J=2.05 Hz, 1H), 7.63 (d, J=7.63 Hz, 1H), 7.41 (d, J=8.80 Hz, 1H), 7.33 (s, 1H), 7.29 (d, J=3.81 Hz, 1H), 7.23 (dt, J=3.96, 7.92 Hz, 2H), 6.85 (dd, J=2.20, 6.60 Hz, 1H), 6.68 (d, J=7.92 Hz, 1H), 4.56 (br. s., 2H), 1.47 (s, 9H).

Compound 40 tert-butyl {4-[({2-[(1-benzofuran-2-ylsulfonyl)amino]-4-chlorophenyl}sulfonyl)methyl]-1-oxidopyridin-2-yl}carbamate

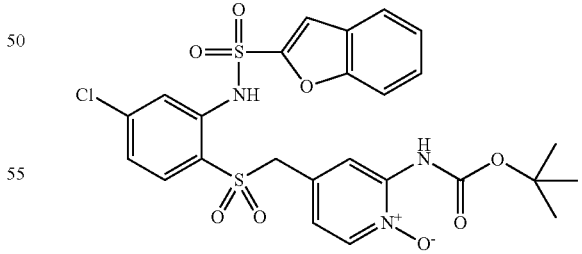

Following General Procedure D, the title compound (82 mg) was prepared from tert-butyl {4-[({2-[(1-benzofuran-2-ylsulfonyl)amino]-4-chlorophenyl}thio)methyl]pyridin-2-yl}carbamate.

1H NMR (600 MHz, CD₃OD) δ 8.22 (d, J=6.46 Hz, 1H), 7.96 (s, 1H), 7.76 (d, J=16.73 Hz, 1H), 7.60-7.68 (m, 1H), 7.43 (d, J=8.51 Hz, 1H), 7.37 (s, 1H), 7.31 (br. s., 1H), 7.21-7.27 (m, 1H), 7.09 (d, J=6.46 Hz, 1H), 6.85 (d, J=6.75 Hz, 1H), 6.72 (d, J=7.63 Hz, 1H), 4.60 (br. s., 2H), 1.55 (s, 9H).

Compound 41

N-(2-{[(2-aminopyridin-4-yl)methyl]sulfonyl}-5-chlorophenyl)-1-benzofuran-2-sulfonamide

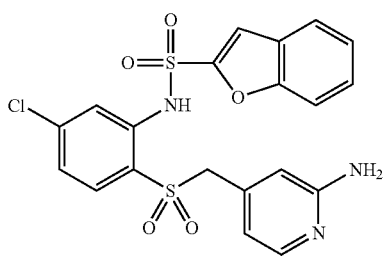 [SMILES: Nc1cc(CS(=O)(=O)c2ccc(Cl)cc2NS(=O)(=O)c2cc3ccccc3o2)ccn1]

Following General Procedure E, the title compound (32 mg, 100%) was prepared from tert-butyl {4-[({2-[(1-benzofuran-2-ylsulfonyl)amino]-4-chlorophenyl}sulfonyl)methyl]pyridin-2-yl}carbamate.

1H NMR (600 MHz, acetone-d6) δ 7.74-7.85 (m, 3H), 7.61-7.70 (m, 2H), 7.52-7.58 (m, 1H), 7.45 (td, J=1.17, 7.92 Hz, 1H), 7.28-7.38 (m, 1H), 7.09 (dd, J=2.05, 8.51 Hz, 1H), 6.88 (s, 1H), 6.57-6.66 (m, 1H), 4.89 (s, 2H).

Compound 42

N-(2-{[(2-amino-1-oxidopyridin-4-yl)methyl]sulfonyl}-5-chlorophenyl)-1-benzofuran-2-sulfonamide

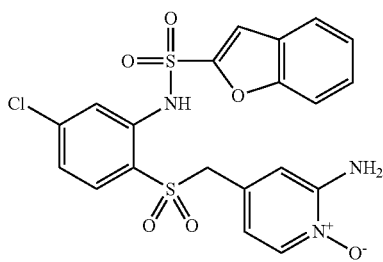 [SMILES: Nc1cc(CS(=O)(=O)c2ccc(Cl)cc2NS(=O)(=O)c2cc3ccccc3o2)cc[n+]1[O-]]

Following General Procedure E, the title compound (43 mg, 67%) was prepared from tert-butyl {4-[({2-[(1-benzofuran-2-ylsulfonyl)amino]-4-chlorophenyl}sulfonyl)methyl]-1-oxidopyridin-2-yl}carbamate (77 mg, 0.130 mmol).

1H NMR (600 MHz, acetone-d6) δ 8.07 (d, J=4.70 Hz, 3H), 7.76-7.81 (m, 2H), 7.74 (s, 1H), 7.64 (d, J=8.51 Hz, 1H), 7.58 (d, J=8.51 Hz, 1H), 7.46-7.49 (m, 1H), 7.32-7.37 (m, 1H), 7.15 (dd, J=1.32, 8.36 Hz, 1H), 6.94 (br. s., 1H), 6.52 (d, J=4.99 Hz, 1H), 4.76 (s, 2H).

Compound 43

N-(2-{[(2-aminopyridin-4-yl)methyl]sulfinyl}-5-chlorophenyl)-1-benzofuran-2-sulfonamide

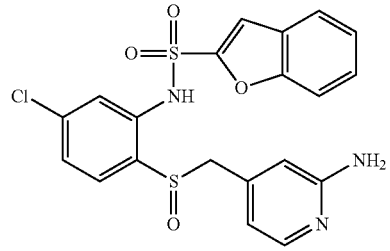

Following General Procedure C and General Procedure E, the title compound (103 mg) was prepared from tert-butyl {4-[({2-[(1-benzofuran-2-ylsulfonyl)amino]-4-chlorophenyl}thio)methyl]pyridin-2-yl}carbamate.

1H NMR (600 MHz, acetone-d6) δ 8.29 (br. s., 1H), 7.74 (dd, J=7.04, 18.19 Hz, 2H), 7.40-7.61 (m, 4H), 7.25-7.37 (m, 2H), 7.05 (d, J=7.04 Hz, 1H), 6.84 (s, 1H), 6.49 (d, J=6.16 Hz, 1H), 4.50 (d, J=12.62 Hz, 2H), 4.40 (d, J=12.62 Hz, 1H).

Intermediate 16

3-((2-amino-4-chlorophenyl)thio)-N,N-dimethylpropanamide

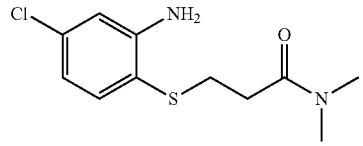 [SMILES: CN(C)C(=O)CCSc1ccc(Cl)cc1N]

The solution of 2-amino-4-chlorobenzenethiol (824 mg, 5.126 mmol), N,N-dimethylacrylamide (512 mg, 5.162 mmol), and HOAc (1 ml) in CH$_2$Cl$_2$ (10 ml) was stirred at room temperature for 4 days. The solvent was removed and the residue was loaded on silica column and purified to yield a white solid (1.08 g, 83%).

1H NMR (600 MHz, CD$_3$OD) δ 7.26 (d, J=8.22 Hz, 1H), 6.76 (d, J=2.05 Hz, 1H), 6.56 (dd, J=2.05, 8.22 Hz, 1H), 2.93-2.97 (m, 5H), 2.90 (s, 3H), 2.58 (t, J=7.04 Hz, 2H).

Compound 44

3-{[4-chloro-2-({[4-chloro-3-(trifluoromethyl)phenyl]sulfonyl}amino)phenyl]sulfonyl}-N,N-dimethylpropanamide

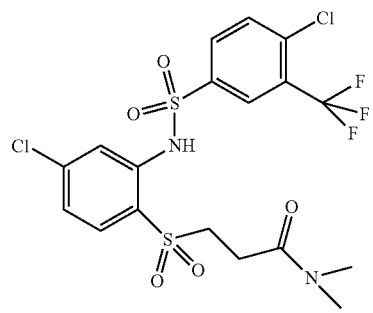 [SMILES: CN(C)C(=O)CCS(=O)(=O)c1ccc(Cl)cc1NS(=O)(=O)c1ccc(Cl)c(C(F)(F)F)c1]

Following General Procedure B and D, the title compound (73 mg) was prepared from 3-((2-amino-4-chlorophenyl)thio)-N,N-dimethylpropanamide (104 mg, 0.405 mmol) and 4-chloro-3-(trifluoromethyl)benzene-1-sulfonyl chloride (113 mg, 0.405 mmol).

1H NMR (600 MHz, CD$_3$OD) δ 8.31 (d, J=1.47 Hz, 1H), 8.12 (dd, J=1.76, 8.51 Hz, 1H), 7.70 (dd, J=8.51, 18.49 Hz, 2H), 7.58 (s, 1H), 6.90 (s., 1H), 3.73 (br. s., 2H), 3.01 (s, 3H), 2.95 (s, 3H), 2.78 (t, J=6.75 Hz, 2H).

Compound 45

3-[(4-chloro-2-{[(2,4-difluorophenyl)sulfonyl]amino}phenyl)thio]-N,N-dimethylpropanamide

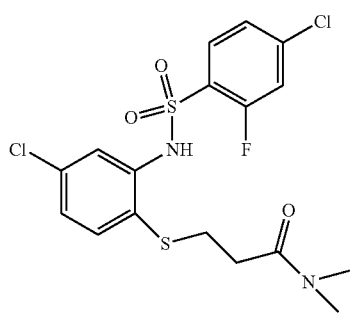 [SMILES: CN(C)C(=O)CCSc1ccc(Cl)cc1NS(=O)(=O)c1ccc(Cl)cc1F]

Following General Procedure B, the title compound (364 mg, 72%) was prepared from 3-((2-amino-4-chlorophenyl)thio)-N,N-dimethylpropanamide (300 mg, 1.167 mmol) and 2,4-difluorobenzene-1-sulfonyl chloride (248 mg, 1.167 mmol) in pyridine (5 ml).

1H NMR (600 MHz, CD$_3$OD) δ 7.86 (td, J=6.02, 8.44 Hz, 1H), 7.38-7.45 (m, 2H), 7.13-7.21 (m, 2H), 7.09 (tdd, J=0.88, 2.49, 8.44 Hz, 1H), 2.95-3.01 (m, 5H), 2.93 (s, 3H), 2.56 (t, J=7.04 Hz, 2H).

Compound 46

3-[(4-chloro-2-{[(2,4-difluorophenyl)sulfonyl]amino}phenyl)sulfinyl]-N,N-dimethylpropanamide

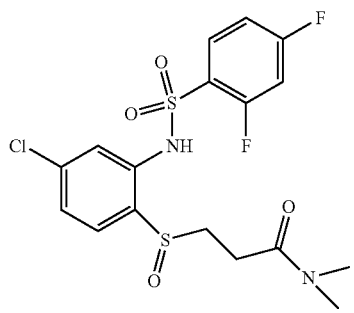 [SMILES: CN(C)C(=O)CCS(=O)c1ccc(Cl)cc1NS(=O)(=O)c1ccc(F)cc1F]

Following General Procedure C, the title compound (130 mg, 88%) was prepared from 3-[(4-chloro-2-{[(2,4-difluorophenyl)sulfonyl]amino}phenyl)thio]-N,N-dimethylpropanamide.

1H NMR (600 MHz, CD$_3$OD) δ 7.90 (td, J=5.87, 8.51 Hz, 1H), 7.69 (d, J=8.51 Hz, 1H), 7.43 (dd, J=2.05, 8.51 Hz, 1H), 7.31 (d, J=2.05 Hz, 1H), 7.20-7.27 (m, 1H), 7.11-7.17 (m, 1H), 3.24-3.29 (m, 1H), 3.12-3.20 (m, 1H), 3.05 (s, 3H), 2.93 (s, 3H), 2.85-2.92 (m, J=4.40 Hz, 1H), 2.72-2.80 (m, J=6.46, 6.46, 17.02 Hz, 1H).

Compound 47

3-[(4-chloro-2-{[(2,4-difluorophenyl)sulfonyl]amino}phenyl)sulfonyl]-N,N-dimethylpropanamide

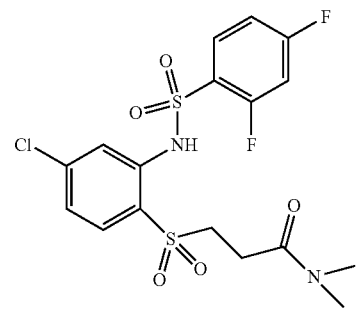 [SMILES: CN(C)C(=O)CCS(=O)(=O)c1ccc(Cl)cc1NS(=O)(=O)c1ccc(F)cc1F]

Following General Procedure D, the title compound (70 mg, 71%) was prepared from 3-[(4-chloro-2-{[(2,4-difluorophenyl)sulfonyl]amino}phenyl)thio]-N,N-dimethylpropanamide.

1H NMR (600 MHz, CD$_3$OD) δ 8.01-8.12 (m, 1H), 7.76 (d, J=8.51 Hz, 2H), 7.49-7.60 (m, 2H), 6.95-7.24 (m, 3H), 3.72 (br. s., 2H), 3.01 (s, 3H), 2.90 (s, 3H), 2.78 (t, J=7.04 Hz, 2H).

Compound 48

3-[(4-chloro-2-{[(4-chloro-2-fluorophenyl)sulfonyl]amino}phenyl)thio]-N,N-dimethylpropanamide

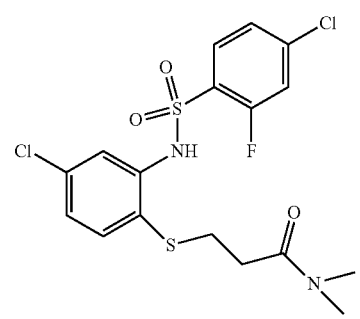 [SMILES: CN(C)C(=O)CCSc1ccc(Cl)cc1NS(=O)(=O)c1ccc(Cl)cc1F]

Following General Procedure B, the title compound (476 mg, 75%) was prepared from 3-((2-amino-4-chlorophenyl)thio)-N,N-dimethylpropanamide (364 mg, 1.42 mmol) and 4-chloro-2-fluorobenzene-1-sulfonyl chloride (325 mg, 1.42 mmol) in pyridine (5 ml).

1H NMR (600 MHz, acetone-d$_6$) δ 9.57 (br. s., 1H), 7.86 (t, J=8.07 Hz, 1H), 7.50-7.56 (m, 2H), 7.45 (dd, J=1.91, 9.83 Hz, 1H), 7.40 (dd, J=1.91, 8.36 Hz, 1H), 7.17 (dd, J=2.35, 8.22 Hz, 1H), 2.94-3.01 (m, 5H), 2.91 (s, 3H), 2.54 (t, J=6.46 Hz, 3H).

Compound 49

3-[(4-chloro-2-{[(4-chloro-2-fluorophenyl)sulfonyl]amino}phenyl)sulfinyl]-N,N-dimethylpropanamide

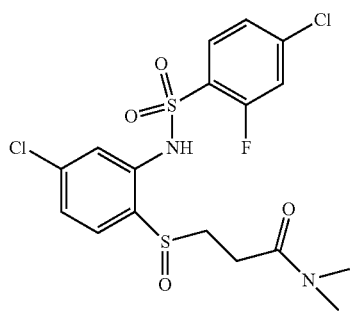 [SMILES: CN(C)C(=O)CCS(=O)c1ccc(Cl)cc1NS(=O)(=O)c1ccc(Cl)cc1F]

Following General Procedure C, the title compound (90 mg, 55%) was prepared from 3-[(4-chloro-2-{[(4-chloro-2-fluorophenyl)sulfonyl]amino}phenyl)thio]-N,N-dimethylpropanamide.

1H NMR (600 MHz, CD$_3$OD) δ 7.78-7.90 (m, 1H), 7.48 (d, J=8.51 Hz, 1H), 7.27-7.34 (m, 2H), 7.26 (d, J=2.05 Hz, 1H), 7.03 (d, J=7.92 Hz, 1H), 3.43 (ddd, J=6.31, 9.02, 13.43 Hz, 1H), 3.16 (ddd, J=5.58, 9.10, 13.50 Hz, 1H), 2.99 (s, 3H), 2.92 (s, 3H), 2.79-2.88 (m, J=6.46, 9.17, 16.07 Hz, 1H), 2.52-2.64 (m, 1H).

Compound 50

3-[(4-chloro-2-{[(4-chloro-2-fluorophenyl)sulfonyl]amino}phenyl)sulfonyl]-N,N-dimethylpropanamide

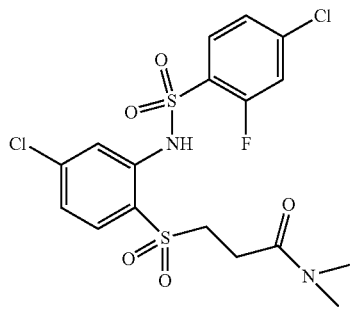 [SMILES: CN(C)C(=O)CCS(=O)(=O)c1ccc(Cl)cc1NS(=O)(=O)c1ccc(Cl)cc1F]

Following General Procedure D, the title compound (81 mg, 48%) was prepared from 3-[(4-chloro-2-{[(4-chloro-2-fluorophenyl)sulfonyl]amino}phenyl)thio]-N,N-dimethylpropanamide.

1H NMR (600 MHz, CD$_3$OD) δ 7.89-7.98 (m, 1H), 7.69 (d, J=8.51 Hz, 1H), 7.46 (d, J=2.05 Hz, 1H), 7.20-7.30 (m, 2H), 6.76 (d, J=7.63 Hz, 1H), 3.86 (t, J=7.19 Hz, 2H), 2.97 (s, 3H), 2.93 (s, 3H), 2.70 (t, J=7.34 Hz, 2H).

Intermediate 17 tert-butyl (5-(hydroxymethyl)-4H-1,2,4-triazol-3-yl)carbamate

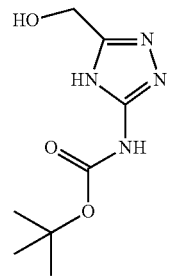

(5-amino-4H-1,2,4-triazol-3-yl)methanol (467 mg, 4.093 mmol), di-tert-butyl dicarbonate (1.16 g, 5.32 mmol), in t-BuOH (20 ml) was stirred at room temperature overnight. The solvent was removed and added ethyl acetate, filtered away the solid and the filtrate was concentrated in vacuo. The residue was purified by column chromatography (10% MeOH in CH$_2$Cl$_2$) to give the title compound as a yellow oil (190 mg, 22%).

1H NMR (300 MHz, CD$_3$OD) δ 4.44 (s, 2H), 1.63 (s, 9H).

General Procedure J

Intermediate 18 tert-butyl (5-(((2-amino-4-chlorophenyl)thio)methyl)-4H-1,2,4-triazol-3-yl)carbamate

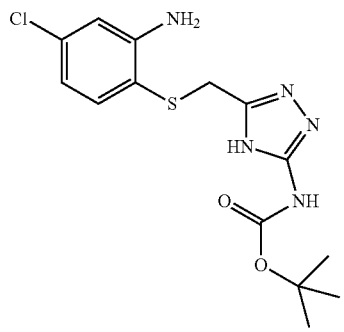 [SMILES: CC(C)(C)OC(=O)Nc1nnc(CSc2ccc(Cl)cc2N)[nH]1]

A solution of tert-butyl (5-(hydroxymethyl)-4H-1,2,4-triazol-3-yl)carbamate (190 mg, 0.888 mmol), 2-amino-4-chlorobenzenethiol (213 mg, 1.332 mmol), PPh3 (466 mg, 1.776 mmol) and di-tert-butylazodicarboxylate (409 mg, 1.776 mmol) in CH2Cl2 (10 ml) was stirred at room temperature for 2 days. The solvent was then removed and the crude residues was loaded on silica gel column to get the title compound.

1H NMR (600 MHz, CD$_3$OD) δ 7.18 (s, 1H), 6.73 (d, J=2.35 Hz, 1H), 6.49 (dd, J=2.35, 8.22 Hz, 2H), 3.68 (s, 2H), 1.60 (s, 9H).

Intermediate 19 tert-butyl (5-(((2-(benzofuran-2-sulfonamido)-4-chlorophenyl)thio)methyl)-4H-1,2,4-triazol-3-yl)carbamate

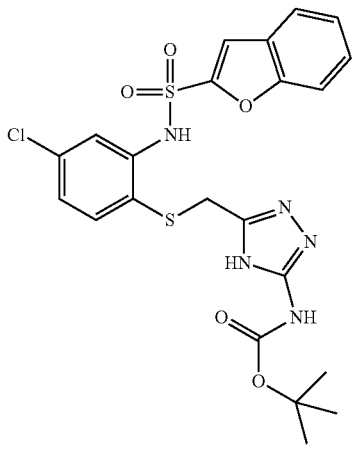 [SMILES: CC(C)(C)OC(=O)Nc1nnc(CSc2ccc(Cl)cc2NS(=O)(=O)c2cc3ccccc3o2)[nH]1]

Following General Procedure B, the title compound was prepared from tert-butyl (5-(((2-amino-4-chlorophenyl)thio)methyl)-4H-1,2,4-triazol-3-yl)carbamate (330 mg, 0.925 mmol) and benzofuran-2-sulfonyl chloride (200 mg, 0.925 mmol) in pyridine (2 ml).

1H NMR (600 MHz, CD$_3$OD) δ 7.69 (dd, J=0.88, 7.92 Hz, 1H), 7.45-7.57 (m, 4H), 7.40 (s, 1H), 7.29-7.35 (m, 1H), 7.16 (dd, J=2.35, 8.22 Hz, 1H), 3.70 (s, 2H), 1.61 (s, 9H).

Compound 51

N-(2-{[(5-amino-4H-1,2,4-triazol-3-yl)methyl]thio}-5-chlorophenyl)-1-benzofuran-2-sulfonamide

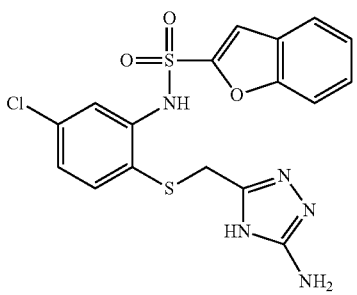 [SMILES: Nc1nnc(CSc2ccc(Cl)cc2NS(=O)(=O)c2cc3ccccc3o2)[nH]1]

Following General Procedure E, the title compound (13 mg) was prepared from tert-butyl (5-(((2-(benzofuran-2-sulfonamido)-4-chlorophenyl)thio)methyl)-4H-1,2,4-triazol-3-yl)carbamate.

1H NMR (600 MHz, CD$_3$OD) δ 7.71 (d, J=7.92 Hz, 1H), 7.55 (d, J=8.51 Hz, 1H), 7.39-7.51 (m, 5H), 7.31-7.37 (m, 1H), 7.16 (d, J=7.04 Hz, 1H), 3.82 (s, 2H).

Compound 52

N-(2-{[(5-amino-4H-1,2,4-triazol-3-yl)methyl]sulfinyl}-5-chlorophenyl)-1-benzofuran-2-sulfonamide

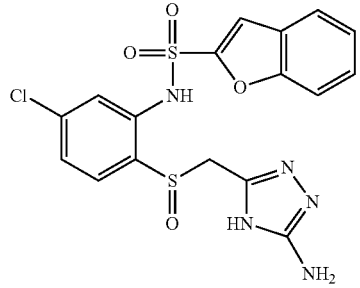 [SMILES: Nc1nnc(CS(=O)c2ccc(Cl)cc2NS(=O)(=O)c2cc3ccccc3o2)[nH]1]

Following General Procedure C and E, the title compound (15 mg) was prepared from tert-butyl (5-(((2-(benzofuran-2-sulfonamido)-4-chlorophenyl)thio)methyl)-4H-1,2,4-triazol-3-yl)carbamate.

1H NMR (600 MHz, CD$_3$OD) δ 7.75 (dd, J=1.17, 7.92 Hz, 1H), 7.57-7.64 (m, 2H), 7.51-7.55 (m, 1H), 7.50 (d, J=0.88 Hz, 1H), 7.44 (dd, J=1.91, 8.36 Hz, 1H), 7.35-7.41 (m, 1H), 7.20 (d, J=2.05 Hz, 1H), 4.45 (d, J=14.09 Hz, 1H), 4.24 (d, J=14.09 Hz, 1H).

Intermediate 20

5-chloro-2-((2-(pyridin-2-yl)ethyl)thio)aniline

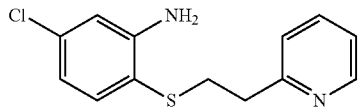 [SMILES: Nc1cc(Cl)ccc1SCCc1ccccn1]

2-(Pyridin-2-yl)ethanol (1 g, 8.12 mmol) was first treated with SOCl$_2$ (3 ml) in CH$_2$Cl$_2$ (10 ml) at rt for 3 hrs. The solvent was removed to get a crude 2-(2-chloroethyl)pyridine. Then following General Procedure A, the title compound (1.69 g, 79%) was prepared from 2-amino-4-chlorobenzenethiol (1.6 g, 9.74 mmol), K$_2$CO$_3$ (3.36 g, 24.36 mmol) in DMF (20 ml).

1H NMR (600 MHz, CD$_3$OD) δ 8.39-8.42 (m, 1H), 7.73 (td, J=1.76, 7.63 Hz, 1H), 7.28 (d, J=7.63 Hz, 1H), 7.23 (d, J=8.22 Hz, 2H), 6.75 (d, J=2.35 Hz, 1H), 6.55 (dd, J=2.35, 8.22 Hz, 1H), 3.06-3.10 (m, 2H), 2.96-3.01 (m, 2H).

Compound 53

N-{5-chloro-2-[(2-pyridin-2-ylethyl)thio]phenyl}-1-benzofuran-2-sulfonamide

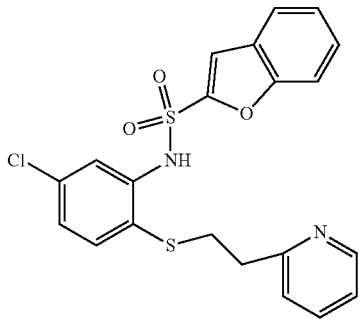 [SMILES: O=S(=O)(Nc1cc(Cl)ccc1SCCc1ccccn1)c1cc2ccccc2o1]

Following General Procedure B, the title compound was prepared from 5-chloro-2-((2-(pyridin-2-yl)ethyl)thio) aniline (439 mg, 1.663 mmol) and benzofuran-2-sulfonyl chloride (2×359 mg, 2×1.663 mmol) in pyridine (5 ml).

1H NMR (600 MHz, CD$_3$OD) δ 8.54-8.62 (m, 1H), 7.85 (s, 1H), 7.71-7.78 (m, 1H), 7.67 (dt, J=1.03, 7.92 Hz, 1H), 7.56 (d, J=2.35 Hz, 1H), 7.39-7.48 (m, 2H), 7.36 (s, 1H), 7.27-7.32 (m, 2H), 7.15-7.22 (m, 2H), 2.98 (t, J=7.04 Hz, 2H), 2.74 (t, J=6.90 Hz, 2H).

Compound 54

N-{5-chloro-2-[(2-pyridin-2-ylethyl)sulfinyl]phenyl}-1-benzofuran-2-sulfonamide

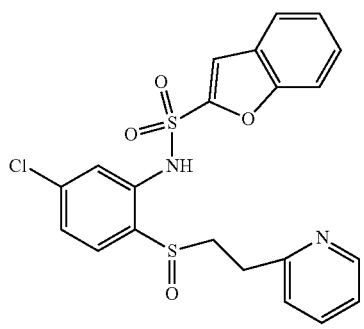 [SMILES: O=S(CCc1ccccn1)c1ccc(Cl)cc1NS(=O)(=O)c1cc2ccccc2o1]

Following General Procedure C, the title compound (45 mg, 79%) was prepared from N-{5-chloro-2-[(2-pyridin-2-ylethyl)thio]phenyl}-1-benzofuran-2-sulfonamide.

1H NMR (600 MHz, CD$_3$OD) δ 8.52-8.60 (m, 1H), 7.81 (td, J=1.76, 7.63 Hz, 1H), 7.64-7.71 (m, 2H), 7.26-7.47 (m, 8H), 3.40-3.50 (m, 1H), 3.29-3.37 (m, 1H), 3.16-3.26 (m, 0H), 2.83-2.95 (m, J=7.48, 7.48, 14.97 Hz, 1H).

Compound 55

N-{5-chloro-2-[(2-pyridin-2-ylethyl)sulfonyl]phenyl}-1-benzofuran-2-sulfonamide

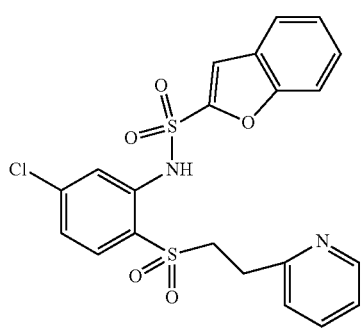 [SMILES: O=S(=O)(CCc1ccccn1)c1ccc(Cl)cc1NS(=O)(=O)c1cc2ccccc2o1]

Following General Procedure D, the title compound (20 mg) was prepared from N-{5-chloro-2-[(2-pyridin-2-ylethyl)thio]phenyl}-1-benzofuran-2-sulfonamide.

1H NMR (600 MHz, CD$_3$OD) δ 8.30 (ddd, J=1.47, 1.61, 4.55 Hz, 1H), 7.71-7.76 (m, 2H), 7.61-7.68 (m, 2H), 7.52 (d, J=0.88 Hz, 1H), 7.31-7.36 (m, 1H), 7.24-7.31 (m, 2H), 7.18-7.23 (m, 2H), 7.05 (dd, J=2.05, 8.51 Hz, 1H), 3.84-3.89 (m, 2H), 3.00-3.14 (m, 2H).

Intermediate 21

2-((2-(1H-pyrazol-4-yl)ethyl)thio)-5-chloroaniline

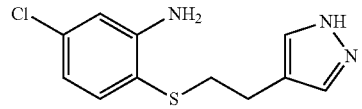 [SMILES: Nc1cc(Cl)ccc1SCCc1cn[nH]c1]

Following the General Procedure J, the title intermediate was prepared from 2-(1H-pyrazol-4-yl) ethanol (472 mg, 4.218 mmol), 2-amino-4-chlorobenzenethiol (1.01 g, 6.327 mmol), PPh$_3$ (2.21 g, 8.436 mmol) and di-tert-butylazodicarboxylate (1.9 g, 8.436 mmol) in CH$_2$Cl$_2$ (20 ml).

1H NMR (600 MHz, CD$_3$OD) δ 7.98 (d, J=0.88 Hz, 1H), 7.64 (s, 1H), 7.23 (d, J=8.22 Hz, 1H), 6.76 (d, J=2.35 Hz, 1H), 6.55 (dd, J=2.05, 8.22 Hz, 1H), 2.89-3.00 (m, 2H), 2.65-2.77 (m, 2H).

Compound 56

N-(5-chloro-2-{[2-(1H-pyrazol-4-yl)ethyl]thio}phenyl)-1-benzofuran-2-sulfonamide

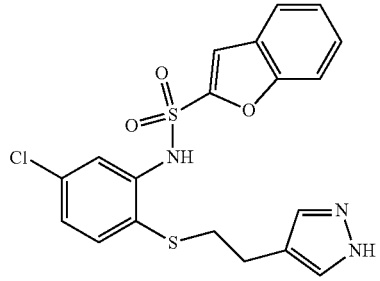 [SMILES: O=S(=O)(Nc1cc(Cl)ccc1SCCc1cn[nH]c1)c1cc2ccccc2o1]

Following General Procedure B, the title compound (123 mg) was prepared from 2-((2-(1H-pyrazol-4-yl)ethyl)thio)-5-chloroaniline (157 mg, 0.618 mmol) and benzofuran-2-sulfonyl chloride (133 mg, 0.618 mmol) in pyridine (3 ml).

1H NMR (600 MHz, CD$_3$OD) δ 7.70 (d, J=7.92 Hz, 1H), 7.43-7.53 (m, 3H), 7.39 (s, 1H), 7.28-7.36 (m, 4H), 7.17 (dd, J=1.76, 8.51 Hz, 1H), 2.82 (t, J=7.63 Hz, 2H), 2.45 (t, J=7.63 Hz, 2H).

Compound 57

N-(5-chloro-2-{[2-(1H-pyrazol-4-yl)ethyl]sulfinyl}phenyl)-1-benzofuran-2-sulfonamide

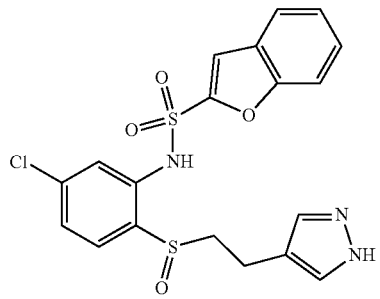 [SMILES: O=S(CCc1cn[nH]c1)c1ccc(Cl)cc1NS(=O)(=O)c1cc2ccccc2o1]

Following General Procedure C, the title compound (52 mg, 40%) was prepared from N-{5-chloro-2-[(2-pyridin-2-ylethyl)thio]phenyl}-1-benzofuran-2-sulfonamide.

1H NMR (600 MHz, CD$_3$OD) δ 7.75-7.81 (m, 1H), 7.72 (td, J=1.76, 7.63 Hz, 1H), 7.67 (d, J=0.88 Hz, 1H), 7.48-7.59 (m, 3H), 7.40-7.45 (m, 2H), 7.19-7.34 (m, 3H), 7.17 (d, J=2.35 Hz, 1H), 3.19-3.26 (m, 3H), 2.87 (t, J=7.63 Hz, 2H).

Compound 58

N-(5-chloro-2-{[2-(1H-pyrazol-4-yl)ethyl]sulfonyl}phenyl)-1-benzofuran-2-sulfonamide

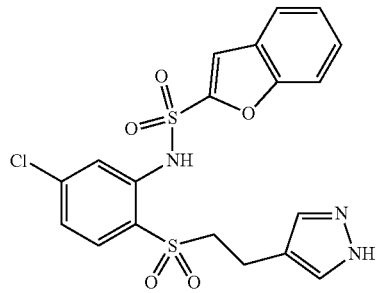 [SMILES: O=S(=O)(CCc1cn[nH]c1)c1ccc(Cl)cc1NS(=O)(=O)c1cc2ccccc2o1]

Following General Procedure D, the title compound (75 mg, 73%) was prepared from N-{5-chloro-2-[(2-pyridin-2-ylethyl)thio]phenyl}-1-benzofuran-2-sulfonamide.

1H NMR (600 MHz, CD$_3$OD) δ 7.67-7.74 (m, 2H), 7.62 (d, J=7.63 Hz, 1H), 7.39 (s, 2H), 7.31 (t, J=7.19 Hz, 2H), 7.22-7.26 (m, 1H), 7.17 (d, J=8.22 Hz, 1H), 6.80-6.90 (m, 1H), 3.89 (br. s., 2H), 2.71-2.81 (m, 2H).

Intermediate 22

5-Chloro-2-[2-(3,5-dimethyl-1H-pyrazol-4-yl)-ethylsulfanyl]-phenylamine

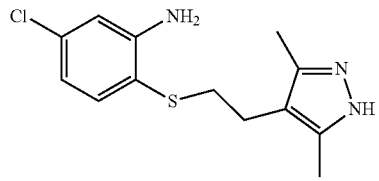 [SMILES: Cc1n[nH]c(C)c1CCSc1ccc(Cl)cc1N]

Following General Procedure A, the title compound (517 mg, 74%) was prepared from 2-Amino-4-chloro-benzenethiol (590 mg, 3.693 mmol) and 4-(2-bromo-ethyl)-3,5-dimethyl-1H-pyrazole (500 mg, 2.462 mmol), K$_2$CO$_3$ (1.7 g, 12.31 mmol) in DMF (20 ml).

1H NMR (600 MHz, CD$_3$OD) δ 7.24 (d, J=8.22 Hz, 1H), 6.77 (d, J=2.05 Hz, 1H), 6.56 (dd, J=2.35, 8.22 Hz, 1H), 2.75-2.80 (m, 2H), 2.53-2.61 (m, 2H), 2.08 (s, 6H).

Compound 59

N-(5-chloro-2-{[2-(3,5-dimethyl-1H-pyrazol-4-yl)ethyl]thio}phenyl)-1-benzofuran-2-sulfonamide

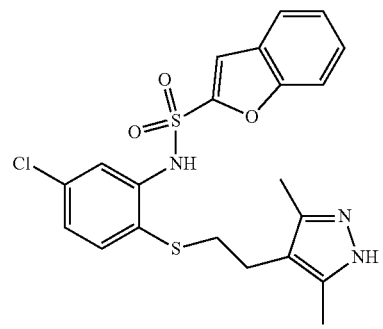 [SMILES: Cc1n[nH]c(C)c1CCSc1ccc(Cl)cc1NS(=O)(=O)c1cc2ccccc2o1]

Following General Procedure B, the title compound (235 mg) was prepared from 2-((2-(1H-pyrazol-4-yl)ethyl)thio)-5-chloroaniline (157 mg, 0.618 mmol) and benzofuran-2-sulfonyl chloride (133 mg, 0.618 mmol) in pyridine (3 ml).

1H NMR (600 MHz, CD$_3$OD) δ 7.68 (dd, J=0.88, 7.92 Hz, 1H), 7.52 (d, J=2.35 Hz, 1H), 7.39-7.47 (m, 3H), 7.27-7.35 (m, 2H), 7.18 (dd, J=2.35, 8.51 Hz, 1H), 2.65-2.72 (m, J=7.63 Hz, 2H), 2.28-2.35 (m, 2H), 1.97 (s, 6H).

Intermediate 23

5-chloro-2-(((2-fluoropyridin-3-yl)methyl)thio)aniline

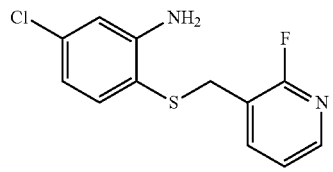 [SMILES: Nc1cc(Cl)ccc1SCc1cccnc1F]

(2-Fluoropyridin-3-yl)methanol (508 mg, 3.998 mmol) was first treated with SOCl$_2$ (1.5 ml) in CH$_2$Cl$_2$ (5 ml) at rt for 3 hrs. The solvent was removed to get a crude 3-(chloromethyl)-2-fluoropyridine. Then following General Procedure A, the title compound (910 mg, 85%) was prepared from 2-amino-4-chlorobenzenethiol (957 mg, 5.995 mmol), K$_2$CO$_3$ (2.7 g, 19.98 mmol) in DMF (20 ml).

1H NMR (600 MHz, CD$_3$OD) δ 8.01 (dt, J=0.88, 4.99 Hz, 1H), 7.42 (ddd, J=1.91, 7.48, 9.68 Hz, 1H), 7.10 (ddd, J=1.76, 5.14, 7.19 Hz, 1H), 6.91 (d, J=8.22 Hz, 1H), 6.73 (d, J=2.05 Hz, 1H), 6.42 (dd, J=2.35, 8.22 Hz, 1H), 3.90 (s, 2H).

Compound 60

N-(5-chloro-2-{[(2-fluoropyridin-3-yl)methyl]thio}phenyl)-1-benzofuran-2-sulfonamide

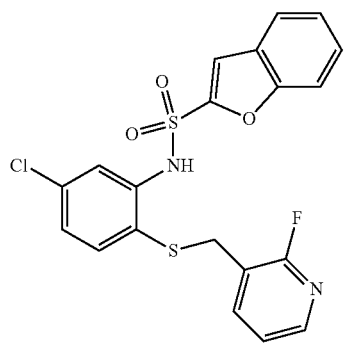 [SMILES: O=S(=O)(Nc1cc(Cl)ccc1SCc1cccnc1F)c1cc2ccccc2o1]

Following General Procedure B, the title compound (235 mg) was prepared from 5-chloro-2-(((2-fluoropyridin-3-yl)methyl)thio)aniline (522 mg, 1.948 mmol) and benzofuran-2-sulfonyl chloride (421 mg, 1.948 mmol) in pyridine (5 ml).

1H NMR (600 MHz, acetone-d6) δ 9.00 (br. s., 1H), 8.05 (dt, J=1.47, 4.70 Hz, 1H), 7.79 (d, J=6.75 Hz, 1H), 7.55-7.63 (m, 3H), 7.43-7.54 (m, 2H), 7.33-7.40 (m, 1H), 7.26 (d, J=8.22 Hz, 1H), 7.07-7.17 (m, 2H), 4.01 (s, 2H).

Compound 61

N-(5-chloro-2-{[(2-fluoropyridin-3-yl)methyl]sulfinyl}phenyl)-1-benzofuran-2-sulfonamide

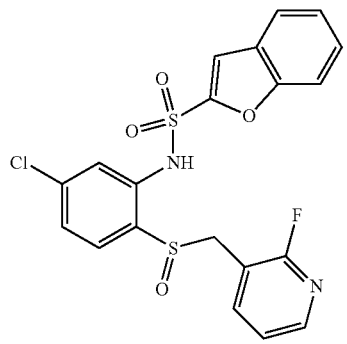 [SMILES: O=S(Cc1cccnc1F)c1ccc(Cl)cc1NS(=O)(=O)c1cc2ccccc2o1]

Following General Procedure C, the title compound (100 mg, 59%) was prepared from N-(5-chloro-2-{[(2-fluoropyridin-3-yl)methyl]thio}phenyl)-1-benzofuran-2-sulfonamide.

1H NMR (600 MHz, CD3OD) δ 7.99 (dd, J=1.91, 4.84 Hz, 1H), 7.65 (d, J=7.34 Hz, 1H), 7.49 (d, J=2.05 Hz, 1H), 7.38 (d, J=8.51 Hz, 1H), 7.28-7.33 (m, 1H), 7.19-7.26 (m, 3H), 7.00 (ddd, J=1.47, 5.21, 7.12 Hz, 1H), 6.81 (d, J=8.22 Hz, 1H), 6.70 (dd, J=2.05, 8.22 Hz, 1H), 4.43-4.59 (m, 2H).

Compound 62

N-(5-chloro-2-{[(2-fluoropyridin-3-yl)methyl]sulfonyl}phenyl)-1-benzofuran-2-sulfonamide

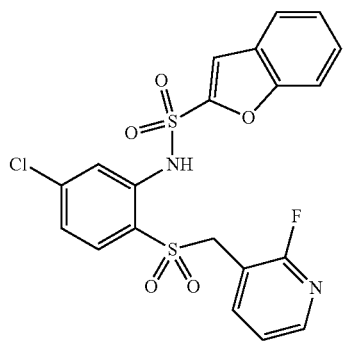 [SMILES: O=S(=O)(Cc1cccnc1F)c1ccc(Cl)cc1NS(=O)(=O)c1cc2ccccc2o1]

Following General Procedure D, the title compound (176 mg, 67%) was prepared from N-(5-chloro-2-{[(2-fluoropyridin-3-yl)methyl]thio}phenyl)-1-benzofuran-2-sulfonamide.

1H NMR (600 MHz, acetone-d6) δ 8.04 (d, J=4.70 Hz, 1H), 7.91 (d, J=2.05 Hz, 1H), 7.70 (d, J=7.63 Hz, 1H), 7.18-7.44 (m, 6H), 6.90 (t, J=5.43 Hz, 1H), 6.67 (d, J=7.63 Hz, 1H), 4.96 (s, 2H).

Intermediate 24

2-(benzylthio)-5-chloroaniline

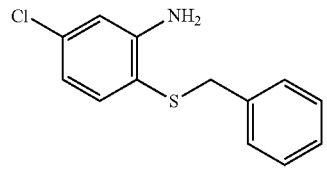 [SMILES: Nc1cc(Cl)ccc1SCc1ccccc1]

Following General Procedure A, the title compound (819 mg, 100%) was prepared from 2-amino-4-chlorobenzenethiol (700 mg, 4.39 mmol), (bromomethyl)benzene (560 mg, 2.92 mmol), K2CO3 (2.0 g, 14.62 mmol) in DMF (20 ml).

1H NMR (600 MHz, CD3OD) δ 7.15-7.24 (m, 3H), 7.07-7.13 (m, 2H), 6.97 (d, J=8.22 Hz, 1H), 6.73 (d, J=2.05 Hz, 1H), 6.43 (dd, J=2.05, 8.22 Hz, 1H), 3.86 (s, 2H).

Compound 63

N-[2-(benzylthio)-5-chlorophenyl]-1-benzofuran-2-sulfonamide

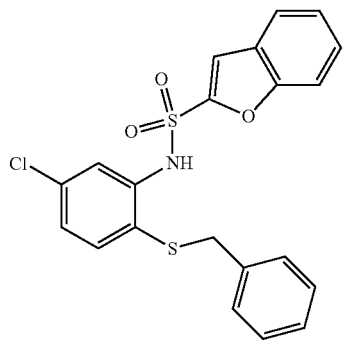 [SMILES: O=S(=O)(Nc1cc(Cl)ccc1SCc1ccccc1)c1cc2ccccc2o1]

Following General Procedure B, the title compound (235 mg) was prepared from 2-(benzylthio)-5-chloroaniline (509 mg, 2.052 mmol) and benzofuran-2-sulfonyl chloride (443 mg, 2.052 mmol) in pyridine (5 ml).

1H NMR (600 MHz, CD$_3$OD) δ 7.73 (d, J=7.92 Hz, 3H), 7.45-7.56 (m, 3H), 7.42 (s, 1H), 7.32-7.38 (m, 1H), 7.10-7.18 (m, 4H), 7.04-7.08 (m, 1H), 6.85-6.94 (m, 2H), 3.81 (s, 2H).

Compound 64

N-[2-(benzylsulfinyl)-5-chlorophenyl]-1-benzofuran-2-sulfonamide

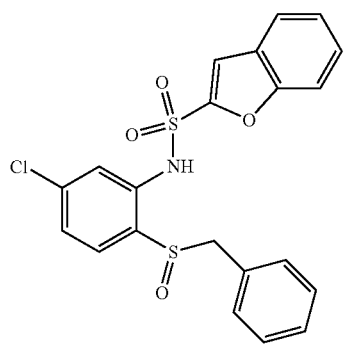 [SMILES: O=S(Cc1ccccc1)c1ccc(Cl)cc1NS(=O)(=O)c1cc2ccccc2o1]

Following General Procedure C, the title compound (139 mg, 84%) was prepared from N-[2-(benzylthio)-5-chlorophenyl]-1-benzofuran-2-sulfonamide.

1H NMR (600 MHz, CD$_3$OD) δ 7.65 (d, J=7.92 Hz, 1H), 7.49 (d, J=2.05 Hz, 1H), 7.37 (dd, J=0.73, 8.36 Hz, 1H), 7.28-7.33 (m, 1H), 7.16-7.27 (m, 3H), 7.08-7.14 (m, 2H), 7.01 (d, J=6.75 Hz, 2H), 6.97 (d, J=8.51 Hz, 1H), 6.73 (dd, J=1.91, 8.36 Hz, 1H), 4.50 (d, J=12.91 Hz, 1H), 4.14 (d, J=12.91 Hz, 1H).

Compound 65

N-[2-(benzylsulfonyl)-5-chlorophenyl]-1-benzofuran-2-sulfonamide

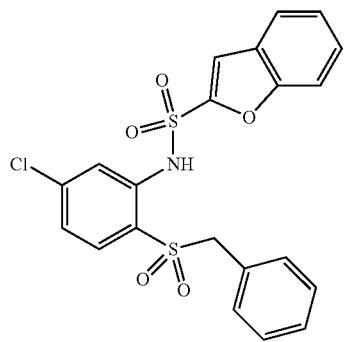 [SMILES: O=S(=O)(Cc1ccccc1)c1ccc(Cl)cc1NS(=O)(=O)c1cc2ccccc2o1]

Following General Procedure D, the title compound (212 mg, 95%) was prepared from N-[2-(benzylthio)-5-chlorophenyl]-1-benzofuran-2-sulfonamide.

1H NMR (600 MHz, CD$_3$OD) δ 7.63-7.73 (m, 2H), 7.40 (dd, J=0.73, 8.36 Hz, 1H), 7.30-7.37 (m, 3H), 7.23-7.29 (m, 1H), 7.08-7.16 (m, 3H), 6.98-7.05 (m, 2H), 6.60 (dd, J=2.05, 8.51 Hz, 1H), 4.99 (s, 2H).

General Procedure K

Intermediate 25

2-amino-4-fluorobenzenethiol

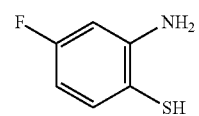

A solution of 5-fluoro-2-methylbenzo[d]thiazole (1.2 g, 7.18 mmol) in ethylene glycol and NaOH (5N, 2 ml) was degassed under N$_2$ for 10 min, then refluxed at 129° C. for 3 hours. The solution was cooled to 0° C. and then acidified to pH 3~4 using c. HCl. The mixture was extracted with EtOAc (2×50 ml). The organic layer was washed with brine and dried with Na$_2$SO$_4$ and concentrated in vacuo. The crude residue (1.01 g, 98%) was used directly in the next step without purification.

1H NMR (600 MHz, CD$_3$OD) δ 7.24 (dd, J=6.16, 8.51 Hz, 1H), 6.97 (dd, J=6.46, 8.51 Hz, 1H), 6.20 (td, J=2.79, 8.58 Hz, 1H).

Intermediate 26

5-fluoro-2((3-nitrobenzyl)thio)aniline

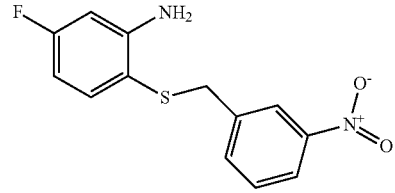 [SMILES: Nc1cc(F)ccc1SCc1cccc([N+](=O)[O-])c1]

Following General Procedure A, the title compound (460 mg, 97%) was prepared from 2-amino-4-fluorobenzenethiol (562 g, 3.93 mmol), 1-(bromomethyl)-3-nitrobenzene (566 mg, 2.62 mmol), K$_2$CO$_3$ (1.8 g, 13.10 mmol) in DMF (10 ml).

1H NMR (600 MHz, CD$_3$OD) δ 8.04 (dt, J=2.09, 7.26 Hz, 1H), 7.89 (s, 1H), 7.34-7.54 (m, 2H), 6.93 (dd, J=6.46, 8.51 Hz, 1H), 6.35-6.53 (m, 1H), 6.15 (td, J=2.64, 8.51 Hz, 1H), 3.95 (s, 2H).

Compound 66

N-(5-fluoro-2-((3-nitrobenzyl)thio)phenyl)benzofuran-2-sulfonamide

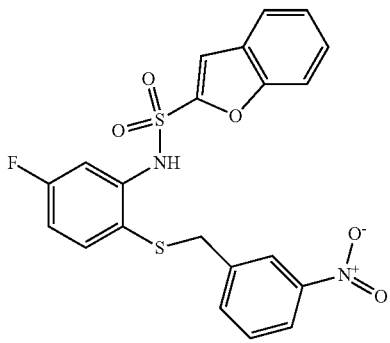 [SMILES: O=[N+]([O-])c1cccc(CSc2ccc(F)cc2NS(=O)(=O)c2cc3ccccc3o2)c1]

Following General Procedure B, the title compound (474 mg, 63%) was prepared from 2-((3-aminobenzyl)thio)-5-fluoroaniline (460 mg, 1.655 mmol) and benzofuran-2-sulfonyl chloride (357 mg, 1.655 mmol) in pyridine (5 ml).

1H NMR (600 MHz, CD$_3$OD) δ 7.98 (ddd, J=0.88, 2.35, 8.22 Hz, 1H), 7.68-7.79 (m, 2H), 7.49-7.54 (m, 2H), 7.42-7.48 (m, 1H), 7.25-7.39 (m, 4H), 7.16 (dd, J=6.16, 8.80 Hz, 1H), 6.78 (td, J=2.93, 8.36 Hz, 1H), 3.91 (s, 2H).

General Procedure L

Compound 67

N-{2-[(3-aminobenzyl)thio]-5-fluorophenyl}-1-benzofuran-2-sulfonamide

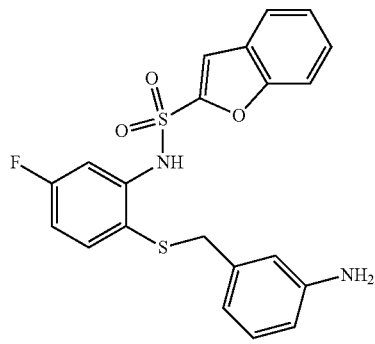 [SMILES: Nc1cccc(CSc2ccc(F)cc2NS(=O)(=O)c2cc3ccccc3o2)c1]

N-(5-fluoro-2-((3-nitrobenzyl)thio)phenyl)benzofuran-2-sulfonamide (91 mg, 0.199 mmol) was dissolved in MeOH (2 ml). Zn (322 mg, 4.967 mmol) and NH$_4$Cl (1 ml) was added to the solution. After the mixture was stirred for 30 min at room temperature, the solid was filtered and the filtrate was concentrated in vacuo and then the crude residue was purified by column chromatography (0~30% EtOAc in hexane) to afford the title product (50 mg, 59%).

1H NMR (600 MHz, CD$_3$OD) δ 7.71 (d, J=7.92 Hz, 1H), 7.50-7.54 (m, 1H), 7.48 (d, J=0.88 Hz, 1H), 7.46 (ddd, J=1.32, 7.26, 8.44 Hz, 1H), 7.28-7.38 (m, 2H), 7.19 (dd, J=6.16, 8.80 Hz, 1H), 6.83-6.89 (m, 1H), 6.77 (td, J=2.79, 8.44 Hz, 1H), 6.46-6.54 (m, 1H), 6.36 (t, J=1.76 Hz, 1H), 6.22 (d, J=7.63 Hz, 1H), 3.63 (s, 2H).

Compound 68

N-{2-[(3-aminobenzyl)sulfinyl]-5-fluorophenyl}-1-benzofuran-2-sulfonamide

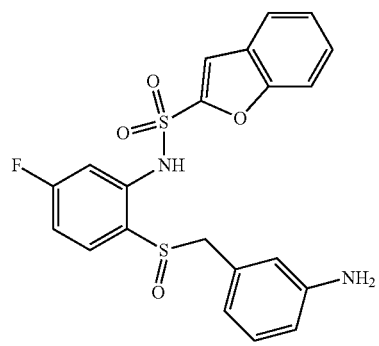 [SMILES: Nc1cccc(CS(=O)c2ccc(F)cc2NS(=O)(=O)c2cc3ccccc3o2)c1]

Following General Procedure L, the title compound (130 mg, 84%) was prepared from N-{5-fluoro-2-[(3-nitrobenzyl)sulfinyl]phenyl}-1-benzofuran-2-sulfonamide.

1H NMR (600 MHz, CD$_3$OD) δ 7.75 (dd, J=0.88, 7.92 Hz, 1H), 7.53-7.60 (m, 2H), 7.48 (ddd, J=1.32, 7.26, 8.44 Hz, 1H), 7.33-7.38 (m, 1H), 7.28 (dd, J=6.16, 8.80 Hz, 1H), 7.14 (dd, J=2.64, 10.27 Hz, 1H), 6.88-7.02 (m, 2H), 6.71 (dt, J=1.06, 8.14 Hz, 1H), 6.57 (s, 1H), 6.41 (d, J=7.63 Hz, 1H), 4.24 (d, J=12.62 Hz, 1H), 4.06 (d, J=12.91 Hz, 1H).

Compound 69

N-{5-fluoro-2-[(3-nitrobenzyl)sulfonyl]phenyl}-1-benzofuran-2-sulfonamide

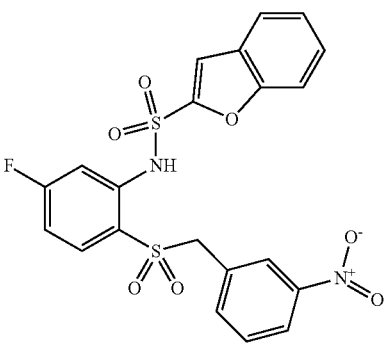 [SMILES: O=[N+]([O-])c1cccc(CS(=O)(=O)c2ccc(F)cc2NS(=O)(=O)c2cc3ccccc3o2)c1]

Following General Procedure D, the title compound (136 mg, 74%) was prepared from N-(5-fluoro-2-((3-nitrobenzyl)thio)phenyl)benzofuran-2-sulfonamide.

1H NMR (600 MHz, CD$_3$OD) δ 8.10 (ddd, J=1.17, 2.13, 8.14 Hz, 1H), 7.72-7.81 (m, 3H), 7.65 (dd, J=6.02, 8.95 Hz, 1H), 7.55 (d, J=8.51 Hz, 1H), 7.45-7.51 (m, 3H), 7.41-7.45 (m, 1H), 7.33-7.39 (m, 1H), 6.80-7.09 (m, 1H), 4.70 (s, 2H).

Compound 70

N-{2-[(3-aminobenzyl)sulfonyl]-5-fluorophenyl}-1-benzofuran-2-sulfonamide

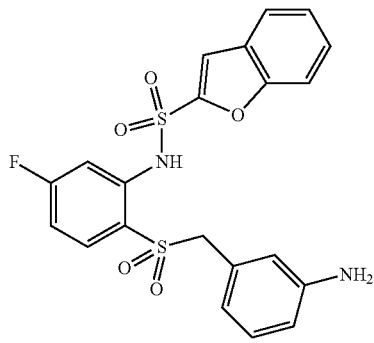 [SMILES: Nc1cccc(CS(=O)(=O)c2ccc(F)cc2NS(=O)(=O)c2cc3ccccc3o2)c1]

Following General Procedure L, the title compound (91 mg, 81%) was prepared from N-{5-fluoro-2-[(3-nitrobenzyl)sulfonyl]phenyl}-1-benzofuran-2-sulfonamide.

1H NMR (600 MHz, acetone-d6) δ 7.87 (br. s., 1H), 7.84 (d, J=7.92 Hz, 2H), 7.57-7.65 (m, 2H), 7.50-7.56 (m, 2H), 7.39 (t, J=7.48 Hz, 1H), 6.94-7.02 (m, 1H), 6.83 (t, J=7.78 Hz, 1H), 6.53 (d, J=8.80 Hz, 1H), 6.38 (s, 1H), 6.13 (d, J=7.34 Hz, 1H), 4.38 (s, 2H).

Intermediate 27

5-methoxy-2-((3-nitrobenzyl)thio)aniline

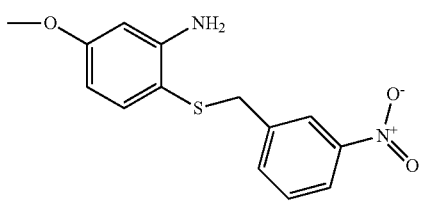 [SMILES: COc1ccc(SCc2cccc([N+](=O)[O-])c2)c(N)c1]

Following General Procedure K and A, the title compound (474 mg) was prepared from 5-methoxy-2-methylbenzo[d]thiazole.

1H NMR (600 MHz, CD$_3$OD) δ 8.03 (dt, J=2.05, 7.34 Hz, 1H), 7.84 (d, J=1.76 Hz, 1H), 7.34-7.48 (m, 2H), 6.83 (d, J=8.51 Hz, 1H), 6.32 (s, 1H), 6.06 (dd, J=2.79, 8.36 Hz, 1H), 3.90 (s, 2H), 3.69 (s, 3H).

Compound 71

N-{2-[(3-aminobenzyl)thio]-5-methoxyphenyl}-1-benzofuran-2-sulfonamide

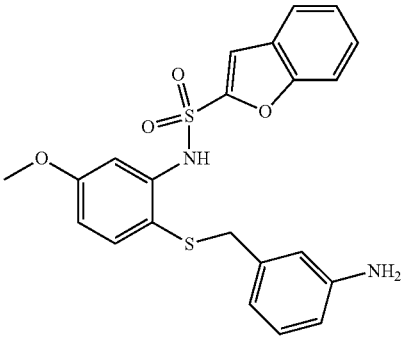 [SMILES: COc1ccc(SCc2cccc(N)c2)c(NS(=O)(=O)c2cc3ccccc3o2)c1]

Following General Procedure L, the title compound (82 mg, 70%) was prepared from N-(5-methoxy-2-((3-nitrobenzyl)thio)phenyl)benzofuran-2-sulfonamide.

1H NMR (600 MHz, CD$_3$OD) δ 7.69 (d, J=7.92 Hz, 1H), 7.50 (dd, J=0.88, 8.51 Hz, 1H), 7.40-7.47 (m, 2H), 7.31 (ddd, J=1.03, 7.19, 7.92 Hz, 1H), 7.07-7.13 (m, 2H), 6.84-6.90 (m, 1H), 6.57 (dd, J=2.79, 8.66 Hz, 1H), 6.50-6.54 (m, 1H), 6.37 (t, J=1.91 Hz, 1H), 6.25 (d, J=7.63 Hz, 1H), 3.72 (s, 3H), 3.57 (s, 2H).

Compound 72

N-{5-methoxy-2-[(3-nitrobenzyl)sulfinyl]phenyl}-1-benzofuran-2-sulfonamide

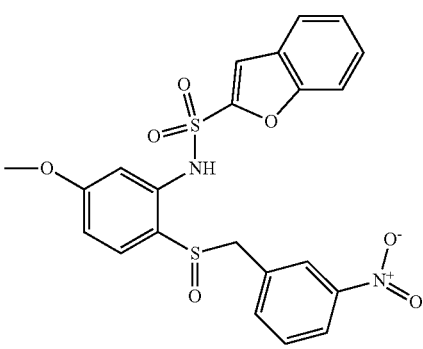 [SMILES: COc1ccc(S(=O)Cc2cccc([N+](=O)[O-])c2)c(NS(=O)(=O)c2cc3ccccc3o2)c1]

Following General Procedure C, the title compound (95 mg, 46%) was prepared from N-(5-methoxy-2-((3-nitrobenzyl)thio)phenyl)benzofuran-2-sulfonamide.

1H NMR (600 MHz, acetone-d6) δ 10.74 (br. s., 1H), 8.16 (ddd, J=0.88, 2.35, 8.22 Hz, 1H), 7.78-7.86 (m, 2H), 7.75 (s, 1H), 7.61 (dd, J=0.88, 8.51 Hz, 1H), 7.56 (t, J=7.92 Hz, 1H), 7.44-7.52 (m, 2H), 7.35-7.40 (m, 1H), 7.09 (d, J=2.35 Hz, 1H), 7.06 (d, J=8.80 Hz, 1H), 6.69 (dd, J=2.49, 8.66 Hz, 1H), 4.45-4.53 (m, 2H), 3.77 (s, 3H).

Compound 73

N-{2-[(3-aminobenzyl)sulfinyl]-5-methoxyphenyl}-1-benzofuran-2-sulfonamide

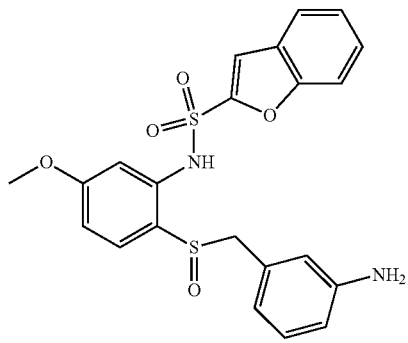 [SMILES: COc1ccc(S(=O)Cc2cccc(N)c2)c(NS(=O)(=O)c2cc3ccccc3o2)c1]

Following General Procedure L, the title compound (55 mg, 65%) was prepared from N-{5-methoxy-2-[(3-nitrobenzyl)sulfinyl]phenyl}-1-benzofuran-2-sulfonamide.

1H NMR (600 MHz, acetone-d6) δ 7.75-7.85 (m, 2H), 7.59 (dd, J=0.59, 8.51 Hz, 1H), 7.44-7.53 (m, 1H), 7.32-7.40 (m, 1H), 7.25 (s, 1H), 6.93 (d, J=8.51 Hz, 1H), 6.85-6.90 (m, 1H), 6.61 (dd, J=2.49, 8.66 Hz, 1H), 6.53-6.58 (m, 1H), 6.40 (t, J=1.76 Hz, 1H), 6.21 (d, J=7.92 Hz, 1H), 4.25 (d, J=12.32 Hz, 1H), 4.08 (d, J=11.74 Hz, 2H), 3.78 (s, 3H).

Compound 74

N-(5-methoxy-2-((3-nitrobenzyl)sulfonyl)phenyl)benzofuran-2-sulfonamide

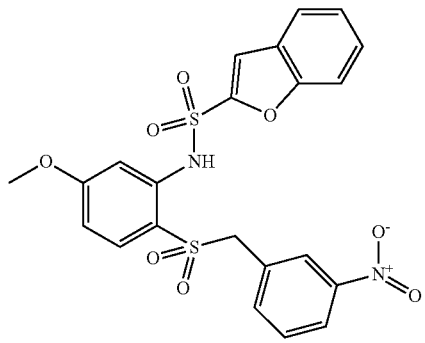 [SMILES: COc1ccc(S(=O)(=O)Cc2cccc([N+](=O)[O-])c2)c(NS(=O)(=O)c2cc3ccccc3o2)c1]

Following General Procedure D, the title compound (165 mg, 83%) was prepared from N-(5-methoxy-2-((3-nitrobenzyl)thio)phenyl)benzofuran-2-sulfonamide.

1H NMR (600 MHz, CDCl3) δ 9.28 (s, 1H), 8.14-8.19 (m, 1H), 7.70 (d, J=7.63 Hz, 1H), 7.64 (s, 1H), 7.58 (s, 1H), 7.41-7.50 (m, 3H), 7.37 (d, J=9.10 Hz, 1H), 7.33 (td, J=1.03, 7.41 Hz, 1H), 7.29 (d, J=2.35 Hz, 1H), 7.26 (d, J=2.35, 8.80 Hz, 1H), 4.38 (s, 2H), 3.86 (s, 3H).

Compound 75

N-{2-[(3-aminobenzyl)sulfonyl]-5-methoxyphenyl}-1-benzofuran-2-sulfonamide

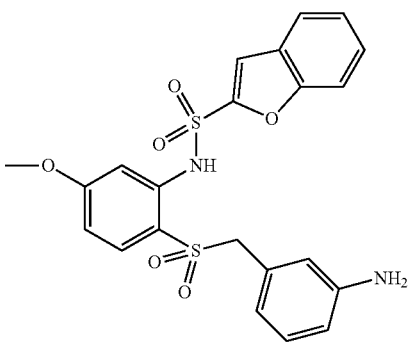 [SMILES: COc1ccc(S(=O)(=O)Cc2cccc(N)c2)c(NS(=O)(=O)c2cc3ccccc3o2)c1]

Following General Procedure L, the title compound (67 mg, 45%) was prepared from N-(5-methoxy-2-((3-nitrobenzyl)sulfonyl)phenyl)benzofuran-2-sulfonamide.

1H NMR (600 MHz, CD3OD) δ 7.70 (d, J=7.63 Hz, 1H), 7.42-7.50 (m, 2H), 7.35-7.41 (m, 1H), 7.33 (d, J=8.80 Hz, 1H), 7.27-7.31 (m, 1H), 7.22 (d, J=2.35 Hz, 1H), 6.76 (t, J=7.78 Hz, 1H), 6.53 (dd, J=1.32, 8.07 Hz, 1H), 6.45 (s, 1H), 6.39 (d, J=8.51 Hz, 1H), 6.27 (d, J=7.63 Hz, 1H), 4.61 (br. s., 2H), 3.76 (s, 3H).

Compound 76

Benzofuran-2-sulfonic acid [2-(3-nitro-benzylsulfanyl)-phenyl]-amide

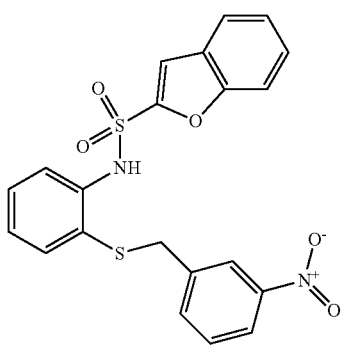 [SMILES: O=[N+]([O-])c1cccc(CSc2ccccc2NS(=O)(=O)c2cc3ccccc3o2)c1]

Following General Procedure B, the title compound (520 mg, 41%) was prepared from 2-((3-nitrobenzyl)thio)aniline (741 mg, 2.85 mmol), benzofuran-2-sulfonyl chloride (616 mg, 2.85 mmol) in pyridine (10 ml).

1H NMR (600 MHz, CD$_3$OD) δ 7.97-8.04 (m, 1H), 7.79-7.89 (m, 1H), 7.70 (d, J=0.88 Hz, 1H), 7.50 (d, J=0.88 Hz, 1H), 7.29-7.47 (m, 6H), 7.15-7.25 (m, 2H), 7.02-7.11 (m, 1H), 3.99 (s, 2H).

Compound 77

N-{2-[(3-aminobenzyl)thio]phenyl}-1-benzofuran-2-sulfonamide

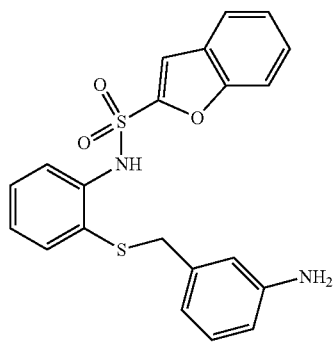 [SMILES: Nc1cccc(CSc2ccccc2NS(=O)(=O)c2cc3ccccc3o2)c1]

Following General Procedure L, the title compound (67 mg, 45%) was prepared from benzofuran-2-sulfonic acid [2-(3-nitro-benzylsulfanyl)-phenyl]-amide.

1H NMR (600 MHz, CD$_3$OD) δ 7.66 (d, J=7.92 Hz, 1H), 7.47-7.52 (m, 1H), 7.38-7.46 (m, 2H), 7.26-7.35 (m, 2H), 7.12-7.22 (m, 2H), 7.04 (td, J=1.47, 7.63 Hz, 1H), 6.88 (t, J=7.78 Hz, 1H), 6.54 (dd, J=1.47, 7.92 Hz, 1H), 6.43 (t, J=1.76 Hz, 1H), 6.28 (d, J=7.63 Hz, 1H), 3.69 (s, 2H).

Compound 78

N-{2-[(3-nitrobenzyl)sulfinyl]phenyl}-1-benzofuran-2-sulfonamide

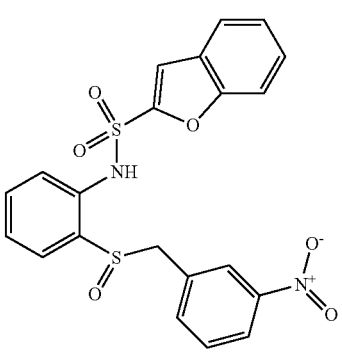 [SMILES: O=[N+]([O-])c1cccc(CS(=O)c2ccccc2NS(=O)(=O)c2cc3ccccc3o2)c1]

Following General Procedure C, the title compound (172 mg, 73%) was prepared from benzofuran-2-sulfonic acid [2-(3-nitro-benzylsulfanyl)-phenyl]-amide.

1H NMR (600 MHz, acetone-d6) δ 10.45 (br. s., 1H), 8.15 (d, J=8.22 Hz, 1H), 7.85 (s, 1H), 7.80 (d, J=7.92 Hz, 1H), 7.66 (d, J=0.88 Hz, 1H), 7.59-7.63 (m, 1H), 7.42-7.57 (m, 5H), 7.34-7.40 (m, 1H), 7.13-7.24 (m, 2H), 4.54-4.60 (m, 1H), 4.45-4.51 (m, 1H).

Compound 79

N-{2-[(3-aminobenzyl)sulfinyl]phenyl}-1-benzofuran-2-sulfonamide

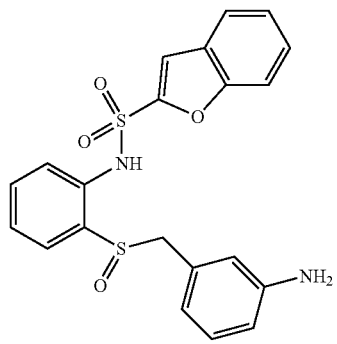 [SMILES: Nc1cccc(CS(=O)c2ccccc2NS(=O)(=O)c2cc3ccccc3o2)c1]

Following General Procedure L, the title compound (122 mg, 90%) was prepared from N-{2-[(3-nitrobenzyl)sulfinyl]phenyl}-1-benzofuran-2-sulfonamide.

1H NMR (600 MHz, CD$_3$OD) δ 7.73 (d, J=7.63 Hz, 1H), 7.59 (d, J=8.22 Hz, 1H), 7.43-7.53 (m, 3H), 7.29-7.42 (m, 3H), 7.20 (d, J=7.63 Hz, 1H), 6.97 (t, J=7.63 Hz, 1H), 6.66 (d, J=7.34 Hz, 1H), 6.57 (br. s., 1H), 6.43 (d, J=7.34 Hz, 1H), 4.27 (d, J=12.91 Hz, 1H), 3.99 (d, J=12.91 Hz, 1H).

Compound 80

N-{2-[(3-aminobenzyl)sulfonyl]phenyl}-1-benzofuran-2-sulfonamide

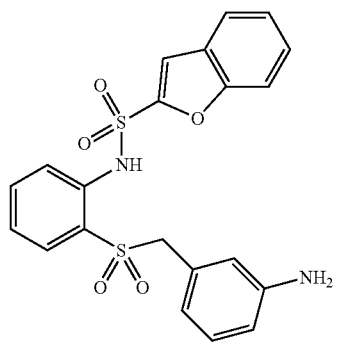 [SMILES: Nc1cccc(CS(=O)(=O)c2ccccc2NS(=O)(=O)c2cc3ccccc3o2)c1]

Following General Procedure L, the title compound (75 mg, 82%) was prepared from N-{2-[(3-nitrobenzyl)sulfonyl]phenyl}-1-benzofuran-2-sulfonamide.

1H NMR (600 MHz, acetone-d6)) δ 7.75-7.85 (m, 3H), 7.62-7.70 (m, 1H), 7.59 (d, J=8.51 Hz, 1H), 7.56 (dd, J=1.76, 7.92 Hz, 1H), 7.49 (td, J=1.17, 7.92 Hz, 1H), 7.36 (t, J=7.48

Hz, 1H), 7.16-7.22 (m, 1H), 6.83 (t, J=7.78 Hz, 1H), 6.57 (dd, J=1.47, 7.92 Hz, 1H), 6.43 (t, J=1.91 Hz, 1H), 6.15 (d, J=7.34 Hz, 1H), 4.37 (s, 2H).

Intermediate 28

5-chloro-2-((4-nitrobenzyl)thio)aniline

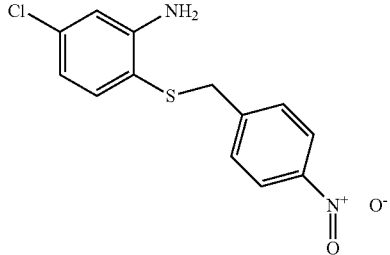

Following General Procedure A, the title compound (624 mg, 92%) was prepared from 2-amino-4-chlorobenzenethiol (555 mg, 3.10 mmol), 1-(bromomethyl)-4-nitrobenzene (490 mg, 2.268 mmol) and $K_2CO_3$ (1.3 g, 9.50 mmol) in DMF (20 ml).

1H NMR (600 MHz, $CD_3OD$) δ 8.07 (d, J=8.80 Hz, 2H), 7.30 (d, J=8.80 Hz, 2H), 6.93 (d, J=8.22 Hz, 1H), 6.73 (d, J=2.35 Hz, 1H), 6.43 (dd, J=2.35, 8.22 Hz, 1H), 3.97 (s, 2H).

Compound 81

N-{5-chloro-2-[(4-nitrobenzyl)thio]phenyl}-1-benzofuran-2-sulfonamide

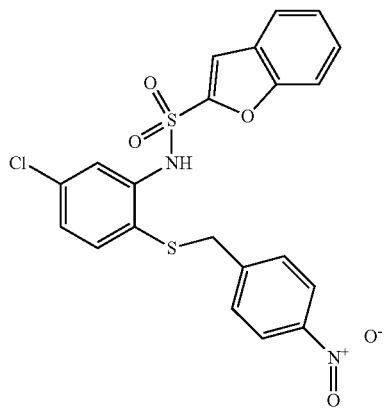

Following General Procedure B, the title compound (475 mg, 72%) was prepared from 5-chloro-2-((4-nitrobenzyl)thio)aniline (411 mg, 1.40 mmol) and benzofuran-2-sulfonyl chloride (303 mg, 1.40 mmol) in pyridine (5 ml).

1H NMR (600 MHz, $CD_3OD$) δ 7.94-8.00 (m, 2H), 7.72 (d, J=7.92 Hz, 1H), 7.50-7.55 (m, 1H), 7.45-7.49 (m, 2H), 7.43 (s, 1H), 7.31-7.38 (m, 1H), 7.11-7.19 (m, 3H), 7.07 (dd, J=2.35, 8.51 Hz, 1H), 3.96 (s, 2H).

Compound 82

N-{5-chloro-2-[(4-nitrobenzyl)sulfonyl]phenyl}-1-benzofuran-2-sulfonamide

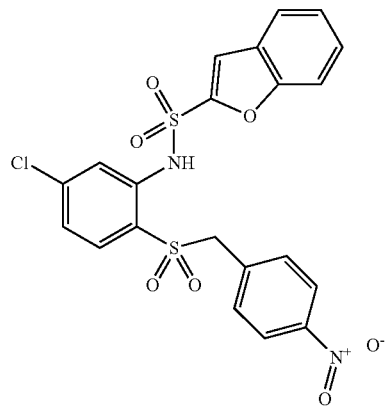

Following General Procedure D, the title compound (120 mg, 85%) was prepared from N-{5-chloro-2-[(4-nitrobenzyl)thio]phenyl}-1-benzofuran-2-sulfonamide.

1H NMR (600 MHz, acetone-d6) δ 9.59 (br. s., 1H), 8.01 (d, J=7.34 Hz, 2H), 7.86 (s, 1H), 7.76 (d, J=7.92 Hz, 1H), 7.72 (s, 1H), 7.52 (d, J=8.51 Hz, 1H), 7.39-7.49 (m, 2H), 7.25-7.36 (m, 3H), 7.00 (s, 1H), 4.96 (s, 2H).

Compound 83

N-{2-[(4-aminobenzyl)sulfonyl]-5-chlorophenyl}-1-benzofuran-2-sulfonamide

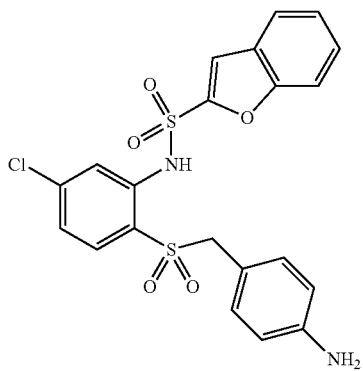 [SMILES: Nc1ccc(CS(=O)(=O)c2ccc(Cl)cc2NS(=O)(=O)c2cc3ccccc3o2)cc1]

Following General Procedure L, the title compound (68 mg, 81%) was prepared from N-{5-chloro-2-[(4-nitrobenzyl)sulfonyl]phenyl}-1-benzofuran-2-sulfonamide.

1H NMR (600 MHz, acetone-d6) δ 7.75-7.88 (m, 3H), 7.61 (d, J=8.51 Hz, 1H), 7.44-7.54 (m, 2H), 7.34-7.41 (m, 1H), 7.22 (dd, J=1.76, 8.51 Hz, 1H), 6.69 (d, J=8.51 Hz, 2H), 6.49 (d, J=8.51 Hz, 2H), 4.38 (s, 2H).

Intermediate 29

5-chloro-2-((2-nitrobenzyl)thio)aniline

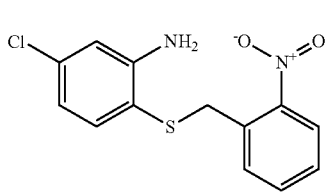

Following General Procedure A, the title compound (548 mg, 95%) was prepared from 2-amino-4-chlorobenzenethiol (441 mg, 2.76 mmol), 1-(bromomethyl)-2-nitrobenzene (398 mg, 1.84 mmol) and K$_2$CO$_3$ (1.27 g, 9.21 mmol) in DMF (20 ml).

1H NMR (600 MHz, CD$_3$OD) δ 7.89-7.98 (m, 1H), 7.37-7.46 (m, 2H), 6.99-7.04 (m, 1H), 6.81 (d, J=8.22 Hz, 1H), 6.71 (d, J=2.05 Hz, 1H), 6.37 (dd, J=2.05, 8.22 Hz, 1H), 4.22 (s, 2H).

Compound 84

N-(5-chloro-2-((2-nitrobenzyl)thio)phenyl)benzofuran-2-sulfonamide

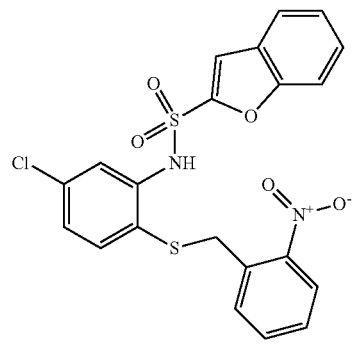 [SMILES: O=[N+]([O-])c1ccccc1CSc1ccc(Cl)cc1NS(=O)(=O)c1cc2ccccc2o1]

Following General Procedure B, the title compound (485 mg, 69%) was prepared from 5-chloro-2-((2-nitrobenzyl)thio)aniline (435 mg, 1.48 mmol) and benzofuran-2-sulfonyl chloride (320 mg, 1.48 mmol) in pyridine (5 ml).

1H NMR (600 MHz, CDCl$_3$) δ 8.03 (dd, J=1.47, 7.92 Hz, 1H), 7.65-7.71 (m, 2H), 7.48-7.53 (m, 2H), 7.43-7.48 (m, 1H), 7.31-7.42 (m, 3H), 7.03 (d, J=8.22 Hz, 1H), 6.90 (dd, J=2.05, 8.22 Hz, 1H), 6.76 (dd, J=1.32, 7.48 Hz, 1H), 4.16 (s, 2H).

Compound 85

N-{2-[(2-aminobenzyl)thio]-5-chlorophenyl}-1-benzofuran-2-sulfonamide

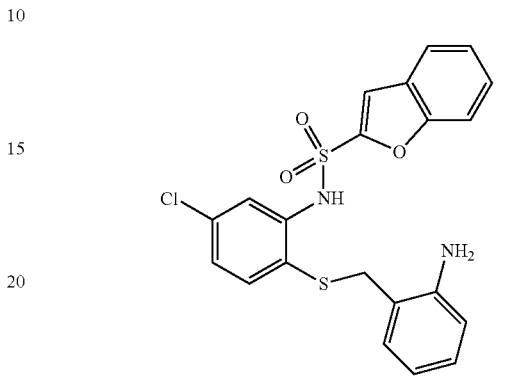

Following General Procedure L, the title compound (44 mg, 40%) was prepared from N-(5-chloro-2-((2-nitrobenzyl)thio)phenyl)benzofuran-2-sulfonamide.

1H NMR (600 MHz, acetone-d6) δ 7.77 (d, J=7.92 Hz, 1H), 7.59 (dd, J=0.88, 8.51 Hz, 1H), 7.47-7.55 (m, 3H), 7.31-7.41 (m, 2H), 7.10 (dd, J=2.35, 8.51 Hz, 1H), 6.86-6.95 (m, 1H), 6.72 (dd, J=0.88, 7.92 Hz, 1H), 6.57 (dd, J=1.32, 7.48 Hz, 1H), 6.38 (td, J=1.03, 7.41 Hz, 1H), 3.97 (s, 2H).

Compound 86

N-{5-chloro-2-[(2-nitrobenzyl)sulfinyl]phenyl}-1-benzofuran-2-sulfonamide

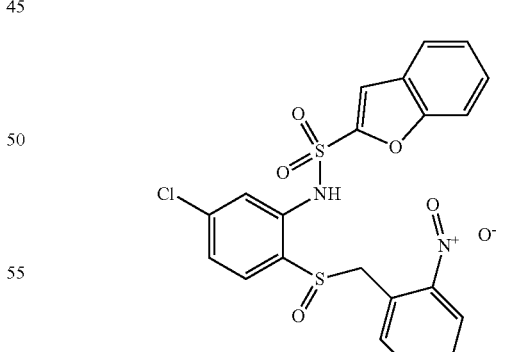

Following General Procedure C, the title compound (160 mg, 79%) was prepared from N-(5-chloro-2-((2-nitrobenzyl)thio)phenyl)benzofuran-2-sulfonamide.

1H NMR (600 MHz, acetone-d6) δ 7.92 (d, J=8.22 Hz, 1H), 7.71 (dd, J=0.73, 7.78 Hz, 1H), 7.59 (d, J=2.05 Hz, 1H), 7.47 (d, J=8.51 Hz, 1H), 7.39-7.44 (m, 1H), 7.33-7.38 (m, 2H), 7.19-7.30 (m, 2H), 6.71-6.80 (m, 2H), 6.67 (d, J=8.22 Hz, 1H), 5.13 (d, J=12.91 Hz, 2H), 4.73 (d, J=12.62 Hz, 2H).

Compound 87

N-{2-[(2-aminobenzyl)sulfinyl]-5-chlorophenyl}-1-benzofuran-2-sulfonamide

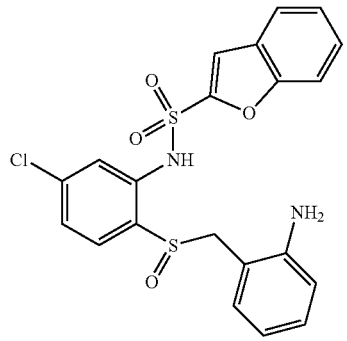 [SMILES: Nc1ccccc1CS(=O)c1ccc(Cl)cc1NS(=O)(=O)c1cc2ccccc2o1]

Following General Procedure L, the title compound (67 mg, 50%) was prepared from N-{5-chloro-2-[(2-nitrobenzyl)sulfinyl]phenyl}-1-benzofuran-2-sulfonamide.

1H NMR (600 MHz, CD$_3$OD) δ 7.72 (d, J=7.92 Hz, 1H), 7.56 (d, J=7.63 Hz, 1H), 7.44-7.52 (m, 2H), 7.41 (d, J=8.51 Hz, 2H), 7.31-7.37 (m, 1H), 7.28 (d, J=1.47 Hz, 1H), 7.21 (dd, J=1.76, 8.22 Hz, 1H), 7.06-7.13 (m, 1H), 6.88 (d, J=7.92 Hz, 1H), 6.75 (d, J=7.04 Hz, 1H), 6.60-6.67 (m, 1H), 4.50 (d, J=13.50 Hz, 2H), 4.23 (d, J=12.91 Hz, 2H).

Compound 88

N-{2-[(2-aminobenzyl)sulfonyl]-5-chlorophenyl}-1-benzofuran-2-sulfonamide

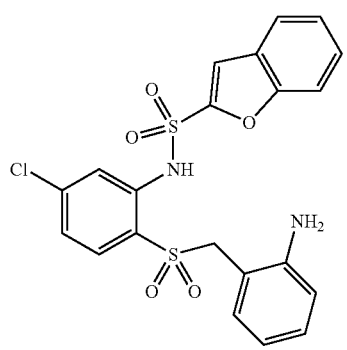 [SMILES: Nc1ccccc1CS(=O)(=O)c1ccc(Cl)cc1NS(=O)(=O)c1cc2ccccc2o1]

Following General Procedure D and K, the title compound (52 mg) was prepared from N-(5-chloro-2-((2-nitrobenzyl)thio)phenyl)benzofuran-2-sulfonamide.

1H NMR (300 MHz, CD$_3$OD) δ 7.69-7.78 (m, 2H), 7.56-7.65 (m, 2H), 7.50-7.55 (m, 1H), 7.45 (td, J=1.17, 7.77 Hz, 1H), 7.28-7.38 (m, 1H), 6.99-7.15 (m, 2H), 6.88 (d, J=7.03 Hz, 1H), 6.67-6.75 (m, 1H), 6.58-6.66 (m, 1H), 4.68 (s, 2H).

Intermediate 30

5-chloro-2-((pyrimidin-2-ylmethyl)thio)aniline

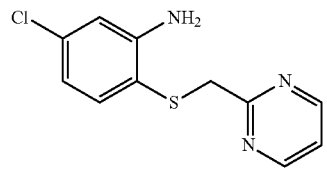 [SMILES: Nc1cc(Cl)ccc1SCc1ncccn1]

Following General Procedure A, the title compound (284 mg, 39%) was prepared from 2-amino-4-chlorobenzenethiol (529 mg, 3.33 mmol), 2-(chloromethyl)pyrimidine (366 mg, 2.22 mmol) and K$_2$CO$_3$ (1.53 g, 11.09 mmol) in DMF (10 ml).

1H NMR (600 MHz, CD$_3$OD) δ 8.65 (d, J=4.99 Hz, 2H), 7.31 (t, J=4.99 Hz, 1H), 7.03 (d, J=8.22 Hz, 1H), 6.70 (s, 1H), 6.43 (dd, J=2.05, 8.22 Hz, 1H), 4.07 (s, 2H).

Compound 89

N-{5-chloro-2-[(pyrimidin-2-ylmethyl)thio]phenyl}-1-benzofuran-2-sulfonamide

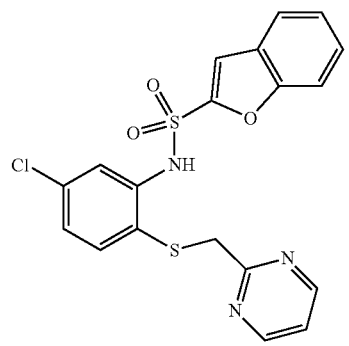 [SMILES: O=S(=O)(Nc1cc(Cl)ccc1SCc1ncccn1)c1cc2ccccc2o1]

Following General Procedure B, the title compound (243 mg, 51%) was prepared from 5-chloro-2-((pyrimidin-2-ylmethyl)thio)aniline (280 mg, 1.11 mmol) and benzofuran-2-sulfonyl chloride (240 mg, 1.11 mmol) in pyridine (3 ml).

1H NMR (600 MHz, acetone-d6) δ 11.69 (br. s., 1H), 8.87 (d, J=4.99 Hz, 2H), 7.74 (dd, J=0.88, 7.92 Hz, 1H), 7.66 (s, 1H), 7.62 (d, J=8.22 Hz, 1H), 7.59 (d, J=0.59 Hz, 1H), 7.45-7.52 (m, 3H), 7.33 (ddd, J=1.76, 6.38, 8.00 Hz, 1H), 7.14 (dd, J=2.20, 8.36 Hz, 1H), 4.24 (s, 2H).

Compound 90

N-{5-chloro-2-[(pyrimidin-2-ylmethyl)sulfinyl]phenyl}-1-benzofuran-2-sulfonamide

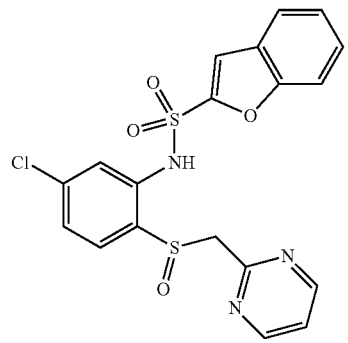 [SMILES: O=S(Cc1ncccn1)c1ccc(Cl)cc1NS(=O)(=O)c1cc2ccccc2o1]

Following General Procedure C, the title compound (82 mg) was prepared from N-{5-chloro-2-[(pyrimidin-2-ylmethyl)thio]phenyl}-1-benzofuran-2-sulfonamide.

1H NMR (600 MHz, CD₃OD) δ 8.68 (dd, J=1.47, 4.99 Hz, 2H), 7.73 (d, J=7.92 Hz, 1H), 7.53-7.60 (m, 2H), 7.45-7.52 (m, 2H), 7.30-7.41 (m, 4H), 4.63 (d, J=13.50 Hz, 1H), 4.46 (d, J=13.50 Hz, 1H).

Compound 91

N-{5-chloro-2-[(pyrimidin-2-ylmethyl)sulfonyl]phenyl}-1-benzofuran-2-sulfonamide

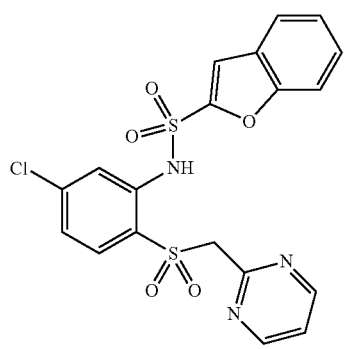 [SMILES: O=S(=O)(Cc1ncccn1)c1ccc(Cl)cc1NS(=O)(=O)c1cc2ccccc2o1]

Following General Procedure D, the title compound (60 mg) was prepared from N-{5-chloro-2-[(pyrimidin-2-ylmethyl)thio]phenyl}-1-benzofuran-2-sulfonamide.

1H NMR (600 MHz, DMSO-d6) δ 8.68 (dd, J=1.47, 4.99 Hz, 2H), 7.76 (s, 1H), 7.68 (br. s., 1H), 7.61 (d, J=8.22 Hz, 1H), 7.54-7.58 (m, 2H), 7.46 (t, J=7.34 Hz, 1H), 7.41 (t, J=4.84 Hz, 1H), 7.30-7.37 (m, 1H), 7.19 (d, J=7.92 Hz, 1H), 5.11-5.19 (m, 2H).

General Procedure M

Intermediate 31

4-mercapto-3-nitrobenzonitrile

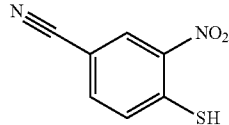 [SMILES: N#Cc1ccc(S)c([N+](=O)[O-])c1]

To a solution of 4-chloro-3-nitrobenzonitrile (530 mg, 2.88 mmol) in dioxane (5 ml)/water (1 ml) was added Na₂S.9H₂O 9692 mg, 2.88 mmol). After it was stirred at room temperature for 2 hours, the reaction was quenched with HCl (1N). The mixture was extracted with EtOAc (2×50 ml). The organic layer was washed with water, brine, dried over Na₂SO₄ and concentrated in vacuo. The title compound was purified by silica gel column chromatography (0~30% EtOAc in hexane).

1H NMR (600 MHz, acetone-d6) δ 8.67 (d, J=1.76 Hz, 1H), 8.01 (s, 1H), 7.93 (dd, J=1.76, 8.51 Hz, 1H), 5.30 (s, 1H).

Intermediate 32

4-(benzylthio)-3-nitrobenzonitrile

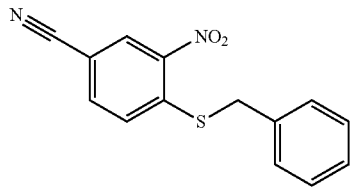

Following General Procedure A, the title compound (580 mg, 82%) was prepared from 4-mercapto-3-nitrobenzonitrile (473 mg, 2.63 mmol), (bromomethyl)benzene (449 mg, 2.63 mmol), K₂CO₃ (1.81 g, 13.14 mmol) in DMF (10 ml).

1H NMR (600 MHz, DMSO-d₆) δ 8.68 (d, J=1.76 Hz, 1H), 8.10 (dd, J=1.47, 8.51 Hz, 1H), 7.88 (d, J=8.51 Hz, 1H), 7.43 (d, J=7.34 Hz, 2H), 7.34 (t, J=7.63 Hz, 2H), 7.25-7.30 (m, 1H), 4.44 (s, 2H).

Intermediate 33

3-amino-4-(benzylthio)benzonitrile

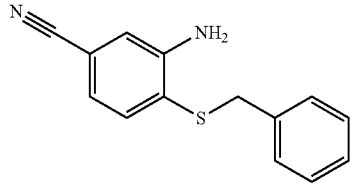 [SMILES: N#Cc1ccc(SCc2ccccc2)c([N+](=O)[O-])c1]

Following General Procedure L, the title compound (372 mg, 81%) was prepared from 4-(benzylthio)-3-nitrobenzonitrile (518 mg, 1.92 mmol).

1H NMR (600 MHz, CD₃OD) δ 7.11-7.25 (m, 6H), 6.96 (d, J=1.76 Hz, 1H), 6.71-6.78 (m, 1H), 4.00 (s, 2H).

Compound 92

N-[2-(benzylthio)-5-cyanophenyl]-1-benzofuran-2-sulfonamide

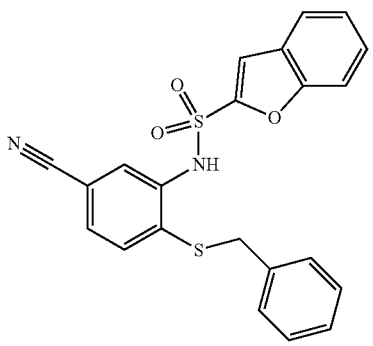 [SMILES: N#Cc1ccc(SCc2ccccc2)c(NS(=O)(=O)c2cc3ccccc3o2)c1]

Following General Procedure B, the title compound (419 mg, 65%) was prepared from 3-amino-4-(benzylthio)benzonitrile (370 mg, 1.54 mmol) and benzofuran-2-sulfonyl chloride (333 mg, 1.54 mmol) in pyridine (3 ml).

1H NMR (600 MHz, CD$_3$OD) δ 7.73 (d, J=8.51 Hz, 1H), 7.65 (d, J=1.17 Hz, 1H), 7.50-7.56 (m, 2H), 7.48 (dd, J=1.47, 8.22 Hz, 1H), 7.39 (ddd, J=2.05, 6.16, 7.92 Hz, 1H), 7.31-7.36 (m, 2H), 7.09-7.20 (m, 3H), 6.92 (d, J=7.04 Hz, 2H), 3.97 (s, 2H).

Compound 93

N-[2-(benzylsulfinyl)-5-cyanophenyl]-1-benzofuran-2-sulfonamide

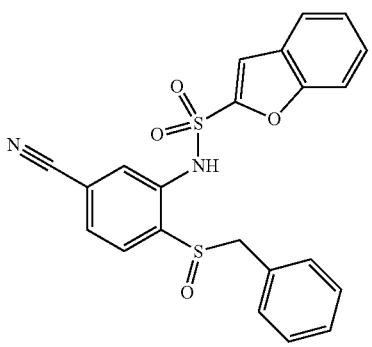 [SMILES: N#Cc1ccc(S(=O)Cc2ccccc2)c(NS(=O)(=O)c2cc3ccccc3o2)c1]

Following General Procedure C, the title compound (109 mg) was prepared from N-[2-(benzylthio)-5-cyanophenyl]-1-benzofuran-2-sulfonamide.

1H NMR (600 MHz, CD$_3$OD) δ 7.74 (d, J=7.63 Hz, 1H), 7.66 (s, 1H), 7.53 (d, J=8.51 Hz, 1H), 7.50 (s, 1H), 7.45 (t, J=7.48 Hz, 1H), 7.30-7.39 (m, 2H), 7.28 (d, J=7.92 Hz, 1H), 7.20-7.25 (m, 1H), 7.16 (t, J=7.48 Hz, 2H), 6.96 (d, J=7.34 Hz, 2H), 4.47 (d, J=13.21 Hz, 1H), 4.21 (d, J=12.91 Hz, 1H).

Compound 94

N-[2-(benzylsulfonyl)-5-cyanophenyl]-1-benzofuran-2-sulfonamide

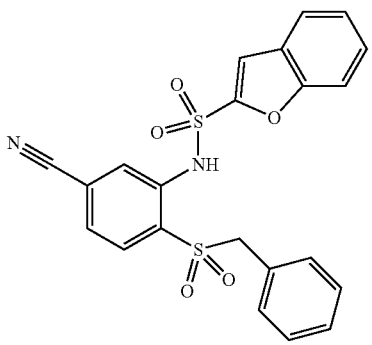 [SMILES: N#Cc1ccc(S(=O)(=O)Cc2ccccc2)c(NS(=O)(=O)c2cc3ccccc3o2)c1]

Following General Procedure D, the title compound (230 mg) was prepared from N-[2-(benzylthio)-5-cyanophenyl]-1-benzofuran-2-sulfonamide.

1H NMR (600 MHz, CD$_3$OD) δ 7.97 (d, J=1.47 Hz, 1H), 7.68 (d, J=7.63 Hz, 1H), 7.52 (d, J=8.22 Hz, 1H), 7.43 (s, 1H), 7.32-7.38 (m, 2H), 7.24-7.30 (m, 1H), 7.09-7.18 (m, 3H), 6.98-7.06 (m, 2H), 6.87 (dd, J=1.47, 8.22 Hz, 1H), 5.05 (s, 2H).

Compound 95

4-chloro-N-[5-chloro-2-(methylsulfonyl)phenyl]-3-(trifluoromethyl)benzenesulfonamide

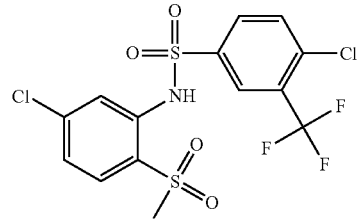 [SMILES: CS(=O)(=O)c1ccc(Cl)cc1NS(=O)(=O)c1ccc(Cl)c(C(F)(F)F)c1]

Following General Procedure B and D, the title compound was prepared from 5-chloro-2-(methylthio)aniline and 4-chloro-3-(trifluoromethyl)benzene-1-sulfonyl chloride.

1H NMR (300 MHz, CD$_3$OD) δ 8.26 (s, 1H), 8.11 (d, J=8.50 Hz, 1H), 7.74-7.87 (m, 2H), 7.58 (d, J=1.47 Hz, 1H), 7.16 (d, J=8.50 Hz, 1H), 3.19 (s, 3H).

Compound 96

4-chloro-N-[5-chloro-2-(methylthio)phenyl]-3-(trifluoromethyl)benzenesulfonamide

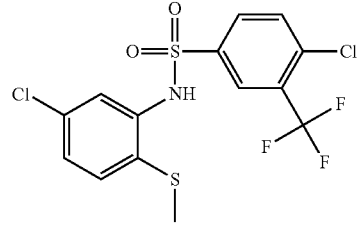 [SMILES: CSc1ccc(Cl)cc1NS(=O)(=O)c1ccc(Cl)c(C(F)(F)F)c1]

Following General Procedure B, the title compound was prepared from 5-chloro-2-(methylthio)aniline and 4-chloro-3-(trifluoromethyl)benzene-1-sulfonyl chloride.

1H NMR (300 MHz, CDCl$_3$) δ 8.13 (d, J=1.47 Hz, 1H), 7.88 (dd, J=1.90, 8.35 Hz, 1H), 7.60 (dd, J=2.64, 12.60 Hz, 2H), 7.28 (d, J=8.50 Hz, 1H), 7.10 (dd, J=2.05, 8.50 Hz, 1H), 2.21 (s, 3H).

Compound 97

4-chloro-N-[5-chloro-2-(isopropylthio)phenyl]-3-(trifluoromethyl)benzenesulfonamide

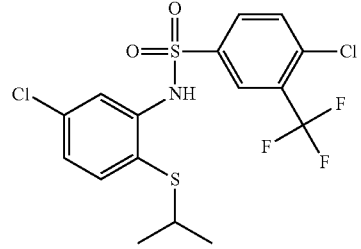 [SMILES: CC(C)Sc1ccc(Cl)cc1NS(=O)(=O)c1ccc(Cl)c(C(F)(F)F)c1]

Following General Procedure A and B, the title compound was prepared from 2-amino-4-chloro-benzenethiol, 2-iodopropane, and 4-chloro-3-(trifluoromethyl)benzene-1-sulfonyl chloride.

1H NMR (300 MHz, CD$_3$OD) δ 8.13 (d, J=1.47 Hz, 1H), 7.92 (dd, J=2.05, 8.50 Hz, 1H), 7.76 (d, J=8.50 Hz, 1H), 7.53 (d, J=2.05 Hz, 1H), 7.33 (d, J=8.50 Hz, 1H), 7.15-7.23 (m, 1H), 3.03-3.21 (m, 1H), 1.06 (d, J=6.45 Hz, 6H).

Compound 98

4-chloro-N-{5-chloro-2-[(2-hydroxyethyl)thio]phenyl}-3-(trifluoromethyl)benzenesulfonamide

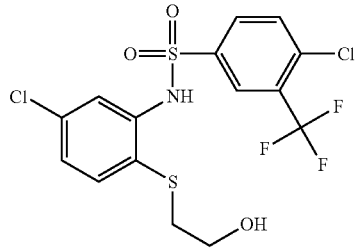 [SMILES: O=S(=O)(Nc1cc(Cl)ccc1SCCO)c1ccc(Cl)c(C(F)(F)F)c1]

Following General Procedure A and B, the title compound was prepared from 2-amino-4-chloro-benzenethiol, 2-bromo-ethanol, and 4-chloro-3-(trifluoromethyl)benzene-1-sulfonyl chloride.

1H NMR (300 MHz, CD$_3$OD) δ 8.09 (d, J=1.47 Hz, 1H), 7.92 (dd, J=1.90, 8.35 Hz, 1H), 7.76 (d, J=8.50 Hz, 1H), 7.51 (d, J=2.34 Hz, 1H), 7.41 (d, J=8.50 Hz, 1H), 7.20 (dd, J=2.20, 8.35 Hz, 1H), 3.49 (t, J=6.15 Hz, 2H), 2.80 (t, J=6.15 Hz, 2H).

Compound 99

4-chloro-N-[5-chloro-2-(isopropylsulfinyl)phenyl]-3-(trifluoromethyl)benzenesulfonamide

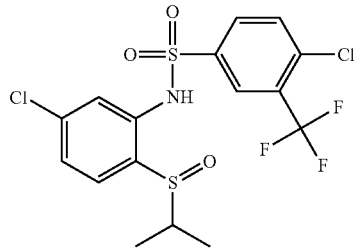 [SMILES: CC(C)S(=O)c1ccc(Cl)cc1NS(=O)(=O)c1ccc(Cl)c(C(F)(F)F)c1]

Following General Procedure C, the title compound (55 mg) was prepared from 4-chloro-N-[5-chloro-2-(isopropylthio)phenyl]-3-(trifluoromethyl)benzenesulfonamide.

Compound 100

4-chloro-N-{5-chloro-2-[(2-hydroxyethyl)sulfinyl]phenyl}-3-(trifluoromethyl)benzenesulfonamide

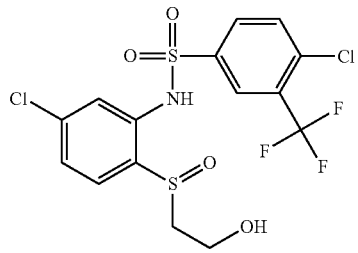 [SMILES: O=S(CCO)c1ccc(Cl)cc1NS(=O)(=O)c1ccc(Cl)c(C(F)(F)F)c1]

Following General Procedure C, the title compound (109 mg) was prepared from 4-chloro-N-{5-chloro-2-[(2-hydroxyethyl)thio]phenyl}-3-(trifluoromethyl)benzenesulfonamide.

1H NMR (300 MHz, CD$_3$OD) δ 8.09 (d, J=1.17 Hz, 1H), 7.96-8.03 (m, 1H), 7.84 (d, J=8.20 Hz, 1H), 7.71 (d, J=8.50 Hz, 1H), 7.44 (dd, J=1.76, 8.50 Hz, 1H), 7.21 (d, J=1.76 Hz, 1H), 3.98 (td, J=4.10, 8.06 Hz, 1H), 3.77-3.88 (m, 1H), 3.19 (ddd, J=5.27, 8.42, 13.26 Hz, 1H), 2.95-3.06 (m, 1H).

Compound 101

4-chloro-N-{5-chloro-2-[(2-hydroxyethyl)sulfonyl]phenyl}-3-(trifluoromethyl)benzenesulfonamide

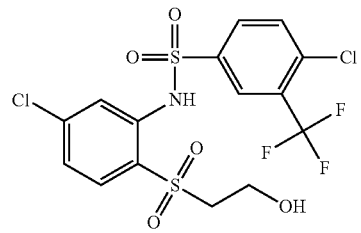 [SMILES: O=S(=O)(CCO)c1ccc(Cl)cc1NS(=O)(=O)c1ccc(Cl)c(C(F)(F)F)c1]

Following General Procedure D, the title compound was prepared from 4-chloro-N-{5-chloro-2-[(2-hydroxyethyl)thio]phenyl}-3-(trifluoromethyl)benzenesulfonamide.

1H NMR (600 MHz, CD$_3$OD) δ 8.27 (d, J=1.47 Hz, 1H), 8.11 (dd, J=2.05, 8.51 Hz, 1H), 7.74 (dd, J=8.51, 14.97 Hz, 2H), 7.54-7.59 (m, 1H), 6.96-7.08 (m, 1H), 3.82 (t, J=6.02 Hz, 2H), 3.57-3.68 (m, 2H).

Compound 102 methyl 3-{[4-chloro-2-({[4-chloro-3-(trifluoromethyl)phenyl]sulfonyl}amino)phenyl]sulfinyl}propanoate

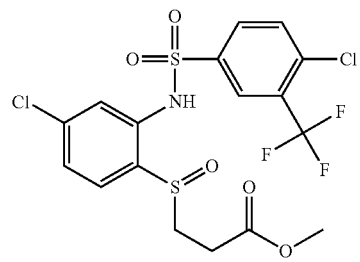 [SMILES: COC(=O)CCS(=O)c1ccc(Cl)cc1NS(=O)(=O)c1ccc(Cl)c(C(F)(F)F)c1]

Following General Procedure H, B, and C, the title compound was prepared from 2-amino-4-chlorobenzenethiol.

1H NMR (300 MHz, CD$_3$OD) δ 8.09 (s, 1H), 7.99 (dd, J=1.76, 8.50 Hz, 1H), 7.85 (d, J=8.20 Hz, 1H), 7.71 (d, J=8.50 Hz, 1H), 7.47 (dd, J=1.61, 8.35 Hz, 1H), 7.11 (d, J=1.76 Hz, 1H), 3.63 (s, 3H), 3.24-3.39 (m, 1H), 3.08-3.22 (m, 1H), 2.54-2.82 (m, 2H).

Compound 103

4-chloro-N-{5-chloro-2-[(pyridin-2-ylmethyl)thio]phenyl}-3-(trifluoromethyl)benzenesulfonamide

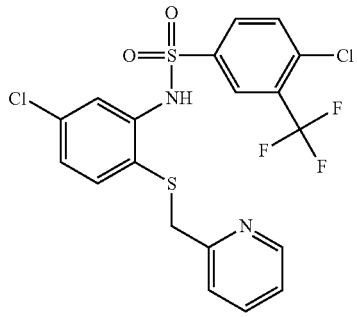 [SMILES: O=S(=O)(Nc1cc(Cl)ccc1SCc1ccccn1)c1ccc(Cl)c(C(F)(F)F)c1]

Following General Procedure A and B, the title compound was prepared from 2-amino-4-chlorobenzenethiol.

1H NMR (600 MHz, CD$_3$OD) δ 8.63 (d, J=3.81 Hz, 1H), 8.03 (d, J=2.35 Hz, 1H), 7.87 (dd, J=2.20, 8.36 Hz, 1H), 7.75 (td, J=1.76, 7.63 Hz, 1H), 7.70 (d, J=8.51 Hz, 1H), 7.54 (d, J=2.35 Hz, 1H), 7.37 (d, J=8.51 Hz, 1H), 7.32-7.35 (m, 1H), 7.21 (d, J=7.63 Hz, 1H), 7.13 (dd, J=2.35, 8.22 Hz, 1H), 4.00 (s, 2H).

Compound 104

4-chloro-N-{5-chloro-2-[(pyridin-3-ylmethyl)thio]phenyl}-3-(trifluoromethyl)benzenesulfonamide

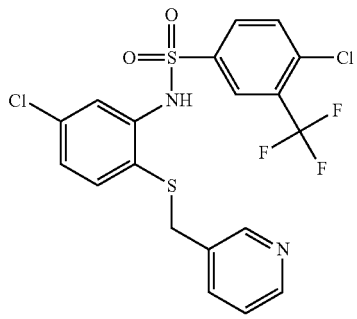 [SMILES: O=S(=O)(Nc1cc(Cl)ccc1SCc1cccnc1)c1ccc(Cl)c(C(F)(F)F)c1]

Following General Procedure A and B, the title compound was prepared from 2-amino-4-chlorobenzenethiol.

1H NMR (600 MHz, CD$_3$OD) δ 8.38 (d, J=3.82 Hz, 1H), 8.25 (br. s., 1H), 8.11 (d, J=2.35 Hz, 1H), 7.93 (dd, J=2.05, 8.51 Hz, 1H), 7.78 (d, J=8.51 Hz, 1H), 7.60 (dt, J=1.91, 7.92 Hz, 1H), 7.39 (d, J=2.35 Hz, 1H), 7.33 (dd, J=4.84, 7.78 Hz, 1H), 7.20 (d, J=8.51 Hz, 1H), 7.14 (s, J=2.35, 2.35, 8.51, 8.51 Hz, 1H), 3.95 (s, 2H).

Compound 105

4-chloro-N-{5-chloro-2-[(pyridin-2-ylmethyl)sulfinyl]phenyl}-3-(trifluoromethyl)benzenesulfonamide

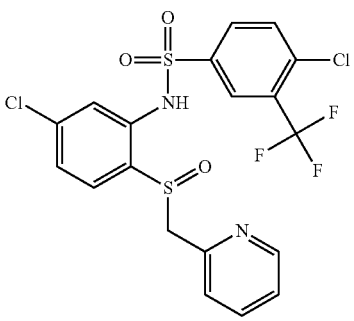 [SMILES: O=S(Cc1ccccn1)c1ccc(Cl)cc1NS(=O)(=O)c1ccc(Cl)c(C(F)(F)F)c1]

Following General Procedure C, the title compound was prepared from 4-chloro-N-{5-chloro-2-[(pyridin-2-ylmethyl)thio]phenyl}-3-(trifluoromethyl)benzenesulfonamide.

1H NMR (600 MHz, DMSO-d6) δ 8.44 (d, J=4.40 Hz, 1H), 8.03 (d, J=2.05 Hz, 1H), 7.98 (dd, J=2.05, 8.22 Hz, 1H), 7.88 (d, J=8.22 Hz, 1H), 7.74 (t, 1H), 7.25-7.33 (m, 2H), 7.20 (d, J=7.63 Hz, 1H), 7.14 (br. s., 1H), 7.03 (d, J=1.47 Hz, 1H), 4.49 (d, J=12.62 Hz, 1H), 4.06 (d, J=12.91 Hz, 1H).

Compound 106

4-chloro-N-{5-chloro-2-[(pyridin-3-ylmethyl)sulfinyl]phenyl}-3-(trifluoromethyl)benzenesulfonamide

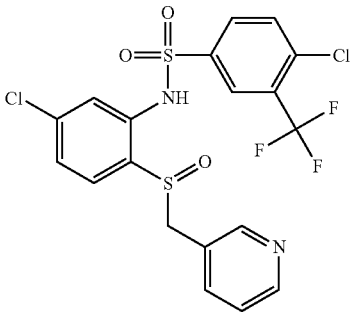 [SMILES: O=S(Cc1cccnc1)c1ccc(Cl)cc1NS(=O)(=O)c1ccc(Cl)c(C(F)(F)F)c1]

Following General Procedure C, the title compound was prepared from 4-chloro-N-{5-chloro-2-[(pyridin-3-ylmethyl)thio]phenyl}-3-(trifluoromethyl)benzenesulfonamide.

1H NMR (600 MHz, CD$_3$OD) δ 8.35 (dd, J=1.61, 4.84 Hz, 1H), 8.24 (d, J=2.35 Hz, 1H), 8.07 (d, J=2.05 Hz, 1H), 8.03 (d, J=1.76 Hz, 1H), 7.71 (d, J=8.51 Hz, 1H), 7.38 (s, 1H), 7.27 (d, J=2.05 Hz, 1H), 7.23-7.26 (m, 1H), 6.75 (d, J=8.22 Hz, 1H), 6.65 (dd, J=1.91, 8.36 Hz, 1H), 4.45 (d, J=13.50 Hz, 1H), 4.37 (d, J=13.21 Hz, 1H).

General Procedure N

Intermediate 34

4-Chloro-N-(5-chloro-2-mercapto-phenyl)-3-trifluoromethyl-benzenesulfonamide

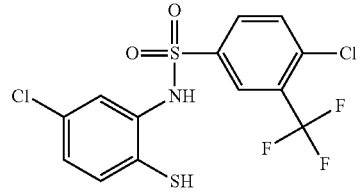 [SMILES: O=S(=O)(Nc1cc(Cl)ccc1S)c1ccc(Cl)c(C(F)(F)F)c1]

To a solution of N,N'-[dithiobis(5-chloro-2,1-phenylene)]bis[4-chloro-3-(trifluoromethyl)benzenesulfonamide] Intermediate 5 (106 mg, 0.13 mmol) in THF (3 ml) at 0° C. was added $NaBH_4$ (20 mg, 0.53 mmol), the mixture was stirred at room temperature for 1 h, diluted with $H_2O$, acidified carefully with 6 M HCl, extracted with EtOAc. The organic layer was washed with brine, dried over $Na_2SO_4$, and concentrated in vacuo to yield 109 mg off-white solid as the title compound.

$^1$H NMR (600 MHz, METHANOL-$d_4$) δ 8.05 (s, 1H), 7.91 (d, J=8.51 Hz, 1H), 7.78 (d, J=8.51 Hz, 1H), 7.30 (dd, J=1.47, 8.22 Hz, 1H), 7.23-7.25 (m, 1H), 7.14 (dd, J=2.20, 8.36 Hz, 1H).

Compound 107 ethyl {[4-chloro-2-({[4-chloro-3-(trifluoromethyl)phenyl]sulfonyl}amino)phenyl]sulfinyl}acetate

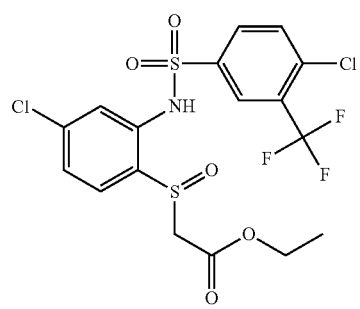 [SMILES: CCOC(=O)CS(=O)c1ccc(Cl)cc1NS(=O)(=O)c1ccc(Cl)c(C(F)(F)F)c1]

Following General Procedure A and C, the title compound was prepared from 4-Chloro-N-(5-chloro-2-mercapto-phenyl)-3-trifluoromethyl-benzenesulfonamide Intermediate 34 and ethyl 2-bromoacetate.

1H NMR (300 MHz, $CD_3OD$) δ 8.06 (s, 1H), 7.96 (d, J=8.50 Hz, 1H), 7.84 (dd, J=8.50, 10.84 Hz, 2H), 7.52 (dd, J=1.61, 8.64 Hz, 1H), 7.06 (d, J=1.47 Hz, 1H), 4.17 (q, J=7.23 Hz, 2H), 4.06 (d, J=14.65 Hz, 1H), 3.88 (d, J=14.36 Hz, 1H), 1.22 (t, J=7.18 Hz, 3H).

General Procedure O

Intermediate 35

4-Chloro-N-[5-chloro-2-(3-oxo-cyclopentylsulfanyl)-phenyl]-3-trifluoromethyl-benzenesulfonamide

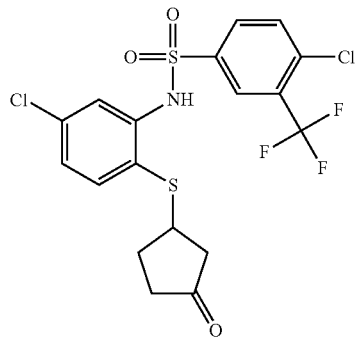 [SMILES: O=C1CCC(Sc2ccc(Cl)cc2NS(=O)(=O)c2ccc(Cl)c(C(F)(F)F)c2)C1]

To a solution of N,N'-[dithiobis(5-chloro-2,1-phenylene)]bis[4-chloro-3-(trifluoromethyl)benzenesulfonamide] Intermediate 5 (105 mg, 0.13 mmol) in $CH_2Cl_2$ (2 ml), MeOH (0.5 ml), and $H_2O$ (0.25 ml) was added polymer-bound triphenylphosphine (~3 mmol/g triphenylphosphine loading, 87 mg, 0.26 mmol), cyclopent-2-enone (33 μl, 0.39 mmol), and PTSA (catalytic amount). The reaction was stirred at room temperature for 4 h and was directly purified by column chromatography on silica gel (0→100% ethyl acetate in hexane) to yield the title compound as an off-white solid (133 mg, 100%).

$^1$H NMR (600 MHz, CHLOROFORM-d) δ 8.16 (d, J=2.35 Hz, 1H), 7.93 (dd, J=2.35, 8.51 Hz, 1H), 7.89 (s, 1H), 7.62-7.65 (m, 2H), 7.35 (d, J=8.22 Hz, 1H), 7.07 (dd, J=2.20, 8.36 Hz, 1H), 3.46 (quin, J=6.53 Hz, 1H), 2.44-2.49 (m, 1H), 2.38-2.44 (m, 1H), 2.21 (s, 2H), 2.05-2.11 (m, 1H), 1.84-1.90 (m, 1H).

Compound 108

4-chloro-N-{5-chloro-2-[(3-hydroxycyclopentyl)sulfinyl]phenyl}-3-(trifluoromethyl)benzenesulfonamide

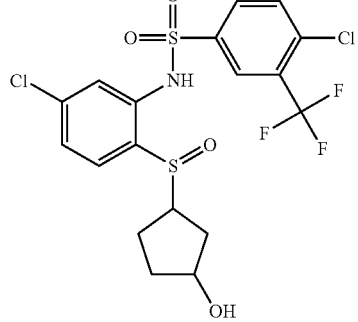

Following General Procedure D, followed by treatment of the crude product with $NaBH_4$ in MeOH, the title compound was prepared from 4-Chloro-N-[5-chloro-2-(3-oxo-cyclopentylsulfanyl)-phenyl]-3-trifluoromethyl-benzenesulfonamide (Intermediate 35).

1H NMR (600 MHz, CD$_3$OD) δ 8.13 (d, J=2.05 Hz, 1H), 7.99 (dd, J=2.20, 8.36 Hz, 1H), 7.73 (d, J=8.51 Hz, 1H), 7.46 (d, J=8.51 Hz, 1H), 7.34 (d, J=2.05 Hz, 1H), 7.06 (dd, J=2.05, 8.51 Hz, 1H), 4.17-4.22 (m, 1H), 3.70-3.77 (m, 1H), 2.19-2.26 (m, 1H), 1.90-2.00 (m, 1H), 1.78-1.86 (m, 1H), 1.62-1.76 (m, 2H), 1.29-1.38 (m, 1H).

Compound 109

4-chloro-N-[5-chloro-2-(ethylsulfonyl)phenyl]-3-(trifluoromethyl)benzenesulfonamide

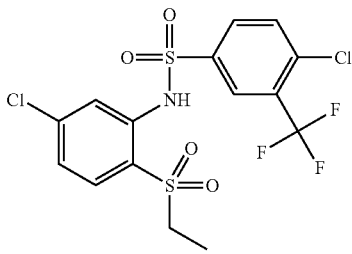 [SMILES: CCS(=O)(=O)c1ccc(Cl)cc1NS(=O)(=O)c1ccc(Cl)c(C(F)(F)F)c1]

Following General Procedure D, the title compound was prepared from 4-chloro-N-[5-chloro-2-(ethylthio)phenyl]-3-(trifluoromethyl)benzenesulfonamide.

1H NMR (600 MHz, CD$_3$OD) δ 8.30 (d, J=1.76 Hz, 1H), 8.14 (dd, J=2.20, 8.36 Hz, 1H), 7.72-7.80 (m, 2H), 7.64 (d, J=2.05 Hz, 1H), 7.10 (br. s., 1H), 3.30-3.38 (m, 2H), 1.09 (t, J=7.34 Hz, 3H)

Compound 110

2-{[4-chloro-2-({[4-chloro-3-(trifluoromethyl)phenyl]sulfonyl}amino)phenyl]thio}-N,N-dimethylacetamide

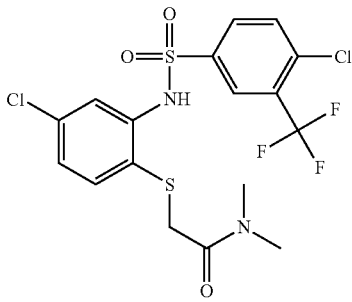 [SMILES: CN(C)C(=O)CSc1ccc(Cl)cc1NS(=O)(=O)c1ccc(Cl)c(C(F)(F)F)c1]

Following General Procedure G, the title compound was prepared from N,N'-[dithiobis(5-chloro-2,1-phenylene)]bis[4-chloro-3-(trifluoromethyl)benzenesulfonamide] Intermediate 5 and 2-chloro-N,N-dimethyl-acetamide.

1H NMR (600 MHz, CD$_3$OD) δ 8.09 (d, J=2.35 Hz, 1H), 7.94 (dd, J=2.05, 8.51 Hz, 1H), 7.76 (d, J=8.22 Hz, 1H), 7.47-7.50 (m, 2H), 7.18 (dd, J=2.35, 8.51 Hz, 1H), 3.68 (s, 2H), 2.97 (s, 3H), 2.93 (s, 3H).

Compound 111

2-{[4-chloro-2-({[4-chloro-3-(trifluoromethyl)phenyl]sulfonyl}amino)phenyl]thio}-N-methylacetamide

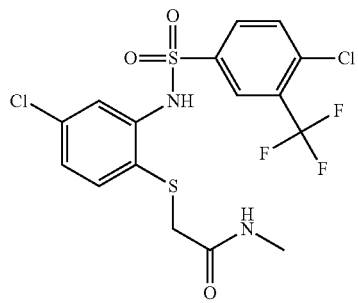 [SMILES: CNC(=O)CSc1ccc(Cl)cc1NS(=O)(=O)c1ccc(Cl)c(C(F)(F)F)c1]

Following General Procedure G, the title compound was prepared from N,N'-[dithiobis(5-chloro-2,1-phenylene)]bis[4-chloro-3-(trifluoromethyl)benzenesulfonamide] Intermediate 5 and 2-chloro-N-methyl-acetamide.

1H NMR (600 MHz, CD$_3$OD) δ 8.09 (d, J=2.35 Hz, 1H), 7.93 (dd, J=2.35, 8.51 Hz, 1H), 7.76 (d, J=8.51 Hz, 1H), 7.48 (d, J=2.35 Hz, 1H), 7.44 (d, J=8.22 Hz, 1H), 7.20 (dd, J=2.35, 8.51 Hz, 1H), 3.40 (s, 2H), 2.69 (s, 3H).

Compound 112

2-{[4-chloro-2-({[4-chloro-3-(trifluoromethyl)phenyl]sulfonyl}amino)phenyl]sulfinyl}-N,N-dimethylacetamide

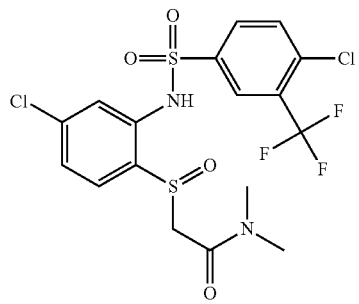 [SMILES: CN(C)C(=O)CS(=O)c1ccc(Cl)cc1NS(=O)(=O)c1ccc(Cl)c(C(F)(F)F)c1]

Following General Procedure C, the title compound was prepared from 2-{[4-chloro-2-({[4-chloro-3-(trifluoromethyl)phenyl]sulfonyl}amino)phenyl]thio}-N,N-dimethylacetamide.

1H NMR (600 MHz, CD$_3$OD) δ 8.16 (d, J=2.35 Hz, 1H), 8.01 (dd, J=2.05, 8.22 Hz, 1H), 7.68 (d, J=8.51 Hz, 1H), 7.45 (d, J=8.51 Hz, 1H), 7.28 (d, J=1.76 Hz, 1H), 6.90 (dd, J=2.05, 8.22 Hz, 1H), 4.65-4.71 (m, 1H), 3.51-3.57 (m, 1H), 3.11 (s, 3H), 2.98 (s, 3H).

Compound 113

2-{[4-chloro-2-({[4-chloro-3-(trifluoromethyl)phenyl]sulfonyl}amino)phenyl]sulfonyl}-N,N-dimethylacetamide

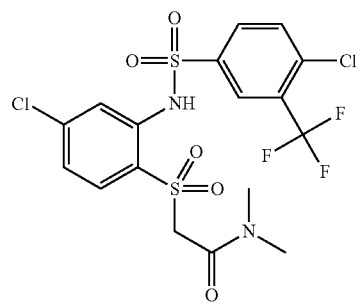 [SMILES: CN(C)C(=O)CS(=O)(=O)c1ccc(Cl)cc1NS(=O)(=O)c1ccc(Cl)c(C(F)(F)F)c1]

Following General Procedure D, the title compound was prepared from 2-{[4-chloro-2-({[4-chloro-3-(trifluoromethyl)phenyl]sulfonyl}amino)phenyl]thio}-N,N-dimethylacetamide.

$^1$H NMR (600 MHz, CD$_3$OD) δ 8.29 (d, J=2.05 Hz, 1H), 8.09-8.14 (m, 1H), 7.72 (d, J=8.51 Hz, 1H), 7.68 (d, J=8.51 Hz, 1H), 7.48 (d, J=1.76 Hz, 1H), 6.81 (d, J=8.22 Hz, 1H), 3.16 (s, 3H), 3.00 (s, 3H).

Compound 114

2-{[4-chloro-2-({[4-chloro-3-(trifluoromethyl)phenyl]sulfonyl}amino)phenyl]sulfinyl}-N-methylacetamide

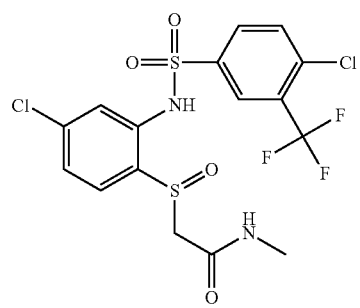 [SMILES: CNC(=O)CS(=O)c1ccc(Cl)cc1NS(=O)(=O)c1ccc(Cl)c(C(F)(F)F)c1]

Following General Procedure C, the title compound was prepared from 2-{[4-chloro-2-({[4-chloro-3-(trifluoromethyl)phenyl]sulfonyl}amino)phenyl]thio}-N-methylacetamide.

$^1$H NMR (600 MHz, CD$_3$OD) δ 8.15 (d, J=2.05 Hz, 1H), 8.01 (dd, J=2.20, 8.36 Hz, 1H), 7.72 (d, J=8.51 Hz, 1H), 7.51 (d, J=8.22 Hz, 1H), 7.22 (d, J=2.05 Hz, 1H), 7.02 (dd, J=1.91, 8.36 Hz, 1H), 4.21 (d, J=13.50 Hz, 1H), 3.49 (d, J=13.21 Hz, 1H), 2.76 (s, 3H)

Compound 115

2-{[4-chloro-2-({[4-chloro-3-(trifluoromethyl)phenyl]sulfonyl}amino)phenyl]sulfonyl}-N-methylacetamide

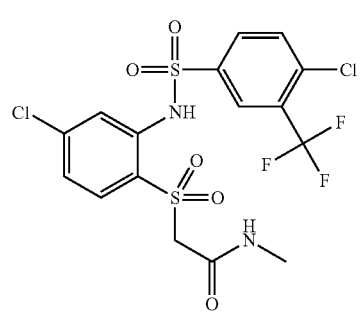 [SMILES: CNC(=O)CS(=O)(=O)c1ccc(Cl)cc1NS(=O)(=O)c1ccc(Cl)c(C(F)(F)F)c1]

Following General Procedure D, the title compound was prepared from 2-{[4-chloro-2-({[4-chloro-3-(trifluoromethyl)phenyl]sulfonyl}amino)phenyl]thio}-N-methylacetamide.

$^1$H NMR (600 MHz, CD$_3$OD) δ 8.29 (d, J=2.05 Hz, 1H), 8.09-8.13 (m, 1H), 7.69 (d, J=8.51 Hz, 1H), 7.66 (d, J=8.22 Hz, 1H), 7.44 (d, J=2.05 Hz, 1H), 6.75 (dd, J=1.91, 8.66 Hz, 1H), 2.77 (s, 3H).

Compound 116

N-{2-[(2-aminoethyl)thio]-5-chlorophenyl}-4-chloro-3-(trifluoromethyl)benzenesulfonamide

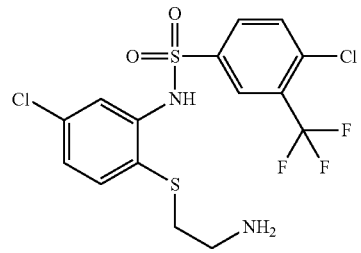 [SMILES: NCCSc1ccc(Cl)cc1NS(=O)(=O)c1ccc(Cl)c(C(F)(F)F)c1]

Following General Procedure G, the title compound was prepared from N,N'-[dithiobis(5-chloro-2,1-phenylene)]bis[4-chloro-3-(trifluoromethyl)benzenesulfonamide] Intermediate 5 and 2-bromo-ethylamine hydrobromide.

$^1$H NMR (600 MHz, CD$_3$OD) δ 8.18 (d, J=2.05 Hz, 1H), 7.99 (dd, J=2.05, 8.22 Hz, 1H), 7.65 (d, J=8.51 Hz, 1H), 7.38 (d, J=8.22 Hz, 1H), 7.30 (d, J=2.35 Hz, 1H), 6.72 (dd, J=2.35, 8.22 Hz, 1H), 2.96-3.05 (m, 4H).

Compound 117

N-{2-[(2-aminoethyl)sulfonyl]-5-chlorophenyl}-4-chloro-3-(trifluoromethyl)benzenesulfonamide

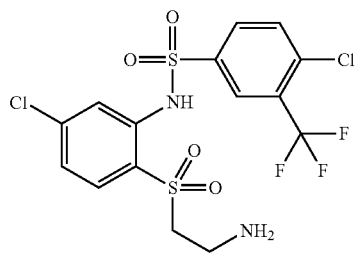 [SMILES: NCCS(=O)(=O)c1ccc(Cl)cc1NS(=O)(=O)c1ccc(Cl)c(C(F)(F)F)c1]

Following General Procedure D, followed by treatment of the crude product with excess zinc dust in MeOH, aqueous NH$_4$Cl and HOAc at room temperature for 2 h, the title compound was prepared from N-{2-[(2-aminoethyl)thio]-5-chlorophenyl}-4-chloro-3-(trifluoromethyl)benzenesulfonamide.

$^1$H NMR (600 MHz, CD$_3$OD) δ 8.27 (d, J=2.05 Hz, 1H), 8.10 (dd, J=1.91, 8.36 Hz, 1H), 7.74 (d, J=8.51 Hz, 1H), 7.67 (d, J=8.51 Hz, 1H), 7.42 (d, J=1.76 Hz, 1H), 6.80 (dd, J=2.05, 8.51 Hz, 1H), 3.88-3.92 (m, 2H), 3.45-3.51 (m, 2H).

Compound 118

N-{2-[(2-aminoethyl)sulfinyl]-5-chlorophenyl}-4-chloro-3-(trifluoromethyl)benzenesulfonamide

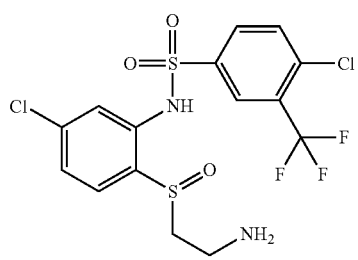 [SMILES: NCCS(=O)c1ccc(Cl)cc1NS(=O)(=O)c1ccc(Cl)c(C(F)(F)F)c1]

Following General Procedure C, the title compound was prepared from N-{2-[(2-aminoethyl)thio]-5-chlorophenyl}-4-chloro-3-(trifluoromethyl)benzenesulfonamide.

$^1$H NMR (300 MHz, CD$_3$OD) δ 8.15 (d, J=1.76 Hz, 1H), 8.00 (dd, J=1.90, 8.35 Hz, 1H), 7.69 (d, J=8.21 Hz, 1H), 7.46 (d, J=8.50 Hz, 1H), 7.25 (d, J=2.05 Hz, 1H), 6.94 (dd, J=1.90, 8.35 Hz, 1H), 3.53-3.67 (m, 1H), 3.36-3.50 (m, 1H), 3.17-3.31 (m, 2H).

Compound 119

3-({2-[(1-benzofuran-2-ylsulfonyl)amino]-4-chlorophenyl}thio)-N,N-dimethylpropanamide

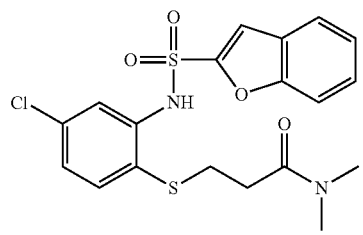 [SMILES: CN(C)C(=O)CCSc1ccc(Cl)cc1NS(=O)(=O)c1cc2ccccc2o1]

Following General Procedure O, the title compound was prepared from N,N'-[dithiobis(5-chloro-2,1-phenylene)]bis(1-benzofuran-2-sulfonamide) Intermediate 8 and N,N-dimethyl-acrylamide.

$^1$H NMR (600 MHz, CD$_3$OD) δ 7.69 (d, J=7.92 Hz, 1H), 7.53-7.56 (m, 1H), 7.45-7.49 (m, 2H), 7.39 (s, 1H), 7.37 (d, J=8.51 Hz, 1H), 7.31-7.35 (m, 1H), 7.17-7.20 (m, 1H), 2.90 (t, J=7.19 Hz, 2H), 2.87 (s, 3H), 2.85 (s, 3H), 2.33 (t, J=7.19 Hz, 2H).

Compound 120

3-({2-[(1-benzofuran-2-ylsulfonyl)amino]-4-chlorophenyl}sulfinyl)-N,N-dimethylpropanamide

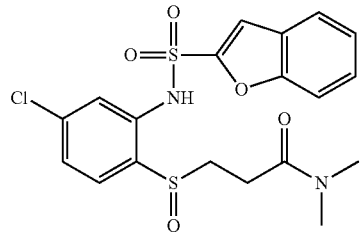 [SMILES: CN(C)C(=O)CCS(=O)c1ccc(Cl)cc1NS(=O)(=O)c1cc2ccccc2o1]

Following General Procedure C, the title compound was prepared from 3-({2-[(1-benzofuran-2-ylsulfonyl)amino]-4-chlorophenyl}thio)-N,N-dimethylpropanamide.

$^1$H NMR (600 MHz, CD$_3$OD) δ 7.72 (d, J=7.34 Hz, 1H), 7.64 (d, J=8.22 Hz, 1H), 7.58 (d, J=8.51 Hz, 1H), 7.46-7.51 (m, 1H), 7.46 (s, 1H), 7.39 (d, J=1.76 Hz, 1H), 7.32-7.37 (m, 2H), 3.27-3.34 (m, 1H), 3.16-3.24 (m, 1H), 2.96 (s, 3H), 2.90 (s, 3H), 2.77-2.86 (m, 1H), 2.59-2.66 (m, 1H).

Compound 121

3-({2-[(1-benzofuran-2-ylsulfonyl)amino]-4-chlorophenyl}sulfonyl)-N,N-dimethylpropanamide

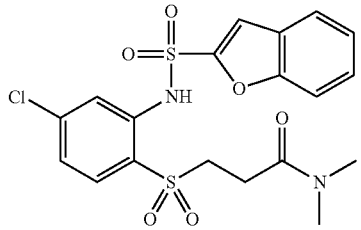 [SMILES: CN(C)C(=O)CCS(=O)(=O)c1ccc(Cl)cc1NS(=O)(=O)c1cc2ccccc2o1]

Following General Procedure D, the title compound was prepared from 3-({2-[(1-benzofuran-2-ylsulfonyl)amino]-4-chlorophenyl}thio)-N,N-dimethylpropanamide.

$^1$H NMR (300 MHz, CD$_3$OD) δ 7.59-7.75 (m, 3H), 7.40-7.49 (m, 1H), 7.30-7.41 (m, 1H), 7.20-7.30 (m, 2H), 6.79 (dd, J=1.76, 8.50 Hz, 1H), 3.94 (t, J=7.47 Hz, 2H), 2.87 (s, 3H), 2.81 (s, 3H), 2.59 (t, J=7.47 Hz, 2H).

Compound 122

N-(2-{[(6-amino-1-oxidopyridin-2-yl)methyl]sulfonyl}-5-chlorophenyl)-1-benzofuran-2-sulfonamide

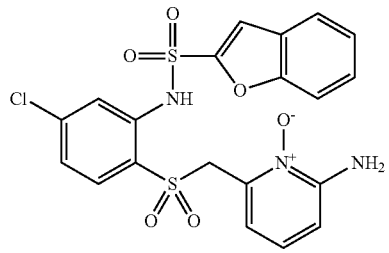 [SMILES: Nc1cccc(CS(=O)(=O)c2ccc(Cl)cc2NS(=O)(=O)c2cc3ccccc3o2)[n+]1[O-]]

Following General Procedure D and E, the title compound was prepared from tert-butyl {6-[({2-[(1-benzofuran-2-ylsulfonyl)amino]-4-chlorophenyl}thio)methyl]pyridin-2-yl}carbamate.

$^1$H NMR (300 MHz, CD$_3$OD) δ 7.77 (d, J=1.76 Hz, 1H), 7.59-7.71 (m, 2H), 7.29-7.44 (m, 3H), 7.20-7.29 (m, 1H), 7.10 (t, J=7.91 Hz, 1H), 6.77-6.88 (m, 2H), 6.57 (d, J=7.33 Hz, 1H), 5.41 (br. s., 2H), 4.57 (br. s., 1H).

General Procedure P

Compound 123

N-(2-{[4-chloro-2-({[4-chloro-3-(trifluoromethyl)phenyl]sulfonyl}amino)phenyl]sulfonyl}ethyl)acetamide

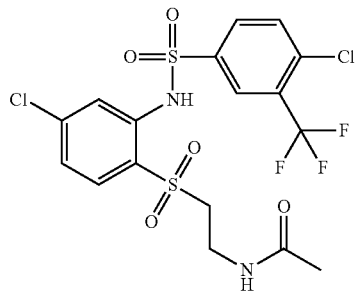 [SMILES: CC(=O)NCCS(=O)(=O)c1ccc(Cl)cc1NS(=O)(=O)c1ccc(Cl)c(C(F)(F)F)c1]

To a solution of N-{2-[(2-aminoethyl)sulfonyl]-5-chlorophenyl}-4-chloro-3-(trifluoromethyl)benzenesulfonamide (23 mg, 0.048 mmol) in CH$_2$Cl$_2$ (2 ml) was added Et$_3$N (14 μl, 0.10 mmol), acetic anhydride (5 μl, 0.053 mmol), and catalytic amount of DMAP. The reaction was stirred at room temperature for 1 h and was concentrated. The crude product was purified by column chromatography on silica gel (0→10% MeOH in ethyl acetate), followed by PTLC (10% MeOH in ethyl acetate) to give the title compound.

$^1$H NMR (600 MHz, CD$_3$OD) δ 8.29 (d, J=2.05 Hz, 1H), 8.13 (dd, J=2.05, 8.51 Hz, 1H), 7.65-7.75 (m, 2H), 7.51 (d, J=2.05 Hz, 1H), 6.82 (dd, J=2.05, 8.51 Hz, 1H), 3.75 (t, J=6.60 Hz, 2H), 3.51 (t, J=6.60 Hz, 2H), 1.86 (s, 3H).

Compound 124

N-(2-{[4-chloro-2-({[4-chloro-3-(trifluoromethyl)phenyl]sulfonyl}amino)phenyl]sulfinyl}ethyl)acetamide

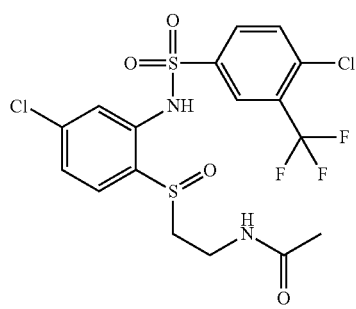 [SMILES: CC(=O)NCCS(=O)c1ccc(Cl)cc1NS(=O)(=O)c1ccc(Cl)c(C(F)(F)F)c1]

Following General Procedure P and C, the title compound was prepared from N-{2-[(2-aminoethyl)thio]-5-chlorophenyl}-4-chloro-3-(trifluoromethyl)benzenesulfonamide.

$^1$H NMR (600 MHz, CD$_3$OD) δ 8.12 (s, 1H), 8.01 (dd, J=1.91, 8.36 Hz, 1H), 7.77 (d, J=8.51 Hz, 1H), 7.56 (d, J=8.22 Hz, 1H), 7.17 (s, 1H), 7.13 (d, J=7.63 Hz, 1H), 3.60-3.71 (m, 1H), 3.44-3.54 (m, 1H), 3.33-3.42 (m, 1H), 3.04-3.15 (m, 1H), 1.98 (s, 3H).

Intermediate 36

4-Chloro-N,N-dimethyl-butyramide

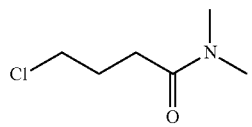

To a solution of 4-chloro-butyryl chloride (1.12 ml, 10.0 mmol) and dimethyl-amine hydrochloride (4.1 g, 50.0 mmol) in THF at 5° C. was added 2M NaOH (30 ml, 60.0 mmol) dropwise over 30 minutes while maintaining reaction temperature between 5-10° C. The reaction was stirred for additional 1.5 h and was concentrated, extracted with EtOAc (×2). The combined organic layer was washed with 1M HCl (×2), brine, dried over Na$_2$SO$_4$, and concentrated in vacuo to yield the title compound as colorless oil (1.5 g, ˜100%). The crude was used without further purification.

Compound 125

4-({2-[(1-benzofuran-2-ylsulfonyl)amino]-4-chlorophenyl}sulfinyl)-N,N-dimethylbutanamide

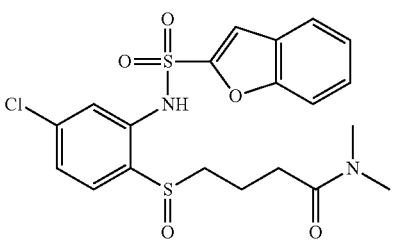 [SMILES: CN(C)C(=O)CCCS(=O)c1ccc(Cl)cc1NS(=O)(=O)c1cc2ccccc2o1]

Following General Procedure G and C, the title compound was prepared from N,N'-[dithiobis(5-chloro-2,1-phenylene)]bis(1-benzofuran-2-sulfonamide) Intermediate 8 and 4-chloro-N,N-dimethyl-butyramide.

$^{1}$H NMR (300 MHz, CD$_{3}$OD) δ 7.68 (d, J=7.62 Hz, 1H), 7.53 (d, J=2.05 Hz, 1H), 7.35-7.49 (m, 3H), 7.32 (d, J=0.88 Hz, 1H), 7.25-7.32 (m, 1H), 6.95 (dd, J=2.05, 8.20 Hz, 1H), 3.33-3.49 (m, 1H), 2.98 (s, 3H), 2.91-3.08 (m, 1H), 2.90 (s, 3H), 2.38-2.57 (m, 2H), 1.92-2.09 (m, 2H).

Compound 126

4-({2-[(1-benzofuran-2-ylsulfonyl)amino]-4-chlorophenyl}sulfonyl)-N,N-dimethylbutanamide

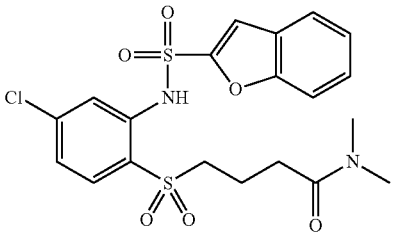 [SMILES: CN(C)C(=O)CCCS(=O)(=O)c1ccc(Cl)cc1NS(=O)(=O)c1cc2ccccc2o1]

Following General Procedure G and D, the title compound was prepared from N,N'-[dithiobis(5-chloro-2,1-phenylene)]bis(1-benzofuran-2-sulfonamide) Intermediate 8 and 4-chloro-N,N-dimethyl-butyramide.

$^{1}$H NMR (600 MHz, CD$_{3}$OD) δ 7.76 (s, 1H), 7.74 (d, J=8.51 Hz, 1H), 7.70 (d, J=7.92 Hz, 1H), 7.38-7.48 (m, 3H), 7.31 (t, J=7.34 Hz, 1H), 6.86-7.05 (m, 1H), 3.46-3.69 (m, 2H), 2.97 (s, 3H), 2.91 (s, 3H), 2.43-2.59 (m, 2H), 1.93-2.09 (m, 2H).

Compound 127

5-chloro-N-[5-chloro-2-(methylsulfinyl)phenyl]-1-benzofuran-2-sulfonamide

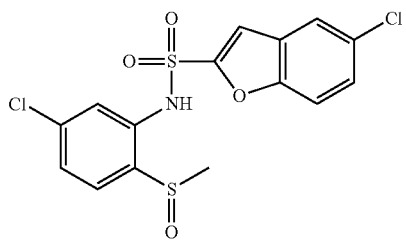 [SMILES: CS(=O)c1ccc(Cl)cc1NS(=O)(=O)c1cc2cc(Cl)ccc2o1]

Following General Procedure B and C, the title compound was prepared from 5-chloro-2-(methylthio)aniline and 5-chloro-benzofuran-2-sulfonyl chloride (CAS #: 128852-02-8) (Bioorganic & Medicinal Chemistry 13 (2005) 3927-3954).

$^{1}$H NMR (300 MHz, CDCl$_{3}$) δ 11.00 (br. s., 1H), 7.80 (d, J=1.47 Hz, 1H), 7.68 (d, J=1.76 Hz, 1H), 7.40-7.54 (m, 3H), 7.05-7.16 (m, 2H), 2.91 (s, 3H).

Compound 128

5-chloro-N-[5-chloro-2-(methylsulfonyl)phenyl]-1-benzofuran-2-sulfonamide

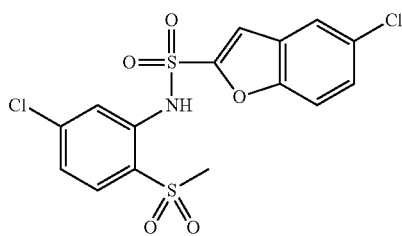 [SMILES: CS(=O)(=O)c1ccc(Cl)cc1NS(=O)(=O)c1cc2cc(Cl)ccc2o1]

Following General Procedure B and D, the title compound was prepared from 5-chloro-2-(methylthio)aniline and 5-chloro-benzofuran-2-sulfonyl chloride (CAS #: 128852-02-8) (Bioorganic & Medicinal Chemistry 13 (2005) 3927-3954).

$^{1}$H NMR (600 MHz, CD$_{3}$OD) δ 7.74 (s, 1H), 7.74 (d, J=5.58 Hz, 1H), 7.64 (d, J=1.76 Hz, 1H), 7.43 (d, J=8.80 Hz, 1H), 7.30-7.35 (m, 2H), 6.88 (dd, J=2.05, 8.51 Hz, 1H), 3.33 (s, 3H).

Compound 129

N-{5-chloro-2-[(1H-pyrazol-3-ylmethyl)sulfinyl]phenyl}-1-benzofuran-2-sulfonamide

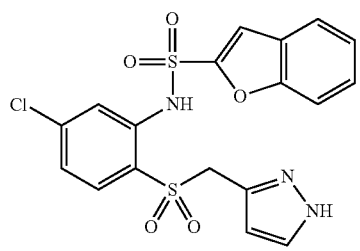 [SMILES: O=S(=O)(Cc1cc[nH]n1)c1ccc(Cl)cc1NS(=O)(=O)c1cc2ccccc2o1]

Following General Procedure C and E, the title compound was prepared from tert-butyl 3-[({2-[(1-benzofuran-2-ylsulfonyl)amino]-4-chlorophenyl}thio)methyl]-1H-pyrazole-1-carboxylate (Compound 22).

¹H NMR (600 MHz, CD₃OD) δ 7.67 (d, J=7.63 Hz, 1H), 7.42-7.47 (m, 2H), 7.41 (d, J=2.05 Hz, 1H), 7.37 (td, J=1.47, 7.78 Hz, 1H), 7.32 (d, J=0.88 Hz, 1H), 7.28 (td, J=0.88, 7.48 Hz, 1H), 7.22 (d, J=8.51 Hz, 1H), 6.96 (dd, J=1.76, 8.51 Hz, 1H), 5.92 (s, 1H), 4.56 (d, J=13.50 Hz, 1H), 4.28 (d, J=13.50 Hz, 1H).

Compound 130

N-[5-chloro-2-(methylsulfinyl)phenyl]-4-isopropyl-benzenesulfonamide

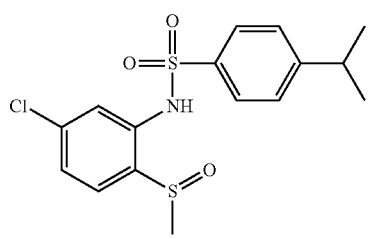 [SMILES: CC(C)c1ccc(S(=O)(=O)Nc2cc(Cl)ccc2S(C)=O)cc1]

Following General Procedure B and C, the title compound was prepared from 5-chloro-2-(methylthio)aniline and 4-isopropyl-benzenesulfonyl chloride.

¹H NMR (600 MHz, CHLOROFORM-d) δ 10.42 (br. s., 1H), 7.80-7.86 (m, 2H), 7.68 (s, 1H), 7.35 (s, 2H), 7.05-7.08 (m, 1H), 7.01-7.03 (m, 1H), 2.94 (spt, J=6.90 Hz, 1H), 2.69 (s, 3H), 1.22 (d, J=7.04 Hz, 6H).

Compound 131

4-bromo-N-[5-chloro-2-(methylthio)phenyl]benzenesulfonamide

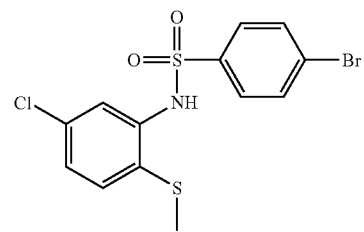 [SMILES: CSc1ccc(Cl)cc1NS(=O)(=O)c1ccc(Br)cc1]

Following General Procedure B, the title compound was prepared from 5-chloro-2-(methylthio)aniline and 4-bromo-benzenesulfonyl chloride.

¹H NMR (600 MHz, CHLOROFORM-d) δ 7.65-7.68 (m, 2H), 7.61-7.63 (m, 2H), 7.58-7.60 (m, 2H), 7.29 (d, J=8.22 Hz, 1H), 7.04 (dd, J=2.20, 8.36 Hz, 1H), 2.17 (s, 3H).

Compound 132

N-[5-chloro-2-(methylthio)phenyl]-4-iodobenzenesulfonamide

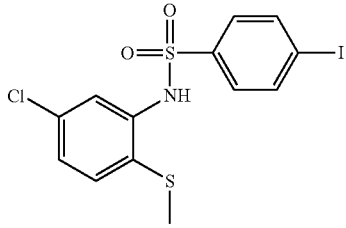 [SMILES: CSc1ccc(Cl)cc1NS(=O)(=O)c1ccc(I)cc1]

Following General Procedure B, the title compound was prepared from 5-chloro-2-(methylthio)aniline and 4-iodo-benzenesulfonyl chloride.

¹H NMR (600 MHz, CHLOROFORM-d) δ 7.80 (d, J=8.80 Hz, 2H), 7.62-7.64 (m, 1H), 7.61 (d, J=2.05 Hz, 1H), 7.49-7.53 (m, 2H), 7.30 (d, J=8.22 Hz, 1H), 7.04 (dd, J=2.20, 8.36 Hz, 1H), 2.17 (s, 3H).

Compound 133

4-bromo-N-[5-chloro-2-(methylsulfinyl)phenyl]benzenesulfonamide

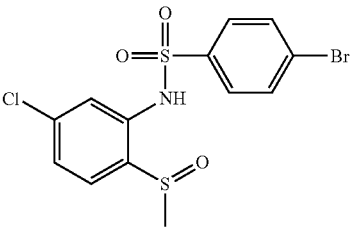 [SMILES: CS(=O)c1ccc(Cl)cc1NS(=O)(=O)c1ccc(Br)cc1]

Following General Procedure C, the title compound was prepared from 4-bromo-N-[5-chloro-2-(methylthio)phenyl]benzenesulfonamide.

¹H NMR (600 MHz, CHLOROFORM-d) δ 10.63-10.77 (m, 1H), 7.79-7.82 (m, 2H), 7.64-7.68 (m, 3H), 7.05 (dd, J=1.17, 2.35 Hz, 2H), 2.79 (s, 3H).

Compound 134

N-[5-chloro-2-(methylsulfinyl)phenyl]-4-iodobenzenesulfonamide

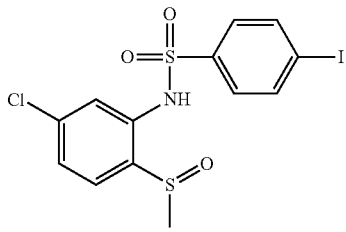 [SMILES: CS(=O)c1ccc(Cl)cc1NS(=O)(=O)c1ccc(I)cc1]

Following General Procedure C, the title compound was prepared from N-[5-chloro-2-(methylthio)phenyl]-4-iodobenzenesulfonamide.

¹H NMR (600 MHz, CHLOROFORM-d) δ 10.69 (br. s., 1H), 7.83-7.91 (m, 2H), 7.61-7.69 (m, 3H), 7.01-7.08 (m, 2H), 2.79 (s, 3H).

Compound 135

4-bromo-N-[5-chloro-2-(methylsulfonyl)phenyl]benzenesulfonamide

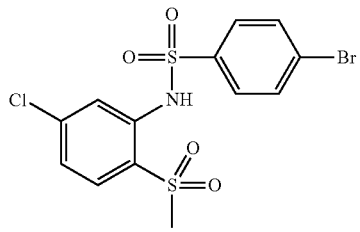 [SMILES: CS(=O)(=O)c1ccc(Cl)cc1NS(=O)(=O)c1ccc(Br)cc1]

Following General Procedure D, the title compound was prepared from 4-bromo-N-[5-chloro-2-(methylthio)phenyl]benzenesulfonamide.
¹H NMR (600 MHz, CHLOROFORM-d) δ 9.20-9.27 (m, 1H), 7.80 (dd, J=1.32, 8.36 Hz, 2H), 7.76 (d, J=8.51 Hz, 1H), 7.68 (dd, J=1.47, 8.80 Hz, 2H), 7.25 (d, J=1.47 Hz, 1H), 7.18-7.21 (m, 1H), 2.93 (d, J=1.47 Hz, 3H).

Compound 136

N-[5-chloro-2-(methylsulfonyl)phenyl]-4-iodobenzenesulfonamide

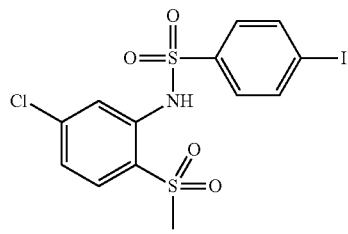 [SMILES: CS(=O)(=O)c1ccc(Cl)cc1NS(=O)(=O)c1ccc(I)cc1]

Following General Procedure D, the title compound was prepared from N-[5-chloro-2-(methylthio)phenyl]-4-iodobenzenesulfonamide.
¹H NMR (600 MHz, CHLOROFORM-d) δ 9.17-9.25 (m, 1H), 7.90 (d, J=8.51 Hz, 2H), 7.76 (d, J=8.51 Hz, 1H), 7.67 (d, J=1.76 Hz, 1H), 7.64 (d, J=8.51 Hz, 2H), 7.19 (dd, J=1.76, 8.51 Hz, 1H), 2.93 (s, 3H).

Compound 137

N-{5-chloro-2-[(pyridin-2-ylmethyl)thio]phenyl}-1-benzofuran-2-sulfonamide

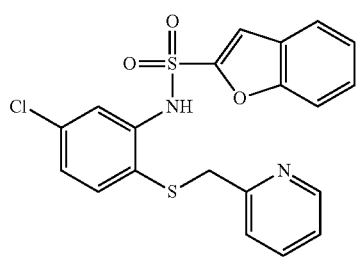 [SMILES: O=S(=O)(Nc1cc(Cl)ccc1SCc1ccccn1)c1cc2ccccc2o1]

Following General Procedure A and B, the title compound was prepared from 2-amino-4-chloro-benzenethiol, 2-bromomethyl-pyridine hydrobromide, and benzofuran-2-sulfonyl chloride.

¹H NMR (600 MHz, CHLOROFORM-d) δ 12.32 (br. s, 1H), 8.87 (dt, J=0.77, 4.92 Hz, 1H), 7.76 (d, J=2.05 Hz, 1H), 7.58-7.65 (m, 2H), 7.44 (dd, J=0.88, 8.22 Hz, 1H), 7.34-7.42 (m, 3H), 7.25-7.30 (m, 2H), 7.06 (d, J=7.63 Hz, 1H), 6.96-7.01 (m, 1H), 3.98 (s, 2H).

Compound 138

N-{5-chloro-2-[(pyridin-3-ylmethyl)thio]phenyl}-1-benzofuran-2-sulfonamide

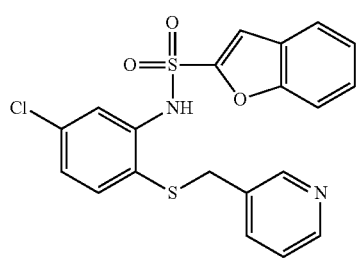 [SMILES: O=S(=O)(Nc1cc(Cl)ccc1SCc1cccnc1)c1cc2ccccc2o1]

Following General Procedure A and B, the title compound was prepared from 2-amino-4-chloro-benzenethiol, 3-bromomethyl-pyridine hydrobromide, and benzofuran-2-sulfonyl chloride.

¹H NMR (600 MHz, CHLOROFORM-d) δ 8.42 (dd, J=1.61, 4.84 Hz, 1H), 8.12 (d, J=1.76 Hz, 2H), 7.66-7.70 (m, 2H), 7.50 (d, J=1.17 Hz, 1H), 7.46-7.49 (m, 1H), 7.42-7.46 (m, 1H), 7.33 (ddd, J=1.17, 6.97, 8.00 Hz, 1H), 7.26-7.29 (m, 1H), 7.13 (ddd, J=0.88, 4.70, 7.92 Hz, 1H), 7.00 (d, J=8.51 Hz, 1H), 6.89 (dd, J=2.20, 8.36 Hz, 1H), 3.75 (s, 2H).

Compound 139

N-{5-chloro-2-[(pyridin-3-ylmethyl)sulfinyl]phenyl}-1-benzofuran-2-sulfonamide

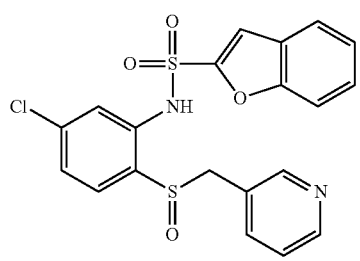 [SMILES: O=S(Cc1cccnc1)c1ccc(Cl)cc1NS(=O)(=O)c1cc2ccccc2o1]

Following General Procedure C, the title compound was prepared from N-{5-chloro-2-[(pyridin-3-ylmethyl)thio]phenyl}-1-benzofuran-2-sulfonamide.

¹H NMR (600 MHz, METHANOL-d₄) δ 8.28 (d, J=4.11 Hz, 1H), 7.86 (br. s., 1H), 7.68-7.71 (m, J=0.73, 1.32 Hz, 1H), 7.54 (d, J=1.76 Hz, 1H), 7.36-7.41 (m, 2H), 7.31-7.35 (m, 1H), 7.25-7.29 (m, J=1.03, 7.78 Hz, 1H), 7.24 (d, J=7.92 Hz,

1H), 7.12 (dd, J=4.99, 7.63 Hz, 1H), 6.73 (d, J=8.51 Hz, 1H), 6.68 (dd, J=2.05, 8.51 Hz, 1H), 4.55 (s, 2H).

Compound 140

N-(5-chloro-2-{[(1-oxidopyridin-3-yl)methyl]sulfinyl}phenyl)-1-benzofuran-2-sulfonamide

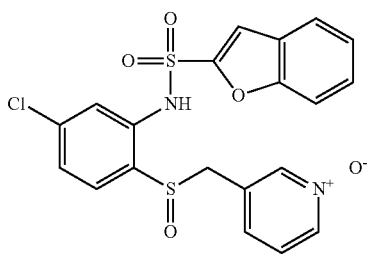

Following General Procedure C, the title compound was prepared from N-{5-chloro-2-[(pyridin-3-ylmethyl)thio]phenyl}-1-benzofuran-2-sulfonamide.

$^1$H NMR (600 MHz, METHANOL-$d_4$) δ 8.10-8.14 (m, 1H), 8.01 (t, J=1.47 Hz, 1H), 7.66-7.68 (m, 1H), 7.42-7.49 (m, 2H), 7.34 (ddd, J=1.17, 7.12, 8.44 Hz, 1H), 7.23-7.29 (m, 2H), 7.14 (dd, J=6.60, 7.78 Hz, 1H), 6.87 (d, J=7.92 Hz, 1H), 6.83 (d, J=8.22 Hz, 1H), 6.71 (dd, J=2.05, 8.22 Hz, 1H), 4.63 (d, J=13.21 Hz, 1H), 4.37 (d, J=13.21 Hz, 1H).

Compound 141

N-{5-chloro-2-[(pyridin-3-ylmethyl)sulfonyl]phenyl}-1-benzofuran-2-sulfonamide

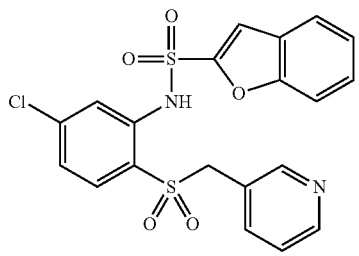 [SMILES: O=S(=O)(Cc1cccnc1)c1ccc(Cl)cc1NS(=O)(=O)c1cc2ccccc2o1]

Following General Procedure D, the title compound was prepared from N-{5-chloro-2-[(pyridin-3-ylmethyl)thio]phenyl}-1-benzofuran-2-sulfonamide.

$^1$H NMR (600 MHz, METHANOL-$d_4$) δ 8.27 (d, J=4.11 Hz, 1H), 8.04 (br. s., 1H), 7.78 (t, J=1.76 Hz, 1H), 7.65 (d, J=7.92 Hz, 1H), 7.46 (d, J=0.88 Hz, 1H), 7.31-7.37 (m, 2H), 7.27-7.31 (m, 1H), 7.21-7.26 (m, 2H), 7.06 (dd, J=5.14, 7.48 Hz, 1H), 6.67 (dt, J=1.76, 8.51 Hz, 1H), 4.98 (s, 2H).

Compound 142

N-(5-chloro-2-{[(1-oxidopyridin-3-yl)methyl]sulfonyl}phenyl)-1-benzofuran-2-sulfonamide

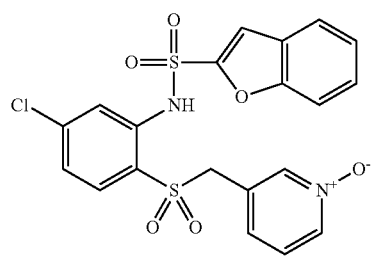 [SMILES: O=S(=O)(Cc1ccc[n+]([O-])c1)c1ccc(Cl)cc1NS(=O)(=O)c1cc2ccccc2o1]

Following General Procedure D, the title compound was prepared from N-{5-chloro-2-[(pyridin-3-ylmethyl)thio]phenyl}-1-benzofuran-2-sulfonamide.

$^1$H NMR (600 MHz, DMSO-$d_6$) δ 8.01-8.08 (m, 2H), 7.68 (d, J=7.92 Hz, 1H), 7.53 (d, J=8.22 Hz, 1H), 7.46-7.48 (m, 1H), 7.31-7.37 (m, 2H), 7.23-7.27 (m, 2H), 7.11-7.15 (m, 1H), 6.98 (d, J=7.92 Hz, 1H), 6.58-6.61 (m, 1H), 5.09 (s, 2H).

Compound 143

N-{5-chloro-2-[(3-nitrobenzyl)thio]phenyl}-1-benzofuran-2-sulfonamide

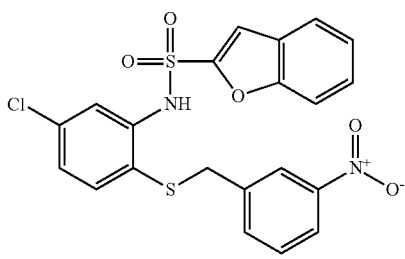 [SMILES: O=[N+]([O-])c1cccc(CSc2ccc(Cl)cc2NS(=O)(=O)c2cc3ccccc3o2)c1]

Following General Procedure G, the title compound was prepared from N,N'-[dithiobis(5-chloro-2,1-phenylene)]bis(1-benzofuran-2-sulfonamide) Intermediate 8 and 1-bromomethyl-3-nitro-benzene.

$^1$H NMR (600 MHz, CHLOROFORM-d) δ 8.08 (s, 1H), 8.02 (ddd, J=1.17, 2.35, 8.22 Hz, 1H), 7.77 (t, J=2.05 Hz, 1H), 7.65-7.69 (m, 2H), 7.50 (d, J=0.88 Hz, 1H), 7.45-7.48 (m, 1H), 7.41-7.45 (m, 1H), 7.30-7.36 (m, 2H), 7.21 (dq, J=0.88, 7.63 Hz, 1H), 7.03 (d, J=8.22 Hz, 1H), 6.89 (dd, J=2.05, 8.22 Hz, 1H), 3.84 (s, 2H).

Compound 144

N-{5-chloro-2-[(3-methoxybenzyl)thio]phenyl}-1-benzofuran-2-sulfonamide

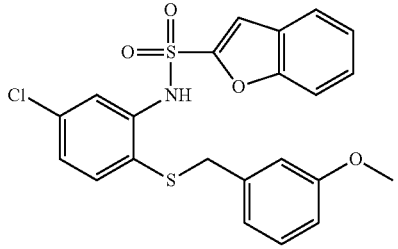 [SMILES: COc1cccc(CSc2ccc(Cl)cc2NS(=O)(=O)c2cc3ccccc3o2)c1]

Following General Procedure G, the title compound was prepared from N,N'-[dithiobis(5-chloro-2,1-phenylene)]bis(1-benzofuran-2-sulfonamide) Intermediate 8 and 1-bromomethyl-3-methoxy-benzene.

¹H NMR (600 MHz, CHLOROFORM-d) δ 8.11 (s, 1H), 7.64-7.68 (m, 2H), 7.40-7.50 (m, 3H), 7.31 (ddd, J=0.88, 7.04, 7.92 Hz, 1H), 7.07-7.13 (m, 2H), 6.90 (dd, J=2.05, 8.22 Hz, 1H), 6.73 (ddd, J=1.17, 2.49, 8.36 Hz, 1H), 6.53-6.56 (m, 1H), 6.48 (t, J=2.35 Hz, 1H), 3.74 (s, 2H), 3.66 (s, 3H).

Compound 145

N-{5-chloro-2-[(pyridin-2-ylmethyl)sulfinyl]phenyl}-1-benzofuran-2-sulfonamide

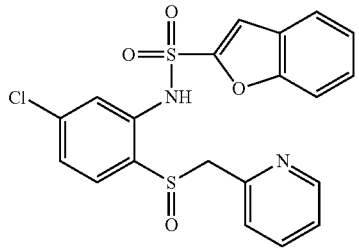

Following General Procedure C, the title compound was prepared from N-{5-chloro-2-[(pyridin-2-ylmethyl)thio]phenyl}-1-benzofuran-2-sulfonamide.

¹H NMR (600 MHz, METHANOL-d₄) δ 8.46 (d, J=4.70 Hz, 1H), 7.64-7.73 (m, 2H), 7.48 (d, J=8.51 Hz, 1H), 7.38-7.45 (m, 3H), 7.25-7.34 (m, 3H), 7.07-7.17 (m, 2H), 4.58 (d, J=12.91 Hz, 1H), 4.35 (d, J=12.91 Hz, 1H).

Compound 146

N-{5-chloro-2-[(pyridin-2-ylmethyl)sulfonyl]phenyl}-1-benzofuran-2-sulfonamide

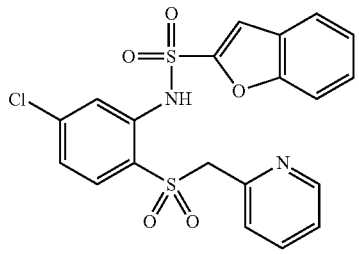 [SMILES: O=S(=O)(Cc1ccccn1)c1ccc(Cl)cc1NS(=O)(=O)c1cc2ccccc2o1]

Following General Procedure D, the title compound was prepared from N-{5-chloro-2-[(pyridin-2-ylmethyl)thio]phenyl}-1-benzofuran-2-sulfonamide.

¹H NMR (600 MHz, METHANOL-d₄) δ 8.42 (dt, J=0.84, 4.77 Hz, 1H), 7.75 (d, J=2.05 Hz, 1H), 7.67 (d, J=7.63 Hz, 1H), 7.41-7.49 (m, 3H), 7.31-7.39 (m, 2H), 7.22-7.29 (m, 2H), 7.07 (d, J=7.63 Hz, 1H), 6.76 (dd, J=1.91, 8.66 Hz, 1H), 5.07 (s, 2H).

Compound 147

N-(5-chloro-2-{[(1-oxidopyridin-2-yl)methyl]sulfonyl}phenyl)-1-benzofuran-2-sulfonamide

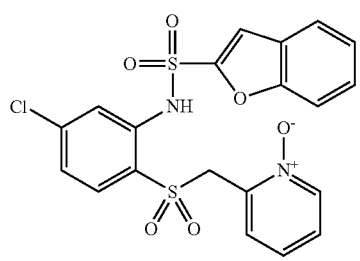 [SMILES: O=S(=O)(Cc1cccc[n+]1[O-])c1ccc(Cl)cc1NS(=O)(=O)c1cc2ccccc2o1]

Following General Procedure D, the title compound was prepared from N-{5-chloro-2-[(pyridin-2-ylmethyl)thio]phenyl}-1-benzofuran-2-sulfonamide ¹H NMR (600 MHz, METHANOL-d₄) δ 8.35 (d, J=6.46 Hz, 1H), 7.74 (d, J=2.05 Hz, 1H), 7.66 (d, J=7.92 Hz, 1H), 7.60 (d, J=8.51 Hz, 1H), 7.38 (s, 2H), 7.34 (d, J=10.56 Hz, 3H), 7.25 (s, 2H), 6.77 (dd, J=1.32, 8.36 Hz, 1H), 5.54 (br. s, 2H).

Compound 148

N-(5-chloro-2-{[(1-oxidopyridin-2-yl)methyl]sulfinyl}phenyl)-1-benzofuran-2-sulfonamide

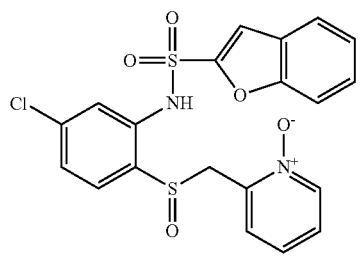 [SMILES: O=S(Cc1cccc[n+]1[O-])c1ccc(Cl)cc1NS(=O)(=O)c1cc2ccccc2o1]

Following General Procedure D, the title compound was prepared from N-{5-chloro-2-[(pyridin-2-ylmethyl)thio]phenyl}-1-benzofuran-2-sulfonamide ¹H NMR (600 MHz, METHANOL-d₄) δ 8.31 (d, J=6.16 Hz, 1H), 7.66 (d, J=7.92 Hz, 1H), 7.46-7.50 (m, 1H), 7.38-7.42 (m, 1H), 7.30-7.38 (m, 2H), 7.28 (s, 3H), 7.19 (d, J=8.51 Hz, 1H), 7.05 (d, J=7.63 Hz, 1H), 6.82 (d, J=8.22 Hz, 1H), 5.14 (d, J=12.62 Hz, 1H), 4.68 (d, J=12.32 Hz, 1H).

Compound 149

N-{2-[(3-aminobenzyl)thio]-5-chlorophenyl}-1-benzofuran-2-sulfonamide

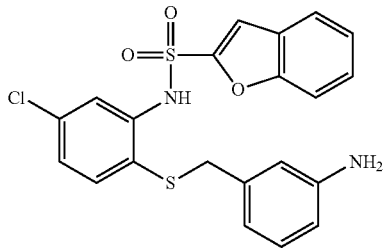

Following General Procedure L, the title compound was prepared from N-{5-chloro-2-[(3-nitrobenzyl)thio]phenyl}-1-benzofuran-2-sulfonamide.

¹H NMR (600 MHz, CHLOROFORM-d) δ 7.64-7.68 (m, 2H), 7.47-7.51 (m, 1H), 7.40-7.46 (m, 2H), 7.29-7.34 (m, 1H), 7.14 (d, J=8.22 Hz, 1H), 6.97 (t, J=7.78 Hz, 1H), 6.92 (dd, J=2.35, 8.22 Hz, 1H), 6.48-6.52 (m, 1H), 6.35 (dd, J=0.59, 7.63 Hz, 1H), 6.28 (t, J=1.91 Hz, 1H), 3.67 (s, 2H).

Compound 150

N-{2-[(3-aminobenzyl)sulfinyl]-5-chlorophenyl}-1-benzofuran-2-sulfonamide

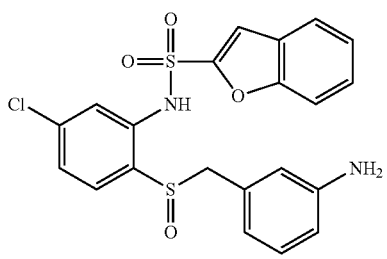

Following General Procedure C and K, the title compound was prepared from N-{5-chloro-2-[(3-nitrobenzyl)thio]phenyl}-1-benzofuran-2-sulfonamide.

¹H NMR (600 MHz, METHANOL-d₄) δ 7.69 (d, J=7.92 Hz, 1H), 7.48 (d, J=8.51 Hz, 1H), 7.37-7.43 (m, 3H), 7.30 (td, J=0.88, 7.48 Hz, 1H), 7.20 (d, J=8.51 Hz, 1H), 7.01 (dd, J=2.05, 8.51 Hz, 1H), 6.95 (t, J=7.78 Hz, 1H), 6.70-6.74 (m, 1H), 6.64 (t, J=1.76 Hz, 1H), 6.45 (d, J=7.63 Hz, 1H), 4.40 (d, J=12.62 Hz, 1H), 4.00 (d, J=12.62 Hz, 1H).

Compound 151

N-{2-[(3-aminobenzyl)sulfonyl]-5-chlorophenyl}-1-benzofuran-2-sulfonamide

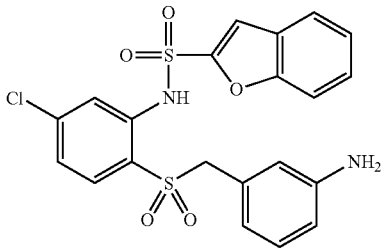 [SMILES: Nc1cccc(CS(=O)(=O)c2ccc(Cl)cc2NS(=O)(=O)c2cc3ccccc3o2)c1]

Following General Procedure D and K, the title compound was prepared from N-{5-chloro-2-[(3-nitrobenzyl)thio]phenyl}-1-benzofuran-2-sulfonamide.

¹H NMR (600 MHz, METHANOL-d₄) δ 7.80 (d, J=2.05 Hz, 1H), 7.69 (d, J=7.63 Hz, 1H), 7.52 (d, J=0.59 Hz, 1H), 7.40 (d, J=8.51 Hz, 1H), 7.35 (td, J=1.32, 7.70 Hz, 1H), 7.31 (d, J=8.51 Hz, 1H), 7.26-7.30 (m, J=7.92 Hz, 1H), 6.78 (dd, J=2.05, 8.51 Hz, 1H), 6.65 (t, J=7.78 Hz, 1H), 6.49 (dd, J=1.91, 7.78 Hz, 1H), 6.33 (t, J=1.76 Hz, 1H), 6.05 (d, J=7.34 Hz, 1H), 4.66 (s, 2H).

Compound 152

N-{5-chloro-2-[(3-hydroxybenzyl)thio]phenyl}-1-benzofuran-2-sulfonamide

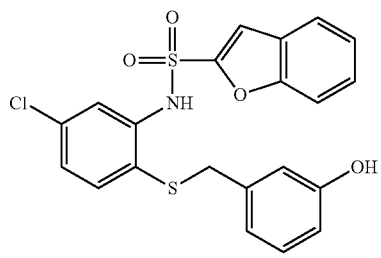 [SMILES: O=S(=O)(Nc1cc(Cl)ccc1SCc1cccc(O)c1)c1cc2ccccc2o1]

To a solution of N-{5-chloro-2-[(3-methoxybenzyl)thio]phenyl}-1-benzofuran-2-sulfonamide (315 mg, 0.69 mmol) in CH₂Cl₂ (5 ml) at room temperature was added BBr₃ (1M solution in CH₂Cl₂, 2.1 ml, 2.1 mmol) and the reaction was stirred for 2 h, diluted with EtOAc, washed with brine, dried over Na₂SO₄, concentrated in vacuo. The crude product was purified by column chromatography on silica gel (25% ethyl acetate in hexane) to give the title compound (196 mg, 64%).

¹H NMR (600 MHz, CHLOROFORM-d) δ 8.10 (br. s., 1H), 7.63-7.69 (m, 2H), 7.41-7.51 (m, 3H), 7.32 (td, J=0.88, 7.48 Hz, 1H), 7.12 (d, J=8.22 Hz, 1H), 7.05 (t, J=7.92 Hz, 1H), 6.91 (dd, J=2.35, 8.22 Hz, 1H), 6.66 (ddd, J=0.73, 2.57, 8.14 Hz, 1H), 6.51 (d, J=7.92 Hz, 1H), 6.45-6.48 (m, 1H), 5.07 (br. s., 1H), 3.71 (s, 2H).

Compound 153

N-{5-chloro-2-[(3-hydroxybenzyl)sulfinyl]phenyl}-1-benzofuran-2-sulfonamide

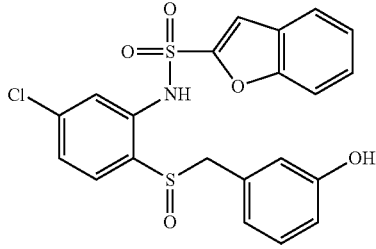 [SMILES: O=S(Cc1cccc(O)c1)c1ccc(Cl)cc1NS(=O)(=O)c1cc2ccccc2o1]

Following General Procedure C, the title compound was prepared from N-{5-chloro-2-[(3-hydroxybenzyl)thio]phenyl}-1-benzofuran-2-sulfonamide $^1$H NMR (600 MHz, CHLOROFORM-d) δ 10.27-11.14 (m, 1H), 7.73 (d, J=2.05 Hz, 1H), 7.67 (d, J=7.92 Hz, 1H), 7.53 (s, 1H), 7.43-7.47 (m, 1H), 7.38-7.42 (m, 1H), 7.28-7.33 (m, 1H), 7.04 (t, J=7.92 Hz, 1H), 6.92 (dd, J=1.47, 8.22 Hz, 1H), 6.79 (d, J=8.22 Hz, 1H), 6.74 (dd, J=2.05, 8.22 Hz, 1H), 6.59 (s, 1H), 6.40 (d, J=7.34 Hz, 1H), 4.33 (d, J=12.32 Hz, 1H), 4.16 (d, J=12.62 Hz, 1H).

Compound 154

N-{5-chloro-2-[(3-hydroxybenzyl)sulfonyl]phenyl}-1-benzofuran-2-sulfonamide

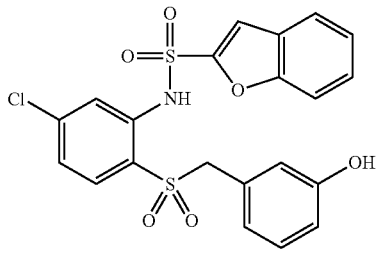 [SMILES: O=S(=O)(Cc1cccc(O)c1)c1ccc(Cl)cc1NS(=O)(=O)c1cc2ccccc2o1]

Following General Procedure D, the title compound was prepared from N-{5-chloro-2-[(3-hydroxybenzyl)thio]phenyl}-1-benzofuran-2-sulfonamide $^1$H NMR (600 MHz, CHLOROFORM-d) δ 7.76 (br. s., 1H), 7.65-7.72 (m, 1H), 7.56 (br. s., 1H), 7.44 (br. s., 3H), 7.33 (s, 1H), 7.02 (br. s., 2H), 6.77 (br. s., 1H), 6.58 (br. s., 1H), 6.39-6.47 (m, 1H), 4.28 (br. s., 2H).

Intermediate 37 benzofuran-2-sulfonic acid (5-chloro-2-mercapto-phenyl)-amide

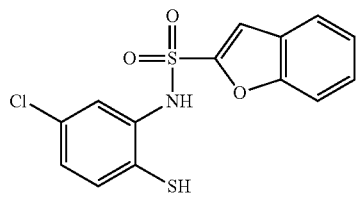 [SMILES: O=S(=O)(Nc1cc(Cl)ccc1S)c1cc2ccccc2o1]

Following General Procedure N, the title compound was prepared from N,N'-[dithiobis(5-chloro-2,1-phenylene)]bis(1-benzofuran-2-sulfonamide) Intermediate 8 and was used without further purification.

Compound 155

N-{5-chloro-2-[(trifluoromethyl)thio]phenyl}-1-benzofuran-2-sulfonamide

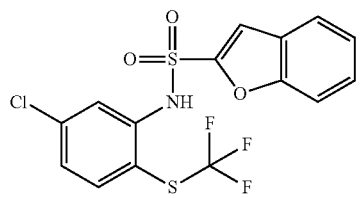 [SMILES: O=S(=O)(Nc1cc(Cl)ccc1SC(F)(F)F)c1cc2ccccc2o1]

To a solution of benzofuran-2-sulfonic acid (5-chloro-2-mercapto-phenyl)-amide (332 mg, 0.98 mmol) in CH$_2$Cl$_2$ (10 ml) at −78° C. was added 3,3-dimethyl-1-(trifluoromethyl)-1,2-benziodoxole (CAS #: 887144-97-0, 354 mg, 1.07 mmol) and the reaction was stirred for 1 h, and was concentrated in vacuo. The crude product was purified by column chromatography on silica gel (CH$_2$Cl$_2$) to give the title compound (375 mg, 94%).

$^1$H NMR (600 MHz, CHLOROFORM-d) δ 7.88 (s, 1H), 7.82 (d, J=2.05 Hz, 1H), 7.67 (dd, J=0.59, 7.92 Hz, 1H), 7.49-7.54 (m, 3H), 7.44-7.49 (m, 1H), 7.33 (td, J=1.03, 7.56 Hz, 1H), 7.11 (dd, J=2.20, 8.36 Hz, 1H).

Compound 156

N-{5-chloro-2-[(trifluoromethyl)sulfonyl]phenyl}-1-benzofuran-2-sulfonamide

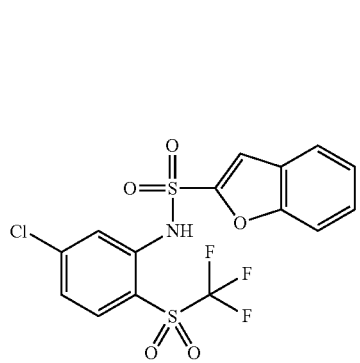 [SMILES: O=S(=O)(Nc1cc(Cl)ccc1S(=O)(=O)C(F)(F)F)c1cc2ccccc2o1]

Following General Procedure D using 10 equivalents of mCPBA in refluxing CH$_2$Cl$_2$, the title compound was prepared from N-{5-chloro-2-[(trifluoromethyl)thio]phenyl}-1-benzofuran-2-sulfonamide.

$^1$H NMR (600 MHz, acetone-d6) δ 7.90 (d, J=2.05 Hz, 1H), 7.78 (d, J=8.80 Hz, 1H), 7.71 (d, J=7.92 Hz, 1H), 7.51 (d, J=8.22 Hz, 1H), 7.36-7.43 (m, 2H), 7.29 (t, J=7.48 Hz, 1H), 6.92 (d, J=6.46 Hz, 1H).

Compound 157

N-{5-chloro-2-[(trifluoromethyl)sulfinyl]phenyl}-1-benzofuran-2-sulfonamide

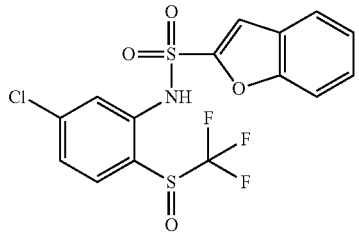 [SMILES: O=S(c1ccc(Cl)cc1NS(=O)(=O)c1cc2ccccc2o1)C(F)(F)F]

Following General Procedure D using 10 equivalents of mCPBA in refluxing CH$_2$Cl$_2$, the title compound was prepared from N-{5-chloro-2-[(trifluoromethyl)thio]phenyl}-1-benzofuran-2-sulfonamide.

$^1$H NMR (600 MHz, acetone-d6) δ 10.00 (br. s., 1H), 7.89 (d, J=8.22 Hz, 1H), 7.78-7.81 (m, 1H), 7.63-7.66 (m, 1H), 7.50-7.59 (m, 4H), 7.39 (ddd, J=0.88, 7.26, 8.00 Hz, 1H).

Compound 158

N-{2-[(3-aminobenzyl)thio]-5-chlorophenyl}-2,4-difluorobenzenesulfonamide

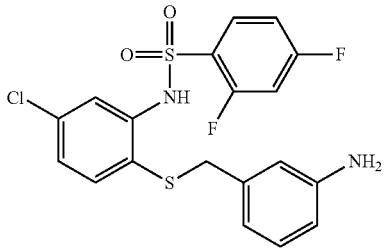

Following General Procedure A, B, and K, the title compound was prepared from 2-amino-4-chloro-benzenethiol, 1-bromomethyl-3-nitro-benzene, and 2,4-difluoro-benzenesulfonyl chloride.

$^1$H NMR (600 MHz, CHLOROFORM-d) δ 7.92 (td, J=6.16, 8.51 Hz, 1H), 7.47 (d, J=2.35 Hz, 1H), 7.19 (d, J=8.22 Hz, 1H), 7.01-7.06 (m, 1H), 6.95-7.01 (m, 1H), 6.88-6.94 (m, 2H), 6.57 (dd, J=1.47, 8.80 Hz, 1H), 6.40-6.45 (m, 2H), 3.72 (s, 2H).

Compound 159

N-{2-[(3-aminobenzyl)sulfonyl]-5-chlorophenyl}-2,4-difluorobenzenesulfonamide

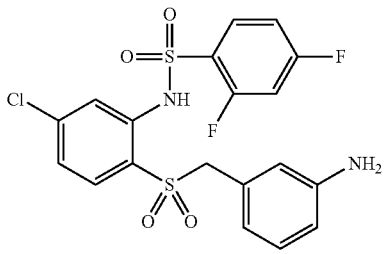 [SMILES: Nc1cccc(CS(=O)(=O)c2ccc(Cl)cc2NS(=O)(=O)c2ccc(F)cc2F)c1]

Following General Procedure A, B, D, and K, the title compound was prepared from 2-amino-4-chloro-benzenethiol, 1-bromomethyl-3-nitro-benzene, and 2,4-difluoro-benzenesulfonyl chloride.

$^1$H NMR (600 MHz, METHANOL-d$_4$) δ 8.05 (td, J=6.16, 8.51 Hz, 1H), 7.48-7.54 (m, 2H), 7.14-7.25 (m, 2H), 7.09 (dd, J=2.05, 8.51 Hz, 1H), 6.96 (t, J=7.78 Hz, 1H), 6.66-6.71 (m, 1H), 6.54 (t, J=1.91 Hz, 1H), 6.34 (d, J=7.63 Hz, 1H), 4.44 (s, 2H).

Compound 160

N-{2-[(3-aminobenzyl)sulfonyl]-5-chlorophenyl}-4-chloro-2-fluorobenzenesulfonamide

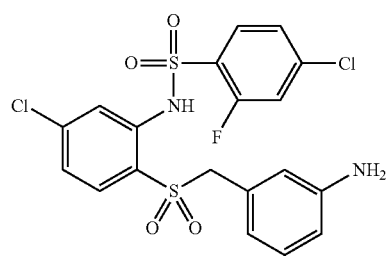 [SMILES: Nc1cccc(CS(=O)(=O)c2ccc(Cl)cc2NS(=O)(=O)c2ccc(Cl)cc2F)c1]

Following General Procedure A, B, D, and K, the title compound was prepared from 2-amino-4-chloro-benzenethiol, 1-bromomethyl-3-nitro-benzene, and 4-chloro-2-fluoro-benzenesulfonyl chloride.

$^1$H NMR (600 MHz, METHANOL-d$_4$) δ 7.97 (t, J=8.51 Hz, 1H), 7.54 (d, J=8.51 Hz, 1H), 7.43-7.52 (m, 3H), 7.13-7.17 (m, 1H), 6.98 (t, J=7.78 Hz, 1H), 6.67-6.72 (m, 1H), 6.53 (s, 1H), 6.33 (d, J=7.63 Hz, 1H), 4.42 (s, 2H).

Compound 161

N-{2-[(3-aminobenzyl)sulfinyl]-5-chlorophenyl}-4-chloro-2-fluorobenzenesulfonamide

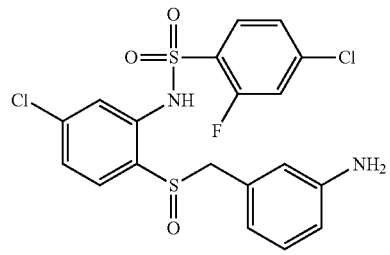 [SMILES: Nc1cccc(CS(=O)c2ccc(Cl)cc2NS(=O)(=O)c2ccc(Cl)cc2F)c1]

Following General Procedure A, B, C, and K, the title compound was prepared from 2-amino-4-chloro-benzenethiol, 1-bromomethyl-3-nitro-benzene, and 4-chloro-2-fluoro-benzenesulfonyl chloride.

¹H NMR (600 MHz, METHANOL-d₄) δ 7.85 (t, J=8.07 Hz, 1H), 7.49 (dd, J=1.76, 9.98 Hz, 1H), 7.40 (dd, J=1.91, 8.36 Hz, 1H), 7.33 (d, J=8.22 Hz, 1H), 7.23 (dd, J=1.91, 8.36 Hz, 1H), 7.16 (d, J=2.05 Hz, 1H), 7.04 (t, J=7.78 Hz, 1H), 6.72-6.75 (m, 1H), 6.63 (t, J=1.91 Hz, 1H), 6.50 (d, J=7.34 Hz, 1H), 4.30 (d, J=12.91 Hz, 1H), 4.04 (d, J=12.62 Hz, 1H).

Compound 162

N-{2-[(3-aminobenzyl)thio]-5-chlorophenyl}benzenesulfonamide

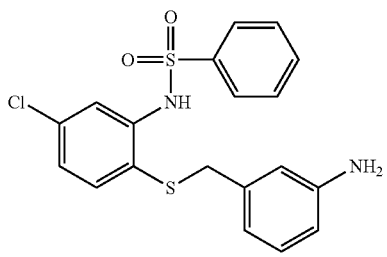 [SMILES: Nc1cccc(CSc2ccc(Cl)cc2NS(=O)(=O)c2ccccc2)c1]

Following General Procedure A, B, and K, the title compound was prepared from 2-amino-4-chloro-benzenethiol, 1-bromomethyl-3-nitro-benzene, and benzenesulfonyl chloride.

¹H NMR (600 MHz, METHANOL-d₄) δ 7.75-7.79 (m, 2H), 7.57-7.62 (m, 1H), 7.48-7.53 (m, 2H), 7.44 (d, J=2.05 Hz, 1H), 7.14 (d, J=8.22 Hz, 1H), 6.99 (dd, J=2.35, 8.22 Hz, 1H), 6.95 (t, J=7.78 Hz, 1H), 6.56-6.60 (m, 1H), 6.45 (t, J=1.91 Hz, 1H), 6.35 (d, J=7.34 Hz, 1H), 3.58 (s, 2H).

Compound 163

N-{2-[(3-aminobenzyl)thio]-5-chlorophenyl}-4-chlorobenzenesulfonamide

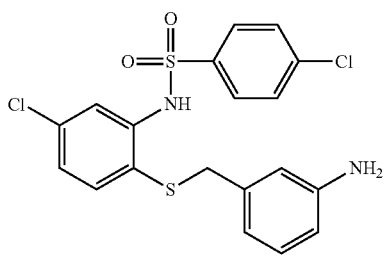 [SMILES: Nc1cccc(CSc2ccc(Cl)cc2NS(=O)(=O)c2ccc(Cl)cc2)c1]

Following General Procedure A, B, and K, the title compound was prepared from 2-amino-4-chloro-benzenethiol, 1-bromomethyl-3-nitro-benzene, and 4-chloro-benzenesulfonyl chloride.

¹H NMR (600 MHz, CHLOROFORM-d) δ 7.69-7.72 (m, 2H), 7.54 (d, J=2.35 Hz, 1H), 7.40-7.44 (m, 2H), 7.17 (d, J=8.22 Hz, 1H), 7.03 (t, J=7.78 Hz, 1H), 6.95 (dd, J=2.20, 8.36 Hz, 1H), 6.58 (dd, J=1.76, 7.92 Hz, 1H), 6.34-6.39 (m, 2H), 3.61 (s, 2H).

Compound 164

N-{2-[(3-aminobenzyl)thio]-5-chlorophenyl}-3-chlorobenzenesulfonamide

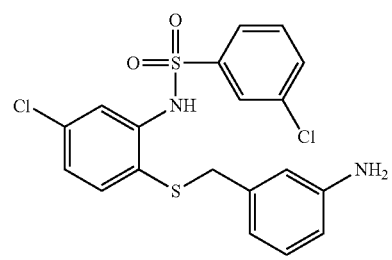 [SMILES: Nc1cccc(CSc2ccc(Cl)cc2NS(=O)(=O)c2cccc(Cl)c2)c1]

Following General Procedure A, B, and K, the title compound was prepared from 2-amino-4-chloro-benzenethiol, 1-bromomethyl-3-nitro-benzene, and 3-chloro-benzenesulfonyl chloride.

¹H NMR (600 MHz, CHLOROFORM-d) δ 7.80 (t, J=1.91 Hz, 1H), 7.63-7.66 (m, 1H), 7.56 (d, J=2.35 Hz, 1H), 7.52 (ddd, J=0.88, 1.98, 8.00 Hz, 1H), 7.39 (t, J=7.92 Hz, 1H), 7.16 (d, J=8.51 Hz, 1H), 7.02 (t, J=7.78 Hz, 1H), 6.96 (dd, J=2.05, 8.22 Hz, 1H), 6.55-6.59 (m, 1H), 6.35 (d, J=7.63 Hz, 1H), 6.32 (t, J=1.91 Hz, 1H), 3.56 (s, 2H).

Compound 165

N-{2-[(3-aminobenzyl)sulfonyl]-5-chlorophenyl}benzenesulfonamide

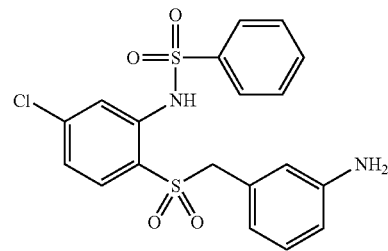

Following General Procedure A, B, D, and K, the title compound was prepared from 2-amino-4-chloro-benzenethiol, 1-bromomethyl-3-nitro-benzene, and benzenesulfonyl chloride.

¹H NMR (600 MHz, METHANOL-d₄) δ 7.90-7.93 (m, 2H), 7.63-7.68 (m, 1H), 7.56-7.62 (m, 3H), 7.42 (d, J=8.51 Hz, 1H), 7.11 (dd, J=2.05, 8.51 Hz, 1H), 6.93 (t, J=7.78 Hz, 1H), 6.66 (ddd, J=0.73, 2.27, 8.14 Hz, 1H), 6.39 (t, J=1.91 Hz, 1H), 6.16 (d, J=7.34 Hz, 1H), 4.18 (s, 2H).

Compound 166

N-{2-[(3-aminobenzyl)sulfinyl]-5-chlorophenyl}benzenesulfonamide

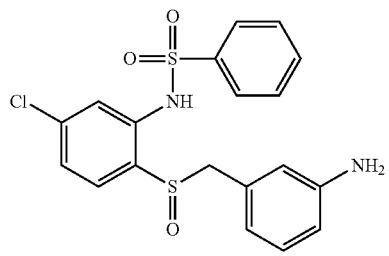 [SMILES: Nc1cccc(CS(=O)c2ccc(Cl)cc2NS(=O)(=O)c2ccccc2)c1]

Following General Procedure A, B, C, and K, the title compound was prepared from 2-amino-4-chloro-benzenethiol, 1-bromomethyl-3-nitro-benzene, and benzenesulfonyl chloride.

$^1$H NMR (600 MHz, METHANOL-$d_4$) δ 7.82-7.86 (m, 2H), 7.64-7.69 (m, 1H), 7.56-7.62 (m, 2H), 7.27-7.31 (m, 1H), 7.22-7.27 (m, 1H), 7.08 (d, J=2.05 Hz, 1H), 6.99 (t, J=7.78 Hz, 1H), 6.67 (ddd, J=0.88, 2.35, 8.22 Hz, 1H), 6.50 (t, J=1.91 Hz, 1H), 6.36 (d, J=7.63 Hz, 1H), 4.12 (d, J=12.62 Hz, 1H), 3.95 (d, J=12.91 Hz, 1H).

Compound 167

N-{2-[(3-aminobenzyl)sulfonyl]-5-chlorophenyl}-4-chlorobenzenesulfonamide

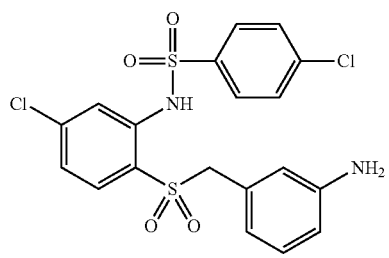 [SMILES: Nc1cccc(CS(=O)(=O)c2ccc(Cl)cc2NS(=O)(=O)c2ccc(Cl)cc2)c1]

Following General Procedure A, B, D, and K, the title compound was prepared from 2-amino-4-chloro-benzenethiol, 1-bromomethyl-3-nitro-benzene, and 4-chlorobenzenesulfonyl chloride.

$^1$H NMR (600 MHz, METHANOL-$d_4$) δ 7.85-7.88 (m, 2H), 7.58-7.62 (m, 2H), 7.55 (d, J=2.05 Hz, 1H), 7.49 (d, J=8.51 Hz, 1H), 7.15 (dd, J=1.91, 8.66 Hz, 1H), 6.95 (t, J=7.78 Hz, 1H), 6.68 (ddd, J=0.88, 2.20, 8.07 Hz, 1H), 6.45 (t, J=1.91 Hz, 1H), 6.21 (d, J=7.63 Hz, 1H), 4.28 (s, 2H).

Compound 168

N-{2-[(3-aminobenzyl)sulfinyl]-5-chlorophenyl}-4-chlorobenzenesulfonamide

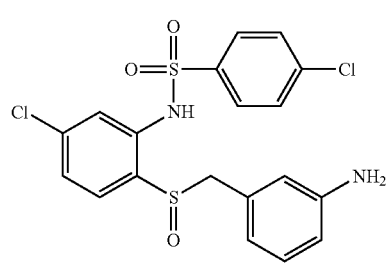 [SMILES: Nc1cccc(CS(=O)c2ccc(Cl)cc2NS(=O)(=O)c2ccc(Cl)cc2)c1]

Following General Procedure A, B, C, and K, the title compound was prepared from 2-amino-4-chloro-benzenethiol, 1-bromomethyl-3-nitro-benzene, and 4-chlorobenzenesulfonyl chloride.

$^1$H NMR (600 MHz, METHANOL-$d_4$) δ 7.79 (d, J=8.51 Hz, 2H), 7.59 (d, J=8.80 Hz, 2H), 7.32 (d, J=8.51 Hz, 1H), 7.24-7.29 (m, 1H), 7.06 (d, J=1.76 Hz, 1H), 6.99 (t, J=7.78 Hz, 1H), 6.65-6.69 (m, 1H), 6.52 (s, 1H), 6.38 (d, J=7.34 Hz, 1H), 4.16 (d, J=12.91 Hz, 1H), 3.97 (d, J=12.91 Hz, 1H).

Compound 169

N-{2-[(3-aminobenzyl)sulfonyl]-5-chlorophenyl}-3-chlorobenzenesulfonamide

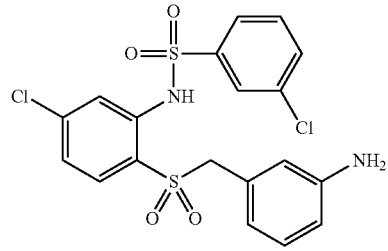 [SMILES: Nc1cccc(CS(=O)(=O)c2ccc(Cl)cc2NS(=O)(=O)c2cccc(Cl)c2)c1]

Following General Procedure A, B, D, and K, the title compound was prepared from 2-amino-4-chloro-benzenethiol, 1-bromomethyl-3-nitro-benzene, and 3-chlorobenzenesulfonyl chloride.

$^1$H NMR (600 MHz, METHANOL-$d_4$) δ 8.00 (t, J=1.91 Hz, 1H), 7.89-7.93 (m, 1H), 7.42-7.51 (m, 3H), 7.38 (d, J=8.51 Hz, 1H), 6.89 (t, J=7.78 Hz, 1H), 6.66 (ddd, J=1.76, 8.51 Hz, 1H), 6.59 (d, J=8.22 Hz, 1H), 6.55 (s, 1H), 6.37 (d, J=7.63 Hz, 1H), 4.69 (s, 2H).

Compound 170

N-{2-[(3-aminobenzyl)sulfinyl]-5-chlorophenyl}-3-chlorobenzenesulfonamide

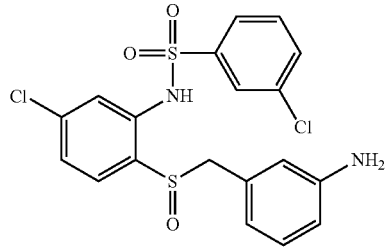 [SMILES: Nc1cccc(CS(=O)c2ccc(Cl)cc2NS(=O)(=O)c2cccc(Cl)c2)c1]

Following General Procedure A, B, C, and K, the title compound was prepared from 2-amino-4-chloro-benzenethiol, 1-bromomethyl-3-nitro-benzene, and 3-chloro-benzenesulfonyl chloride.

$^1$H NMR (600 MHz, METHANOL-$d_4$) δ 7.85 (s, 1H), 7.77 (d, J=7.63 Hz, 1H), 7.51-7.55 (m, 1H), 7.47 (t, J=7.92 Hz, 1H), 7.22 (d, J=8.22 Hz, 1H), 7.19 (d, J=1.76 Hz, 1H), 6.93-7.00 (m, 2H), 6.65 (dd, J=2.20, 8.07 Hz, 1H), 6.58 (s, 1H), 6.43 (d, J=7.63 Hz, 1H), 4.35 (d, J=12.91 Hz, 1H), 3.82 (d, J=12.91 Hz, 1H).

Compound 171

3-{[4-chloro-2-({[4-chloro-3-(trifluoromethyl)phenyl]sulfonyl}amino)phenyl]thio}-N-isopropylpropanamide

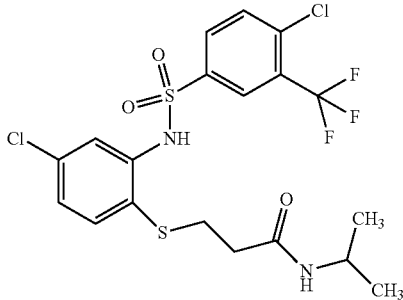 [SMILES: CC(C)NC(=O)CCSc1ccc(Cl)cc1NS(=O)(=O)c1ccc(Cl)c(C(F)(F)F)c1]

Following General Procedure H, B, the title compound was prepared from 2-amino-4-chloro-benzenethiol, N-isopropyl-acrylamide, and 4-chloro-3-trifluoromethyl-benzenesulfonyl chloride.

$^1$H NMR (300 MHz, CD$_3$OD) δ 8.19 (d, J=1.47 Hz, 1H), 7.98 (d, J=8.20 Hz, 1H), 7.60 (d, J=8.20 Hz, 1H), 7.23 (d, J=2.05 Hz, 1H), 7.06 (d, J=8.20 Hz, 1H), 6.75 (dd, J=2.20, 8.35 Hz, 1H), 3.85-4.03 (m, 1H), 3.00 (t, J=7.33 Hz, 2H), 2.39 (t, J=7.47 Hz, 2H), 1.12 (d, 6H).

Compound 172

3-{[4-chloro-2-{[4-chloro-3-(trifluoromethyl)phenyl]sulfonyl}amino)phenyl]thio}-N,N-dimethylpropanamide

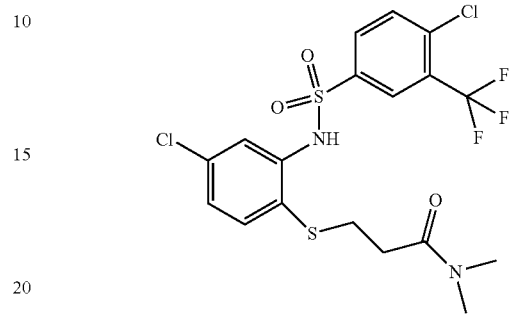

Following General Procedure H, B, the title compound was prepared from 2-amino-4-chloro-benzenethiol, N,N-dimethyl-acrylamide, and 4-chloro-3-trifluoromethyl-benzenesulfonyl chloride.

$^1$H NMR (300 MHz, CD$_3$OD) δ 8.11 (s, 1H), 7.90 (d, J=7.91 Hz, 1H), 7.71-7.79 (m, 1H), 7.49 (d, J=2.34 Hz, 1H), 7.39 (d, J=8.50 Hz, 1H), 7.21 (none, J=2.34, 8.50 Hz, 1H), 2.96 (d, J=7.62 Hz, 6H), 2.90 (t, J=7.03 Hz, 2H), 2.51 (t, J=7.03 Hz, 2H).

Compound 173

3-{[4-chloro-2-{[4-chloro-3-(trifluoromethyl)phenyl]sulfonyl}amino)phenyl]sulfinyl}-N-isopropyl-propanamide

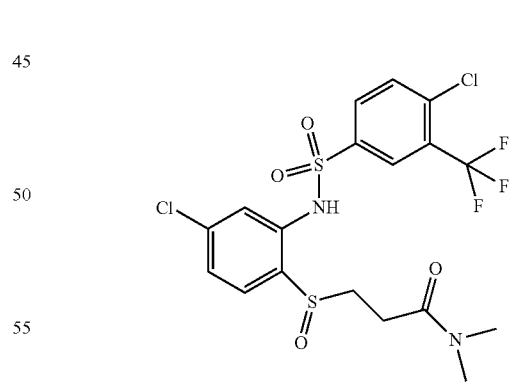

Following General Procedure C, the title compound was prepared from 3-{[4-chloro-2-({[4-chloro-3-(trifluoromethyl)phenyl]sulfonyl}amino)phenyl]thio}-N,N-dimethyl-propanamide $^1$H NMR (300 MHz, CD$_3$OD) δ 8.17 (d, J=1.76 Hz, 1H), 8.01 (d, J=8.20 Hz, 1H), 7.67 (d, J=8.50 Hz, 1H), 7.39 (d, J=8.20 Hz, 1H), 7.24 (d, J=1.76 Hz, 1H), 6.88 (dd, J=1.90, 8.35 Hz, 1H), 3.91 (quin, J=6.59 Hz, 1H), 3.37-3.52 (m, 1H), 3.09-3.25 (m, 1H), 2.58 (ddd, J=5.71, 9.89, 15.16 Hz, 1H), 2.26 (ddd, J=5.86, 9.74, 15.16 Hz, 1H), 1.10 (dd, 4H).

Compound 174

3-{[4-chloro-2-({[4-chloro-3-(trifluoromethyl)phenyl]sulfonyl}amino)phenyl]sulfinyl}propanamide

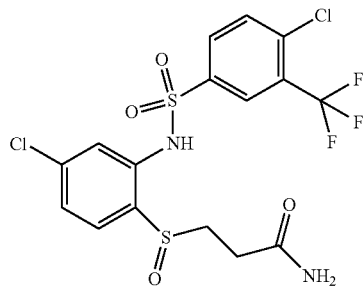 [SMILES: NC(=O)CCS(=O)c1ccc(Cl)cc1NS(=O)(=O)c1ccc(Cl)c(C(F)(F)F)c1]

Following General Procedure H, B, the title compound was prepared from 2-amino-4-chloro-benzenethiol, acrylamide, and 4-chloro-3-trifluoromethyl-benzenesulfonyl chloride.

¹H NMR (600 MHz, CD₃OD) δ 8.16 (d, J=1.76 Hz, 1H), 8.00 (dd, J=2.05, 8.22 Hz, 1H), 7.75 (d, J=8.51 Hz, 1H), 7.57 (d, J=8.51 Hz, 1H), 7.32 (s, 1H), 7.21 (d, J=7.92 Hz, 1H), 3.26 (br. s., 1H), 3.18 (br. s., 1H), 2.99-3.07 (m, 3H), 2.95 (s, 3H), 2.88 (dt, J=7.37, 16.95 Hz, 1H), 2.62-2.77 (m, 1H).

Compound 175

N-[5-chloro-2-(methylsulfinyl)phenyl]benzenesulfonamide

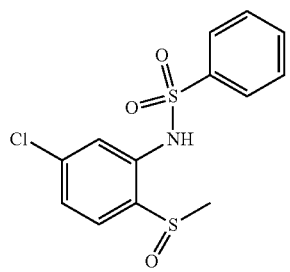 [SMILES: CS(=O)c1ccc(Cl)cc1NS(=O)(=O)c1ccccc1]

Following General Procedure B, C, the title compound was prepared from 5-chloro-2-(methylsulfinyl)aniline and benzenesulfonyl chloride.

¹H NMR (300 MHz, acetone-d6) δ 10.64 (br. s., 1H), 7.93 (d, J=7.03 Hz, 2H), 7.59-7.79 (m, 3H), 7.55 (d, J=1.76 Hz, 1H), 7.45 (d, J=8.50 Hz, 1H), 7.26 (dd, J=1.90, 8.35 Hz, 1H), 2.74 (s, 3H).

Compound 176

N-[5-chloro-2-(methylthio)phenyl]thiophene-2-sulfonamide

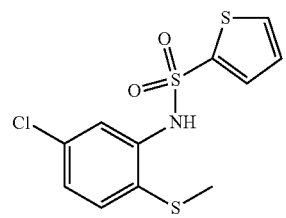 [SMILES: CSc1ccc(Cl)cc1NS(=O)(=O)c1cccs1]

Following General Procedure B, the title compound was prepared from 5-chloro-2-(methylsulfinyl)aniline and thiophene-2-sulfonyl chloride.

¹H NMR (300 MHz, CD₃OD) δ 7.75 (dd, J=1.17, 4.98 Hz, 1H), 7.50 (dd, J=1.32, 3.66 Hz, 1H), 7.40 (d, J=2.05 Hz, 1H), 7.26-7.34 (m, 1H), 7.15-7.24 (m, 1H), 7.08 (dd, J=3.81, 4.98 Hz, 1H), 2.23 (s, 3H).

Compound 177

N-[5-chloro-2-(methylsulfinyl)phenyl]thiophene-2-sulfonamide

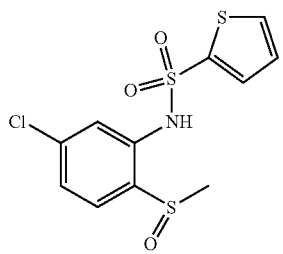 [SMILES: CS(=O)c1ccc(Cl)cc1NS(=O)(=O)c1cccs1]

Following General Procedure C, the title compound was prepared from N-[5-chloro-2-(methylthio)phenyl]thiophene-2-sulfonamide ¹H NMR (600 MHz, CD₃OD) δ 7.81 (d, J=4.40 Hz, 1H), 7.75 (d, J=8.51 Hz, 1H), 7.51-7.57 (m, 1H), 7.43 (d, J=7.92 Hz, 1H), 7.15 (dd, J=4.84, 8.66 Hz, 2H), 2.79 (s, 3H).

Compound 178

N-{2-[(3-nitrobenzyl)sulfonyl]phenyl}-1-benzofuran-2-sulfonamide

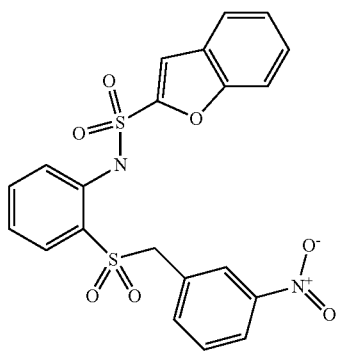 [SMILES: O=[N+]([O-])c1cccc(CS(=O)(=O)c2ccccc2NS(=O)(=O)c2cc3ccccc3o2)c1]

Following General Procedure D, the title compound (136 mg, 82%) was prepared from benzofuran-2-sulfonic acid [2-(3-nitro-benzylsulfanyl)-phenyl]-amide.

1H NMR (600 MHz, acetone-d6) δ 9.57 (br. s., 1H), 8.17 (dt, J=2.53, 6.38 Hz, 1H), 7.93 (d, J=0.88 Hz, 1H), 7.74-7.83 (m, 3H), 7.69 (td, J=1.47, 7.92 Hz, 1H), 7.63 (dd, J=1.47, 7.92

Hz, 1H), 7.52-7.59 (m, 3H), 7.47 (ddd, J=1.17, 7.41, 8.44 Hz, 1H), 7.30-7.38 (m, 1H), 7.23 (t, J=7.63 Hz, 1H), 4.85 (s, 2H).

Compound 179

N-(5-chloro-2-{[2-(3,5-dimethyl-1H-pyrazol-4-yl)ethyl]sulfinyl}phenyl)-1-benzofuran-2-sulfonamide

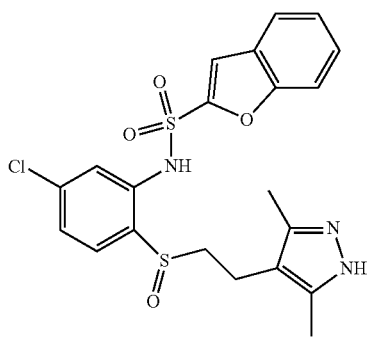 [SMILES: Cc1n[nH]c(C)c1CCS(=O)c1ccc(Cl)cc1NS(=O)(=O)c1cc2ccccc2o1]

Following General Procedure C, the title compound (79 mg, 73%) was prepared from N-(5-chloro-2-{[2-(3,5-dimethyl-1H-pyrazol-4-yl)ethyl]thio}phenyl)-1-benzofuran-2-sulfonamide.

1H NMR (600 MHz, CD$_3$OD) δ 7.61 (d, J=7.92 Hz, 1H), 7.46 (d, J=2.05 Hz, 1H), 7.44 (d, J=8.22 Hz, 1H), 7.28-7.32 (m, 1H), 7.21-7.26 (m, 1H), 7.19 (dd, J=0.73, 8.36 Hz, 1H), 7.15 (d, J=0.88 Hz, 1H), 6.92 (dd, J=1.91, 8.36 Hz, 1H), 3.52-3.62 (m, 1H), 2.80-2.91 (m, 2H), 2.56-2.65 (m, 1H), 2.11 (s, 6H).

Compound 180

4-chloro-N-{5-chloro-2-[(3-hydroxycyclopentyl)sulfonyl]phenyl}-3-(trifluoromethyl)benzenesulfonamide

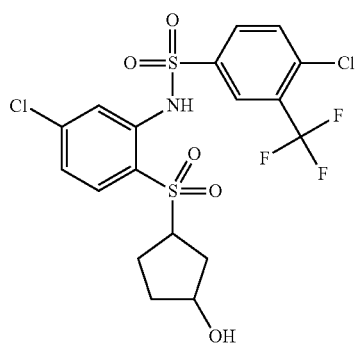 [SMILES: O=S(=O)(Nc1cc(Cl)ccc1S(=O)(=O)C1CCC(O)C1)c1ccc(Cl)c(C(F)(F)F)c1]

Following General Procedure D, followed by treatment of the crude product with NaBH$_4$ in MeOH, the title compound was prepared from 4-Chloro-N-[5-chloro-2-(3-oxo-cyclopentylsulfanyl)-phenyl]-3-trifluoromethyl-benzenesulfonamide (Intermediate 35).

1H NMR (600 MHz, CD$_3$OD) δ 8.34 (s, 1H), 8.18 (dd, J=1.91, 8.36 Hz, 1H), 7.70-7.79 (m, 2H), 7.65 (s, 1H), 7.00 (br. s., 1H), 4.12-4.18 (m, 2H), 1.98-2.10 (m, 2H), 1.72-1.84 (m, 2H), 1.63-1.71 (m, 2H).

Compound 181

N-[5-chloro-2-(methylthio)phenyl]-4-methyl-3-nitrobenzenesulfonamide

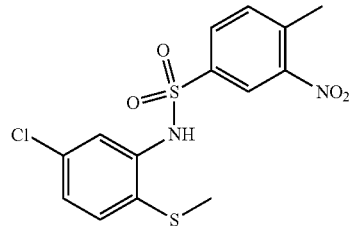 [SMILES: CSc1ccc(Cl)cc1NS(=O)(=O)c1ccc(C)c([N+](=O)[O-])c1]

Following General Procedure B, the title compound (197 mg, 61%) was prepared from 5-Chloro-2-methylsulfanylphenylamine (150 mg, 0.87 mmol) and 4-Methyl-3-nitrobenzenesulfonyl chloride (235 mg, 0.87 mmol).

$^1$H NMR (600 MHz, CD$_3$OD) δ 8.29 (d, J=1.76 Hz, 1H), 7.85 (dd, J=1.91, 8.07 Hz, 1H), 7.57 (d, J=8.22 Hz, 1H), 7.39 (d, J=2.05 Hz, 1H), 7.17-7.25 (m, 2H), 2.60 (s, 3H), 2.20 (s, 3H).

Compound 182 chloro-2-(methylsulfinyl)phenyl]-4-methyl-3-nitrobenzenesulfonamide

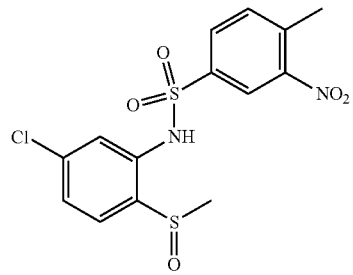 [SMILES: Cc1ccc(S(=O)(=O)Nc2cc(Cl)ccc2S(C)=O)cc1[N+](=O)[O-]]

Following General Procedure C, the title compound was prepared from N-[5-chloro-2-(methylthio)phenyl]-4-methyl-3-nitrobenzenesulfonamide $^1$H NMR (600 MHz, CDCL$_3$) δ 10.88 (br. s., 1H), 8.53 (d, J=2.05 Hz, 1H), 8.05 (dd, J=1.91, 8.07 Hz, 1H), 7.64 (d, J=1.76 Hz, 1H), 7.54 (d, J=8.22 Hz, 1H), 7.04-7.16 (m, 2H), 2.87 (s, 3H), 2.67 (s, 3H).

Compound 183

N-[5-chloro-2-(methylsulfonyl)phenyl]-4-methyl-3-nitrobenzenesulfonamide

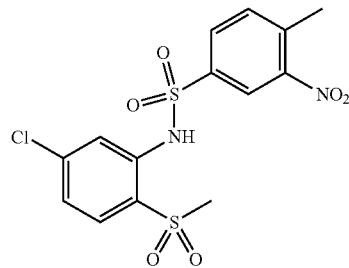 [SMILES: Cc1ccc(S(=O)(=O)Nc2cc(Cl)ccc2S(C)(=O)=O)cc1[N+](=O)[O-]]

Following General Procedure D, the title compound was prepared from N-[5-chloro-2-(methylthio)phenyl]-4-methyl-3-nitrobenzenesulfonamide $^1$H NMR (600 MHz, CDCL$_3$) δ 9.36 (br. s., 1H), 8.52 (d, J=2.05 Hz, 1H), 8.05 (dd, J=2.05, 8.22 Hz, 1H), 7.79 (d, J=8.51 Hz, 1H), 7.67 (d, J=2.05 Hz, 1H), 7.58 (d, J=7.92 Hz, 1H), 7.23 (dd, J=1.76, 8.51 Hz, 1H), 3.04 (s, 3H), 2.68 (s, 3H).

Compound 184

4-chloro-N-[5-chloro-2-(methylthio)phenyl]benzene-sulfonamide

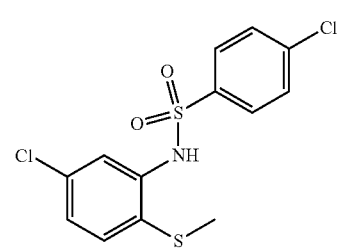 [SMILES: CSc1ccc(Cl)cc1NS(=O)(=O)c1ccc(Cl)cc1]

Following General Procedure B, the title compound (150 mg, 68%) was prepared from 5-Chloro-2-methylsulfanyl-phenylamine (110 mg, 0.64 mmol) and 4-Chloro-benzene-sulfonyl chloride (134 mg, 0.64 mmol).

$^1$H NMR (600 MHz, CD$_3$OD) δ 7.72 (d, J=9.10 Hz, 2H), 7.51 (d, J=8.80 Hz, 2H), 7.37 (d, J=2.05 Hz, 1H), 7.25 (d, J=8.51 Hz, 1H), 7.19 (dd, J=2.05, 8.22 Hz, 1H), 2.20 (s, 3H).

Compound 185

4-chloro-N-[5-chloro-2-(methylsulfinyl)phenyl]benzenesulfonamide

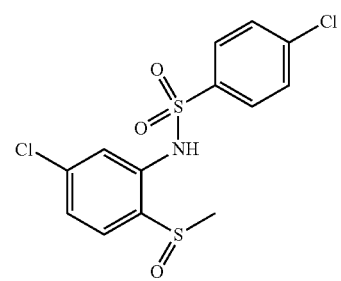 [SMILES: CS(=O)c1ccc(Cl)cc1NS(=O)(=O)c1ccc(Cl)cc1]

Following General Procedure C, the title compound was prepared from 4-chloro-N-[5-chloro-2-(methylthio)phenyl]benzenesulfonamide $^1$H NMR (600 MHz, CDCL$_3$) δ 10.67 (br. s., 1H), 7.89 (d, J=8.80 Hz, 2H), 7.66 (d, J=1.76 Hz, 1H), 7.50 (d, J=8.80 Hz, 2H), 6.91-7.16 (m, 2H), 2.80 (none, 3H).

Compound 186

4-chloro-N-[5-chloro-2-(methylsulfonyl)phenyl]benzenesulfonamide

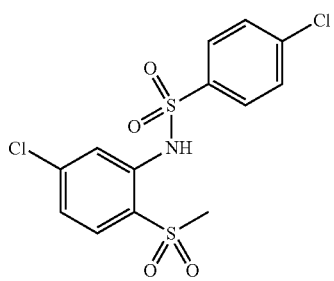 [SMILES: CS(=O)(=O)c1ccc(Cl)cc1NS(=O)(=O)c1ccc(Cl)cc1]

Following General Procedure D, the title compound was prepared from 4-chloro-N-[5-chloro-2-(methylthio)phenyl]benzenesulfonamide $^1$H NMR (600 MHz, CDCL$_3$) δ 7.89 (d, J=8.80 Hz, 2H), 7.78 (d, J=8.51 Hz, 1H), 7.68 (d, J=1.76 Hz, 1H), 7.53 (d, J=8.80 Hz, 2H), 7.20 (dd, J=2.05, 8.51 Hz, 1H), 2.96 (s, 3H).

Compound 187

4-chloro-N-[5-chloro-2-(methylthio)phenyl]-3-methylbenzenesulfonamide

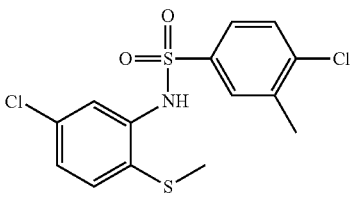 [SMILES: CSc1ccc(Cl)cc1NS(=O)(=O)c1ccc(Cl)c(C)c1]

Following General Procedure B, the title compound (205 mg, 59%) was prepared from 5-chloro-2-methylsulfanyl-phenylamine (165 mg, 0.95 mmol) and 4-chloro-3-methyl-benzenesulfonyl chloride (215 mg, 0.95 mmol).

$^1$H NMR (600 MHz, CDCL$_3$) δ 7.71 (d, 1H), 7.65 (s, 1H), 7.62 (d, J=2.05 Hz, 1H), 7.57 (dd, J=2.05, 8.22 Hz, 1H), 7.41 (d, J=8.22 Hz, 1H), 7.32 (d, J=8.51 Hz, 1H), 7.04 (dd, J=2.20, 8.36 Hz, 1H), 2.39 (s, 3H), 2.19 (s, 3H).

Compound 188

4-chloro-N-[5-chloro-2-(methylsulfinyl)phenyl]-3-methylbenzenesulfonamide

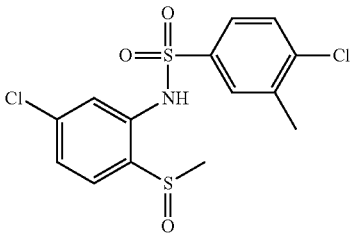 [SMILES: Cc1cc(S(=O)(=O)Nc2cc(Cl)ccc2S(C)=O)ccc1Cl]

Following General Procedure C, the title compound was prepared from 4-chloro-N-[5-chloro-2-(methylthio)phenyl]-3-methylbenzenesulfonamide $^{1}$H NMR (600 MHz, CDCL$_{3}$) δ 10.62 (s, 1H), 7.82 (d, J=2.05 Hz, 1H), 7.71 (dd, J=1.91, 8.36 Hz, 1H), 7.63 (d, J=2.05 Hz, 1H), 7.48 (d, J=8.51 Hz, 1H), 7.02-7.15 (m, 2H), 2.81 (s, 3H), 2.43 (s, 3H).

Compound 189

4-chloro-N-[5-chloro-2-(methylsulfonyl)phenyl]-3-methylbenzenesulfonamide

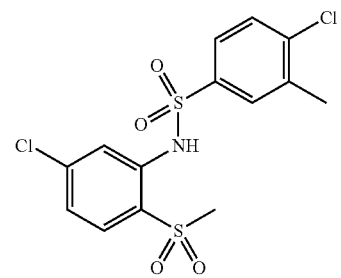 [SMILES: Cc1cc(S(=O)(=O)Nc2cc(Cl)ccc2S(C)(=O)=O)ccc1Cl]

Following General Procedure D, the title compound was prepared from 4-chloro-N-[5-chloro-2-(methylthio)phenyl]-3-methylbenzenesulfonamide $^{1}$H NMR (600 MHz, CDCL$_{3}$) δ 9.24 (br. s., 1H), 7.83 (d, J=2.05 Hz, 1H), 7.78 (d, J=8.51 Hz, 1H), 7.71 (dd, J=2.05, 8.51 Hz, 1H), 7.67 (d, J=1.76 Hz, 1H), 7.50 (d, J=8.22 Hz, 1H), 7.19 (dd, J=1.76, 8.51 Hz, 1H), 2.97 (s, 3H), 2.44 (s, 3H).

Compound 190

N-[5-chloro-2-(methylthio)phenyl]-3-nitro-4-(trifluoromethyl)benzenesulfonamide

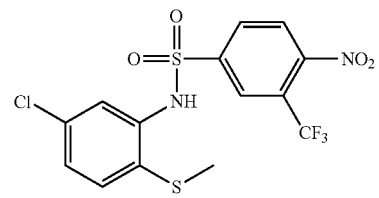 [SMILES: CSc1ccc(Cl)cc1NS(=O)(=O)c1ccc([N+](=O)[O-])c(C(F)(F)F)c1]

Following General Procedure B, the title compound (176 mg, 43%) was prepared from 5-chloro-2-methylsulfanyl-phenylamine (167 mg, 0.95 mmol) and 4-nitro-3-trifluoromethyl-benzenesulfonyl chloride (278 mg, 0.95 mmol).

$^{1}$H NMR (300 MHz, CD$_{3}$OD) δ 8.04-8.22 (m, 3H), 7.42 (d, J=2.05 Hz, 1H), 7.16-7.32 (m, 2H), 2.20 (s, 3H).

Compound 191

N-[5-chloro-2-(methylsulfonyl)phenyl]-3-nitro-4-(trifluoromethyl)benzenesulfonamide

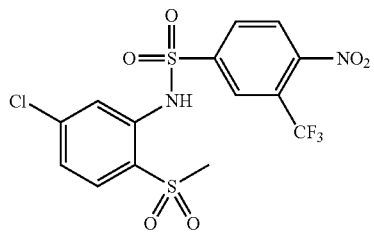 [SMILES: CS(=O)(=O)c1ccc(Cl)cc1NS(=O)(=O)c1ccc([N+](=O)[O-])c(C(F)(F)F)c1]

Following General Procedure D, the title compound was prepared from N-[5-chloro-2-(methylthio)phenyl]-3-nitro-4-(trifluoromethyl)benzenesulfonamide $^{1}$H NMR (600 MHz, acetone-d6) δ 9.64 (br. s., 1H), 8.49-8.65 (m, 2H), 8.33 (d, J=8.51 Hz, 1H), 7.89 (d, J=8.51 Hz, 1H), 7.70 (d, J=1.76 Hz, 1H), 7.39 (d, J=8.22 Hz, 1H), 3.24 (s, 3H).

Compound 192

N-[5-chloro-2-(methylsulfinyl)phenyl]-3-nitro-4-(trifluoromethyl)benzenesulfonamide

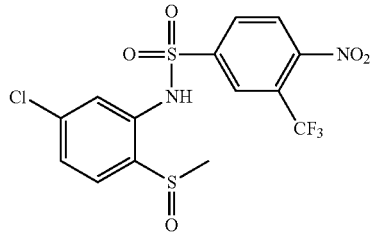 [SMILES: CS(=O)c1ccc(Cl)cc1NS(=O)(=O)c1ccc([N+](=O)[O-])c(C(F)(F)F)c1]

Following General Procedure D, the title compound was prepared from N-[5-chloro-2-(methylthio)phenyl]-3-nitro-4-(trifluoromethyl)benzenesulfonamide $^{1}$H NMR (600 MHz, acetone-d6) δ 8.25-8.35 (m, 2H), 8.11 (d, J=8.22 Hz, 1H), 7.39-7.48 (m, 2H), 6.75 (dd, J=2.05, 8.22 Hz, 1H), 2.70 (s, 3H).

Compound 193

N-[5-chloro-2-(methylthio)phenyl]-2,4-difluorobenzenesulfonamide

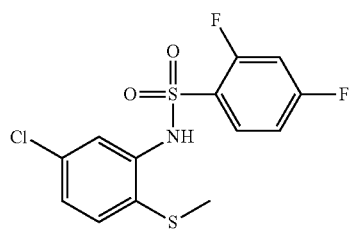 [SMILES: CSc1ccc(Cl)cc1NS(=O)(=O)c1ccc(F)cc1F]

Following General Procedure B, the title compound (358 mg, 94%) was prepared from 5-chloro-2-methylsulfanyl-phenylamine (189 mg, 1.09 mmol) and 2,4-Difluoro-benzenesulfonyl chloride (231 mg, 1.09 mmol).

$^1$H NMR (300 MHz, CD$_3$OD) δ 7.82 (td, J=6.15, 8.50 Hz, 1H), 7.34 (d, J=2.05 Hz, 1H), 7.16-7.30 (m, 3H), 7.00-7.16 (m, 1H), 2.27 (s, 3H).

Compound 194

N-[5-chloro-2-(methylsulfonyl)phenyl]-2,4-difluorobenzenesulfonamide

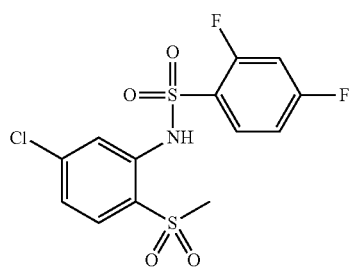 [SMILES: CS(=O)(=O)c1ccc(Cl)cc1NS(=O)(=O)c1ccc(F)cc1F]

Following General Procedure D, the title compound was prepared from N-[5-chloro-2-(methylthio)phenyl]-2,4-difluorobenzenesulfonamide $^1$H NMR (300 MHz, acetone-d6) δ 9.81 (br. s., 1H), 8.15-8.32 (m, 1H), 7.91 (d, J=8.50 Hz, 1H), 7.63 (d, J=1.76 Hz, 1H), 7.24-7.46 (m, 3H), 3.27 (s, 3H).

Compound 195

N-[5-chloro-2-(methylsulfinyl)phenyl]-2,4-difluorobenzenesulfonamide

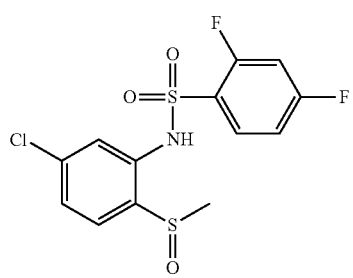 [SMILES: CS(=O)c1ccc(Cl)cc1NS(=O)(=O)c1ccc(F)cc1F]

Following General Procedure D, the title compound was prepared from N-[5-chloro-2-(methylthio)phenyl]-2,4-difluorobenzenesulfonamide $^1$H NMR (600 MHz, acetone-d6) δ 10.97 (br. s., 1H), 8.10 (td, J=6.16, 8.51 Hz, 1H), 7.51 (d, J=8.22 Hz, 1H), 7.46 (d, J=2.05 Hz, 1H), 7.30-7.38 (m, 1H), 7.24-7.31 (m, 2H), 2.90 (s, 3H).

Compound 196

N-[5-chloro-2-(methylthio)phenyl]-5-methylfuran-2-sulfonamide

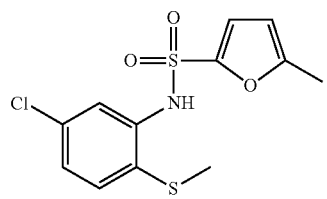 [SMILES: CSc1ccc(Cl)cc1NS(=O)(=O)c1ccc(C)o1]

Following General Procedure B, the title compound (212 mg, 48%) was prepared from 5-chloro-2-methylsulfanyl-phenylamine (189 mg, 1.09 mmol) and 5-methyl-furan-2-sulfonyl chloride (250 mg, 1.38 mmol).

$^1$H NMR (300 MHz, acetone-d6) δ 8.53 (br. s., 1H), 7.37-7.49 (m, 2H), 7.25 (dd, J=2.34, 8.50 Hz, 1H), 6.96 (d, J=3.22 Hz, 1H), 6.24 (d, J=2.64 Hz, 1H), 2.38 (s, 3H), 2.34 (s, 3H).

Compound 197

N-[5-chloro-2-(methylsulfinyl)phenyl]-5-methylfuran-2-sulfonamide

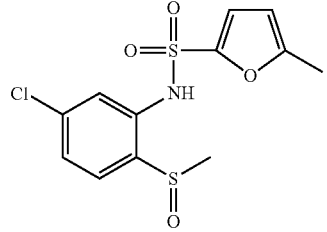 [SMILES: Cc1ccc(S(=O)(=O)Nc2cc(Cl)ccc2S(C)=O)o1]

Following General Procedure C, the title compound was prepared from N-[5-chloro-2-(methylthio)phenyl]-5-methyl-furan-2-sulfonamide $^1$H NMR (600 MHz, acetone-d6) δ 10.74 (br. s., 1H), 7.55 (d, J=2.05 Hz, 1H), 7.51 (d, J=8.22 Hz, 1H), 7.30 (dd, J=1.91, 8.36 Hz, 1H), 7.18 (d, J=3.23 Hz, 1H), 6.24-6.35 (m, 1H), 2.90 (s, 3H), 2.34 (s, 3H).

Compound 198

N-[5-chloro-2-(methylsulfonyl)phenyl]-5-methylfuran-2-sulfonamide

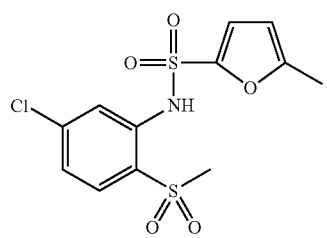 [SMILES: Cc1ccc(S(=O)(=O)Nc2cc(Cl)ccc2S(C)(=O)=O)o1]

Following General Procedure D, the title compound was prepared from N-[5-chloro-2-(methylthio)phenyl]-5-methyl-furan-2-sulfonamide ¹H NMR (600 MHz, acetone-d6) δ 9.54 (br. s., 1H), 7.90 (d, J=8.51 Hz, 1H), 7.73 (d, J=2.05 Hz, 1H), 7.39 (dd, J=1.76, 8.51 Hz, 1H), 7.31 (d, J=3.52 Hz, 1H), 6.32 (d, J=3.23 Hz, 1H), 3.24 (s, 3H), 2.33 (s, 3H).

Compound 199

N-[5-chloro-2-(methylthio)phenyl]furan-2-sulfonamide

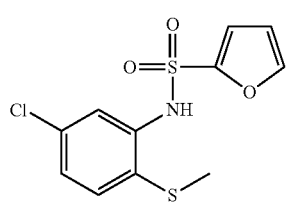 [SMILES: CSc1ccc(Cl)cc1NS(=O)(=O)c1ccco1]

Following General Procedure B, the title compound (215 mg, 47%) was prepared from 5-chloro-2-methylsulfanyl-phenylamine (260 mg, 1.50 mmol) and furan-2-sulfonyl chloride (250 mg, 1.50 mmol).

¹H NMR (300 MHz, acetone-d6) δ 8.67 (br. s., 1H), 7.84 (s, 1H), 7.32-7.46 (m, 2H), 7.26 (dd, J=2.20, 8.35 Hz, 1H), 7.07 (d, J=3.52 Hz, 1H), 6.63 (dd, J=1.76, 3.52 Hz, 1H), 2.36 (s, 3H).

Compound 200

N-[5-chloro-2-(methylsulfinyl)phenyl]furan-2-sulfonamide

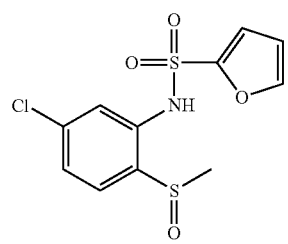 [SMILES: CS(=O)c1ccc(Cl)cc1NS(=O)(=O)c1ccco1]

¹H NMR (600 MHz, acetone-d6) δ 10.85 (br. s., 1H), 7.89 (s, 1H), 7.49-7.59 (m, 2H), 7.28-7.36 (m, 2H), 6.68 (dd, J=1.76, 3.52 Hz, 1H), 2.88 (s, 3H).

Following General Procedure C, the title compound was prepared from N-[5-chloro-2-(methylthio)phenyl]furan-2-sulfonamide Compound 201

N-[5-chloro-2-(methylsulfonyl)phenyl]furan-2-sulfonamide

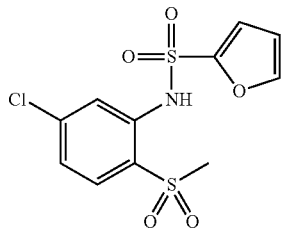 [SMILES: CS(=O)(=O)c1ccc(Cl)cc1NS(=O)(=O)c1ccco1]

Following General Procedure D, the title compound was prepared from N-[5-chloro-2-(methylthio)phenyl]furan-2-sulfonamide ¹H NMR (600 MHz, acetone-d6) δ 9.62 (br. s., 1H), 7.90 (d, J=8.51 Hz, 2H), 7.74 (d, J=2.05 Hz, 1H), 7.27-7.48 (m, 2H), 6.70 (dd, J=1.76, 3.52 Hz, 1H), 3.22 (s, 3H).

Compound 202

4-chloro-N-[5-chloro-2-(methylthio)phenyl]-2-fluoro-benzenesulfonamide

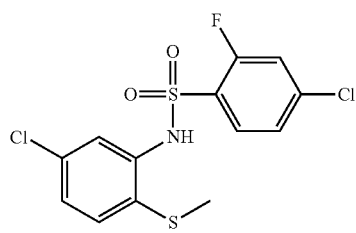 [SMILES: CSc1ccc(Cl)cc1NS(=O)(=O)c1ccc(Cl)cc1F]

Following General Procedure B, the title compound (380 mg, 66%) was prepared from 5-chloro-2-methylsulfanyl-phenylamine (273 mg, 1.57 mmol) and 4-chloro-2-fluoro-benzenesulfonyl chloride (360 mg, 1.57 mmol).

¹H NMR (300 MHz, acetone-d6) δ 8.77 (br. s., 1H), 7.84 (t, J=8.06 Hz, 1H), 7.53 (dd, J=1.90, 9.82 Hz, 1H), 7.35-7.48 (m, 3H), 7.25 (dd, J=2.20, 8.35 Hz, 1H), 2.34 (s, 3H).

Compound 203

4-chloro-N-[5-chloro-2-(methylsulfinyl)phenyl]-2-fluorobenzenesulfonamide

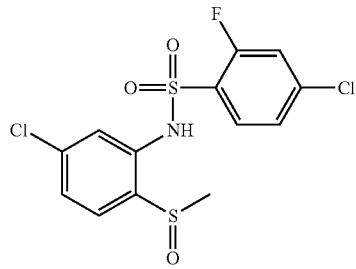 [SMILES: CS(=O)c1ccc(Cl)cc1NS(=O)(=O)c1ccc(Cl)cc1F]

Following General Procedure C, the title compound was prepared from 4-chloro-N-[5-chloro-2-(methylthio)phenyl]-2-fluorobenzenesulfonamide $^1$H NMR (300 MHz, acetone-d6) δ 10.95 (br. s., 1H), 8.03 (t, J=8.20 Hz, 1H), 7.39-7.61 (m, 4H), 7.28 (dd, J=1.90, 8.35 Hz, 1H), 2.93 (s, 3H).

Compound 204

4-chloro-N-[5-chloro-2-(methylsulfonyl)phenyl]-2-fluorobenzenesulfonamide

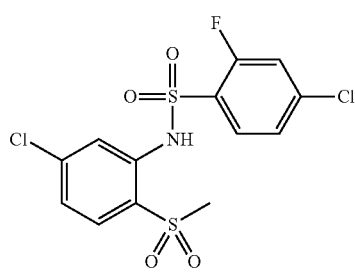 [SMILES: CS(=O)(=O)c1ccc(Cl)cc1NS(=O)(=O)c1ccc(Cl)cc1F]

Following General Procedure D, the title compound was prepared from 4-chloro-N-[5-chloro-2-(methylthio)phenyl]-2-fluorobenzenesulfonamide $^1$H NMR (300 MHz, acetone-d6) δ 9.84 (br. s., 1H), 8.12 (t, J=8.20 Hz, 1H), 7.90 (d, J=8.50 Hz, 1H), 7.46-7.69 (m, 3H), 7.33 (dd, J=1.47, 8.50 Hz, 1H), 3.27 (s, 3H).

Compound 205

3-chloro-N-[5-chloro-2-(methylthio)phenyl]-2-fluorobenzenesulfonamide

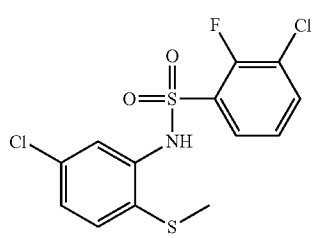 [SMILES: CSc1ccc(Cl)cc1NS(=O)(=O)c1cccc(Cl)c1F]

Following General Procedure B, the title compound (386 mg, 62%) was prepared from 5-chloro-2-methylsulfanylphenylamine (297 mg, 1.71 mmol) and 3-chloro-2-fluorobenzenesulfonyl chloride (392 mg, 1.71 mmol).

$^1$H NMR (300 MHz, acetone-d6) δ 8.87 (br. s., 1H), 7.70-7.93 (m, 2H), 7.32-7.47 (m, 3H), 7.20-7.31 (m, 1H), 2.32 (s, 3H).

Compound 206

3-chloro-N-[5-chloro-2-(methylsulfonyl)phenyl]-2-fluorobenzenesulfonamide

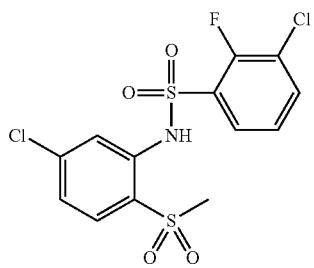 [SMILES: CS(=O)(=O)c1ccc(Cl)cc1NS(=O)(=O)c1cccc(Cl)c1F]

Following General Procedure D, the title compound was prepared from 3-chloro-N-[5-chloro-2-(methylthio)phenyl]-2-fluorobenzenesulfonamide $^1$H NMR (300 MHz, acetone-d6) δ 7.89-8.04 (m, 1H), 7.69 (d, J=8.50 Hz, 1H), 7.55-7.65 (m, 2H), 7.23-7.37 (m, 1H), 6.72 (dd, J=1.90, 8.64 Hz, 1H), 3.22 (s, 3H).

Compound 207

3-chloro-N-[5-chloro-2-(methylsulfinyl)phenyl]-2-fluorobenzenesulfonamide

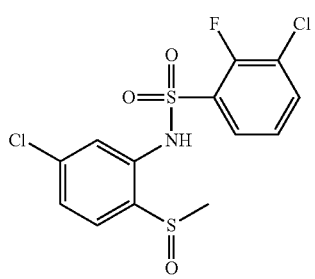 [SMILES: CS(=O)c1ccc(Cl)cc1NS(=O)(=O)c1cccc(Cl)c1F]

Following General Procedure C, the title compound was prepared from 3-chloro-N-[5-chloro-2-(methylthio)phenyl]-2-fluorobenzenesulfonamide $^1$H NMR (300 MHz, acetone-d6) δ 7.94-8.04 (m, 1H), 7.83-7.93 (m, 1H), 7.42-7.59 (m, 3H), 7.29 (dd, J=1.90, 8.35 Hz, 1H), 2.93 (s, 3H).

Compound 208

4-chloro-N-{5-chloro-2-[(1H-imidazol-2-ylmethyl)thio]phenyl}-3-(trifluoromethyl)benzenesulfonamide

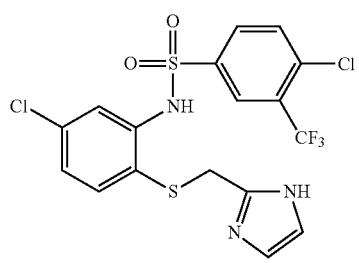 [SMILES: O=S(=O)(Nc1cc(Cl)ccc1SCc1ncc[nH]1)c1ccc(Cl)c(C(F)(F)F)c1]

Following General Procedure A, B, the title compound was prepared from 2-Amino-4-chloro-benzenethiol, 2-chloromethyl-1H-imidazole and 4-chloro-3-trifluoromethyl-benzenesulfonyl chloride.

¹H NMR (300 MHz, CD₃OD) δ 8.06 (d, J=1.76 Hz, 1H), 7.89 (dd, J=2.05, 8.50 Hz, 1H), 7.63-7.78 (m, 2H), 7.45 (d, J=2.05 Hz, 1H), 7.30 (d, J=8.50 Hz, 1H), 7.14 (dd, J=2.34, 8.50 Hz, 1H), 6.73 (s, 1H), 3.83 (s, 2H).

Compound 209

4-chloro-N-{5-chloro-2-[(1H-imidazol-2-ylmethyl)sulfinyl]phenyl}-3-(trifluoromethyl)benzenesulfonamide

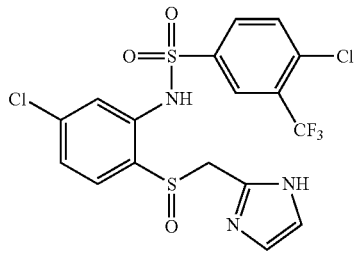 [SMILES: O=S(Cc1ncc[nH]1)c1ccc(Cl)cc1NS(=O)(=O)c1ccc(Cl)c(C(F)(F)F)c1]

Following General Procedure C, the title compound was prepared from 4-chloro-N-{5-chloro-2-[(1H-imidazol-2-ylmethyl)thio]phenyl}-3-(trifluoromethyl)benzenesulfonamide.

¹H NMR (600 MHz, CD₃OD) δ 8.18 (d, 1H), 8.03 (dd, J=1.91, 8.36 Hz, 1H), 7.72 (d, J=8.22 Hz, 1H), 7.41 (s, 2H), 7.20 (d, J=1.76 Hz, 1H), 7.06 (d, J=8.51 Hz, 1H), 6.84 (dd, J=1.91, 8.36 Hz, 1H), 4.76 (d, J=8.22 Hz, 2H).

Compound 210

4-chloro-N-{5-chloro-2-[(1H-imidazol-2-ylmethyl)sulfonyl]phenyl}-3-(trifluoromethyl)benzenesulfonamide

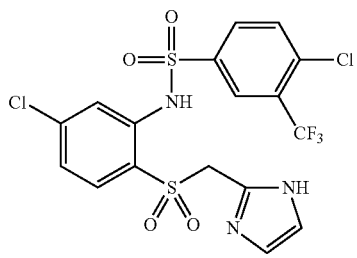 [SMILES: O=S(=O)(Cc1ncc[nH]1)c1ccc(Cl)cc1NS(=O)(=O)c1ccc(Cl)c(C(F)(F)F)c1]

¹H NMR (600 MHz, acetone-d6) δ 8.33 (d, J=1.76 Hz, 1H), 8.18 (dd, J=1.76, 8.22 Hz, 1H), 7.70 (d, J=8.22 Hz, 1H), 7.66 (d, J=8.51 Hz, 1H), 7.58 (d, J=2.05 Hz, 1H), 7.10 (s, 2H), 6.72 (dd, J=1.91, 8.36 Hz, 1H), 4.86 (s, 2H).

Compound 211

4-chloro-N-{5-chloro-2-[(1H-imidazol-4-ylmethyl)thio]phenyl}-3-(trifluoromethyl)benzenesulfonamide

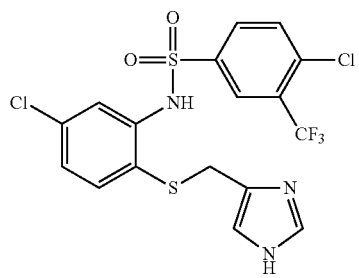 [SMILES: O=S(=O)(Nc1cc(Cl)ccc1SCc1c[nH]cn1)c1ccc(Cl)c(C(F)(F)F)c1]

Following General Procedure A, B, the title compound was prepared from 2-Amino-4-chloro-benzenethiol, 4-chloromethyl-1H-imidazole hydrogen chloride and 4-chloro-3-trifluoromethyl-benzenesulfonyl chloride.

¹H NMR (600 MHz, acetone-d6) δ 8.07 (d, J=2.05 Hz, 1H), 7.89-7.97 (m, 2H), 7.77 (d, J=8.51 Hz, 1H), 7.61 (d, J=2.35 Hz, 1H), 7.56 (d, J=8.22 Hz, 1H), 7.16 (dd, J=2.35, 8.22 Hz, 1H), 7.02 (s, 1H), 3.87 (s, 2H).

Compound 212

4-chloro-N-{5-chloro-2-[(1H-imidazol-4-ylmethyl)sulfinyl]phenyl}-3-(trifluoromethyl)benzenesulfonamide

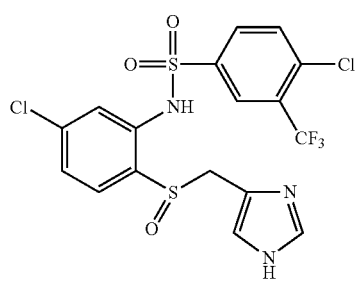 [SMILES: O=S(Cc1c[nH]cn1)c1ccc(Cl)cc1NS(=O)(=O)c1ccc(Cl)c(C(F)(F)F)c1]

Following General Procedure C, the title compound was prepared from 4-chloro-N-{5-chloro-2-[(1H-imidazol-4-ylmethyl)thio]phenyl}-3-(trifluoromethyl)benzenesulfonamide.

¹H NMR (600 MHz, acetone-d6) δ 8.26 (br. s., 1H), 8.17 (s, 1H), 8.08 (dd, J=1.76, 8.51 Hz, 1H), 7.82 (d, J=8.51 Hz, 1H), 7.47 (br. s., 1H), 7.38 (d, J=8.51 Hz, 1H), 7.30 (s, 1H), 7.09 (d, J=7.92 Hz, 1H), 4.48 (dd, J=2.35, 13.79 Hz, 1H), 4.20 (d, J=14.09 Hz, 1H).

Compound 213

N-{5-chloro-2-[(1H-imidazol-2-ylmethyl)thio]phenyl}-1-benzofuran-2-sulfonamide

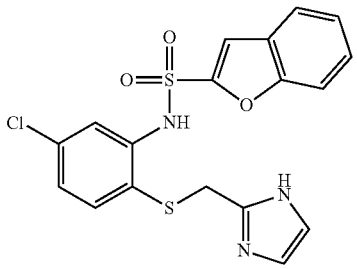 [SMILES: O=S(=O)(Nc1cc(Cl)ccc1SCc1ncc[nH]1)c1cc2ccccc2o1]

Following General Procedure A, B, the title compound was prepared from 2-Amino-4-chloro-benzenethiol, 2-chloromethyl-1H-imidazole and 1-benzofuran-2-sulfonyl chloride.

$^1$H NMR (600 MHz, acetone-d6) δ 7.74 (d, J=7.92 Hz, 1H), 7.64 (d, J=2.35 Hz, 1H), 7.61 (d, J=8.51 Hz, 1H), 7.53 (d, J=8.51 Hz, 1H), 7.46 (td, J=1.17, 7.78 Hz, 1H), 7.41 (s, 1H), 7.33 (t, J=7.48 Hz, 1H), 7.17 (s, 2H), 7.09 (dd, J=2.35, 8.22 Hz, 1H), 4.10 (s, 2H).

Compound 214

N-{5-chloro-2-[(1H-imidazol-2-ylmethyl)sulfinyl]phenyl}-1-benzofuran-2-sulfonamide

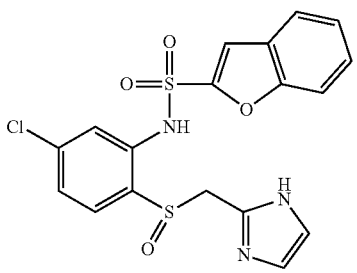 [SMILES: O=S(Cc1ncc[nH]1)c1ccc(Cl)cc1NS(=O)(=O)c1cc2ccccc2o1]

Following General Procedure C, the title compound was prepared from N-{5-chloro-2-[(1H-imidazol-2-ylmethyl)thio]phenyl}-1-benzofuran-2-sulfonamide $^1$H NMR (300 MHz, DMSO-d6) δ 7.68 (d, J=7.62 Hz, 1H), 7.51-7.61 (m, 3H), 7.41 (d, J=2.05 Hz, 1H), 7.32-7.40 (m, 1H), 7.21-7.32 (m, 1H), 7.17 (s, 1H), 6.92 (d, J=8.50 Hz, 1H), 6.74 (dd, J=1.90, 8.06 Hz, 1H), 4.89 (d, J=14.07 Hz, 1H), 4.56 (d, J=13.77 Hz, 1H).

Compound 215

N-{5-chloro-2-[(1H-imidazol-2-ylmethyl)sulfonyl]phenyl}-1-benzofuran-2-sulfonamide

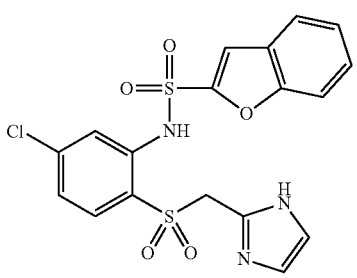 [SMILES: O=S(=O)(Cc1ncc[nH]1)c1ccc(Cl)cc1NS(=O)(=O)c1cc2ccccc2o1]

Following General Procedure D, the title compound was prepared from N-{5-chloro-2-[(1H-imidazol-2-ylmethyl)thio]phenyl}-1-benzofuran-2-sulfonamide $^1$H NMR (300 MHz, acetone-d6) δ 7.69-7.79 (m, 3H), 7.66 (s, 2H), 7.46-7.54 (m, 1H), 7.41 (s, 2H), 7.24-7.34 (m, 1H), 6.88 (dd, J=1.90, 8.64 Hz, 1H), 5.62 (s, 2H).

Compound 216

N-{5-chloro-2-[(1H-imidazol-4-ylmethyl)sulfinyl]phenyl}-1-benzofuran-2-sulfonamide

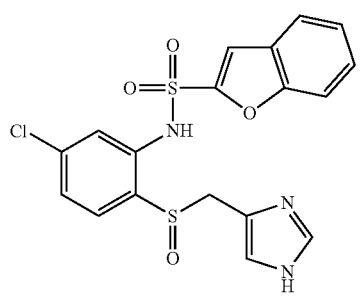 [SMILES: O=S(Cc1c[nH]cn1)c1ccc(Cl)cc1NS(=O)(=O)c1cc2ccccc2o1]

Following General Procedure C, the title compound was prepared from N-{5-chloro-2-[(1H-imidazol-4-ylmethyl)thio]phenyl}-1-benzofuran-2-sulfonamide.

$^1$H NMR (300 MHz, acetone-d6) δ 8.34 (s, 1H), 7.75 (d, J=7.91 Hz, 1H), 7.60 (d, J=2.05 Hz, 1H), 7.47-7.56 (m, 2H), 7.43 (t, J=7.33 Hz, 1H), 7.24-7.38 (m, 3H), 7.03 (d, J=10.55 Hz, 1H), 4.58 (d, J=14.36 Hz, 1H), 4.24 (d, J=13.77 Hz, 1H)

Compound 217

N-{5-chloro-2-[(1H-imidazol-4-ylmethyl)sulfonyl]phenyl}-1-benzofuran-2-sulfonamide

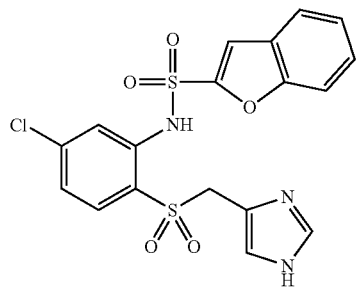 [SMILES: O=S(=O)(Cc1c[nH]cn1)c1ccc(Cl)cc1NS(=O)(=O)c1cc2ccccc2o1]

Following General Procedure D, the title compound was prepared from N-{5-chloro-2-[(1H-imidazol-4-ylmethyl)thio]phenyl}-1-benzofuran-2-sulfonamide $^1$H NMR (300 MHz, acetone-d6) δ 8.20 (br. s., 1H), 7.66-7.81 (m, 3H), 7.35-7.53 (m, 4H), 7.23-7.35 (m, 1H), 6.95 (dd, J=2.05, 8.50 Hz, 1H), 4.87 (s, 2H).

Compound 218

N-[2-({2-[(aminocarbonyl)amino]ethyl}thio)-5-chlorophenyl]-1-benzofuran-2-sulfonamide

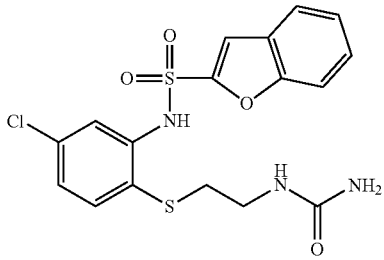 [SMILES: NC(=O)NCCSc1ccc(Cl)cc1NS(=O)(=O)c1cc2ccccc2o1]

Following General Procedure A, B, the title compound was prepared from 2-Amino-4-chloro-benzenethiol, (2-chloroethyl)-urea and 1-benzofuran-2-sulfonyl chloride.

1H NMR (300 MHz, acetone-d6) δ 7.77 (d, J=7.91 Hz, 1H), 7.45-7.66 (m, 5H), 7.31-7.42 (m, 1H), 7.22 (dd, J=2.05, 8.50 Hz, 1H), 6.02 (br. s., 1H), 5.40 (br. s., 2H), 3.14 (q, J=6.15 Hz, 2H), 2.84 (t, J=6.45 Hz, 2H).

Compound 219

N-[2-({2-[(aminocarbonyl)amino]ethyl}sulfinyl)-5-chlorophenyl]-1-benzofuran-2-sulfonamide

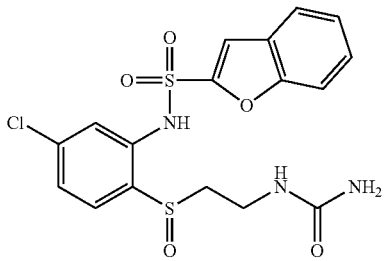 [SMILES: NC(=O)NCCS(=O)c1ccc(Cl)cc1NS(=O)(=O)c1cc2ccccc2o1]

Following General Procedure C, the title compound was prepared from N-[2-({2-[(aminocarbonyl)amino]ethyl}thio)-5-chlorophenyl]-1-benzofuran-2-sulfonamide $^1$H NMR (600 MHz, CD$_3$OD) δ 7.68 (d, J=7.92 Hz, 1H), 7.54 (dd, J=5.28, 8.22 Hz, 2H), 7.42 (t, J=7.92 Hz, 1H), 7.37 (s, 1H), 7.27-7.34 (m, 2H), 7.10 (d, J=6.75 Hz, 1H), 3.58-3.67 (m, 1H), 3.44-3.53 (m, 1H), 3.36-3.43 (m, 1H), 2.98-3.09 (m, 1H).

Compound 220

N-[2-({2-[(aminocarbonyl)amino]ethyl}sulfonyl)-5-chlorophenyl]-1-benzofuran-2-sulfonamide

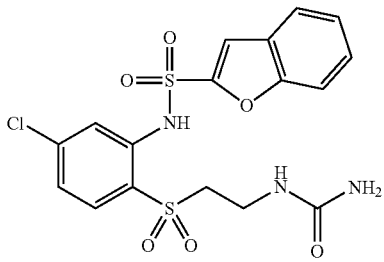 [SMILES: NC(=O)NCCS(=O)(=O)c1ccc(Cl)cc1NS(=O)(=O)c1cc2ccccc2o1]

Following General Procedure D, the title compound was prepared from N-[2-({2-[(aminocarbonyl)amino]ethyl}thio)-5-chlorophenyl]-1-benzofuran-2-sulfonamide.

$^1$H NMR (600 MHz, CD$_3$OD) δ 7.85 (d, J=8.51 Hz, 1H), 7.80 (d, J=2.05 Hz, 1H), 7.77 (d, J=7.92 Hz, 1H), 7.72 (s, 1H), 7.61 (d, J=8.51 Hz, 1H), 7.52 (t, J=7.34 Hz, 1H), 7.31-7.40 (m, 2H), 3.36-3.47 (m, 4H).

Compound 221

N-(5-chloro-2-{[3-(dimethylamino)propyl]thio}phenyl)-1-benzofuran-2-sulfonamide

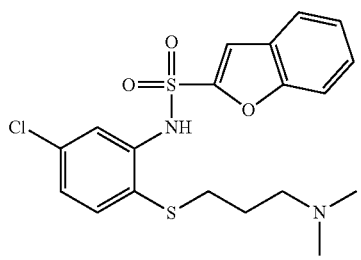 [SMILES: CN(C)CCCSc1ccc(Cl)cc1NS(=O)(=O)c1cc2ccccc2o1]

Following General Procedure A, B, the title compound was prepared from 2-Amino-4-chloro-benzenethiol, (3-chloropropyl)-dimethyl-amine hydrochloride and 1-benzofuran-2-sulfonyl chloride.

$^1$H NMR (600 MHz, acetone-d6) δ 7.62-7.72 (m, 2H), 7.49 (d, J=8.22 Hz, 1H), 7.31-7.38 (m, 2H), 7.25 (t, J=7.48 Hz, 1H), 7.18 (s, 1H), 6.69 (dd, J=2.05, 8.22 Hz, 1H), 3.44 (t, J=5.58 Hz, 2H), 3.30 (s, 3H), 3.12 (s, 3H), 2.97 (t, J=6.31 Hz, 2H), 1.96-2.10 (m, 2H)

Compound 222

N-(5-chloro-2-{[3-(dimethylamino)propyl]sulfinyl}phenyl)-1-benzofuran-2-sulfonamide

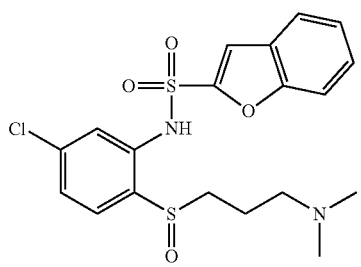 [SMILES: CN(C)CCCS(=O)c1ccc(Cl)cc1NS(=O)(=O)c1cc2ccccc2o1]

Following General Procedure C, the title compound was prepared from N-(5-chloro-2-{[3-(dimethylamino)propyl]thio}phenyl)-1-benzofuran-2-sulfonamide.

$^1$H NMR (600 MHz, acetone-d6) δ 7.67 (d, J=7.92 Hz, 1H), 7.60 (d, J=1.76 Hz, 1H), 7.50 (d, J=8.22 Hz, 1H), 7.41 (d, J=8.22 Hz, 1H), 7.33 (t, J=7.92 Hz, 1H), 7.20-7.28 (m, 2H), 6.83 (dd, J=1.76, 8.22 Hz, 1H), 3.69 (ddd, J=4.99, 8.58, 13.43

Hz, 1H), 3.61 (ddd, J=4.11, 10.71, 14.23 Hz, 1H), 3.48 (ddd, J=5.58, 5.72, 13.35 Hz, 1H), 3.07-3.21 (m, 7H), 2.30-2.42 (m, 1H), 2.16-2.30 (m, 1H).

Compound 223

N-(5-chloro-2-{[3-(dimethylamino)propyl]sulfonyl}phenyl)-1-benzofuran-2-sulfonamide

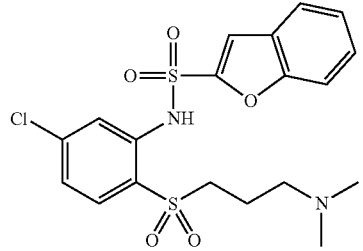 [SMILES: CN(C)CCCS(=O)(=O)c1ccc(Cl)cc1NS(=O)(=O)c1cc2ccccc2o1]

Following General Procedure D, the title compound was prepared from N-(5-chloro-2-{[3-(dimethylamino)propyl]thio}phenyl)-1-benzofuran-2-sulfonamide.

$^1$H NMR (600 MHz, acetone-d6) δ 7.63 (d, J=7.63 Hz, 1H), 7.53 (d, J=1.76 Hz, 1H), 7.48 (d, J=8.22 Hz, 1H), 7.43 (d, J=8.22 Hz, 1H), 7.30 (t, J=7.34 Hz, 1H), 7.21 (t, J=7.21 Hz, 1H), 7.17 (s, 1H), 6.74 (dd, J=2.05, 8.22 Hz, 1H), 3.60-3.69 (m, 2H), 3.36-3.48 (m, 1H), 3.20-3.33 (m, 6H), 2.90-3.01 (br. s., 1H), 2.29-2.42 (m, J=6.75 Hz, 1H), 2.08-2.21 (m, 1H).

Compound 224

N-(5-chloro-2-{[3-(dimethylnitroryl)propyl]sulfonyl}phenyl)-1-benzofuran-2-sulfonamide

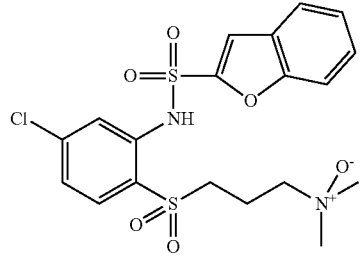 [SMILES: C[N+](C)([O-])CCCS(=O)(=O)c1ccc(Cl)cc1NS(=O)(=O)c1cc2ccccc2o1]

Following General Procedure D, the title compound was prepared from N-(5-chloro-2-{[3-(dimethylamino)propyl]thio}phenyl)-1-benzofuran-2-sulfonamide.

1H NMR (600 MHz, acetone-d6) δ 7.79 (s, 1H), 7.70 (d, J=8.51 Hz, 1H), 7.64 (d, J=7.63 Hz, 1H), 7.52 (d, J=8.51 Hz, 1H), 7.29-7.38 (m, 2H), 7.19-7.28 (m, 1H), 6.74 (d, J=8.51 Hz, 1H), 3.74-3.84 (m, 2H), 3.60-3.65 (m., 2H), 3.26 (s, 6H), 2.27-2.39 (m, 2H).

Compound 225

N-(5-chloro-2-{[(2-oxo-1,3-oxazolidin-5-yl)methyl]sulfinyl}phenyl)-1-benzofuran-2-sulfonamide

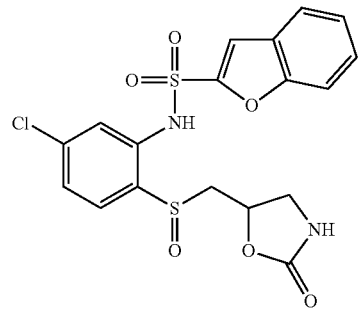 [SMILES: O=C1NCC(CS(=O)c2ccc(Cl)cc2NS(=O)(=O)c2cc3ccccc3o2)O1]

Following General Procedure A, B, C, the title compound was prepared from 2-Amino-4-chloro-benzenethiol, 5-chloromethyl-oxazolidin-2-one and 1-benzofuran-2-sulfonyl chloride.

$^1$H NMR (600 MHz, acetone-d6) δ 7.62 (dd, J=7.92, 11.15 Hz, 1H), 7.44-7.54 (m, 2H), 7.26-7.44 (m, 3H), 7.20 (ddd, J=7.48, 7.63, 11.30 Hz, 1H), 6.87-7.05 (m, 1H), 6.51 (br. s., 1H), 4.69-5.03 (m, 1H), 3.60 (q, J=8.31 Hz, 1H), 3.45-3.55 (m, 1H), 3.23-3.45 (m, 1H), 3.06-3.17 (m, 1H).

Compound 226

N-(5-chloro-2-{[(2-oxo-1,3-oxazolidin-5-yl)methyl]sulfonyl}phenyl)-1-benzofuran-2-sulfonamide

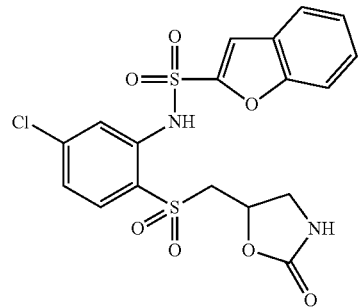 [SMILES: O=C1NCC(CS(=O)(=O)c2ccc(Cl)cc2NS(=O)(=O)c2cc3ccccc3o2)O1]

Following General Procedure D, the title compound was prepared from N-(5-chloro-2-{[(2-oxo-1,3-oxazolidin-5-yl)methyl]thio)phenyl)benzofuran-2-sulfonamide.

$^1$H NMR (600 MHz, acetone-d6) δ 7.81 (d, J=1.76 Hz, 1H), 7.68 (d, J=8.22 Hz, 2H), 7.54 (d, J=8.22 Hz, 1H), 7.29-7.40 (m, 2H), 7.22-7.29 (m, 1H), 6.79 (br. s., 1H), 6.47 (br. s., 1H), 4.94 (dt, J=6.93, 14.01 Hz, 1H), 4.17 (dd, J=5.58, 14.09 Hz, 1H), 3.96 (dd, J=6.90, 14.23 Hz, 1H), 3.65 (t, J=8.66 Hz, 1H), 3.32-3.47 (m, 1H).

Compound 227

N-(5-chloro-2-{[(2,6-dioxo-1,2,3,6-tetrahydropyrimidin-4-yl)methyl]thio}phenyl)-1-benzofuran-2-sulfonamide

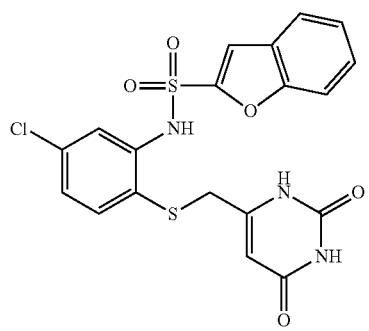 [SMILES: O=c1cc(CSc2ccc(Cl)cc2NS(=O)(=O)c2cc3ccccc3o2)[nH]c(=O)[nH]1]

Following General Procedures A and B the title compound was prepared from 2-amino-4-chloro-benzenethiol, 6-chloromethyl-1H-pyrimidine-2,4-dione and 1-benzofuran-2-sulfonyl chloride.

$^1$H NMR (600 MHz, CD$_3$OD) δ 7.72 (d, J=7.92 Hz, 1H), 7.57 (d, J=8.22 Hz, 1H), 7.45-7.51 (m, 1H), 7.44 (d, J=2.05 Hz, 1H), 7.42 (s, 1H), 7.27-7.37 (m, 2H), 7.09 (br. s., 1H), 5.05 (s, 1H), 3.64 (s, 2H).

Compound 228

N-(5-chloro-2-{[(2,6-dioxo-1,2,3,6-tetrahydropyrimidin-4-yl)methyl]sulfinyl}phenyl)-1-benzofuran-2-sulfonamide

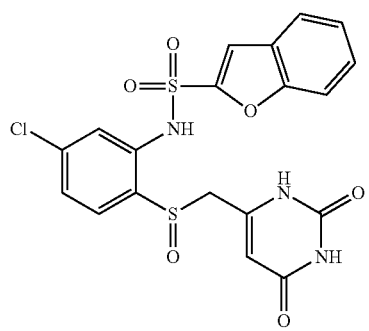 [SMILES: O=c1cc(CS(=O)c2ccc(Cl)cc2NS(=O)(=O)c2cc3ccccc3o2)[nH]c(=O)[nH]1]

Following General Procedure C, the title compound was prepared from N-(5-chloro-2-{[(2,6-dioxo-1,2,3,6-tetrahydropyrimidin-4-yl)methyl]thio}phenyl)-1-benzofuran-2-sulfonamide.

$^1$H NMR (600 MHz, CD$_3$OD) δ 7.68 (d, J=7.92 Hz, 1H), 7.52 (d, J=8.51 Hz, 1H), 7.49 (d, J=8.51 Hz, 1H), 7.41 (t, J=7.92 Hz, 1H), 7.32-7.37 (m, 2H), 7.27-7.32 (m, 1H), 7.09 (d, J=8.22 Hz, 1H), 5.32 (s, 1H), 4.40 (d, J=13.21 Hz, 1H), 3.89 (d, J=12.91 Hz, 1H).

Compound 229

N-(5-chloro-2-{[(2,6-dioxo-1,2,3,6-tetrahydropyrimidin-4-yl)methyl]sulfonyl}phenyl)-1-benzofuran-2-sulfonamide

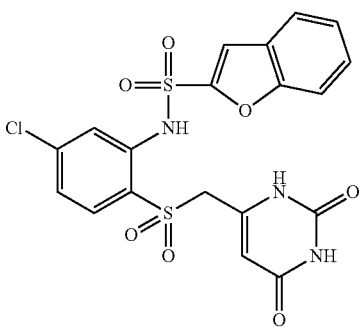 [SMILES: O=c1cc(CS(=O)(=O)c2ccc(Cl)cc2NS(=O)(=O)c2cc3ccccc3o2)[nH]c(=O)[nH]1]

Following General Procedure D, the title compound was prepared from N-(5-chloro-2-{[(2,6-dioxo-1,2,3,6-tetrahydropyrimidin-4-yl)methyl]thio}phenyl)-1-benzofuran-2-sulfonamide.

$^1$H NMR (600 MHz, acetone-d6) δ 10.36 (br. s., 1H), 10.15 (br. s., 1H), 7.78 (br. s., 1H), 7.70 (d, J=8.51 Hz, 1H), 7.65 (d, J=7.92 Hz, 1H), 7.42-7.51 (m, 2H), 7.35 (t, J=7.63 Hz, 1H), 7.26 (t, J=7.48 Hz, 1H), 6.87 (d, J=6.75 Hz, 1H), 5.48 (br. s., 1H), 4.76 (br. s., 2H).

Compound 230

N-{2-[(3-aminopropyl)thio]-5-chlorophenyl}-1-benzofuran-2-sulfonamide

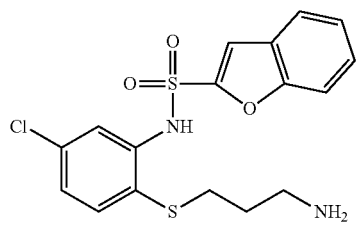 [SMILES: NCCCSc1ccc(Cl)cc1NS(=O)(=O)c1cc2ccccc2o1]

Following General Procedure F, G, the title compound was prepared from 2,2'-dithiobis(5-chloroaniline), 1-benzofuran-2-sulfonyl chloride and 3-bromo-propylamine hydrochloride.

$^1$H NMR (600 MHz, DMSO-d6) δ 8.03 (br. s., 2H), 7.69 (d, J=7.63 Hz, 1H), 7.56 (d, J=8.22 Hz, 1H), 7.37 (t, J=7.78 Hz,

1H), 7.23-7.32 (m, 2H), 7.05-7.20 (m, 2H), 6.60 (br. s., 1H), 3.03 (br. s., 2H), 2.91 (t, J=6.60 Hz, 2H), 1.74-1.92 (m, 2H).

Intermediate 38

(3-Bromo-propyl)-carbamic acid tert-butyl ester

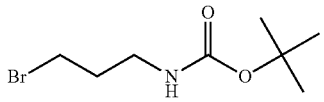

A mixture of 3-bromo-propylamine hydrochloride (523 mg, 2.39 mmol), di-tert-butyl dicarbonate (573 mg, 2.63 mmol), NaOH (1N, 1.5 ml) in MeOH was stirred at rt overnight. The mixture was added water and extracted with EtOAc. The organic layer was washed with brine, dried over $Na_2SO_4$ and concentrated in vacuo. The residue was purified by column chromatography in silica gel.

$^1$H NMR (600 MHz, $CDCl_3$) δ 4.65 (br. s., 1H), 3.38-3.56 (m, 2H), 3.28 (d, J=5.28 Hz, 2H), 1.95-2.14 (m, 2H), 1.45 (br. s., 9H).

Compound 231

N-{2-[(3-aminopropyl)sulfinyl]-5-chlorophenyl}-1-benzofuran-2-sulfonamide

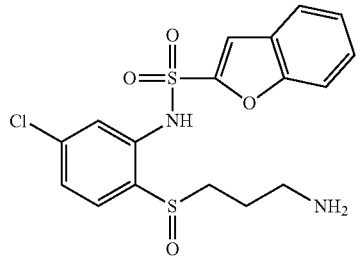 [SMILES: NCCCS(=O)c1ccc(Cl)cc1NS(=O)(=O)c1cc2ccccc2o1]

Following General Procedure F, G, C, E the title compound was prepared from 2,2'-dithiobis(5-chloroaniline), 1-benzofuran-2-sulfonyl chloride and (3-bromo-propyl)-carbamic acid tert-butyl ester.

$^1$H NMR (600 MHz, acetone-d6) δ 7.78 (d, J=7.92 Hz, 1H), 7.63 (d, J=8.51 Hz, 1H), 7.54-7.59 (m, 2H), 7.46-7.52 (m, 2H), 7.32-7.40 (m, 1H), 7.21 (d, J=7.92 Hz, 1H), 4.03-4.14 (m, 1H), 3.88-4.00 (m, 1H), 3.35 (ddd, J=6.97, 7.19, 13.72 Hz, 1H), 3.10 (ddd, J=6.46, 6.60, 13.35 Hz, 1H), 2.16-2.36 (m, 2H).

Compound 232

N-{2-[(3-aminopropyl)sulfonyl]-5-chlorophenyl}-1-benzofuran-2-sulfonamide

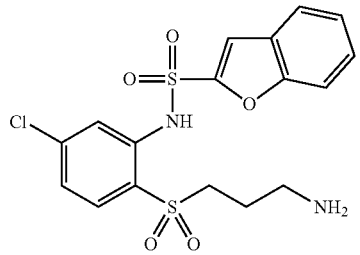 [SMILES: NCCCS(=O)(=O)c1ccc(Cl)cc1NS(=O)(=O)c1cc2ccccc2o1]

Following General Procedure F, G, D, E the title compound was prepared from 2,2'-dithiobis(5-chloroaniline), 1-benzofuran-2-sulfonyl chloride and (3-bromo-propyl)-carbamic acid tert-butyl ester.

$^1$H NMR (600 MHz, $CD_3OD$) δ 7.88 (d, J=8.51 Hz, 1H), 7.79 (d, J=7.92 Hz, 1H), 7.72 (d, J=1.76 Hz, 1H), 7.68 (s, 1H), 7.61 (d, J=8.51 Hz, 1H), 7.53 (t, J=7.78 Hz, 1H), 7.40 (t, J=7.63 Hz, 1H), 7.34 (d, J=8.51 Hz, 1H), 3.47 (t, J=7.04 Hz, 2H), 3.02 (t, J=7.63 Hz, 2H), 2.06 (quin, 2H).

Compound 233

N-(5-chloro-2-{[(2,4-dioxo-1,2,3,4-tetrahydropyrimidin-5-yl)methyl]sulfinyl}phenyl)-1-benzofuran-2-sulfonamide

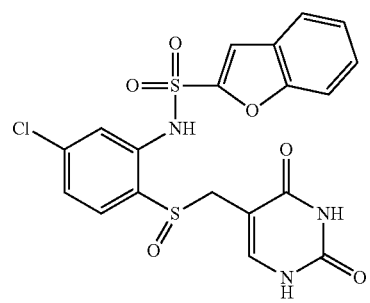 [SMILES: O=c1[nH]cc(CS(=O)c2ccc(Cl)cc2NS(=O)(=O)c2cc3ccccc3o2)c(=O)[nH]1]

Following General Procedure A, B, C, the title compound was prepared from 2-amino-4-chloro-benzenethiol, 5-(chloromethyl)uracil and 1-benzofuran-2-sulfonyl chloride.

$^1$H NMR (600 MHz, DMSO-d6) δ 10.99 (s, 1H), 10.75 (br. s., 1H), 7.61 (d, J=7.63 Hz, 1H), 7.51 (d, J=8.22 Hz, 1H), 7.32 (t, J=7.48 Hz, 1H), 7.16-7.27 (m, 3H), 7.01-7.10 (m, 1H), 6.86 (br. s., 1H), 6.64-6.79 (m, 1H), 4.02 (d, J=13.21 Hz, 1H), 3.85 (d, J=13.21 Hz, 1H).

Compound 234

N-(5-chloro-2-{[(2,4-dioxo-1,2,3,4-tetrahydropyrimidin-5-yl)methyl]sulfonyl}phenyl)-1-benzofuran-2-sulfonamide

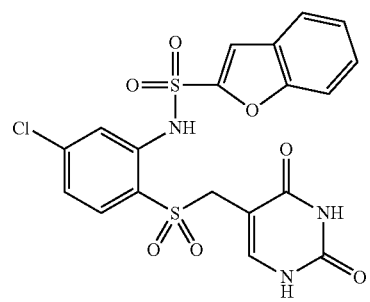 [SMILES: O=c1[nH]cc(CS(=O)(=O)c2ccc(Cl)cc2NS(=O)(=O)c2cc3ccccc3o2)c(=O)[nH]1]

Following General Procedure A, B, D, the title compound was prepared from 2-amino-4-chloro-benzenethiol, 5-(chloromethyl)uracil and 1-benzofuran-2-sulfonyl chloride.

$^1$H NMR (600 MHz, $CD_3OD$) δ 7.69 (d, J=2.05 Hz, 1H), 7.63-7.67 (m, 2H), 7.44 (t, J=8.36 Hz, 1H), 7.32-7.39 (m, 2H), 7.27 (t, J=7.04 Hz, 1H), 7.18 (s, 1H), 6.82 (d, J=7.92 Hz, 1H), 4.70 (s, 2H).

Compound 235

N-{4-[({2-[(1-benzofuran-2-ylsulfonyl)amino]-4-chlorophenyl}thio)methyl]-1,3-thiazol-2-yl}acetamide

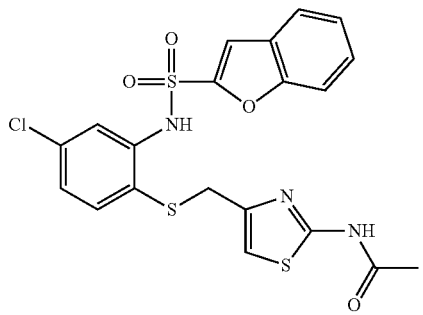 [SMILES: CC(=O)Nc1nc(CSc2ccc(Cl)cc2NS(=O)(=O)c2cc3ccccc3o2)cs1]

Following General Procedure A, B, the title compound was prepared from 2-amino-4-chloro-benzenethiol, N-(4-Chloromethyl-thiazol-2-yl)-acetamide and 1-benzofuran-2-sulfonyl chloride.

1H NMR (600 MHz, CD$_3$OD) δ 7.70 (d, J=7.92 Hz, 1H), 7.49-7.54 (m, 2H), 7.45-7.50 (m, 1H), 7.42 (s, 1H), 7.29-7.36 (m, 2H), 7.11 (dd, J=2.20, 8.36 Hz, 1H), 6.45 (s, 1H), 3.84 (s, 2H), 2.21 (s, 3H).

Compound 236

N-{4-[({2-[(1-benzofuran-2-ylsulfonyl)amino]-4-chlorophenyl}sulfinyl)methyl]-1,3-thiazol-2-yl}acetamide

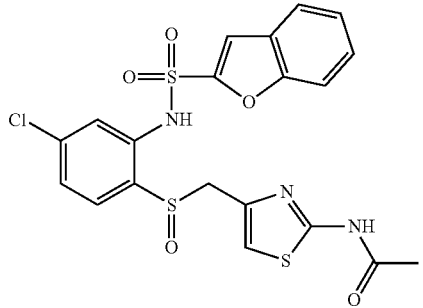 [SMILES: CC(=O)Nc1nc(CS(=O)c2ccc(Cl)cc2NS(=O)(=O)c2cc3ccccc3o2)cs1]

Following General Procedure C, the title compound was prepared from N-{4-[({2-[(1-benzofuran-2-ylsulfonyl)amino]-4-chlorophenyl}thio)methyl]-1,3-thiazol-2-yl}acetamide.

$^1$H NMR (600 MHz, acetone-d6) δ 10.93 (br. s., 1H), 7.83 (d, J=7.92 Hz, 1H), 7.80 (s, 1H), 7.62-7.67 (m, 2H), 7.49-7.58 (m, 1H), 7.39 (t, J=7.48 Hz, 1H), 7.08-7.22 (m, 2H), 6.74 (s, 1H), 4.29-4.46 (m, 2H), 2.23 (s, 3H).

Compound 237

N-{4-[({2-[(1-benzofuran-2-ylsulfonyl)amino]-4-chlorophenyl}sulfonyl)methyl]-1,3-thiazol-2-yl}acetamide

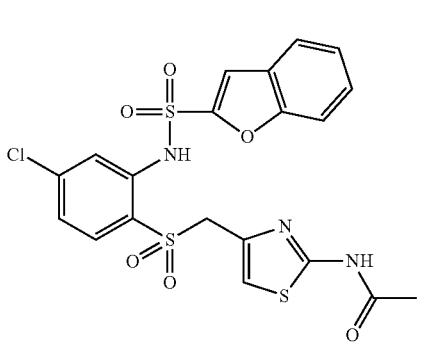 [SMILES: CC(=O)Nc1nc(CS(=O)(=O)c2ccc(Cl)cc2NS(=O)(=O)c2cc3ccccc3o2)cs1]

Following General Procedure D, the title compound was prepared from N-{4-[({2-[(1-benzofuran-2-ylsulfonyl)amino]-4-chlorophenyl}thio)methyl]-1,3-thiazol-2-yl}acetamide.

1H NMR (600 MHz, acetone-d6) δ 10.90 (br. s., 1H), 9.65 (br. s., 1H), 7.81 (d, J=7.34 Hz, 2H), 7.75 (d, J=2.05 Hz, 1H), 7.65 (d, J=8.51 Hz, 1H), 7.60 (s., 1H), 7.51 (s., 1H), 7.38 (t, J=7.19 Hz, 1H), 7.27 (s., 1H), 6.95 (s, 1H), 4.67 (br. s., 2H), 2.21 (s, 3H).

Compound 238

N-(5-chloro-2-{[2-(3,5-dimethyl-1H-pyrazol-4-yl)ethyl]sulfonyl}phenyl)-1-benzofuran-2-sulfonamide

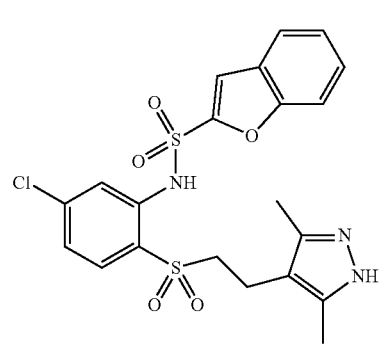 [SMILES: Cc1n[nH]c(C)c1CCS(=O)(=O)c1ccc(Cl)cc1NS(=O)(=O)c1cc2ccccc2o1]

Following General Procedure D, the title compound (53 mg, 38%) was prepared from N-(5-chloro-2-{[2-(3,5-dimethyl-1H-pyrazol-4-yl)ethyl]thio}phenyl)-1-benzofuran-2-sulfonamide.

1H NMR (600 MHz, CD$_3$OD) δ 7.79 (d, J=1.76 Hz, 1H), 7.76 (d, J=8.51 Hz, 1H), 7.67 (d, J=7.92 Hz, 1H), 7.57 (d, J=0.59 Hz, 1H), 7.37 (ddd, J=1.17, 7.19, 8.36 Hz, 1H), 7.26-

7.31 (m, 1H), 7.20-7.24 (m, 1H), 7.15 (dd, J=1.76, 8.51 Hz, 1H), 3.40-3.50 (m, 2H), 2.60-2.72 (m, 2H), 2.01 (s, 6H).

Compound 239

N-{5-fluoro-2-[(3-nitrobenzyl)sulfinyl]phenyl}-1-benzofuran-2-sulfonamide

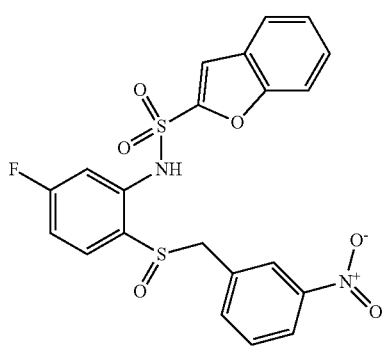 [SMILES: O=[N+]([O-])c1cccc(CS(=O)c2ccc(F)cc2NS(=O)(=O)c2cc3ccccc3o2)c1]

Following General Procedure C, the title compound (174 mg, 79%) was prepared from N-(5-fluoro-2-((3-nitrobenzyl)thio)phenyl)benzofuran-2-sulfonamide.

1H NMR (600 MHz, CD$_3$OD) δ 7.98 (d, J=9.10 Hz, 1H), 7.67 (d, J=7.63 Hz, 1H), 7.49 (br. s., 1H), 7.40 (s, 1H), 7.35 (d, J=8.51 Hz, 1H), 7.26-7.32 (m, 2H), 7.21-7.26 (m, 2H), 7.12 (d, J=7.63 Hz, 1H), 6.74-6.80 (m, 1H), 6.40 (t, J=7.34 Hz, 1H), 4.52-4.64 (m, 2H).

Compound 240

N-{2-[(3-aminobenzyl)sulfinyl]-5-chlorophenyl}-2,4-difluorobenzenesulfonamide

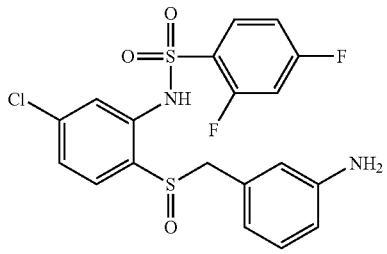 [SMILES: Nc1cccc(CS(=O)c2ccc(Cl)cc2NS(=O)(=O)c2ccc(F)cc2F)c1]

Following General Procedure A, B, C, and K, the title compound was prepared from 2-amino-4-chloro-benzenethiol, 1-bromomethyl-3-nitro-benzene, and 2,4-difluoro-benzenesulfonyl chloride.

$^1$H NMR (600 MHz, METHANOL-d$_4$) δ 7.95 (d, J=6.16 Hz, 1H), 7.19-7.30 (m, 3H), 7.11-7.19 (m, 2H), 7.00 (t, J=7.78 Hz, 1H), 6.72 (dd, J=1.47, 7.92 Hz, 1H), 6.61 (s, 1H), 6.44 (d, J=7.04 Hz, 1H), 4.34 (d, J=12.91 Hz, 1H), 4.07 (d, J=12.90 Hz, 1H).

Compound 241

N-[5-chloro-2-(methylsulfonyl)phenyl]-4-isopropyl-benzenesulfonamide

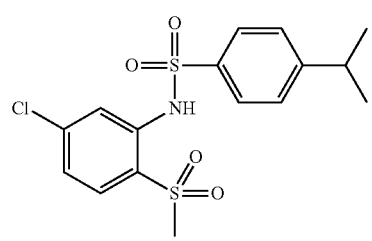 [SMILES: CC(C)c1ccc(S(=O)(=O)Nc2cc(Cl)ccc2S(C)(=O)=O)cc1]

Following General Procedure B and D, the title compound was prepared from 5-chloro-2-(methylthio)aniline and 4-isopropyl-benzenesulfonyl chloride.

$^1$H NMR (600 MHz, CHLOROFORM-d) δ 9.13 (s, 1H), 7.80-7.85 (m, 2H), 7.71-7.76 (m, 2H), 7.34-7.39 (m, 2H), 7.16 (dd, J=2.05, 8.51 Hz, 1H), 2.95 (spt, J=6.90 Hz, 1H), 2.81 (s, 3H), 1.22 (d, J=7.04 Hz, 6H).

Compound 242

N-(5-methoxy-2-((3-nitrobenzyl)thio)phenyl)benzofuran-2-sulfonamide

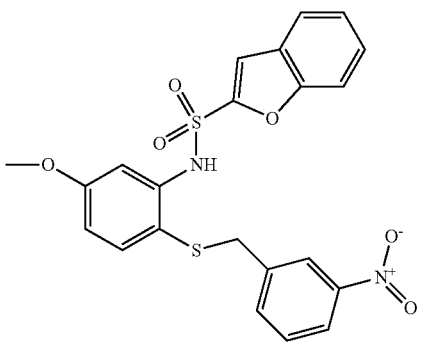 [SMILES: COc1ccc(SCc2cccc([N+](=O)[O-])c2)c(NS(=O)(=O)c2cc3ccccc3o2)c1]

Following General Procedure B, the title compound (406 mg, 56%) was prepared from 5-methoxy-2-((3-nitrobenzyl)thio)aniline (450 mg, 1.552 mmol) and benzofuran-2-sulfonyl chloride (335 mg, 1.552 mmol) in pyridine (5 ml).

1H NMR (600 MHz, CD$_3$OD) δ 8.53 (dd, J=1.76, 5.87 Hz, 1H), 7.96 (ddd, J=1.03, 2.27, 8.14 Hz, 1H), 7.70 (d, J=7.92 Hz, 1H), 7.63 (t, J=1.91 Hz, 1H), 7.51 (s, 1H), 7.42 (dd, J=1.17, 8.22 Hz, 1H), 7.24-7.37 (m, 3H), 7.11 (s, 1H), 7.00 (s, 1H), 6.55 (dd, J=2.79, 8.66 Hz, 1H), 3.83 (s, 2H), 3.71 (s, 3H).

Compound 243

N-{5-chloro-2-[(1H-pyrazol-3-ylmethyl)sulfonyl]phenyl}-1-benzofuran-2-sulfonamide

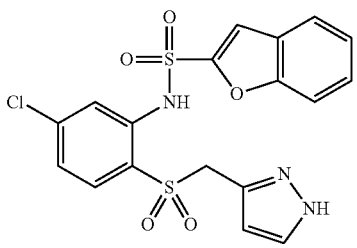 [SMILES: O=S(=O)(Cc1cc[nH]n1)c1ccc(Cl)cc1NS(=O)(=O)c1cc2ccccc2o1]

Following General Procedure D and E, the title compound was prepared from tert-butyl 3-[({2-[(1-benzofuran-2-ylsulfonyl)amino]-4-chlorophenyl}thio)methyl]-1H-pyrazole-1-carboxylate (Compound 22).

$^1$H NMR (600 MHz, CD$_3$OD) δ 7.71 (d, J=1.76 Hz, 1H), 7.66 (d, J=7.92 Hz, 1H), 7.51 (d, J=8.51 Hz, 1H), 7.31-7.43 (m, 4H), 7.24-7.29 (m, 1H), 6.79 (d, J=7.04 Hz, 1H), 5.82 (br. s., 1H), 4.99 (br. s., 2H).

Compound 244

N-{2-[(3-aminobenzyl)thio]-5-chlorophenyl}-4-chloro-2-fluorobenzenesulfonamide

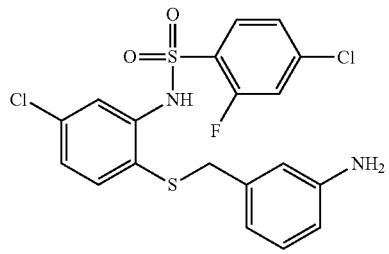

Following General Procedure A, B, and K, the title compound was prepared from 2-amino-4-chloro-benzenethiol, 1-bromomethyl-3-nitro-benzene, and 4-chloro-2-fluoro-benzenesulfonyl chloride.

$^1$H NMR (600 MHz, CHLOROFORM-d) δ 7.84 (t, J=8.22 Hz, 1H), 7.47 (d, J=2.05 Hz, 1H), 7.25 (dt, J=1.03, 8.51 Hz, 1H), 7.17-7.22 (m, 2H), 7.04 (t, J=7.63 Hz, 1H), 6.93 (dd, J=2.35, 8.22 Hz, 1H), 6.58 (dt, J=1.17, 7.92 Hz, 1H), 6.40-6.45 (m, 2H), 3.72 (s, 2H).

Intermediate 39

2-(benzylthio)-5-chloroaniline

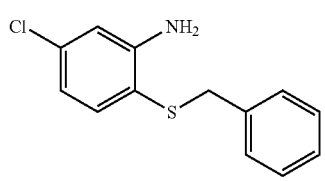 [SMILES: Nc1cc(Cl)ccc1SCc1ccccc1]

Following General Procedure A, the title compound (560 mg, 33%) was prepared from 2-amino-4-chlorobenzenethiol (1.08 g, 6.77 mmol), (bromomethyl)benzene (0.8 ml, 6.77 mmol) and K$_2$CO$_3$ (3.18 g, 23.04 mmol) in DMF (20 ml).

$^1$H NMR (600 MHz, CDCl$_3$) δ 7.18-7.27 (m, 3H), 7.09-7.14 (m, 2H), 7.07 (d, J=8.22 Hz, 1H), 6.69 (d, J=2.35 Hz, 1H), 6.57 (dd, J=2.35, 8.22 Hz, 1H), 4.38 (br. s., 2H), 3.85 (s, 2H).

Compound 245

N-[2-(benzylsulfanyl)-5-chlorophenyl]-4-chloro-3-(trifluoromethyl)benzenesulfonamide

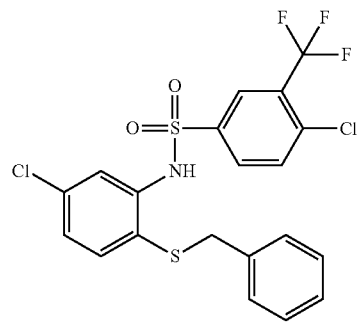 [SMILES: O=S(=O)(Nc1cc(Cl)ccc1SCc1ccccc1)c1ccc(Cl)c(C(F)(F)F)c1]

Following General Procedure B, the title compound (890 mg, 80%) was prepared from 2-(benzylthio)-5-chloroaniline (560 mg, 2.25 mmol) and 4-chloro-3-(trifluoromethyl)benzene-1-sulfonyl chloride (628 mg, 2.25 mmol).

$^1$H NMR (600 MHz, CD$_3$OD) δ 8.08 (d, J=2.35 Hz, 1H), 7.90 (dd, J=2.20, 8.36 Hz, 1H), 7.76 (s, 1H), 7.44 (d, J=2.05

Hz, 1H), 7.18-7.28 (m, 3H), 7.09-7.17 (m, 2H), 7.06 (dd, J=1.61, 7.78 Hz, 2H), 3.84 (s, 2H).

Compound 246

N-[2-(benzylsulfinyl)-5-chlorophenyl]-4-chloro-3-(trifluoromethyl)benzenesulfonamide

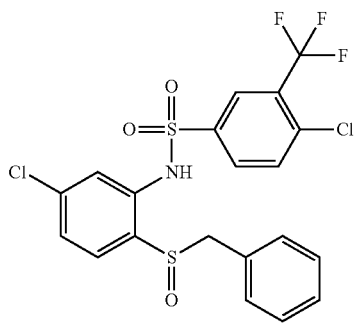 [SMILES: O=S(Cc1ccccc1)c1ccc(Cl)cc1NS(=O)(=O)c1ccc(Cl)c(C(F)(F)F)c1]

Following General Procedure C, the title compound (246 mg, 75%) was prepared from N-[2-(benzylsulfanyl)-5-chlorophenyl]-4-chloro-3-(trifluoromethyl)benzenesulfonamide (316 mg, 0.64 mmol).

$^1$H NMR (600 MHz, CDCL$_3$) δ 8.25 (d, J=2.35 Hz, 1H), 8.04 (dd, J=2.05, 8.51 Hz, 1H), 7.69 (s, 1H), 7.53 (s, 1H), 7.33-7.38 (m, 1H), 7.25-7.31 (m, 2H), 6.90-7.00 (m, 3H), 6.70 (d, J=8.22 Hz, 1H), 4.30 (d, J=12.62 Hz, 1H), 4.21 (d, J=12.62 Hz, 1H).

Compound 247

N-[2-(benzylsulfonyl)-5-chlorophenyl]-4-chloro-3-(trifluoromethyl)benzenesulfonamide

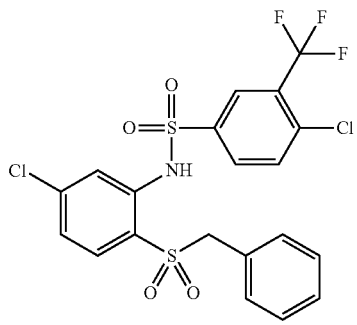 [SMILES: O=S(=O)(Cc1ccccc1)c1ccc(Cl)cc1NS(=O)(=O)c1ccc(Cl)c(C(F)(F)F)c1]

Following General Procedure D, the title compound (286 mg, 66%) was prepared from N-[2-(benzylsulfanyl)-5-chlorophenyl]-4-chloro-3-(trifluoromethyl)benzenesulfonamide (409 mg, 0.83 mmol).

$^1$H NMR (600 MHz, acetone-d6) δ 9.23 (br. s., 1H), 8.30 (d, J=2.05 Hz, 1H), 8.21 (dd, J=2.20, 8.36 Hz, 1H), 7.97 (d, J=8.51 Hz, 1H), 7.54-7.63 (m, 2H), 7.25-7.41 (m, 4H), 7.15 (d, J=7.34 Hz, 2H), 4.63 (s, 2H).

Intermediate 40

4-Amino-3-mercaptobenzonitrile

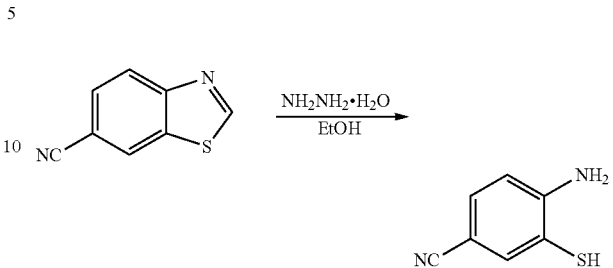

A mixture of 6-cyanobenzothiazole (532 mg, 3.33 mmol) and hydrazine monohydrate (1.2 ml, 24.76 mmol) in EtOH (10 ml) was heated at 80° C. under N$_2$ atmosphere for 2 hours. The solvent was evaporated, H$_2$O was added to the residue, and the solution was adjusted to pH~5-7 with AcOH. The resulting yellow precipitate was filtered and washed with H$_2$O, dried under high vacuum to yield the title compound as yellow solid (486 mg, 97%).

$^1$H NMR (600 MHz, CD$_3$OD) δ 7.57 (d, J=1.76 Hz, 1H), 7.29 (dd, J=1.91, 8.36 Hz, 1H), 6.76 (d, J=8.51 Hz, 1H).

Intermediate 41

4-Amino-3-(benzylthio)benzonitrile

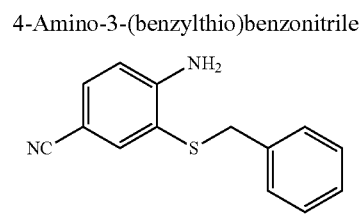

Following General Procedure A, the title compound (615 mg, 79%) was prepared from 4-amino-3-mercaptobenzonitrile (486 mg, 3.24 mmol), (bromomethyl)benzene (0.38 ml, 3.24 mmol) and K$_2$CO$_3$ (2.2 g, 16.20 mmol) in DMF (10 ml).

$^1$H NMR (600 MHz, CD$_3$OD) δ 7.30 (dd, J=1.91, 8.36 Hz, 1H), 7.25 (d, J=1.76 Hz, 1H), 7.19-7.22 (m, 3H), 7.10 (dd, J=1.61, 8.07 Hz, 2H), 6.74 (d, J=8.51 Hz, 1H), 3.91 (s, 2H).

Compound 248

N-[2-(benzylsulfanyl)-4-cyanophenyl]-1-benzofuran-2-sulfonamide

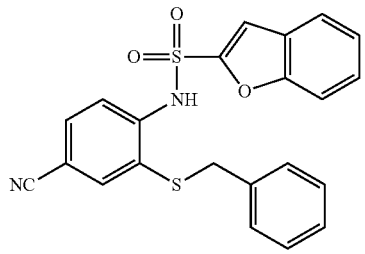 [SMILES: N#Cc1ccc(NS(=O)(=O)c2cc3ccccc3o2)c(SCc2ccccc2)c1]

Following General Procedure B, the title compound (752 mg, 47%) was prepared from 4-amino-3-(benzylthio)benzonitrile (430 mg, 1.80 mmol), benzofuran-2-sulfonyl chloride (391 mg, 1.80 mmol), and DMAP (cat.) in pyridine (3 ml).

¹H NMR (600 MHz, CDCl₃) δ 8.37 (s, 1H), 7.73 (d, J=8.51 Hz, 1H), 7.67 (d, J=7.92 Hz, 1H), 7.42-7.56 (m, 4H), 7.39 (d, J=2.05 Hz, 1H), 7.29-7.35 (m, 1H), 7.17-7.18 (m, 3H), 6.93 (dd, J=2.49, 7.19 Hz, 2H), 3.84 (s, 2H).

Compound 249

N-[2-(benzylsulfinyl)-4-cyanophenyl]-1-benzofuran-2-sulfonamide

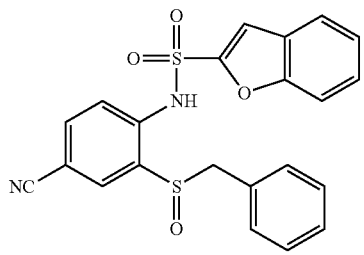 [SMILES: N#Cc1ccc(NS(=O)(=O)c2cc3ccccc3o2)c(S(=O)Cc2ccccc2)c1]

Following General Procedure C, the title compound (98 mg, 61%) was prepared from N-[2-(benzylsulfanyl)-4-cyanophenyl]-1-benzofuran-2-sulfonamide (156 mg, 0.37 mmol).

¹H NMR (600 MHz, CD₃OD) δ 7.62-7.70 (m, 1H), 7.56 (d, J=8.51 Hz, 1H), 7.44 (dd, J=2.20, 8.66 Hz, 1H), 7.39 (dd, J=0.73, 8.36 Hz, 1H), 7.32-7.34 (m, 1H), 7.31 (d, J=0.88 Hz, 1H), 7.22-7.29 (m, 1H), 7.15-7.22 (m, 2H), 7.04-7.11 (m, 2H), 6.94 (dd, J=1.03, 8.07 Hz, 2H), 4.48 (d, J=12.91 Hz, 1H), 4.30 (d, J=12.91 Hz, 1H).

Compound 250

N-[2-(benzylsulfonyl)-4-cyanophenyl]-1-benzofuran-2-sulfonamide

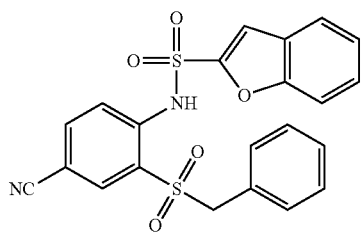 [SMILES: N#Cc1ccc(NS(=O)(=O)c2cc3ccccc3o2)c(S(=O)(=O)Cc2ccccc2)c1]

Following General Procedure D, the title compound (128 mg, 84%) was prepared from N-[2-(benzylsulfanyl)-4-cyanophenyl]-1-benzofuran-2-sulfonamide (142 mg, 0.34 mmol).

¹H NMR (600 MHz, CDCL₃) δ 7.78 (d, J=8.80 Hz, 1H), 7.68 (d, J=8.22 Hz, 1H), 7.62 (s., 1H), 7.49 (d, J=8.51 Hz, 1H), 7.44 (s., 1H), 7.26-7.34 (m, 3H), 7.11-7.19 (m, 1H), 6.94-7.03 (m, 2H), 6.85-6.91 (m, J=5.58 Hz, 2H), 4.76 (s., 2H).

Intermediate 42

6-(Benzylthio)-5-nitro-2,3-dihydro-1H-inden-1-one

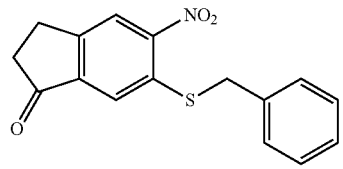 [SMILES: O=C1CCc2cc([N+](=O)[O-])c(SCc3ccccc3)cc21]

Following General Procedure A, the title compound (672 mg, 79%) was prepared from 6-bromo-5-nitro-2,3-dihydro-1H-inden-1-one (1.5 g, 5.86 mmol), phenylmethanethiol (1 ml, 8.79 mmol) and K₂CO₃ (4.0 g, 29.29 mmol) in DMF (20 ml).

¹H NMR (600 MHz, CDCl₃) δ 8.56 (s, 1H), 7.52 (s, 1H), 7.41-7.47 (m, 2H), 7.35-7.39 (m, 2H), 7.30-7.35 (m, 1H), 4.26 (s, 2H), 3.13-3.22 (m, 2H), 2.74-2.82 (m, 2H).

Intermediate 43

5-Amino-6-(benzylthio)-2,3-dihydro-1H-inden-1-one

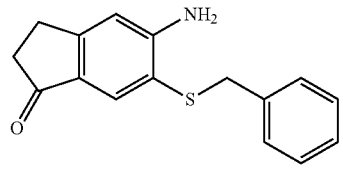 [SMILES: Nc1cc2c(cc1SCc1ccccc1)C(=O)CC2]

Following General Procedure L, the title compound (370 mg, 61%) was prepared from 6-(benzylthio)-5-nitro-2,3-dihydro-1H-inden-1-one (670 mg, 2.24 mmol).

¹H NMR (600 MHz, CDCl₃) δ 7.18-7.30 (m, 6H), 7.04 (s, 1H), 4.05 (s, 2H), 2.92-2.97 (m, 2H), 2.62-2.68 (m, 2H).

Compound 251

N-[6-(benzylsulfanyl)-1-oxo-2,3-dihydro-1H-inden-5-yl]-1-benzofuran-2-sulfonamide

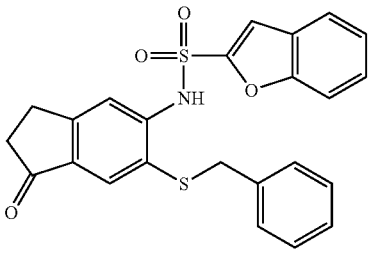 [SMILES: O=C1CCc2cc(NS(=O)(=O)c3cc4ccccc4o3)c(SCc3ccccc3)cc21]

Following General Procedure B, the title compound (752 mg, 47%) was prepared from 5-Amino-6-(benzylthio)-2,3- dihydro-1H-inden-1-one (463 mg, 1.72 mmol) and benzofuran-2-sulfonyl chloride (371 mg, 1.72 mmol) in pyridine (3 ml).

¹H NMR (600 MHz, CDCl₃) δ 7.90 (s, 1H), 7.85 (s, 1H), 7.61-7.70 (m, 1H), 7.42-7.50 (m, 3H), 7.29-7.36 (m, 1H), 7.20-7.24 (m, 3H), 6.98-7.06 (m, 2H), 3.94 (s, 2H), 2.90-2.98 (m, 2H), 2.61-2.68 (m, 2H).

Compound 252

N-[6-(benzylsulfinyl)-1-oxo-2,3-dihydro-1H-inden-5-yl]-1-benzofuran-2-sulfonamide

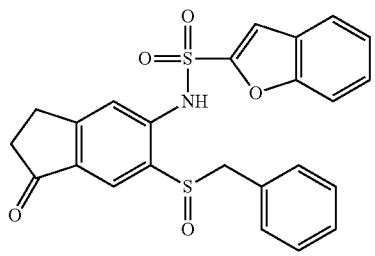 [SMILES: O=C1CCc2cc(NS(=O)(=O)c3cc4ccccc4o3)c(S(=O)Cc3ccccc3)cc21]

Following General Procedure C, the title compound (99 mg, 61%) was prepared from N-[6-(benzylsulfanyl)-1-oxo-2,3-dihydro-1H-inden-5-yl]-1-benzofuran-2-sulfonamide (143 mg, 0.32 mmol).

¹H NMR (600 MHz, CD₃OD) δ 7.69 (s, 1H), 7.59 (s, 1H), 7.29-7.42 (m, 3H), 7.09-7.27 (m, 5H), 6.96 (d, J=7.63 Hz, 2H), 4.38 (d, J=12.91 Hz, 1H), 4.18 (d, J=12.91 Hz, 1H), 2.80-2.95 (m, J=4.99 Hz, 2H), 2.51-2.66 (m, 2H).

Compound 253

N-[6-(benzylsulfonyl)-1-oxo-2,3-dihydro-1H-inden-5-yl]-1-benzofuran-2-sulfonamide

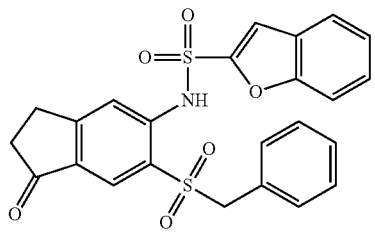 [SMILES: O=C1CCc2cc(NS(=O)(=O)c3cc4ccccc4o3)c(S(=O)(=O)Cc3ccccc3)cc21]

Following General Procedure D, the title compound (92 mg, 63%) was prepared from N-[6-(benzylsulfanyl)-1-oxo-2,3-dihydro-1H-inden-5-yl]-1-benzofuran-2-sulfonamide (137 mg, 0.31 mmol).

¹H NMR (600 MHz, CDCl₃) δ 8.05 (s, 1H), 7.71 (dt, J=1.03, 7.92 Hz, 1H), 7.65 (d, J=0.88 Hz, 1H), 7.60 (s, 1H), 7.48-7.53 (m, 1H), 7.41-7.47 (m, 1H), 7.29-7.37 (m, 2H), 7.19-7.28 (m, 2H), 7.03 (d, J=7.04 Hz, 2H), 4.43 (s, 2H), 2.90-3.07 (m, 2H), 2.63-2.78 (m, 2H).

Intermediate 44

Methyl 4-(((2-amino-4-chlorophenyl)thio)methyl)benzoate

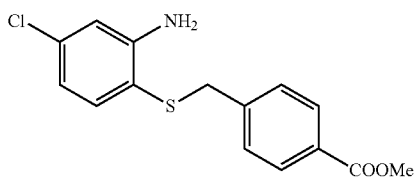 [SMILES: COC(=O)c1ccc(CSc2ccc(Cl)cc2N)cc1]

Following General Procedure A, the title compound (2.2 g, 88%) was prepared from 2-amino-4-chlorobenzenethiol (1.3 g, 8.14 mmol), methyl 4-(bromomethyl)benzoate (1.86 g, 8.14 mmol) and K₂CO₃ (5.6 g, 40.73 mmol) in DMF (20 ml).

¹H NMR (600 MHz, CDCl₃) δ 7.89 (d, J=8.22 Hz, 2H), 7.13 (d, J=8.22 Hz, 2H), 6.99 (d, J=8.22 Hz, 1H), 6.67 (d, J=2.35 Hz, 1H), 6.53 (dd, J=2.05, 8.22 Hz, 1H), 4.30 (br. s., 2H), 3.89 (s, 3H), 3.85 (s, 2H)

Compound 254

Methyl 4-(((4-chloro-2-(4-chloro-3-(trifluoromethyl)phenylsulfonamido)phenyl)thio)methyl)benzoate

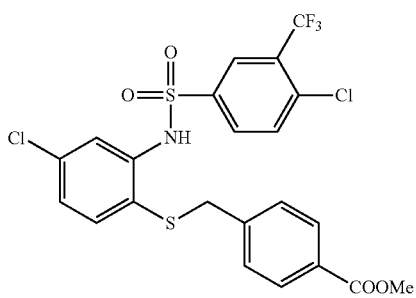 [SMILES: COC(=O)c1ccc(CSc2ccc(Cl)cc2NS(=O)(=O)c2ccc(Cl)c(C(F)(F)F)c2)cc1]

Following General Procedure B, the title compound (635 mg, 66%) was prepared from 4-(((2-amino-4-chlorophenyl)thio)methyl)benzoate (535 mg, 1.74 mmol) and 4-chloro-3-(trifluoromethyl)benzene-1-sulfonyl chloride (486 mg, 1.74 mmol) in pyridine (5 ml).

¹H NMR (600 MHz, CDCl₃) δ 8.11 (d, J=2.35 Hz, 1H), 7.91 (d, J=8.51 Hz, 2H), 7.82 (dd, J=2.35, 8.51 Hz, 1H), 7.64

(b.s, 1H), 7.59 (d, J=8.51 Hz, 1H), 7.53 (d, J=2.05 Hz, 1H), 7.01-7.06 (m, 3H), 6.95 (dd, J=2.20, 8.36 Hz, 1H), 3.91 (s, 3H), 3.76 (s, 2H).

General Procedure Q

Compound 255

4-({[4-chloro-2-({[4-chloro-3-(trifluoromethyl)phenyl]sulfonyl}amino)phenyl]sulfanyl}methyl)benzoic acid

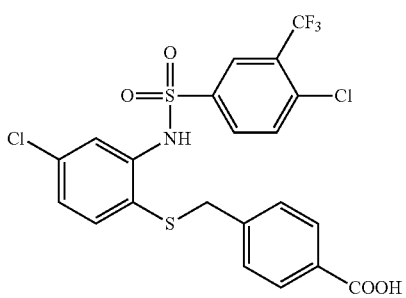 [SMILES: O=C(O)c1ccc(CSc2ccc(Cl)cc2NS(=O)(=O)c2ccc(Cl)c(C(F)(F)F)c2)cc1]

A mixture of methyl 4-(((4-chloro-2-(4-chloro-3-(trifluoromethyl)phenylsulfonamido)phenyl)thio)methyl)benzoate (635 mg, 1.155 mmol), NaOH (5M, 2 ml) in MeOH (10 ml) was stirred at room temperature overnight. The solvent was removed and the residue was diluted with water, acidified with 10% HCl. The mixture was extracted with EtOAc (2×20 ml). The combined organic layer was washed with brine and concentrated under vacuum. The desire product was purified by MPLC (50% to 100% EtOAc/Hexane).

$^1$H NMR (600 MHz, CDCl$_3$) δ 8.12 (d, J=2.05 Hz, 1H), 7.98 (d, J=8.22 Hz, 2H), 7.84 (dd, J=2.35, 8.51 Hz, 1H), 7.66 (s, 1H), 7.61 (d, J=8.51 Hz, 1H), 7.54 (d, J=2.35 Hz, 1H), 7.05-7.08 (m, 3H), 6.96 (dd, J=2.20, 8.36 Hz, 1H), 3.78 (s, 2H).

Compound 256

4-({[4-chloro-2-({[4-chloro-3-(trifluoromethyl)phenyl]sulfonyl}amino)phenyl]sulfinyl}methyl)benzoic acid

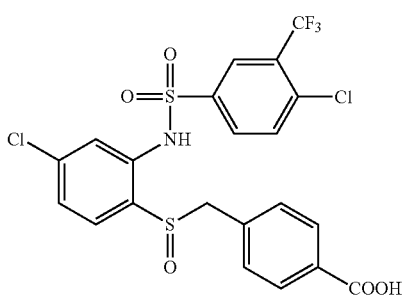 [SMILES: O=C(O)c1ccc(CS(=O)c2ccc(Cl)cc2NS(=O)(=O)c2ccc(Cl)c(C(F)(F)F)c2)cc1]

Following General Procedure C, the title compound (179 mg, 86%) was prepared from 4-({[4-chloro-2-({[4-chloro-3-(trifluoromethyl)phenyl]sulfonyl}amino)phenyl]sulfanyl}methyl)benzoic acid (203 mg, 0.38 mmol).

$^1$H NMR (600 MHz, CD$_3$OD) δ 8.21 (d, J=2.05 Hz, 1H), 8.01 (d, J=2.35 Hz, 1H), 7.98 (d, J=8.22 Hz, 2H), 7.74 (d, J=8.51 Hz, 1H), 7.21 (s, 1H), 7.13-7.16 (m, 4H), 7.06 (d, J=8.22 Hz, 1H), 4.37 (d, J=12.91 Hz, 1H), 4.27 (d, J=12.91 Hz, 1H).

Compound 257

4-({[4-chloro-2-({[4-chloro-3-(trifluoromethyl)phenyl]sulfonyl}amino)phenyl]sulfonyl}methyl)benzoic acid

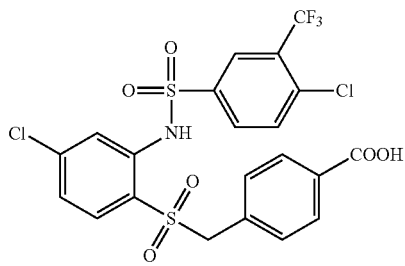 [SMILES: O=C(O)c1ccc(CS(=O)(=O)c2ccc(Cl)cc2NS(=O)(=O)c2ccc(Cl)c(C(F)(F)F)c2)cc1]

Following General Procedure D, the title compound (170 mg, 79%) was prepared from 4-({[4-chloro-2-({[4-chloro-3-(trifluoromethyl)phenyl]sulfonyl}amino)phenyl]sulfanyl}methyl)benzoic acid (203 mg, 0.38 mmol).

$^1$H NMR (600 MHz, CDCl$_3$) δ 8.20 (d, J=2.05 Hz, 1H), 7.97 (dd, J=2.20, 8.36 Hz, 1H), 7.91 (d, J=8.22 Hz, 2H), 7.65 (d, J=8.51 Hz, 1H), 7.44 (d, J=2.05 Hz, 1H), 7.32 (d, J=8.80 Hz, 1H), 7.07 (d, J=7.92 Hz, 2H), 6.97 (d, J=9.68 Hz, 1H), 4.38 (s, 2H).

General Procedure R

Compound 258 tert-butyl ({[4-({[4-chloro-2-({[4-chloro-3-(trifluoromethyl)phenyl]sulfonyl}amino)phenyl]sulfanyl}methyl)phenyl]carbonyl}amino)acetate

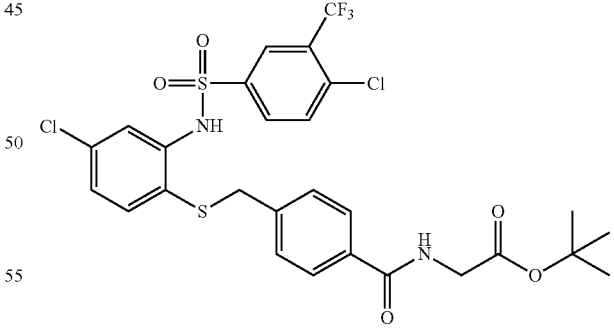

A mixture of 4-({[4-chloro-2-({[4-chloro-3-(trifluoromethyl)phenyl]sulfonyl}amino)phenyl]sulfanyl}methyl)benzoic acid (98 mg, 0.18 mmol), glycine t-butyl ester (36 mg, 0.27 mmol), 4-methyl morpholine (60 µl, 0.55 mmol) and EDC (53 mg, 0.27 mmol) in DMF (3 ml) was stirred at room temperature overnight. The reaction was quenched with water and extracted with EtOAc (2×5 ml). The combined organic layer was washed with brine, dried over Na$_2$SO$_4$, and concentrated in vacuo. The residue was purified by flash column chromatography on silica gel (30%-100% EtOAc in hexane) to afford the title compound (92 mg, 78%).

¹H NMR (600 MHz, CDCl₃) δ 8.10 (d, J=2.05 Hz, 1H), 7.81 (dd, J=2.20, 8.36 Hz, 1H), 7.67 (d, J=8.22 Hz, 2H), 7.59 (d, J=8.51 Hz, 1H), 7.48 (d, J=2.35 Hz, 1H), 6.98-7.08 (m, 3H), 6.94 (dd, J=2.05, 8.22 Hz, 1H), 6.69 (t, J=4.55 Hz, 1H), 4.10 (d, J=4.99 Hz, 2H), 3.74 (s, 2H), 1.48 (s, 9H).

Compound 259 tert-butyl ({[4-({[4-chloro-2-({[4-chloro-3-(trifluoromethyl)phenyl]sulfonyl}amino)phenyl]sulfinyl}methyl)phenyl]carbonyl}amino)acetate

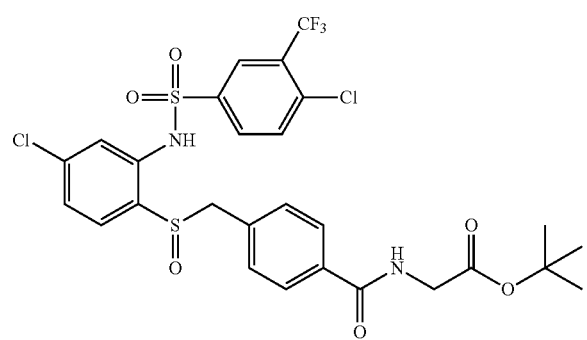 [SMILES: CC(C)(C)OC(=O)CNC(=O)c1ccc(CS(=O)c2ccc(Cl)cc2NS(=O)(=O)c2ccc(Cl)c(C(F)(F)F)c2)cc1]

Following General Procedure R, the title compound (98 mg, 81%) was prepared from 4-({[4-chloro-2-({[4-chloro-3-(trifluoromethyl)phenyl]sulfonyl}amino)phenyl]sulfinyl}methyl)benzoic acid (100 mg, 0.18 mmol).

¹H NMR (600 MHz, CDCl₃) δ 8.21 (d, J=1.76 Hz, 1H), 7.97 (dd, J=1.91, 8.36 Hz, 1H), 7.61 (d, J=7.92 Hz, 2H), 7.57 (d, J=8.51 Hz, 1H), 7.38 (d, J=1.47 Hz, 1H), 6.90 (d, J=7.63 Hz, 2H), 6.74-6.83 (m, 2H), 4.25 (d, J=12.62 Hz, 1H), 4.06-4.13 (m, 3H), 1.47 (s, 9H).

Compound 260 tert-butyl ({[4-({[4-chloro-2-({[4-chloro-3-(trifluoromethyl)phenyl]sulfonyl}amino)phenyl]sulfonyl}methyl)phenyl]carbonyl}amino)acetate

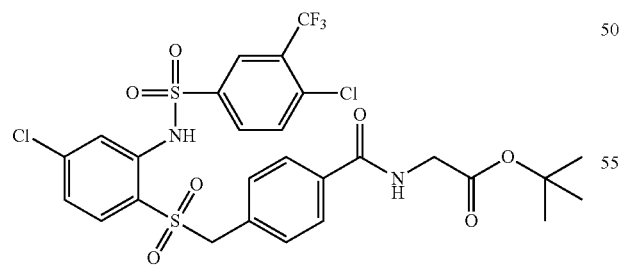

Following General Procedure R, the title compound (92 mg, 64%) was prepared from 4-({[4-chloro-2-({[4-chloro-3-(trifluoromethyl)phenyl]sulfonyl}amino)phenyl]sulfonyl}methyl)benzoic acid (119 mg, 0.21 mmol).

¹H NMR (600 MHz, CDCl₃) δ 8.21 (d, J=1.47 Hz, 1H), 7.98 (d, J=8.22 Hz, 1H), 7.41-7.53 (m, 3H), 7.36 (br. s., 1H), 7.17 (d, J=8.51 Hz, 1H), 6.81 (t, J=4.99 Hz, 1H), 6.71 (d, J=7.63 Hz, 2H), 6.53 (dd, J=1.76, 8.51 Hz, 1H), 4.47 (br. s., 2H), 4.02 (d, J=4.99 Hz, 2H), 1.43 (s, 9H).

General Procedure S

Compound 261

({[4-({[4-chloro-2-({[4-chloro-3-(trifluoromethyl)phenyl]sulfonyl}amino)phenyl]sulfanyl}methyl)phenyl]carbonyl}amino)acetic acid

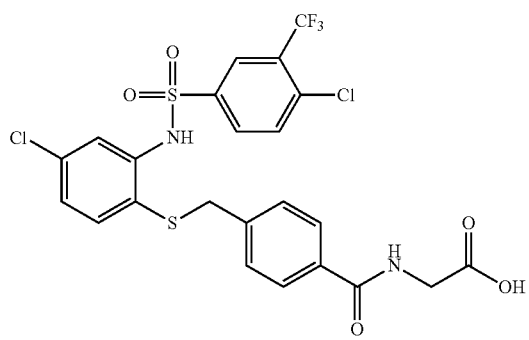 [SMILES: O=C(O)CNC(=O)c1ccc(CSc2ccc(Cl)cc2NS(=O)(=O)c2ccc(Cl)c(C(F)(F)F)c2)cc1]

A mixture of tert-butyl ({[4-({[4-chloro-2-({[4-chloro-3-(trifluoromethyl)phenyl]sulfonyl}amino)phenyl]sulfanyl}methyl)phenyl]carbonyl}amino)acetate (90 mg, 0.14 mmol) in formic acid (2 ml) was stirred at room temperature overnight. Formic acid was removed under vacuum and the desired product (72 mg, 88%) was re-crystallized from 10% MeOH in CH₂Cl₂.

¹H NMR (600 MHz, CD₃OD) δ 8.10 (d, J=2.05 Hz, 1H), 7.91 (dd, J=2.05, 8.51 Hz, 1H), 7.71-7.81 (m, 3H), 7.41 (s, 1H), 7.19 (d, J=8.22 Hz, 2H), 7.08-7.17 (m, 2H), 4.05 (br. s., 2H), 3.92 (s, 2H).

Compound 262

({[4-({[4-chloro-2-({[4-chloro-3-(trifluoromethyl)phenyl]sulfonyl}amino)phenyl]sulfinyl}methyl)phenyl]carbonyl}amino)acetic acid

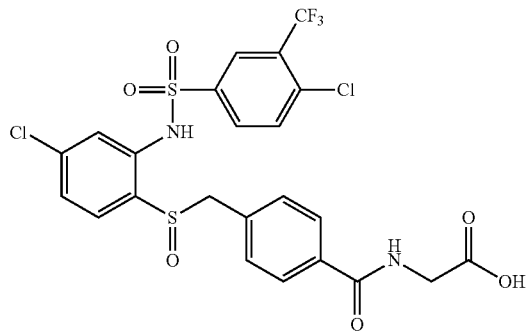 [SMILES: O=C(O)CNC(=O)c1ccc(CS(=O)c2ccc(Cl)cc2NS(=O)(=O)c2ccc(Cl)c(C(F)(F)F)c2)cc1]

Following General Procedure S, the title compound (58 mg, 70%) was prepared from tert-butyl ({[4-({[4-chloro-2-({[4-chloro-3-(trifluoromethyl)phenyl]sulfonyl}amino)phenyl]sulfinyl}methyl)phenyl]carbonyl}amino) acetate (90 mg, 0.14 mmol).

¹H NMR (600 MHz, CD₃OD) δ 8.13 (d, J=2.05 Hz, 1H), 8.02 (dd, J=2.20, 8.36 Hz, 1H), 7.84 (d, J=8.51 Hz, 1H), 7.76

(d, J=8.22 Hz, 2H), 7.12-7.30 (m, 4H), 7.03 (s, 1H), 4.46 (d, J=12.91 Hz, 1H), 4.24 (d, J=12.91 Hz, 1H), 4.08 (s, 2H).

Compound 263

({[4-({[4-chloro-2-({[4-chloro-3-(trifluoromethyl)phenyl]sulfonyl}amino)phenyl]sulfonyl}methyl)phenyl]carbonyl}amino)acetic acid

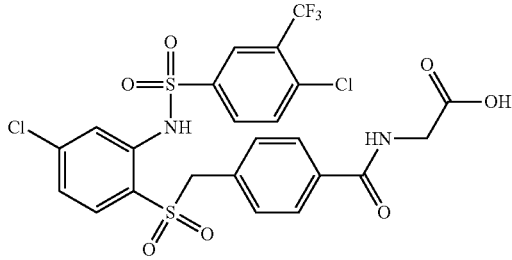 [SMILES: O=C(O)CNC(=O)c1ccc(CS(=O)(=O)c2ccc(Cl)cc2NS(=O)(=O)c2ccc(Cl)c(C(F)(F)F)c2)cc1]

Following General Procedure S, the title compound (60 mg, 73%) was prepared from tert-butyl ({[4-({[4-chloro-2-({[4-chloro-3-(trifluoromethyl)phenyl]sulfonyl}amino)phenyl]sulfonyl}methyl)phenyl]carbonyl}amino)acetate (89 mg, 0.13 mmol).

$^1$H NMR (600 MHz, CD$_3$OD) δ 8.36 (s, 1H), 8.10-8.21 (m, 2H), 7.72 (d, J=8.22 Hz, 2H), 7.45-7.53 (m, 1H), 7.38 (d, J=8.51 Hz, 1H), 7.35 (d, J=8.22 Hz, 2H), 6.73 (s., 1H), 4.97 (s, 2H), 4.05 (s, 2H).

Intermediate 45

Methyl 3-(((2-amino-4-chlorophenyl)thio)methyl)benzoate

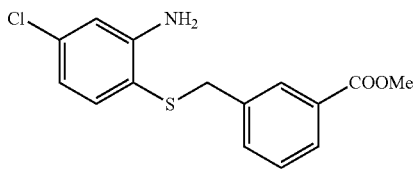 [SMILES: COC(=O)c1cccc(CSc2ccc(Cl)cc2N)c1]

Following General Procedure A, the title compound (1.4 g, 42%) was prepared from 2-amino-4-chlorobenzenethiol (1.7 g, 10.90 mmol), methyl 3-(bromomethyl)benzoate (2.5 g, 10.90 mmol) and K$_2$CO$_3$ (7.5 g, 54.50 mmol) in DMF (30 ml).

$^1$H NMR (600 MHz, CDCl$_3$) δ 7.88 (dt, J=1.47, 7.63 Hz, 1H), 7.78 (t, J=1.76 Hz, 1H), 7.26-7.33 (m, 1H), 6.97-7.05 (m, 2H), 6.70 (d, J=2.35 Hz, 1H), 6.67 (d, J=2.05 Hz, 1H), 4.32 (br.s., 2H), 3.89 (s, 3H), 3.87 (s, 2H).

Compound 264

Methyl 3-({[4-chloro-2-({[4-chloro-3-(trifluoromethyl)phenyl]sulfonyl}amino)phenyl]sulfanyl}methyl)benzoate

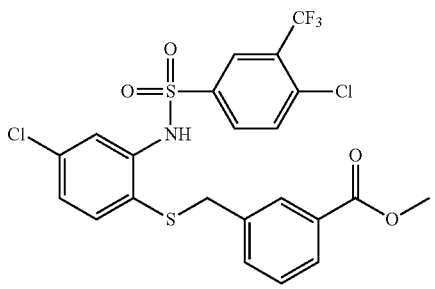 [SMILES: COC(=O)c1cccc(CSc2ccc(Cl)cc2NS(=O)(=O)c2ccc(Cl)c(C(F)(F)F)c2)c1]

Following General Procedure B, the title compound (1.65 g, 65%) was prepared from methyl 3-(((2-amino-4-chlorophenyl)thio)methyl)benzoate (1.41 g, 4.59 mmol) and 4-chloro-3-(trifluoromethyl)benzene-1-sulfonyl chloride (1.28 g, 4.59 mmol) in pyridine (10 ml).

$^1$H NMR (600 MHz, CDCL$_3$) δ 8.10 (d, J=2.05 Hz, 1H), 7.92 (d, J=7.92 Hz, 1H), 7.83 (dd, J=2.20, 8.36 Hz, 1H), 7.65 (br.s, 1H), 7.60 (d, J=8.51 Hz, 1H), 7.54 (d, J=2.05 Hz, 1H), 7.25-7.39 (m, 2H), 7.14 (d, J=7.04 Hz, 1H), 7.08 (s, 1H), 6.96 (dd, J=2.20, 8.36 Hz, 1H), 3.90 (s, 3H), 3.77 (s, 2H).

Compound 265 methyl 3-({[4-chloro-2-({[4-chloro-3-(trifluoromethyl)phenyl]sulfonyl}amino)phenyl]sulfinyl}methyl)benzoate

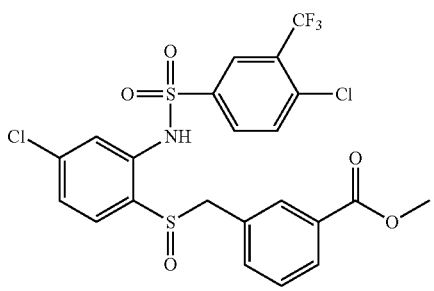 [SMILES: COC(=O)c1cccc(CS(=O)c2ccc(Cl)cc2NS(=O)(=O)c2ccc(Cl)c(C(F)(F)F)c2)c1]

Following General Procedure C, the title compound (36 mg, 88%) was prepared from Methyl 3-({[4-chloro-2-({[4-chloro-3-(trifluoromethyl)phenyl]sulfonyl}amino)phenyl]sulfanyl}methyl)benzoate (40 mg, 0.07 mmol).

$^1$H NMR (600 MHz, CD$_3$OD) δ 8.11 (d, J=2.05 Hz, 1H), 8.02 (dd, J=2.20, 8.36 Hz, 1H), 7.91-7.97 (m, 1H), 7.86 (d, J=8.22 Hz, 2H), 7.57 (br.s, 1H), 7.37-7.42 (m, 1H), 7.32 (d,

J=7.92 Hz, 1H), 7.20-7.28 (m, 2H), 7.01 (d, J=1.47 Hz, 1H), 4.43 (d, J=13.20 Hz, 1H), 4.23 (d, J=13.20 Hz, 1H), 3.87 (s, 3H).

Compound 266 methyl 3-({[4-chloro-2-({[4-chloro-3-(trifluoromethyl)phenyl]sulfonyl}amino)phenyl]sulfonyl}methyl)benzoate

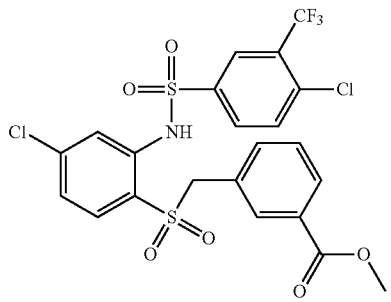 [SMILES: COC(=O)c1cccc(CS(=O)(=O)c2ccc(Cl)cc2NS(=O)(=O)c2ccc(Cl)c(C(F)(F)F)c2)c1]

Following General Procedure D, the title compound (61 mg, 89%) was prepared from 4-({[4-chloro-2-({[4-chloro-3-(trifluoromethyl)phenyl]sulfonyl}amino)phenyl]sulfanyl}methyl)benzoic acid (65 mg, 0.12 mmol).

$^1$H NMR (600 MHz, DMSO-$d_6$) δ 8.26 (d, J=1.76 Hz, 1H), 8.14 (dd, J=2.35, 8.22 Hz, 1H), 7.93 (d, J=7.92 Hz, 1H), 7.84-7.90 (m, 2H), 7.76 (s, 1H), 7.38-7.48 (m, 3H), 7.38 (d, J=2.05 Hz, 1H), 7.11 (br. s., 1H), 4.95 (s, 2H), 3.82 (s, 3H).

Compound 267

3-({[4-chloro-2-({[4-chloro-3-(trifluoromethyl)phenyl]sulfonyl}amino)phenyl]sulfanyl}methyl)benzoic acid

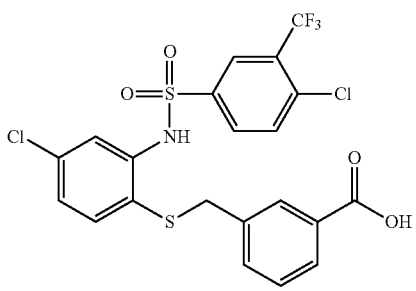 [SMILES: O=C(O)c1cccc(CSc2ccc(Cl)cc2NS(=O)(=O)c2ccc(Cl)c(C(F)(F)F)c2)c1]

Following General Procedure Q, the title compound (1.2 g, 75%) was prepared from methyl 3-({[4-chloro-2-({[4-chloro-3-(trifluoromethyl)phenyl]sulfonyl}amino)phenyl]sulfanyl}methyl)benzoate (1.65 g, 3 mmol).

$^1$H NMR (600 MHz, CD$_3$OD) δ 8.08 (d, J=2.05 Hz, 1H), 7.92 (dd, J=2.35, 8.51 Hz, 1H), 7.88 (d, J=7.63 Hz, 1H), 7.73-7.79 (m, 2H), 7.44 (d, J=2.35 Hz, 1H), 7.27-7.38 (m, 2H), 7.10-7.18 (m, 2H), 3.91 (s, 2H).

Compound 268

3-({[4-chloro-2-({[4-chloro-3-(trifluoromethyl)phenyl]sulfonyl}amino)phenyl]sulfonyl}methyl)benzoic acid

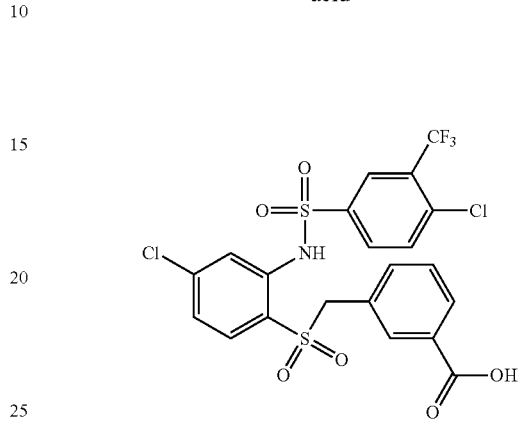

Following General Procedure D, the title compound (74 mg, 64%) was prepared from 3-({[4-chloro-2-({[4-chloro-3-(trifluoromethyl)phenyl]sulfonyl}amino)phenyl]sulfanyl}methyl)benzoic acid (109 mg, 0.20 mmol).

$^1$H NMR (600 MHz, DMSO-$d_6$) δ 8.24 (d, J=2.35 Hz, 1H), 8.11 (dd, J=2.05, 8.51 Hz, 1H), 7.92 (d, J=8.51 Hz, 1H), 7.85 (d, J=7.63 Hz, 1H), 7.74-7.79 (m, 1H), 7.46 (d, J=8.51 Hz, 1H), 7.27-7.41 (m, 3H), 7.17 (s, 1H), 4.90 (s, 2H).

Compound 269

3-({[4-chloro-2-({[4-chloro-3-(trifluoromethyl)phenyl]sulfonyl}amino)phenyl]sulfinyl}methyl)benzoic acid

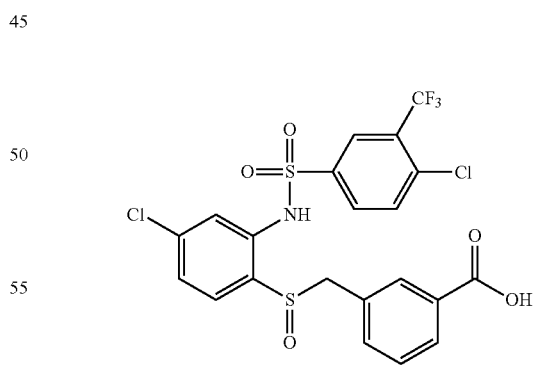

Following General Procedure C, the title compound (30 mg, 21%) was prepared from 3-({[4-chloro-2-({[4-chloro-3-(trifluoromethyl)phenyl]sulfonyl}amino)phenyl]sulfanyl}methyl)benzoic acid (140 mg, 0.26 mmol).

$^1$H NMR (600 MHz, CDCl$_3$) δ 8.24 (d, J=2.35 Hz, 1H), 8.09 (d, J=7.92 Hz, 1H), 8.02 (dd, J=2.35, 8.51 Hz, 1H), 7.63-7.68 (m, 2H), 7.55 (d, J=1.76 Hz, 1H), 7.39-7.46 (m,

1H), 7.25 (s, 1H), 6.95 (dd, J=1.91, 8.36 Hz, 1H), 6.72 (d, J=8.22 Hz, 1H), 4.23-4.38 (m, 2H).

Compound 270

3-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide

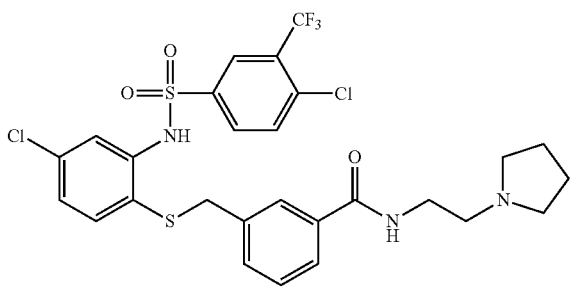 [SMILES: O=C(NCCN1CCCC1)c1cccc(CSc2ccc(Cl)cc2NS(=O)(=O)c2ccc(Cl)c(C(F)(F)F)c2)c1]

Following General Procedure R, the title compound (388 mg, 80%) was prepared from 3-({[4-chloro-2-({[4-chloro-3-(trifluoromethyl)phenyl]sulfonyl}amino)phenyl]sulfanyl}methyl)benzoic acid (411 mg, 0.77 mmol), 2-(pyrrolidin-1-yl)ethanamine (0.15 ml, 1.15 mmol), EDC (294 mg, 1.53 mmol) and DMAP (cat.) in DMF (10 ml).

$^1$H NMR (600 MHz, CDCl$_3$) δ 8.22 (t, J=4.99 Hz, 1H), 8.05 (d, J=2.05 Hz, 1H), 7.53-7.74 (m, 3H), 7.41 (d, J=8.51 Hz, 1H), 7.37 (d, J=2.35 Hz, 1H), 7.21 (d, J=7.92 Hz, 1H), 7.09-7.18 (m, 1H), 6.93 (d, J=8.51 Hz, 1H), 6.78 (dd, J=2.20, 8.36 Hz, 1H), 3.80 (s, 2H), 3.75 (q, J=5.48 Hz, 2H), 3.21 (t, J=5.43 Hz, 2H), 3.09 (br. s., 4H), 1.77-1.88 (m, 4H).

Compound 271

3-({[4-chloro-2-({[4-chloro-3-(trifluoromethyl)phenyl]sulfonyl}amino)phenyl]sulfinyl}methyl)-N-[2-(1-oxidopyrrolidin-1-yl)ethyl]benzamide

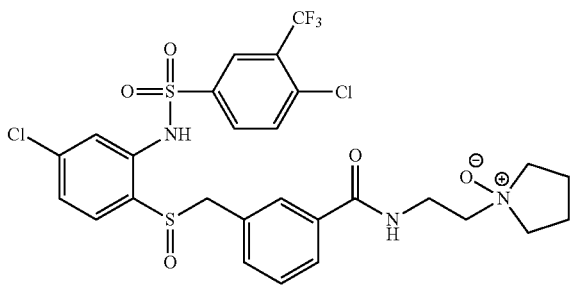 [SMILES: O=C(NCC[N+]1([O-])CCCC1)c1cccc(CS(=O)c2ccc(Cl)cc2NS(=O)(=O)c2ccc(Cl)c(C(F)(F)F)c2)c1]

Following General Procedure D, the title compound (42 mg, 28%) was prepared from 3-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide (144 mg, 0.23 mmol).

$^1$H NMR (300 MHz, CD$_3$OD) δ 8.22 (d, J=2.34 Hz, 1H), 8.06 (dd, J=1.90, 8.06 Hz, 1H), 7.67-7.81 (m, 3H), 7.21-7.38 (m, 2H), 7.18 (d, J=2.05 Hz, 1H), 6.99 (d, J=8.20 Hz, 1H), 6.72 (dd, J=2.05, 8.20 Hz, 1H), 4.53 (d, J=12.89 Hz, 1H), 4.23 (d, J=13.19 Hz, 1H), 3.90-4.00 (m, 2H), 3.58-3.85 (m, 6H), 2.08-2.39 (m, 4H).

Compound 272

3-({[4-chloro-2-({[4-chloro-3-(trifluoromethyl)phenyl]sulfonyl}amino)phenyl]sulfinyl}methyl)-N-[2-(pyrrolidin-1-yl)ethyl]benzamide

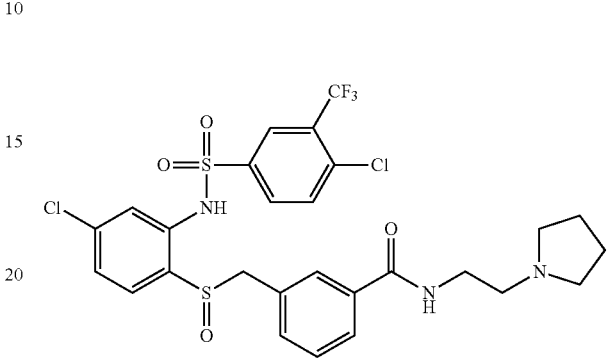

Following General Procedure R, the title compound (17 mg, 19%) was prepared from 3-({[4-chloro-2-({[4-chloro-3-(trifluoromethyl)phenyl]sulfonyl}amino)phenyl]sulfinyl}methyl)benzoic acid (76 mg, 0.14 mmol), 2-(pyrrolidin-1-yl)ethanamine (26 µl, 0.21 mmol), EDC (53 mg, 0.28 mmol) and DMAP (cat.) in DMF (2 ml).

$^1$H NMR (300 MHz, CD$_3$OD) δ 8.20 (d, J=2.05 Hz, 1H), 8.05 (dd, J=2.20, 8.35 Hz, 1H), 7.97 (s, 1H), 7.80-7.86 (m, 1H), 7.71 (d, J=8.21 Hz, 1H), 7.23-7.47 (m, 2H), 7.16 (d, J=1.76 Hz, 1H), 7.12 (d, J=8.20 Hz, 1H), 6.76 (dd, J=1.90, 8.35 Hz, 1H), 4.60 (d, J=12.89 Hz, 1H), 4.13 (d, J=13.19 Hz, 1H), 3.65-3.84 (m, 2H), 3.34-3.59 (m, 6H), 1.95-2.21 (m, 4H).

Compound 273

3-({[4-chloro-2-({[4-chloro-3-(trifluoromethyl)phenyl]sulfonyl}amino)phenyl]sulfonyl}methyl)-N-[2-(1-oxidopyrrolidin-1-yl)ethyl]benzamide

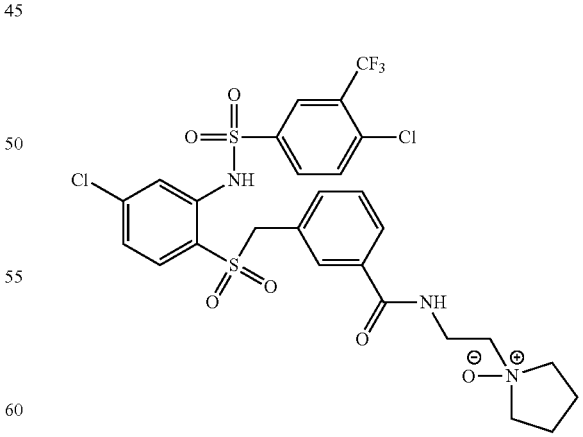

Following General Procedure D, the title compound (63 mg, 40%) was prepared from 3-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide (144 mg, 0.23 mmol).

¹H NMR (300 MHz, CD₃OD) δ 8.38 (d, J=2.05 Hz, 1H), 8.20 (dd, J=2.05, 8.21 Hz, 1H), 7.92 (s, 1H), 7.75 (d, J=7.62 Hz, 1H), 7.69 (d, J=8.50 Hz, 1H), 7.21-7.50 (m, 4H), 6.58 (dd, J=2.05, 8.50 Hz, 1H), 5.00 (s, 2H), 3.88-4.03 (m, 2H), 3.52-3.87 (m, 6H), 1.93-2.45 (m, 4H).

Compound 274

3-({[4-chloro-2-{[4-chloro-3-(trifluoromethyl)phenyl]sulfonyl}amino)phenyl]sulfonyl}methyl)-N-[2-(pyrrolidin-1-yl)ethyl]benzamide

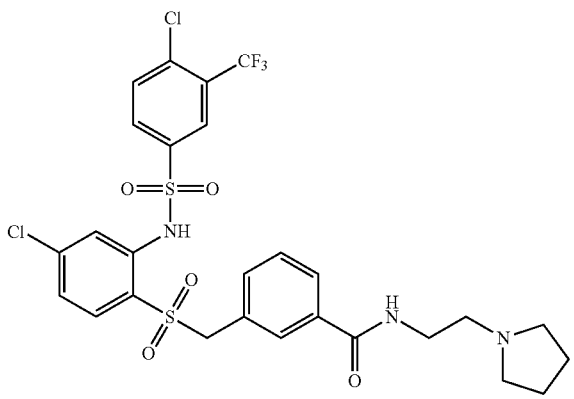 [SMILES: O=C(NCCN1CCCC1)c1cccc(CS(=O)(=O)c2ccc(Cl)cc2NS(=O)(=O)c2ccc(Cl)c(C(F)(F)F)c2)c1]

Following General Procedure R, the title compound (21 mg, 49%) was prepared from 3-({[4-chloro-2-({[4-chloro-3-(trifluoromethyl)phenyl]sulfonyl}amino)phenyl]sulfonyl}methyl)benzoic acid (48 mg, 0.085 mmol), 2-(pyrrolidin-1-yl)ethanamine (16 μl, 0.13 mmol), EDC (32 mg, 0.17 mmol) and DMAP (cat.) in DMF (2 ml).

¹H NMR (300 MHz, CD₃OD) δ 8.36 (s, 1H), 8.12-8.25 (m, 2H), 7.83 (d, J=7.91 Hz, 1H), 7.72 (d, J=8.50 Hz, 1H), 7.57 (d, J=6.74 Hz, 1H), 7.49 (d, J=8.50 Hz, 1H), 7.43 (d, J=7.62 Hz, 1H), 7.29 (d, J=1.76 Hz, 1H), 6.58-6.70 (m, 1H), 5.01 (s, 2H), 3.76 (t, J=5.57 Hz, 2H), 3.39-3.58 (m, 6H), 2.02-2.10 (m, 4H).

Compound 275

4-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide

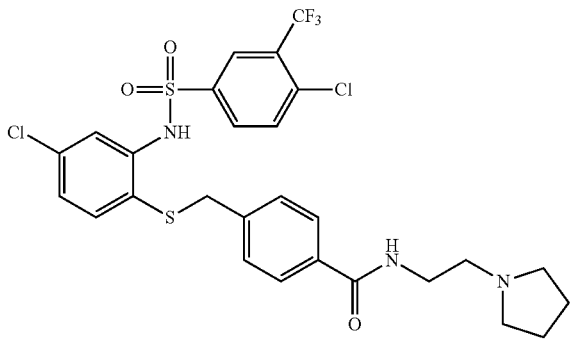 [SMILES: O=C(NCCN1CCCC1)c1ccc(CSc2ccc(Cl)cc2NS(=O)(=O)c2ccc(Cl)c(C(F)(F)F)c2)cc1]

Following General Procedure R, the title compound (345 mg, 71%) was prepared from 4-({[4-chloro-2-({[4-chloro-3-(trifluoromethyl)phenyl]sulfonyl}amino)phenyl]sulfanyl}methyl)benzoic acid (410 mg, 0.765 mmol), 2-(pyrrolidin-1-yl)ethanamine (0.15 ml, 1.15 mmol), EDC (293 mg, 1.53 mmol) and DMAP (cat.) in DMF (5 ml).

¹H NMR (600 MHz, CDCL₃) δ 7.96-8.05 (m, 1H), 7.69-7.76 (m, 1H), 7.63 (d, J=8.51 Hz, 2H), 7.46-7.54 (m, 1H), 7.31-7.38 (m, 1H), 6.98 (d, J=8.22 Hz, 2H), 6.91-6.96 (m, 1H), 6.83-6.90 (m, 1H), 3.70 (s, 2H), 3.46 (t, J=6.02 Hz, 2H), 2.63-2.73 (m, 2H), 2.51-2.62 (m, 4H), 1.62-1.81 (m, 4H).

Compound 276

4-({[4-chloro-2-({[4-chloro-3-(trifluoromethyl)phenyl]sulfonyl}amino)phenyl]sulfanyl}methyl)-N-[2-(1-oxidopyrrolidin-1-yl)ethyl]benzamide

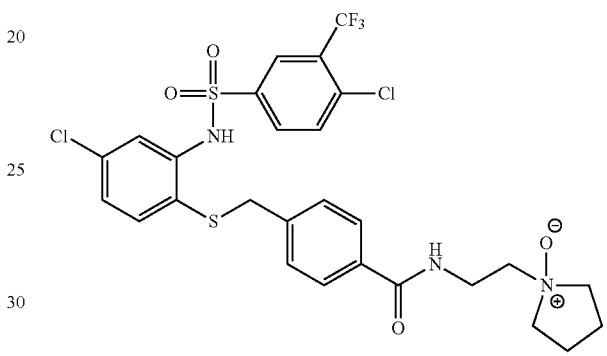

Following General Procedure D, the title compound (52 mg, 40%) was prepared from 4-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide (126 mg, 0.20 mmol).

¹H NMR (300 MHz, CD₃OD) δ 8.11 (d, J=1.76 Hz, 1H), 7.86 (d, J=7.62 Hz, 1H), 7.72 (d, J=8.21 Hz, 2H), 7.29-7.49 (m, 3H), 7.20 (d, J=8.20 Hz, 2H), 7.08-7.16 (m, 1H), 3.87-4.03 (m, 4H), 3.44-3.80 (m, 6H), 2.26-2.48 (m, 2H), 2.00-2.22 (m, 2H).

Compound 277

4-({[4-chloro-2-({[4-chloro-3-(trifluoromethyl)phenyl]sulfonyl}amino)phenyl]sulfinyl}methyl)-N-[2-(1-oxidopyrrolidin-1-yl)ethyl]benzamide

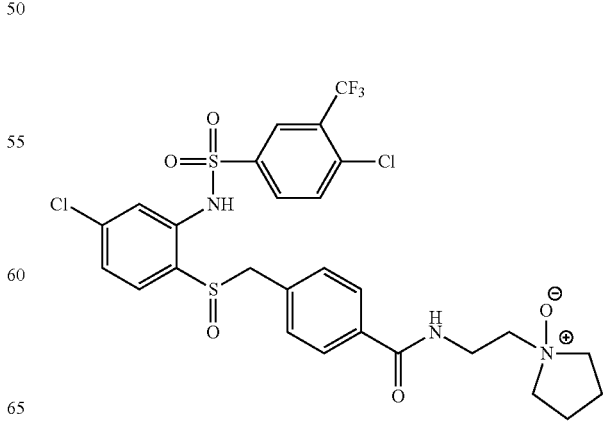

Following General Procedure D, the title compound (53 mg, 40%) was prepared from 4-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide (126 mg, 0.20 mmol).

$^1$H NMR (300 MHz, CD$_3$OD) δ 8.23 (d, J=1.76 Hz, 1H), 8.06 (dd, J=1.90, 8.35 Hz, 1H), 7.61-7.78 (m, 3H), 7.27 (s, 1H), 7.09 (d, J=8.20 Hz, 2H), 6.92 (d, J=8.50 Hz, 1H), 6.70 (dd, J=1.90, 8.35 Hz, 1H), 4.47 (d, J=12.89 Hz, 1H), 4.26 (d, J=12.89 Hz, 1H), 3.83-3.97 (m, 2H), 3.50-3.81 (m, 6H), 2.00-2.43 (m, 4H).

Compound 278

4-({[4-chloro-2-({[4-chloro-3-(trifluoromethyl)phenyl]sulfonyl}amino)phenyl]sulfinyl}methyl)-N-[2-(pyrrolidin-1-yl)ethyl]benzamide

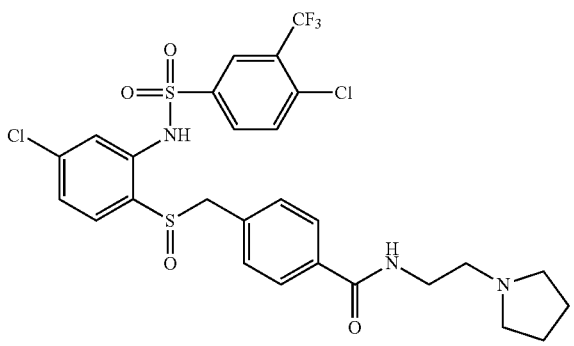 [SMILES: O=C(NCCN1CCCC1)c1ccc(CS(=O)c2ccc(Cl)cc2NS(=O)(=O)c2ccc(Cl)c(C(F)(F)F)c2)cc1]

Following General Procedure L, the title compound (55 mg, 81%) was prepared from 4-({[4-chloro-2-({[4-chloro-3-(trifluoromethyl)phenyl]sulfonyl}amino)phenyl]sulfinyl}methyl)-N-[2-(1-oxidopyrrolidin-1-yl)ethyl]benzamide (70 mg, 0.11 mmol).

$^1$H NMR (600 MHz, CD$_3$OD) δ 8.23 (d, J=2.05 Hz, 1H), 8.06 (dd, J=2.05, 8.22 Hz, 1H), 7.69-7.71 (m, 4H), 7.27 (d, J=2.05 Hz, 1H), 7.11 (d, J=8.22 Hz, 2H), 6.90 (d, J=8.51 Hz, 1H), 6.67 (dd, J=2.05, 8.22 Hz, 1H), 4.47 (d, J=12.91 Hz, 1H), 4.29 (s, 1H), 3.72 (t, J=5.72 Hz, 2H), 3.35-3.56 (m, 6H), 2.03-2.21 (m, 4H).

Compound 279

4-({[4-chloro-2-({[4-chloro-3-(trifluoromethyl)phenyl]sulfonyl}amino)phenyl]sulfonyl}methyl)-N-[2-(1-oxidopyrrolidin-1-yl)ethyl]benzamide

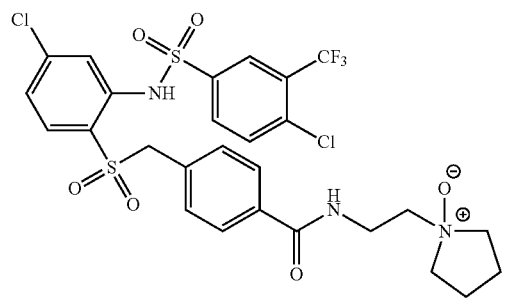 [SMILES: O=C(NCC[N+]1([O-])CCCC1)c1ccc(CS(=O)(=O)c2ccc(Cl)cc2NS(=O)(=O)c2ccc(Cl)c(C(F)(F)F)c2)cc1]

Following General Procedure D, the title compound (97 mg, 69%) was prepared from 4-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide (130 mg, 0.21 mmol).

$^1$H NMR (600 MHz, acetone-d$_6$) δ 8.41 (d, J=2.05 Hz, 1H), 8.19-8.29 (m, 1H), 7.95 (s, 1H), 7.57-7.75 (m, 3H), 7.34 (d, J=8.51 Hz, 1H), 7.26 (d, J=8.22 Hz, 2H), 6.47 (dd, J=2.05, 8.51 Hz, 1H), 4.96 (s, 2H), 3.87-4.01 (m, 2H), 3.65-3.80 (m, 4H), 3.53-3.64 (m, 2H), 2.24-2.39 (m, 2H), 2.07-2.16 (m, 2H).

Compound 280

4-({[4-chloro-2-({[4-chloro-3-(trifluoromethyl)phenyl]sulfonyl}amino)phenyl]sulfonyl}methyl)-N-[2-(pyrrolidin-1-yl)ethyl]benzamide

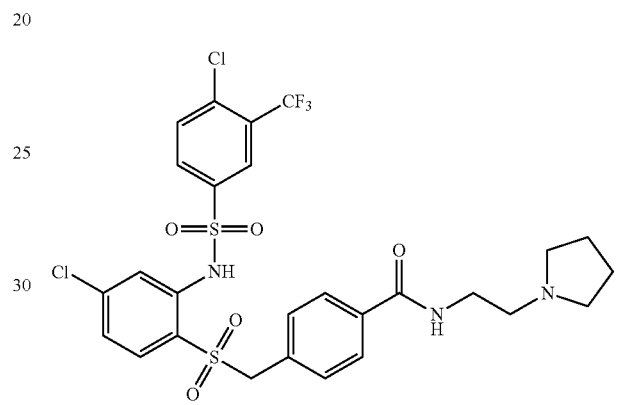

Following General Procedure L, the title compound (59 mg, 92%) was prepared from 4-({[4-chloro-2-({[4-chloro-3-(trifluoromethyl)phenyl]sulfonyl}amino)phenyl]sulfonyl}methyl)-N-[2-(1-oxidopyrrolidin-1-yl)ethyl]benzamide (66 mg, 0.10 mmol).

$^1$H NMR (600 MHz, acetone-d6) δ 8.27 (d, J=2.05 Hz, 1H), 8.24 (t, J=5.72 Hz, 1H), 8.09 (dd, J=2.05, 8.22 Hz, 1H), 7.60-7.65 (m, 3H), 7.48 (d, J=2.05 Hz, 1H), 7.26 (d, J=8.51 Hz, 1H), 7.15 (d, J=8.51 Hz, 2H), 6.42 (dd, J=2.05, 8.51 Hz, 1H), 4.72 (s, 2H), 3.64-3.81 (m, 2H), 3.43-3.59 (m, 6H), 1.93-2.05 (m, 4H).

Intermediate 46

Methyl 2-(((2-amino-4-chlorophenyl)thio)methyl)benzoate

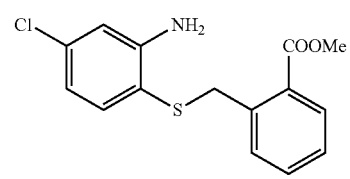 [SMILES: COC(=O)c1ccccc1CSc1ccc(Cl)cc1N]

Following General Procedure A, the title compound (1.6 g, 84%) was prepared from 2-amino-4-chlorobenzenethiol (969 mg, 6.06 mmol), methyl 2-(bromomethyl)benzoate (1.4 g, 6.11 mmol) and K$_2$CO$_3$ (4.2 g, 30.55 mmol) in DMF (50 ml).

¹H NMR (600 MHz, CDCL₃) δ 7.90 (dd, J=1.47, 7.63 Hz, 1H), 7.27-7.41 (m, 2H), 6.95-7.01 (m, 2H), 6.67 (s, 1H), 6.48-6.56 (m, 1H), 4.41 (br. s., 2H), 4.27 (s, 2H), 3.88 (s, 3H).

Compound 281

Methyl 2-({[4-chloro-2-({[4-chloro-3-(trifluoromethyl)phenyl]sulfonyl}amino)phenyl]sulfanyl}methyl)benzoate

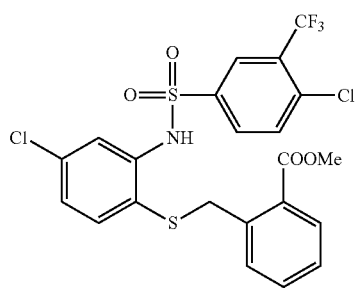 [SMILES: COC(=O)c1ccccc1CSc1ccc(Cl)cc1NS(=O)(=O)c1ccc(Cl)c(C(F)(F)F)c1]

Following General Procedure B, the title compound (936 mg, 37%) was prepared from methyl 2-(((2-amino-4-chlorophenyl)thio)methyl)benzoate (1.41 g, 4.56 mmol) and 4-chloro-3-(trifluoromethyl)benzene-1-sulfonyl chloride (1.3 g, 4.56 mmol) in pyridine (10 ml).

¹H NMR (300 MHz, CD₃OD) δ 8.12 (d, J=1.76 Hz, 1H), 7.86-8.00 (m, 2H), 7.76 (d, J=8.50 Hz, 1H), 7.50 (d, J=1.76 Hz, 1H), 7.27-7.45 (m, 2H), 6.94-7.18 (m, 3H), 4.21 (s, 2H), 3.86 (s, 3H).

Compound 282

2-({[4-chloro-2-({[4-chloro-3-(trifluoromethyl)phenyl]sulfonyl}amino)phenyl]sulfanyl}methyl)benzoic acid

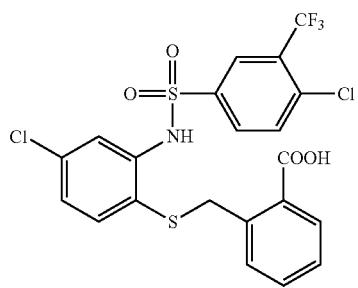 [SMILES: O=C(O)c1ccccc1CSc1ccc(Cl)cc1NS(=O)(=O)c1ccc(Cl)c(C(F)(F)F)c1]

Following General Procedure Q, the title compound (405 mg, 94%) was prepared from methyl 2-({[4-chloro-2-({[4-chloro-3-(trifluoromethyl)phenyl]sulfonyl}amino)phenyl]sulfanyl}methyl)benzoate (444 mg, 0.81 mmol).

¹H NMR (300 MHz, CD₃OD) δ 8.08 (d, J=1.47 Hz, 1H), 7.82-8.01 (m, 2H), 7.75 (d, J=8.20 Hz, 1H), 7.49 (d, J=2.05 Hz, 1H), 7.27-7.38 (m, 2H), 7.20 (d, J=8.50 Hz, 1H), 7.04-7.15 (m, 1H), 6.88-6.99 (m, 1H), 4.21 (s, 2H).

Compound 283

Methyl 2-({[4-chloro-2-({[4-chloro-3-(trifluoromethyl)phenyl]sulfonyl}amino)phenyl]sulfinyl}methyl)benzoate

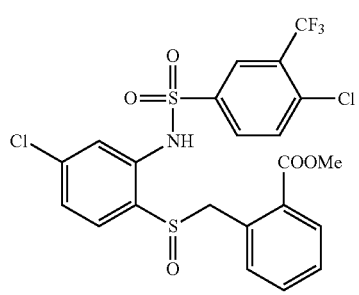 [SMILES: COC(=O)c1ccccc1CS(=O)c1ccc(Cl)cc1NS(=O)(=O)c1ccc(Cl)c(C(F)(F)F)c1]

Following General Procedure C, the title compound (88 mg, 71%) was prepared from methyl 2-({[4-chloro-2-({[4-chloro-3-(trifluoromethyl)phenyl]sulfonyl}amino)phenyl]sulfanyl}methyl)benzoate (120 mg, 0.22 mmol).

¹H NMR (300 MHz, CD₃OD) δ 8.12 (d, J=2.05 Hz, 1H), 7.90-8.06 (m, 2H), 7.83 (d, J=8.50 Hz, 1H), 7.38-7.54 (m, 2H), 6.97-7.35 (m, 4H), 4.61-4.82 (m, 2H), 3.83 (s, 3H).

Compound 284

2-({[4-chloro-2-({[4-chloro-3-(trifluoromethyl)phenyl]sulfonyl}amino)phenyl]sulfinyl}methyl)benzoic acid

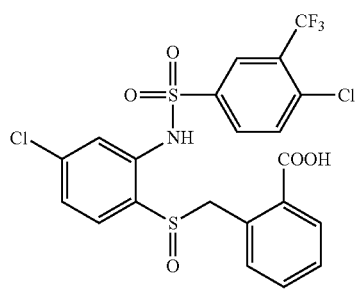 [SMILES: O=C(O)c1ccccc1CS(=O)c1ccc(Cl)cc1NS(=O)(=O)c1ccc(Cl)c(C(F)(F)F)c1]

Following General Procedure Q, the title compound (30 mg, 23%) was prepared from methyl 2-({[4-chloro-2-({[4-chloro-3-(trifluoromethyl)phenyl]sulfonyl}amino)phenyl]sulfinyl}methyl)benzoate (128 mg, 0.24 mmol).

¹H NMR (300 MHz, CDCl₃) δ 8.12-8.28 (m, 2H), 8.00 (d, J=8.21 Hz, 1H), 7.57-7.68 (m, 2H), 7.50 (t, J=5.71 Hz, 2H), 7.03-7.24 (m, 3H), 4.80 (d, J=11.43 Hz, 1H), 4.44 (d, J=11.14 Hz, 1H).

Compound 285

Methyl 2-({[4-chloro-2-({[4-chloro-3-(trifluoromethyl)phenyl]sulfonyl}amino)phenyl]sulfonyl}methyl)benzoate

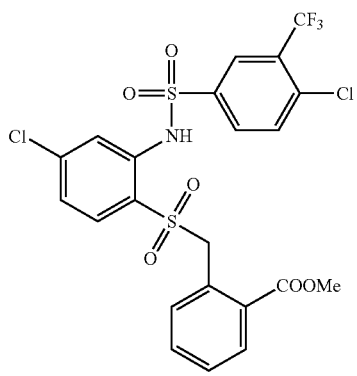 [SMILES: COC(=O)c1ccccc1CS(=O)(=O)c1ccc(Cl)cc1NS(=O)(=O)c1ccc(Cl)c(C(F)(F)F)c1]

Following General Procedure D, the title compound (88 mg, 78%) was prepared from methyl 2-({[4-chloro-2-({[4-chloro-3-(trifluoromethyl)phenyl]sulfonyl}amino)phenyl]sulfanyl}methyl)benzoate (107 mg, 0.20 mmol).

¹H NMR (300 MHz, DMSO-d₆) δ 8.30 (d, J=2.05 Hz, 1H), 8.07-8.20 (m, 1H), 7.94 (d, J=8.50 Hz, 1H), 7.81 (d, J=6.74 Hz, 1H), 7.35-7.58 (m, 3H), 7.29-7.24 (m, 3H), 5.28 (s, 2H), 3.70 (s, 3H).

Compound 286

2-({[4-chloro-2-({[4-chloro-3-(trifluoromethyl)phenyl]sulfonyl}amino)phenyl]sulfonyl}methyl)benzoic acid

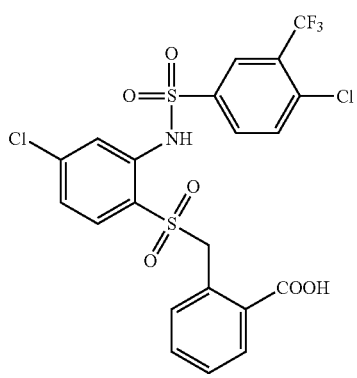 [SMILES: O=C(O)c1ccccc1CS(=O)(=O)c1ccc(Cl)cc1NS(=O)(=O)c1ccc(Cl)c(C(F)(F)F)c1]

Following General Procedure Q, the title compound (67 mg, 50%) was prepared from methyl 2-({[4-chloro-2-({[4-chloro-3-(trifluoromethyl)phenyl]sulfonyl}amino)phenyl]sulfonyl}methyl)benzoate (125 mg, 0.23 mmol).

¹H NMR (300 MHz, CD₃OD) δ 8.41 (d, J=2.05 Hz, 1H), 8.30 (dd, J=2.05, 8.50 Hz, 1H), 7.76 (dd, J=1.03, 7.77 Hz, 1H), 7.76 (dd, J=1.03, 7.77 Hz, 1H), 7.68 (d, J=8.50 Hz, 1H), 7.52 (d, J=8.50 Hz, 1H), 7.29 (td, J=1.17, 7.62 Hz, 1H), 7.16 (td, J=1.47, 7.47 Hz, 1H), 7.00 (d, J=7.62 Hz, 1H), 6.67 (dd, J=1.90, 8.64 Hz, 1H), 5.31 (s, 2H).

Compound 287

2-({[4-chloro-2-({[4-chloro-3-(trifluoromethyl)phenyl]sulfonyl}amino)phenyl]sulfanyl}methyl)benzamide

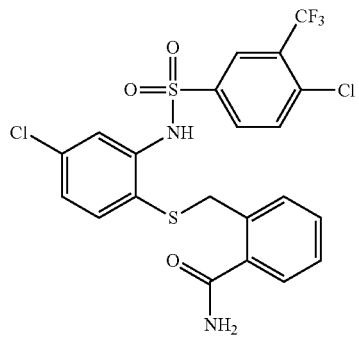 [SMILES: NC(=O)c1ccccc1CSc1ccc(Cl)cc1NS(=O)(=O)c1ccc(Cl)c(C(F)(F)F)c1]

A mixture of 2-({[4-chloro-2-({[4-chloro-3-(trifluoromethyl)phenyl]sulfonyl}amino)phenyl]sulfanyl}methyl)benzoic acid (156 mg, 0.29 mmol), HOBT (59 mg, 0.44 mmol), EDC (84 mg, 0.44 mmol), and NH₃—H₂O (28-30% NH₃ basis, 2×4 ml, excess) in DMF (3 ml) was stirred at room temperature overnight. The mixture was diluted with water, extracted with EtOAc. The organic layer was washed with brine, dried over Na₂SO₄, and concentrated in vacuo. The residue was purified by flash column chromatography on silica gel (40-100% EtOAc in hexane) to yield the title compound (69 mg, 45%).

¹H NMR (300 MHz, CD₃OD) δ 8.09 (d, J=2.05 Hz, 1H), 7.97 (s, 1H), 7.94 (dd, J=2.34, 8.50 Hz, 1H), 7.75 (d, J=8.50 Hz, 1H), 7.48-7.53 (m, 1H), 7.44 (d, J=2.34 Hz, 1H), 7.22-7.34 (m, 3H), 7.09 (dd, J=2.34, 8.50 Hz, 1H), 6.90-6.99 (m, 1H), 4.10 (s, 2H).

Compound 288

2-({[4-chloro-2-({[4-chloro-3-(trifluoromethyl)phenyl]sulfonyl}amino)phenyl]sulfanyl}methyl)-N,N-dimethylbenzamide

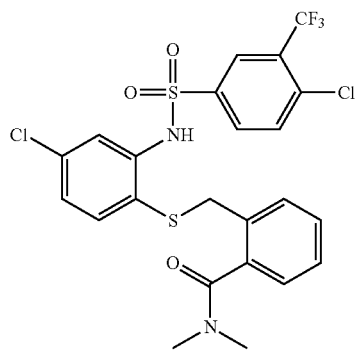 [SMILES: CN(C)C(=O)c1ccccc1CSc1ccc(Cl)cc1NS(=O)(=O)c1ccc(Cl)c(C(F)(F)F)c1]

A mixture of 2-({[4-chloro-2-({[4-chloro-3-(trifluoromethyl)phenyl]sulfonyl}amino)phenyl]sulfanyl}methyl)benzoic acid (304 mg, 0.57 mmol), DMAP (138 mg, 1.13 mmol), EDC (217 mg, 1.13 mmol), and dimethylamine hydrochloride (93 mg, 1.13 mmol) in CH$_2$Cl$_2$ (3 ml) was stirred at room temperature overnight. The mixture was diluted with water, extracted with EtOAc. The organic layer was washed with brine, dried over Na$_2$SO$_4$, and concentrated in vacuo. The residue was purified by flash column chromatography on silica gel (0~30% EtOAc in hexane) to yield the title compound (122 mg, 38%).

$^1$H NMR (300 MHz, CDCL$_3$) δ 8.21 (d, J=2.05 Hz, 1H), 7.84 (dd, J=2.20, 8.35 Hz, 1H), 7.52 (d, J=8.50 Hz, 1H), 7.45 (d, J=2.34 Hz, 1H), 7.33 (d, J=8.20 Hz, 1H), 7.16-7.27 (m, 2H), 7.10 (td, J=2.05, 7.18 Hz, 1H), 7.03 (dd, J=2.34, 8.50 Hz, 1H), 6.74 (d, J=7.33 Hz, 1H), 3.77 (s, 2H), 3.18 (s, 3H), 2.85 (s, 3H).

Compound 289

2-({[4-chloro-2-({[4-chloro-3-(trifluoromethyl)phenyl]sulfonyl}amino)phenyl]sulfanyl}methyl)-N-ethylbenzamide

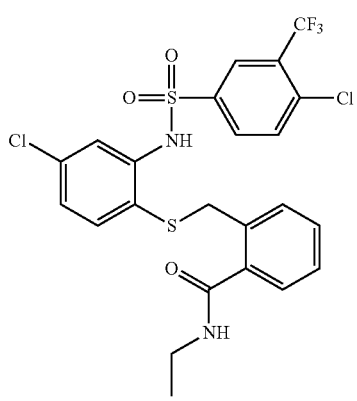 [SMILES: CCNC(=O)c1ccccc1CSc1ccc(Cl)cc1NS(=O)(=O)c1ccc(Cl)c(C(F)(F)F)c1]

A mixture of 2-({[4-chloro-2-({[4-chloro-3-(trifluoromethyl)phenyl]sulfonyl}amino)phenyl]sulfanyl}methyl)benzoic acid (394 mg, 0.74 mmol), HOBT (199 mg, 1.47 mmol), EDC (211 mg, 1.47 mmol), ethylamine hydrochloride (119 mg, 1.47 mmol) in DMF (3 ml) was stirred at room temperature overnight. The mixture was diluted with water, extracted with EtOAc. The organic layer was washed with brine, dried over Na$_2$SO$_4$, and concentrated in vacuo. The residue was purified by flash column chromatography on silica gel (0-30% EtOAc in hexane) to yield the title compound (100 mg, 24%).

$^1$H NMR (300 MHz, acetone-d6) δ 8.29 (d, J=2.05 Hz, 1H), 8.10 (dd, J=2.34, 8.50 Hz, 1H), 7.87 (d, J=8.50 Hz, 1H), 7.75 (br. s., 1H), 7.43-7.52 (m, 3H), 7.22-7.34 (m, 2H), 7.14 (dd, J=2.20, 8.35 Hz, 1H), 7.03-7.10 (m, 1H), 4.17 (s, 2H), 3.50 (qd, J=5.86, 7.23 Hz, 2H), 1.25 (t, J=7.18 Hz, 3H).

Intermediate 47

3-Bromo-N,N-diethylpropanamide

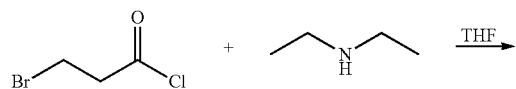

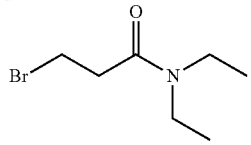

A mixture of 3-bromopropanoyl chloride (1.0 g, 5.8 mmol) and diethylamine (1.9 g, 26 mmol) in THF (20 ml) was stirred at 0° C. for 30 min, the resulting white solid was filtered and the filtrate was concentrated to give a crude oil which was used in the next reaction without further purification.

$^1$H NMR (300 MHz, CDCL$_3$) δ 3.67 (t, J=7.18 Hz, 2H), 3.39 (q, J=7.13 Hz, 2H), 3.31 (q, J=7.33 Hz, 2H), 2.89 (t, J=7.18 Hz, 2H), 1.19 (t, J=7.18 Hz, 3H), 1.12 (t, J=7.18 Hz, 3H).

Intermediate 48

3-((2-amino-4-chlorophenyl)thio)-N,N-diethylpropanamide

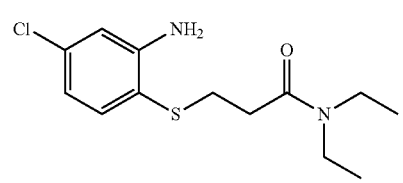 [SMILES: CCN(CC)C(=O)CCSc1ccc(Cl)cc1N]

Following General Procedure A, the title compound (1.0 g, 88%) was prepared from 2-amino-4-chlorobenzenethiol (660 mg, 4.13 mmol), crude 3-bromo-N,N-diethylpropanamide (860 mg, 6.60 mmol) and K$_2$CO$_3$ (2.9 g, 20.67 mmol) in DMF (20 ml).

$^1$H NMR (300 MHz, CDCl$_3$) δ 7.28 (d, J=8.20 Hz, 1H), 6.70 (d, J=2.34 Hz, 1H), 6.62 (dd, J=2.20, 8.06 Hz, 1H), 4.55 (br. s., 2H), 3.36 (q, J=7.03 Hz, 2H), 3.22 (q, J=7.33 Hz, 2H), 3.02 (t, J=7.18 Hz, 2H), 2.52 (t, J=7.18 Hz, 2H), 0.99-1.18 (m, 6H).

Compound 290

3-{[4-chloro-2-({[4-chloro-3-(trifluoromethyl)phenyl]sulfonyl}amino)phenyl]sulfanyl}-N,N-diethylpropanamide

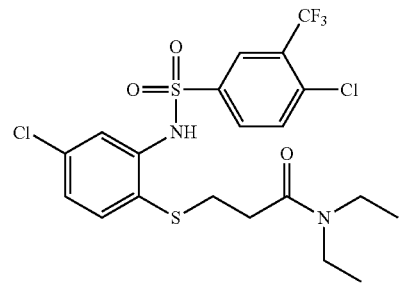 [SMILES: CCN(CC)C(=O)CCSc1ccc(Cl)cc1NS(=O)(=O)c1ccc(Cl)c(C(F)(F)F)c1]

Following General Procedure B, the title compound (999 mg, 85%) was prepared from 3-((2-amino-4-chlorophenyl)thio)-N,N-diethylpropanamide (635 mg, 2.22 mmol) and 4-chloro-3-(trifluoromethyl)benzene-1-sulfonyl chloride (619 mg, 2.22 mmol) in pyridine (6 ml).

¹H NMR (300 MHz, CDCL₃) δ 8.25 (d, J=1.76 Hz, 1H), 7.86 (dd, J=2.34, 8.50 Hz, 1H), 7.70 (s, 1H), 7.54 (d, J=8.21 Hz, 1H), 7.39 (d, J=8.50 Hz, 1H), 7.05 (dd, J=2.34, 8.20 Hz, 1H), 3.48 (q, J=7.03 Hz, 2H), 3.28 (q, J=7.23 Hz, 2H), 2.88 (t, J=6.30 Hz, 2H), 2.47 (t, J=6.30 Hz, 2H), 0.97-1.29 (m, 6H).

Compound 291

3-{[4-chloro-2-({[4-chloro-3-(trifluoromethyl)phenyl]sulfonyl}amino)phenyl]sulfinyl}-N,N-diethylpropanamide

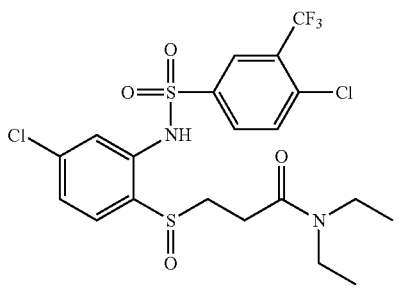 [SMILES: CCN(CC)C(=O)CCS(=O)c1ccc(Cl)cc1NS(=O)(=O)c1ccc(Cl)c(C(F)(F)F)c1]

Following General Procedure C, the title compound (272 mg, 61%) was prepared from 3-{[4-chloro-2-({[4-chloro-3-(trifluoromethyl)phenyl]sulfonyl}amino)phenyl]sulfanyl}-N,N-diethylpropanamide (430 mg, 0.81 mmol).

¹H NMR (300 MHz, CDCl₃) δ 8.21 (d, J=2.05 Hz, 1H), 7.89 (dd, J=2.05, 8.50 Hz, 1H), 7.67 (d, J=1.76 Hz, 1H), 7.58 (d, J=8.50 Hz, 1H), 7.47 (d, J=8.50 Hz, 1H), 7.21 (dd, J=1.90, 8.35 Hz, 1H), 3.44 (q, J=7.23 Hz, 2H), 3.33 (q, J=7.03 Hz, 2H), 3.12-3.25 (m, 1H), 2.95-3.08 (m, 1H), 2.85-2.94 (m, 1H), 2.64-2.77 (m, 1H), 1.11-1.24 (m, 6H)

Compound 292

3-{[4-chloro-2-({[4-chloro-3-(trifluoromethyl)phenyl]sulfonyl}amino)phenyl]sulfonyl}-N,N-diethylpropanamide

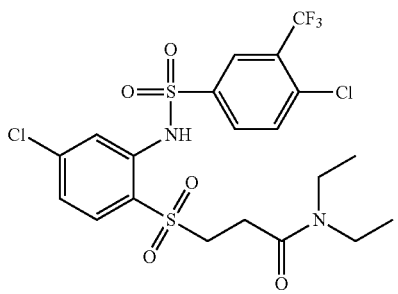 [SMILES: CCN(CC)C(=O)CCS(=O)(=O)c1ccc(Cl)cc1NS(=O)(=O)c1ccc(Cl)c(C(F)(F)F)c1]

Following General Procedure D, the title compound (300 mg, 79%) was prepared from 3-{[4-chloro-2-({[4-chloro-3-(trifluoromethyl)phenyl]sulfonyl}amino)phenyl]sulfanyl}-N,N-diethylpropanamide (357 mg, 0.68 mmol).

¹H NMR (300 MHz, CDCl₃) δ 8.26 (d, J=2.34 Hz, 1H), 8.01 (dd, J=2.34, 8.50 Hz, 1H), 7.70-7.78 (m, 2H), 7.65 (d, J=8.50 Hz, 1H), 7.18 (dd, J=1.90, 8.64 Hz, 1H), 3.43 (t, J=6.89 Hz, 2H), 3.24-3.39 (m, 4H), 2.79 (t, J=7.03 Hz, 2H), 1.19 (t, J=7.18 Hz, 3H), 1.08 (t, J=7.03 Hz, 3H).

Intermediate 49

3-((2-amino-4-chlorophenyl)thio)-1-(pyrrolidin-1-yl)propan-1-one

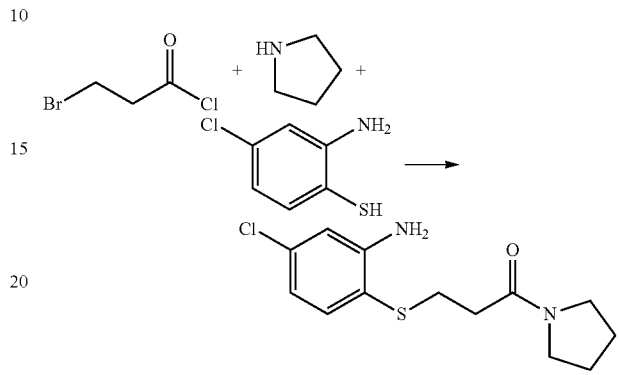

To a solution of K₂CO₃ (3.6 g, 26 mmol) in THF (20 ml) was added pyrrolidine (2.1 ml, 26 mmol) at room temperature, then the mixture was cooled to −78° C. and 3-bromopropanoyl chloride (1.0 g, 5.83 mmol) was added slowly. After it was stirred for 30 min, 2-amino-4-chlorobenzenethiol (837 mg, 5.24 mmol) was added to the mixture and the reaction was stirred at room temperature for 3 hours. The mixture was diluted with water, extracted with EtOAc. The organic layer was washed with brine, dried over Na₂SO₄, and concentrated in vacuo. The residue was purified by flash column chromatography on silica gel (0~30% EtOAc in hexane) to yield the title compound (760 mg, 46%).

¹H NMR (300 MHz, CDCL₃) δ 7.28 (d, J=8.21 Hz, 1H), 6.70 (d, J=2.34 Hz, 1H), 6.61 (dd, J=2.34, 8.21 Hz, 1H), 4.58 (br. s., 2H), 3.45 (t, J=6.74 Hz, 2H), 3.32 (t, J=6.74 Hz, 2H), 3.02 (t, J=7.03 Hz, 2H), 2.47 (t, J=7.03 Hz, 2H), 1.76-2.01 (m, 4H).

Compound 293

4-chloro-N-(5-chloro-2-{[3-oxo-3-(pyrrolidin-1-yl)propyl]sulfanyl}phenyl)-3-(trifluoromethyl)benzenesulfonamide

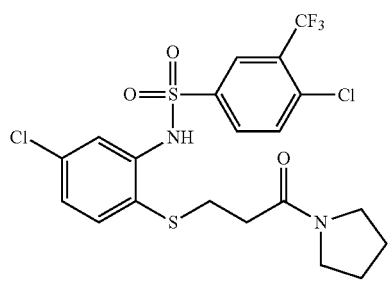 [SMILES: O=C(CCSc1ccc(Cl)cc1NS(=O)(=O)c1ccc(Cl)c(C(F)(F)F)c1)N1CCCC1]

Following General Procedure B, the title compound (242 mg, 17%) was prepared from 3-((2-amino-4-chlorophenyl)thio)-1-(pyrrolidin-1-yl)propan-1-one (758 mg, 2.67 mmol) and 4-chloro-3-(trifluoromethyl)benzene-1-sulfonyl chloride (745 mg, 2.67 mmol) in pyridine (10 ml).

¹H NMR (300 MHz, CDCL₃) δ 9.52 (br. s., 1H), 8.25 (d, J=2.05 Hz, 1H), 7.87 (dd, J=2.20, 8.35 Hz, 1H), 7.67 (d, J=2.34 Hz, 1H), 7.54 (d, J=8.21 Hz, 1H), 7.37 (s, 1H), 7.04 (dd, J=2.20, 8.35 Hz, 1H), 3.56 (t, J=6.89 Hz, 2H), 3.35 (t, J=6.74 Hz, 2H), 2.88 (t, J=6.15 Hz, 2H), 2.40 (t, J=6.30 Hz, 2H), 1.75-2.08 (m, 4H).

Compound 294

4-chloro-N-(5-chloro-2-{[3-oxo-3-(pyrrolidin-1-yl)propyl]sulfinyl}phenyl)-3-(trifluoromethyl)benzenesulfonamide

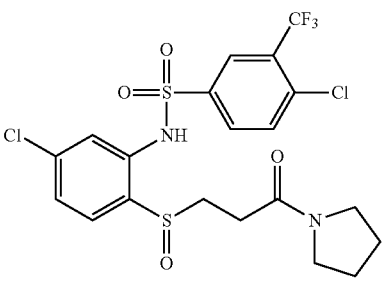 [SMILES: O=C(CCS(=O)c1ccc(Cl)cc1NS(=O)(=O)c1ccc(Cl)c(C(F)(F)F)c1)N1CCCC1]

Following General Procedure C, the title compound (91 mg, 78%) was prepared from 4-chloro-N-(5-chloro-2-{[3-oxo-3-(pyrrolidin-1-yl)propyl]sulfanyl}phenyl)-3-(trifluoromethyl)benzenesulfonamide (113 mg, 0.21 mmol).

¹H NMR (300 MHz, CD₃OD) δ 8.12 (d, J=2.05 Hz, 1H), 7.98 (dd, J=2.05, 8.50 Hz, 1H), 7.78 (d, J=8.50 Hz, 1H), 7.64 (d, J=8.50 Hz, 1H), 7.33 (dd, J=1.90, 8.35 Hz, 1H), 7.26 (d, J=2.05 Hz, 1H), 3.26-3.55 (m, 5H), 3.07-3.22 (m, 1H), 2.71-2.87 (m, 1H), 2.50-2.69 (m, 1H), 1.82-2.05 (m, 4H).

Compound 295

4-chloro-N-(5-chloro-2-{[3-oxo-3-(pyrrolidin-1-yl)propyl]sulfonyl}phenyl)-3-(trifluoromethyl)benzenesulfonamide

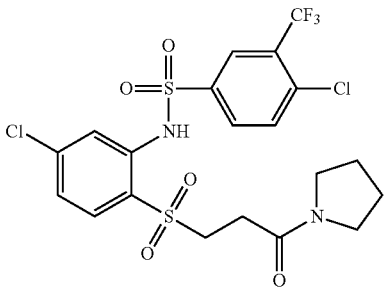 [SMILES: O=C(CCS(=O)(=O)c1ccc(Cl)cc1NS(=O)(=O)c1ccc(Cl)c(C(F)(F)F)c1)N1CCCC1]

Following General Procedure D, the title compound (76 mg, 94%) was prepared from 4-chloro-N-(5-chloro-2-{[3-oxo-3-(pyrrolidin-1-yl)propyl]sulfanyl}phenyl)-3-(trifluoromethyl)benzenesulfonamide (68 mg, 0.13 mmol).

¹H NMR (300 MHz, CD₃OD) δ 8.30 (d, J=2.05 Hz, 1H), 8.12 (dd, J=2.20, 8.35 Hz, 1H), 7.61-7.72 (m, 2H), 7.48 (d, J=2.05 Hz, 1H), 6.75 (dd, J=2.05, 8.50 Hz, 1H), 3.93 (t, J=7.62 Hz, 2H), 3.34-3.46 (m, 4H), 2.63 (t, J=7.62 Hz, 2H), 1.72-2.04 (m, 4H).

Compound 296

Methyl 2-(((2-(benzofuran-2-sulfonamido)-4-chlorophenyl)thio)methyl)benzoate

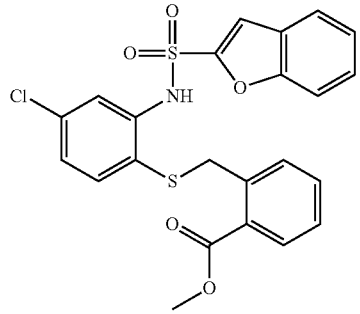 [SMILES: COC(=O)c1ccccc1CSc1ccc(Cl)cc1NS(=O)(=O)c1cc2ccccc2o1]

Following General Procedure B, the title compound (277 mg, 58%) was prepared from methyl 2-(((2-amino-4-chlorophenyl)thio)methyl)benzoate (300 mg, 0.98 mmol) and benzofuran-2-sulfonyl chloride (211 mg, 0.98 mmol) in pyridine (3 ml).

¹H NMR (300 MHz, CD₃OD) δ 7.85 (dd, J=3.81, 5.57 Hz, 1H), 7.66-7.77 (m, 1H), 7.54 (d, J=2.05 Hz, 1H), 7.41-7.52 (m, 3H), 7.30-7.39 (m, 1H), 7.21-7.29 (m, 2H), 6.97-7.12 (m, 2H), 6.81 (dd, J=3.52, 5.57 Hz, 1H), 4.22 (s, 2H), 3.84 (s, 3H).

Compound 297

2-[({2-[(1-benzofuran-2-ylsulfonyl)amino]-4-chlorophenyl}sulfanyl)methyl]benzoic acid

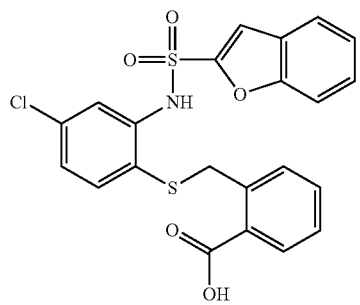 [SMILES: O=C(O)c1ccccc1CSc1ccc(Cl)cc1NS(=O)(=O)c1cc2ccccc2o1]

Following General Procedure Q, the title compound (247 mg, 92%) was prepared from Methyl 2-(((2-(benzofuran-2-sulfonamido)-4-chlorophenyl)thio)methyl)benzoate (277 mg, 0.57 mmol).

¹H NMR (300 MHz, CD₃OD) δ 7.89 (dd, J=1.76, 7.33 Hz, 1H), 7.72 (ddd, J=1.03, 1.17, 7.77 Hz, 1H), 7.53 (d, J=2.34 Hz, 1H), 7.50-7.52 (m, 1H), 7.48 (dd, J=1.17, 7.03 Hz, 1H), 7.46 (d, J=0.88 Hz, 1H), 7.31-7.37 (m, 1H), 7.17-7.29 (m, 2H), 7.09-7.14 (m, 1H), 6.97-7.07 (m, 1H), 6.70 (dd, J=1.61, 7.18 Hz, 1H), 4.23 (s, 2H).

Compound 298

2-[({2-[(1-benzofuran-2-ylsulfonyl)amino]-4-chlorophenyl}sulfinyl)methyl]benzoic acid

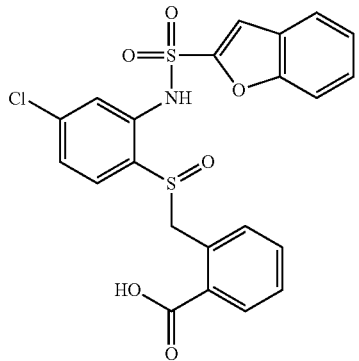 [SMILES: O=C(O)c1ccccc1CS(=O)c1ccc(Cl)cc1NS(=O)(=O)c1cc2ccccc2o1]

Following General Procedure C, the title compound (78 mg, 92%) was prepared from 2-[({2-[(1-benzofuran-2-ylsulfonyl)amino]-4-chlorophenyl}sulfanyl)methyl]benzoic acid (82 mg, 0.17 mmol).

$^1$H NMR (300 MHz, CD$_3$OD) δ 7.96-8.09 (m, 1H), 7.73 (d, J=7.91 Hz, 1H), 7.28-7.62 (m, 7H), 7.13-7.26 (m, 2H), 6.87-6.99 (m, 1H), 4.77 (d, J=12.31 Hz, 1H), 4.67 (d, J=12.31 Hz, 1H).

Compound 299

2-[({2-[(1-benzofuran-2-ylsulfonyl)amino]-4-chlorophenyl}sulfonyl)methyl]benzoic acid

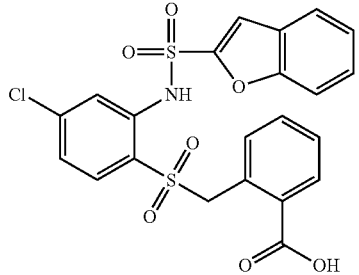 [SMILES: O=C(O)c1ccccc1CS(=O)(=O)c1ccc(Cl)cc1NS(=O)(=O)c1cc2ccccc2o1]

Following General Procedure D, the title compound (68 mg, 83%) was prepared from 2-[({2-[(1-benzofuran-2-ylsul-fonyl)amino]-4-chlorophenyl}sulfanyl)methyl]benzoic acid (77 mg, 0.16 mmol).

$^1$H NMR (300 MHz, acetone-d6) δ 7.98-8.06 (m, 1H), 7.81-7.86 (m, 2H), 7.80 (d, J=2.05 Hz, 1H), 7.60-7.65 (m, 1H), 7.45-7.56 (m, 4H), 7.35-7.43 (m, 1H), 7.14-7.31 (m, 2H), 5.32 (s, 2H).

Intermediate 50

2-amino-4-fluorobenzenethiol

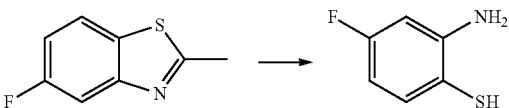

Following General Procedure K, the title compound (1.4 g, 84%) was prepared from 5-fluoro-2-methylbenzo[d]thiazole (1.8 g, 10.8 mmol).

$^1$H NMR (300 MHz, CD$_3$OD) δ 6.83 (dd, J=5.42, 8.06 Hz, 1H), 6.22-6.36 (m, 2H).

Intermediate 51 methyl 2-(((2-amino-4-fluorophenyl)thio)methyl)benzoate

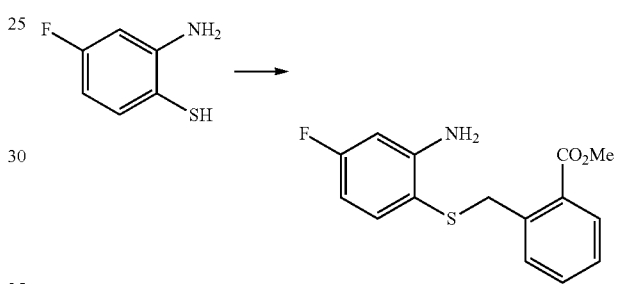

Following General Procedure A, the title compound (1.8 g, 60%) was prepared from 2-amino-4-fluorobenzenethiol (1.4 g, 9.79 mmol) and methyl 2-(bromomethyl)benzoate (2.2 g, 9.79 mmol), K$_2$CO$_3$ (4.0 g, 29.4 mmol) in DMF (50 ml).

$^1$H NMR (300 MHz, CD$_3$OD) δ 7.83 (dd, J=1.76, 7.33 Hz, 1H), 7.30 (td, J=1.76, 6.74 Hz, 2H), 6.97 (dd, J=1.61, 7.18 Hz, 1H), 6.86 (dd, J=6.45, 8.50 Hz, 1H), 6.42 (dd, J=2.64, 11.14 Hz, 1H), 6.13 (td, J=2.64, 8.50 Hz, 1H), 4.24 (s, 2H), 3.86 (s, 3H).

Compound 300 methyl 2-[({2-[(1-benzofuran-2-ylsulfonyl)amino]-4-fluorophenyl}sulfanyl)methyl]benzoate

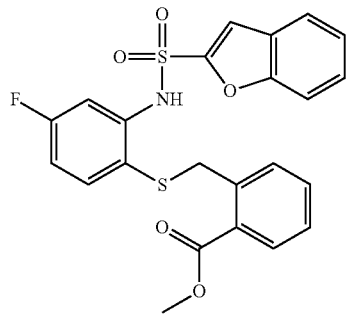 [SMILES: COC(=O)c1ccccc1CSc1ccc(F)cc1NS(=O)(=O)c1cc2ccccc2o1]

Following General Procedure B, the title compound (1.6 g, 55%) was prepared from methyl 2-(((2-amino-4-fluorophenyl)thio)methyl)benzoate (1.8 g, 6.19 mmol) and benzofuran-2-sulfonyl chloride (1.3 g, 6.19 mmol) in pyridine (10 ml).

$^1$H NMR (300 MHz, CD$_3$OD) δ 7.80-7.89 (m, 1H), 7.72 (d, J=7.62 Hz, 1H), 7.42-7.57 (m, 3H), 7.30-7.39 (m, 2H), 7.19-7.28 (m, 2H), 7.10 (dd, J=6.30, 8.64 Hz, 1H), 6.66-6.78 (m, 2H), 4.18 (s, 2H), 3.85 (s, 3H).

Compound 301

2-[({2-[(1-benzofuran-2-ylsulfonyl)amino]-4-fluorophenyl}sulfanyl)methyl]benzoic acid

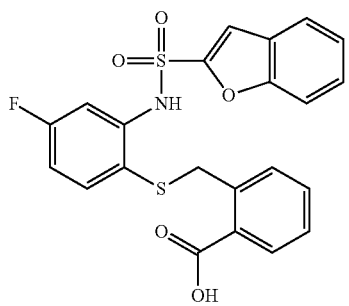 [SMILES: O=C(O)c1ccccc1CSc1ccc(F)cc1NS(=O)(=O)c1cc2ccccc2o1]

Following General Procedure Q, the title compound (130 mg, 99%) was prepared from methyl 2-(((2-(benzofuran-2-sulfonamido)-4-fluorophenyl)thio)methyl)benzoate (137 mg, 0.29 mmol).

$^1$H NMR (300 MHz, CD$_3$OD) δ 7.91 (dd, J=1.61, 7.47 Hz, 1H), 7.70 (d, J=7.91 Hz, 1H), 7.04-7.55 (m, 8H), 6.73 (td, J=2.78, 8.42 Hz, 1H), 6.56-6.66 (m, 1H), 4.19 (s, 2H).

Compound 302 methyl 2-[({2-[(1-benzofuran-2-ylsulfonyl)amino]-4-fluorophenyl}sulfinyl)methyl]benzoate

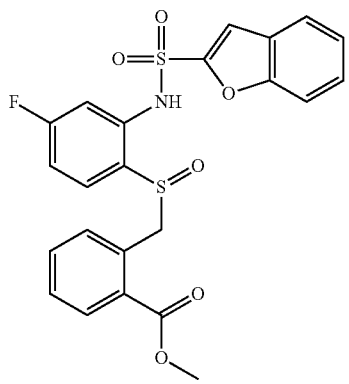 [SMILES: COC(=O)c1ccccc1CS(=O)c1ccc(F)cc1NS(=O)(=O)c1cc2ccccc2o1]

Following General Procedure C, the title compound (416 mg, 85%) was prepared from methyl 2-[({2-[(1-benzofuran-2-ylsulfonyl)amino]-4-fluorophenyl}sulfanyl)methyl]benzoate (476 mg, 1.01 mmol).

$^1$H NMR (300 MHz, CD$_3$OD) δ 7.92-8.00 (m, 1H), 7.75 (d, J=7.91 Hz, 1H), 7.31-7.64 (m, 6H), 7.26 (dd, J=2.34, 10.26 Hz, 1H), 7.16 (dd, J=5.86, 8.79 Hz, 1H), 6.93-7.01 (m, 2H), 4.82 (d, J=12.31 Hz, 1H), 4.70 (d, J=12.31 Hz, 1H), 3.85 (s, 3H).

Compound 303

2-[({2-[(1-benzofuran-2-ylsulfonyl)amino]-4-fluorophenyl}sulfinyl)methyl]benzoic acid

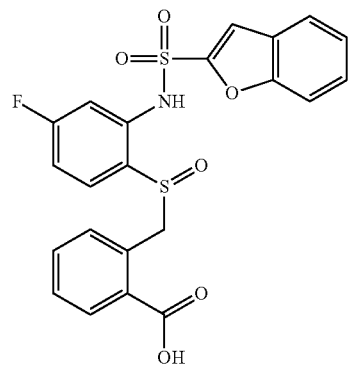 [SMILES: O=C(O)c1ccccc1CS(=O)c1ccc(F)cc1NS(=O)(=O)c1cc2ccccc2o1]

Following General Procedure Q, the title compound (276 mg, 90%) was prepared from methyl 2-[({2-[(1-benzofuran-2-ylsulfonyl)amino]-4-fluorophenyl}sulfinyl)methyl]benzoate (315 mg, 0.65 mmol).

$^1$H NMR (300 MHz, CD$_3$OD) δ 8.05 (dd, J=1.76, 7.33 Hz, 1H), 7.74 (d, J=7.91 Hz, 1H), 7.27-7.66 (m, 7H), 7.20 (dd, J=6.15, 8.79 Hz, 1H), 6.78-7.02 (m, 2H), 4.63-4.80 (m, 2H).

Compound 304 methyl 2-[({2-[(1-benzofuran-2-ylsulfonyl)amino]-4-fluorophenyl}sulfonyl)methyl]benzoate

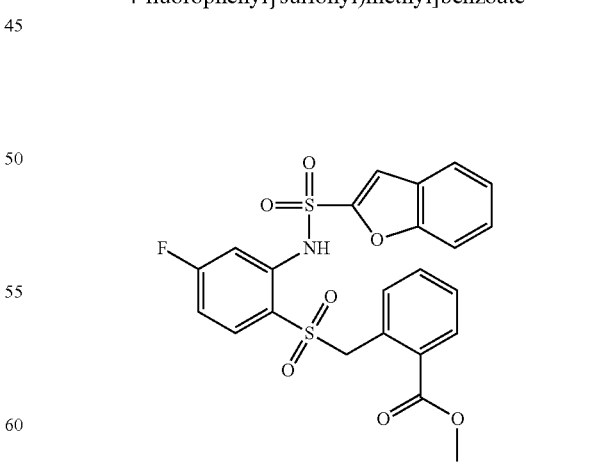

Following General Procedure D, the title compound (386 mg, 86%) was prepared from methyl 2-[({2-[(1-benzofuran-2-ylsulfonyl)amino]-4-fluorophenyl}sulfanyl)methyl]benzoate (422 mg, 0.90 mmol).

¹H NMR (300 MHz, DMSO-d₆) δ 7.71-7.82 (m, 3H), 7.65 (d, J=8.20 Hz, 1H), 7.27-7.52 (m, 6H), 7.15 (d, J=7.33 Hz, 1H), 6.89 (t, J=8.20 Hz, 1H), 5.33 (s, 2H), 3.72 (s, 3H).

Compound 305

2-[({2-[(1-benzofuran-2-ylsulfonyl)amino]-4-fluorophenyl}sulfonyl)methyl]benzoic acid

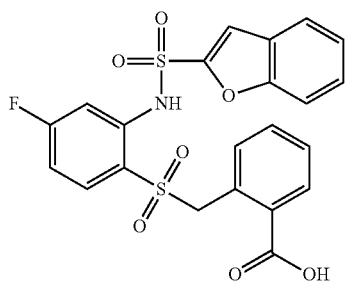 [SMILES: O=C(O)c1ccccc1CS(=O)(=O)c1ccc(F)cc1NS(=O)(=O)c1cc2ccccc2o1]

Following General Procedure Q, the title compound (254 mg, 94%) was prepared from methyl 2-[({2-[(1-benzofuran-2-ylsulfonyl)amino]-4-fluorophenyl}sulfonyl)methyl]benzoate (278 mg, 0.55 mmol).

¹H NMR (300 MHz, CD₃OD) δ 7.91 (d, J=9.08 Hz, 1H), 7.76 (d, J=7.91 Hz, 1H), 7.72 (s, 1H), 7.45-7.61 (m, 4H), 7.31-7.43 (m, 3H), 7.08 (d, J=8.79 Hz, 1H), 6.83-6.97 (m, 1H), 5.19 (s, 2H).

Intermediate 52 methyl 3-(((2-amino-4-fluorophenyl)thio)methyl)benzoate

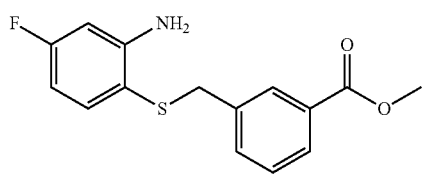 [SMILES: COC(=O)c1cccc(CSc2ccc(F)cc2N)c1]

Following General Procedure A, the title compound (750 mg, 88%) was prepared from 2-amino-4-fluorobenzenethiol (417 mg, 2.92 mmol) and methyl 3-(bromomethyl)benzoate (666 mg, 2.92 mmol), K₂CO₃ (1.21 g, 8.75 mmol) in DMF (10 ml).

¹H NMR (600 MHz, CDCL₃) δ 7.89 (d, J=7.92 Hz, 1H), 7.80 (s, 1H), 7.28-7.32 (m, 1H), 7.22-7.25 (m, 1H), 7.06 (dd, J=6.46, 8.51 Hz, 1H), 6.39 (dd, J=2.64, 10.56 Hz, 1H), 6.29 (td, J=2.64, 8.51 Hz, 1H), 4.41 (br. s., 2H), 3.91 (s, 3H), 3.86 (s, 2H).

Compound 306 methyl 3-[({2-[(1-benzofuran-2-ylsulfonyl)amino]-4-fluorophenyl}sulfanyl)methyl]benzoate

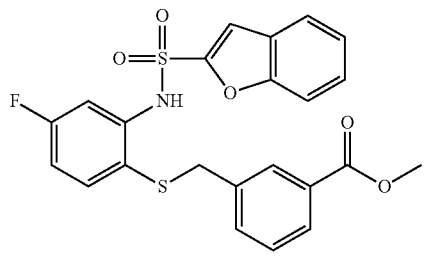 [SMILES: COC(=O)c1cccc(CSc2ccc(F)cc2NS(=O)(=O)c2cc3ccccc3o2)c1]

Following General Procedure B, the title compound (601 mg, 50%) was prepared from methyl 3-(((2-amino-4-fluorophenyl)thio)methyl)benzoate (750 mg, 2.58 mmol) and benzofuran-2-sulfonyl chloride (556 mg, 2.58 mmol) in pyridine (5 ml).

¹H NMR (600 MHz, CDCL₃) δ 8.23 (s, 1H), 7.86 (dt, J=1.36, 7.85 Hz, 1H), 7.62-7.70 (m, 2H), 7.50 (d, J=0.88 Hz, 1H), 7.46-7.49 (m, 1H), 7.39-7.46 (m, 2H), 7.32 (ddd, J=1.03, 7.12, 8.00 Hz, 1H), 7.22-7.26 (m, 1H), 7.02-7.10 (m, 2H), 6.57-6.63 (m, 1H), 3.88 (s, 3H), 3.79 (s, 2H).

Compound 307

3-[({2-[(1-benzofuran-2-ylsulfonyl)amino]-4-fluorophenyl}sulfanyl)methyl]benzoic acid

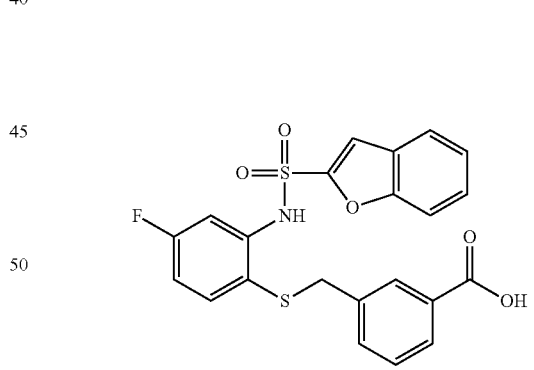

Following General Procedure Q, the title compound (223 mg, 79%) was prepared from methyl 3-[({2-[(1-benzofuran-2-ylsulfonyl)amino]-4-fluorophenyl}sulfanyl)methyl]benzoate (291 mg, 0.62 mmol).

¹H NMR (600 MHz, CDCL₃) δ 8.23 (s, 1H), 7.91 (ddd, J=1.32, 1.47, 7.78 Hz, 1H), 7.64-7.70 (m, 2H), 7.51 (d, J=1.17 Hz, 1H), 7.47-7.50 (m, 1H), 7.40-7.45 (m, 2H), 7.32 (ddd, J=1.03, 7.12, 8.00 Hz, 1H), 7.28 (t, J=7.78 Hz, 1H), 7.12 (d, J=7.92 Hz, 1H), 7.08 (dd, J=6.16, 8.80 Hz, 1H), 6.56-6.66 (m, 1H), 3.80 (s, 2H).

Compound 308 methyl 3-[({2-[(1-benzofuran-2-ylsulfonyl)amino]-4-fluorophenyl}sulfinyl)methyl]benzoate

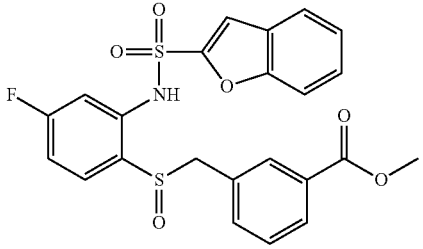 [SMILES: COC(=O)c1cccc(CS(=O)c2ccc(F)cc2NS(=O)(=O)c2cc3ccccc3o2)c1]

Following General Procedure C, the title compound (120 mg, 96%) was prepared methyl 3-[({2-[(1-benzofuran-2-ylsulfonyl)amino]-4-fluorophenyl}sulfanyl)methyl]benzoate (120 mg, 0.26 mmol).

$^1$H NMR (600 MHz, CDCL$_3$) δ 10.92 (br. s., 1H), 7.94 (d, J=7.92 Hz, 1H), 7.68 (d, J=7.63 Hz, 1H), 7.56-7.60 (m, 1H), 7.44-7.48 (m, 1H), 7.36-7.42 (m, 2H), 7.27-7.33 (m, 2H), 7.26 (t, J=3.81 Hz, 1H), 7.10 (d, J=7.63 Hz, 1H), 6.72 (dd, J=5.72, 8.66 Hz, 1H), 6.60 (td, J=2.05, 8.07 Hz, 1H), 4.44 (d, J=12.62 Hz, 1H), 4.31 (d, J=12.62 Hz, 1H), 3.86 (s, 3H).

Compound 309

3-[({2-[(1-benzofuran-2-ylsulfonyl)amino]-4-fluorophenyl}sulfinyl)methyl]benzoic acid

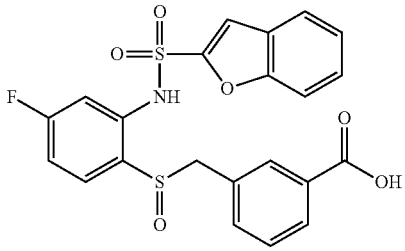 [SMILES: O=C(O)c1cccc(CS(=O)c2ccc(F)cc2NS(=O)(=O)c2cc3ccccc3o2)c1]

Following General Procedure Q, the title compound (33 mg, 48%) was prepared from methyl 3-[({2-[(1-benzofuran-2-ylsulfonyl)amino]-4-fluorophenyl}sulfinyl)methyl]benzoate (74 mg, 0.15 mmol).

$^1$H NMR (600 MHz, DMSO-d$_6$) δ 7.82 (d, J=7.34 Hz, 1H), 7.76 (d, J=7.92 Hz, 1H), 7.68 (d, J=7.92 Hz, 1H), 7.59-7.64 (m, 2H), 7.50 (t, J=7.78 Hz, 1H), 7.32-7.38 (m, 2H), 7.08-7.26 (m, 3H), 7.00 (dd, J=2.05, 10.27 Hz, 1H), 4.39 (d, J=12.91 Hz, 1H), 4.08 (d, J=12.91 Hz, 1H).

Compound 310 methyl 3-[({2-[(1-benzofuran-2-ylsulfonyl)amino]-4-fluorophenyl}sulfonyl)methyl]benzoate

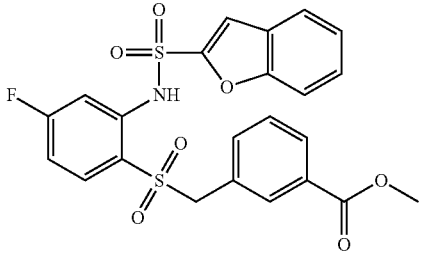 [SMILES: COC(=O)c1cccc(CS(=O)(=O)c2ccc(F)cc2NS(=O)(=O)c2cc3ccccc3o2)c1]

Following General Procedure D, the title compound (125 mg, 94%) was prepared from methyl 3-[({2-[(1-benzofuran-2-ylsulfonyl)amino]-4-fluorophenyl}sulfanyl)methyl]benzoate (125 mg, 0.27 mmol).

$^1$H NMR (600 MHz, CDCL$_3$) δ 9.44 (br. s., 1H), 7.98 (dd, J=1.17, 7.63 Hz, 1H), 7.70 (d, J=7.92 Hz, 1H), 7.60 (s, 1H), 7.58 (s, 1H), 7.54 (dd, J=2.20, 10.42 Hz, 1H), 7.41-7.49 (m, 3H), 7.29-7.36 (m, 2H), 7.17 (d, J=7.63 Hz, 1H), 6.68-6.79 (m, 1H), 4.37 (s, 2H), 3.86 (s, 3H).

Compound 311

3-[({2-[(1-benzofuran-2-ylsulfonyl)amino]-4-fluorophenyl}sulfonyl)methyl]benzoic acid

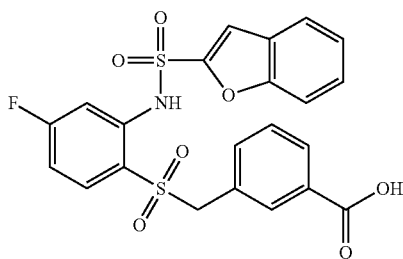 [SMILES: O=C(O)c1cccc(CS(=O)(=O)c2ccc(F)cc2NS(=O)(=O)c2cc3ccccc3o2)c1]

Following General Procedure Q, the title compound (87 mg, 94%) was prepared from methyl 3-[({2-[(1-benzofuran-2-ylsulfonyl)amino]-4-fluorophenyl}sulfonyl)methyl]benzoate (94 mg, 0.19 mmol).

$^1$H NMR (600 MHz, DMSO-d$_6$) δ 7.81 (td, J=1.61, 4.47 Hz, 1H), 7.73-7.78 (m, 2H), 7.60-7.66 (m, 2H), 7.51-7.57 (m, 1H), 7.45 (t, J=7.78 Hz, 1H), 7.34 (t, J=7.48 Hz, 1H), 7.29-7.31 (m, 2H), 7.27 (dd, J=2.49, 11.59 Hz, 1H), 6.91 (s, 1H), 4.93 (s, 2H).

Intermediate 53 methyl 4-(((2-amino-4-fluorophenyl)thio)methyl)benzoate

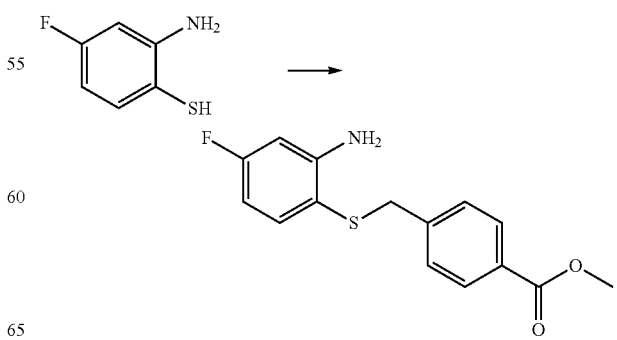

Following General Procedure A, the title compound (873 mg, 94%) was prepared from 2-amino-4-fluorobenzenethiol (456 mg, 3.19 mmol) and methyl 4-(bromomethyl)benzoate (731 mg, 3.19 mmol), K$_2$CO$_3$ (1.32 g, 9.58 mmol) in DMF (20 ml).

$^1$H NMR (600 MHz, CDCL$_3$) δ 7.89 (d, J=8.22 Hz, 2H), 7.12 (d, J=8.22 Hz, 2H), 7.03 (dd, J=6.46, 8.51 Hz, 1H), 6.38 (dd, J=2.64, 10.56 Hz, 1H), 6.27 (td, J=2.64, 8.51 Hz, 1H), 4.36 (br. s., 2H), 3.90 (s, 3H), 3.83 (s, 2H).

Compound 312 methyl 4-[({2-[(1-benzofuran-2-ylsulfonyl)amino]-4-fluorophenyl}sulfanyl)methyl]benzoate

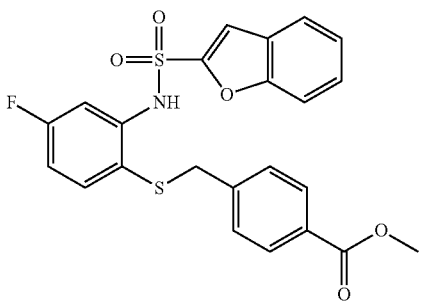 [SMILES: COC(=O)c1ccc(CSc2ccc(F)cc2NS(=O)(=O)c2cc3ccccc3o2)cc1]

Following General Procedure B, the title compound (929 mg, 66%) was prepared from methyl 4-(((2-amino-4-fluorophenyl)thio)methyl)benzoate (873 g, 2.99 mmol) and benzofuran-2-sulfonyl chloride (646 mg, 2.99 mmol) in pyridine (5 ml).

$^1$H NMR (600 MHz, CDCL$_3$) δ 8.25 (br. s., 1H), 7.80-7.88 (m, 2H), 7.68 (dt, J=1.03, 7.92 Hz, 1H), 7.51 (d, J=1.17 Hz, 1H), 7.39-7.49 (m, 3H), 7.31-7.35 (m, 1H), 7.01 (dd, J=6.16, 8.51 Hz, 1H), 6.96 (d, J=8.22 Hz, 2H), 6.49-6.63 (m, 1H), 3.89 (s, 3H), 3.77 (s, 2H).

Compound 313

4-[({2-[(1-benzofuran-2-ylsulfonyl)amino]-4-fluorophenyl}sulfanyl)methyl]benzoic acid

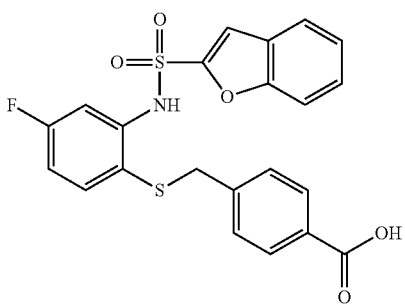 [SMILES: O=C(O)c1ccc(CSc2ccc(F)cc2NS(=O)(=O)c2cc3ccccc3o2)cc1]

Following General Procedure Q, the title compound (516 mg, 86%) was prepared from methyl 4-[({2-[(1-benzofuran-2-ylsulfonyl)amino]-4-fluorophenyl}sulfanyl)methyl]benzoate (620 mg, 1.32 mmol).

$^1$H NMR (600 MHz, CDCL$_3$) δ 8.25 (s, 1H), 7.91 (d, J=8.51 Hz, 2H), 7.69 (s, 1H), 7.40-7.54 (m, 4H), 7.33 (dd, J=0.88, 14.97 Hz, 1H), 7.03 (dd, J=6.16, 8.51 Hz, 1H), 6.99 (d, J=8.51 Hz, 2H), 6.60 (td, J=2.64, 8.22 Hz, 1H), 3.79 (s, 2H).

Compound 314 methyl 4-[({2-[(1-benzofuran-2-ylsulfonyl)amino]-4-fluorophenyl}sulfinyl)methyl]benzoate

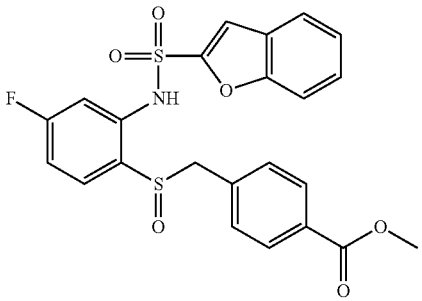 [SMILES: COC(=O)c1ccc(CS(=O)c2ccc(F)cc2NS(=O)(=O)c2cc3ccccc3o2)cc1]

Following General Procedure C, the title compound (55 mg, 44%) was prepared from methyl 4-[({2-[(1-benzofuran-2-ylsulfonyl)amino]-4-fluorophenyl}sulfanyl)methyl]benzoate (120 mg, 0.26 mmol).

$^1$H NMR (600 MHz, CDCL$_3$) δ 10.83 (br. s., 1H), 7.21-7.92 (m, 8H), 6.90 (s, 2H), 6.60 (s, 1H), 6.50 (s, 1H), 4.16-4.61 (m, 2H), 3.82 (s, 3H).

Compound 315

4-[({2-[(1-benzofuran-2-ylsulfonyl)amino]-4-fluorophenyl}sulfinyl)methyl]benzoic acid

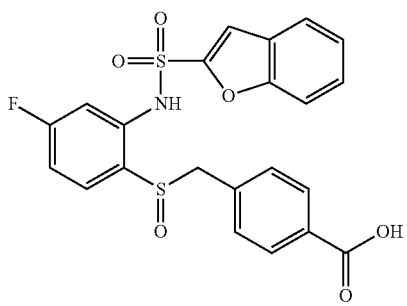 [SMILES: O=C(O)c1ccc(CS(=O)c2ccc(F)cc2NS(=O)(=O)c2cc3ccccc3o2)cc1]

Following General Procedure Q, the title compound (48 mg, 100%) was prepared from methyl 4-[({2-[(1-benzofuran-2-ylsulfonyl)amino]-4-fluorophenyl}sulfinyl)methyl]benzoate (50 mg, 0.103 mmol).

$^1$H NMR (600 MHz, DMSO-d$_6$) δ 7.74-7.80 (m, 3H), 7.69 (d, J=8.51 Hz, 1H), 7.62 (s, 1H), 7.50 (t, J=7.63 Hz, 1H), 7.37 (t, J=7.48 Hz, 1H), 7.19-7.25 (m, 1H), 7.09-7.15 (m, 1H), 7.07 (d, J=7.63 Hz, 2H), 6.99 (d, J=10.27 Hz, 1H), 4.39 (d, J=12.91 Hz, 1H), 4.11 (d, J=12.91 Hz, 1H).

Compound 316 methyl 4-[({2-[(1-benzofuran-2-ylsulfonyl)amino]-4-fluorophenyl}sulfonyl)methyl]benzoate

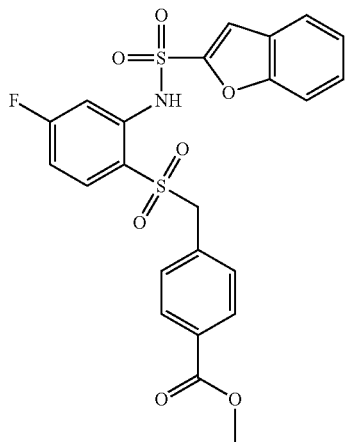 [SMILES: COC(=O)c1ccc(CS(=O)(=O)c2ccc(F)cc2NS(=O)(=O)c2cc3ccccc3o2)cc1]

Following General Procedure D, the title compound (92 mg, 71%) was prepared from methyl 4-[({2-[(1-benzofuran-2-ylsulfonyl)amino]-4-fluorophenyl}sulfanyl)methyl]benzoate (121 mg, 0.26 mmol).

$^1$H NMR (600 MHz, CDCL$_3$) δ 7.88 (d, J=8.22 Hz, 2H), 7.71 (d, J=7.92 Hz, 1H), 7.61 (s, 1H), 7.52-7.57 (m, 1H), 7.42-7.51 (m, 2H), 7.31-7.40 (m, 2H), 7.03 (d, J=8.22 Hz, 2H), 6.67-6.76 (m, 1H), 4.39 (s, 2H), 3.90 (s, 3H).

Compound 317

4-[({2-[(1-benzofuran-2-ylsulfonyl)amino]-4-fluorophenyl}sulfonyl)methyl]benzoic acid

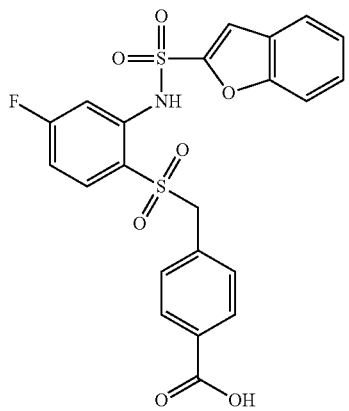 [SMILES: O=C(O)c1ccc(CS(=O)(=O)c2ccc(F)cc2NS(=O)(=O)c2cc3ccccc3o2)cc1]

Following General Procedure Q, the title compound (80 mg, 91%) was prepared from methyl 4-[({2-[(1-benzofuran-2-ylsulfonyl)amino]-4-fluorophenyl}sulfonyl)methyl]benzoate (90 mg, 0.179 mmol).

$^1$H NMR (600 MHz, DMSO-d$_6$) δ 7.77 (d, J=7.92 Hz, 1H), 7.74 (d, J=8.22 Hz, 2H), 7.66 (s, 1H), 7.64 (d, J=8.51 Hz, 1H), 7.50-7.53 (m, 1H), 7.46 (t, J=7.78 Hz, 1H), 7.35 (t, J=7.63 Hz, 1H), 7.25-7.31 (m, 1H), 7.20 (d, J=8.22 Hz, 2H), 6.80-6.96 (m, 1H), 4.93 (s, 2H).

Intermediate 54

Methyl 2-(((2-aminophenyl)thio)methyl)benzoate

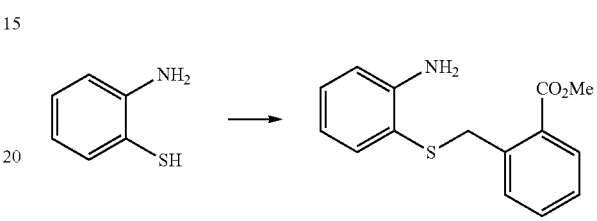

Following General Procedure A, the title compound (1.7 g, 74%) was prepared from 2-aminobenzenethiol (1.1 g, 8.47 mmol), methyl 2-(bromomethyl)benzoate (1.9 g, 8.47 mmol), and K$_2$CO$_3$ (3.5 g, 25.4 mmol) in DMF (50 ml).

$^1$H NMR (300 MHz, CDCL$_3$) δ 7.90 (dd, J=1.90, 7.18 Hz, 1H), 7.22-7.35 (m, 2H), 7.07-7.12 (m, 2H), 6.94-7.01 (m, 1H), 6.68 (d, J=7.62 Hz, 1H), 6.57 (td, J=1.17, 7.47 Hz, 1H), 4.33 (br. s., 2H), 4.30 (s, 2H), 3.88 (s, 3H).

Compound 318 methyl 2-[({2-[(1-benzofuran-2-ylsulfonyl)amino]phenyl}sulfanyl)methyl]benzoate

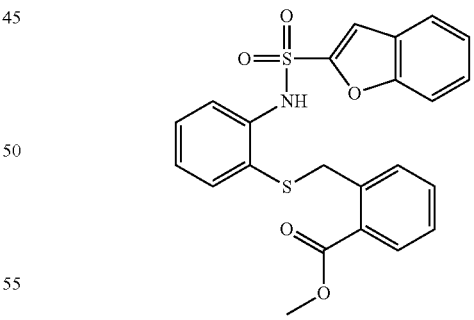

Following General Procedure B, the title compound (803 mg, 74%) was prepared from methyl 2-(((2-aminophenyl)thio)methyl)benzoate (652 mg, 2.39 mmol) and benzofuran-2-sulfonyl chloride (816 mg, 3.78 mmol) in pyridine (10 ml).

$^1$H NMR (300 MHz, CDCL$_3$) δ 8.36 (s, 1H), 7.89-8.02 (m, 1H), 7.63 (t, J=7.62 Hz, 2H), 7.36-7.49 (m, 3H), 7.24-7.33 (m, 4H), 7.20 (dd, J=1.32, 7.77 Hz, 1H), 6.86-7.00 (m, 1H), 6.79 (d, J=5.86 Hz, 1H), 4.25 (s, 2H), 3.93 (s, 3H).

Compound 319

2-[({2-[(1-benzofuran-2-ylsulfonyl)amino]phenyl}sulfanyl)methyl]benzoic acid

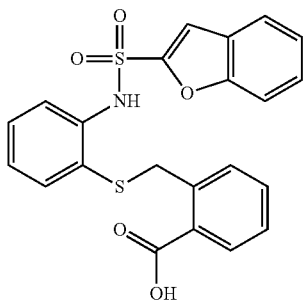 [SMILES: O=C(O)c1ccccc1CSc1ccccc1NS(=O)(=O)c1cc2ccccc2o1]

Following General Procedure Q, the title compound (220 mg, 99%) was prepared from methyl 2-[({2-[(1-benzofuran-2-ylsulfonyl)amino]phenyl}sulfanyl)methyl]benzoate (227 mg, 0.50 mmol).

$^1$H NMR (300 MHz, CDCL$_3$) δ 8.52 (s, 1H), 8.03-8.17 (m, 1H), 7.64 (dd, J=8.06, 13.63 Hz, 2H), 7.17-7.52 (m, 8H), 6.91-7.01 (m, 1H), 6.83-6.90 (m, 1H), 4.29 (s, 2H).

Compound 320 methyl 2-[({2-[(1-benzofuran-2-ylsulfonyl)amino]phenyl}sulfinyl)methyl]benzoate

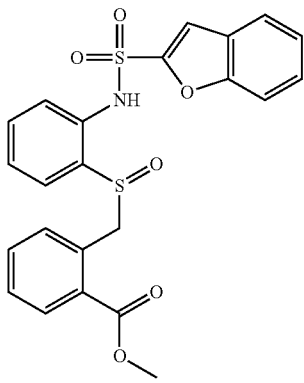 [SMILES: COC(=O)c1ccccc1CS(=O)c1ccccc1NS(=O)(=O)c1cc2ccccc2o1]

Following General Procedure C, the title compound (182 mg, 77%) was prepared from methyl 2-[({2-[(1-benzofuran-2-ylsulfonyl)amino]phenyl}sulfanyl)methyl]benzoate (228 mg, 0.50 mmol).

$^1$H NMR (300 MHz, CDCL$_3$) δ 7.99-8.15 (m, 1H), 7.76 (dd, J=0.88, 8.50 Hz, 1H), 7.58-7.67 (m, 1H), 7.48 (d, J=0.88 Hz, 1H), 7.33-7.45 (m, 5H), 7.21-7.30 (m, 1H), 7.14-7.20 (m, 1H), 6.99-7.12 (m, 2H), 4.82 (d, J=11.72 Hz, 1H), 4.57 (d, J=12.01 Hz, 1H), 3.91 (s, 3H).

Compound 321

2-[({2-[(1-benzofuran-2-ylsulfonyl)amino]phenyl}sulfinyl)methyl]benzoic acid

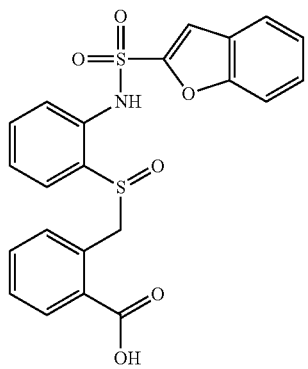 [SMILES: O=C(O)c1ccccc1CS(=O)c1ccccc1NS(=O)(=O)c1cc2ccccc2o1]

Following General Procedure Q, the title compound (145 mg, 96%) was prepared from methyl 2-[({2-[(1-benzofuran-2-ylsulfonyl)amino]phenyl}sulfinyl)methyl]benzoate (155 mg, 0.33 mmol).

$^1$H NMR (300 MHz, CDCL$_3$) δ 10.37 (br.s, 1H), 8.11-8.26 (m, 1H), 7.76 (d, J=8.50 Hz, 1H), 7.64 (d, J=7.62 Hz, 1H), 7.35-7.52 (m, 4H), 7.23-7.33 (m, 4H), 7.06-7.18 (m, 2H), 4.88 (d, J=12.01 Hz, 1H), 4.52 (d, J=12.01 Hz, 1H).

Compound 322 methyl 2-[({2-[(1-benzofuran-2-ylsulfonyl)amino]phenyl}sulfonyl)methyl]benzoate

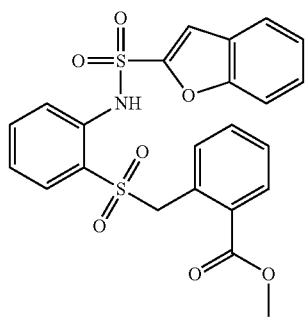 [SMILES: COC(=O)c1ccccc1CS(=O)(=O)c1ccccc1NS(=O)(=O)c1cc2ccccc2o1]

Following General Procedure D, the title compound (201 mg, 63%) was prepared from methyl 2-[({2-[(1-benzofuran-2-ylsulfonyl)amino]phenyl}sulfanyl)methyl]benzoate (300 mg, 0.66 mmol).

$^1$H NMR (300 MHz, CDCL$_3$) δ 7.85-7.94 (m, 1H), 7.76 (d, J=8.50 Hz, 1H), 7.65 (d, J=7.62 Hz, 1H), 7.35-7.57 (m, 7H), 7.24-7.33 (m, 1H), 7.10-7.18 (m, 1H), 6.98-7.08 (m, 1H), 5.10 (s, 2H), 3.75 (s, 3H).

Compound 323

2-[({2-[(1-benzofuran-2-ylsulfonyl)amino]phenyl}sulfonyl)methyl]benzoic acid

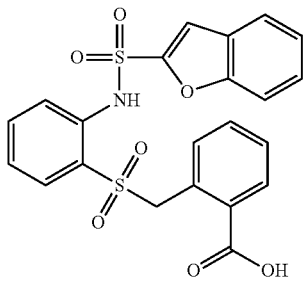 [SMILES: O=C(O)c1ccccc1CS(=O)(=O)c1ccccc1NS(=O)(=O)c1cc2ccccc2o1]

Following General Procedure Q, the title compound (154 mg, 87%) was prepared from methyl 2-[({2-[(1-benzofuran-2-ylsulfonyl)amino]phenyl}sulfonyl)methyl]benzoate (182 mg, 0.38 mmol).

$^1$H NMR (300 MHz, CDCL$_3$) δ 8.06 (dd, J=1.76, 7.33 Hz, 1H), 7.77 (d, J=8.50 Hz, 1H), 7.67 (d, J=7.33 Hz, 1H), 7.39-7.60 (m, 7H), 7.28-7.37 (m, 2H), 7.03-7.14 (m, 1H), 5.13 (s, 2H).

Intermediate 55

Methyl 2-(((4-methyl-2-nitrophenyl)thio)methyl)benzoate

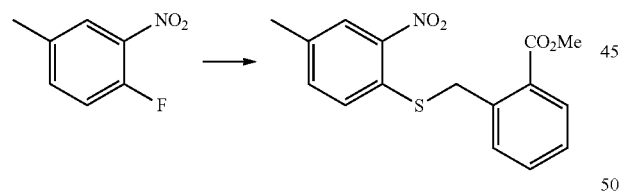

To a solution of 1-fluoro-4-methyl-2-nitrobenzene (1.35 g, 8.70 mmol) in DMF (20 ml) was added Na$_2$S.9H$_2$O (2.09 g, 8.70 mmol) and the reaction was stirred at room temperature for 16 hours, then methyl 2-(bromomethyl)benzoate (1.99 g, 8.70 mmol) and K$_2$CO$_3$ (6.0 g, 43.52 mmol) was added and the reaction was continued for 3 hours, diluted with water, extracted with EtOAc. The organic layer was washed with brine, dried over Na$_2$SO$_4$, and concentrated in vacuo. The residue was purified by flash column chromatography on silica gel (0→20% EtOAc in hexane) to yield the title compound (741 mg, 27%).

$^1$H NMR (600 MHz, CDCL$_3$) δ 7.91-8.02 (m, 2H), 7.42-7.52 (m, 2H), 7.29-7.39 (m, 3H), 4.66 (s, 2H), 3.90 (s, 3H), 2.39 (s, 3H).

Intermediate 56

Methyl 2-(((2-amino-4-methylphenyl)thio)methyl)benzoate

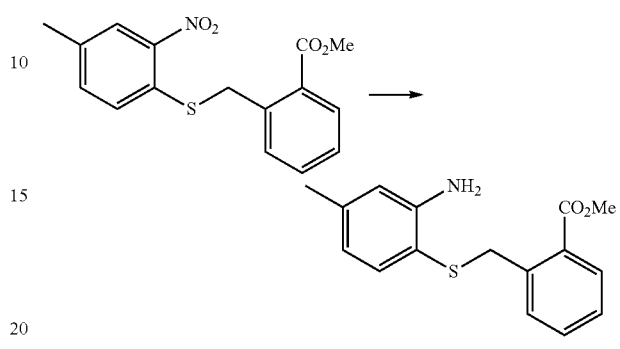

Following General Procedure L, the title compound (567 mg, 85%) was prepared from methyl 2-(((4-methyl-2-nitrophenyl)thio)methyl)benzoate (741 mg, 2.34 mmol), Zn (3.7 g, 58.44 mmol) and saturated aqueous NH$_4$Cl (1 ml) in MeOH (20 ml).

$^1$H NMR (300 MHz, CDCL$_3$) δ 7.90 (d, J=7.62 Hz, 1H), 7.22-7.38 (m, 2H), 6.99 (d, J=7.91 Hz, 2H), 6.53 (s, 1H), 6.40 (d, J=7.62 Hz, 1H), 4.26 (s, 2H), 3.88 (s, 3H), 2.23 (s, 3H).

Compound 324

Methyl 2-[({2-[(1-benzofuran-2-ylsulfonyl)amino]-4-methylphenyl}sulfanyl)methyl]benzoate

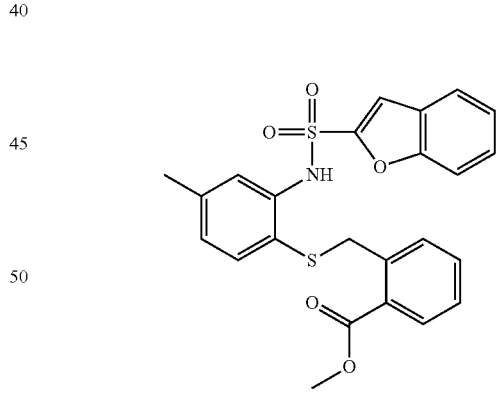

Following General Procedure B, the title compound (688 mg, 75%) was prepared from methyl 2-(((2-amino-4-methylphenyl)thio)methyl)benzoate (567 mg, 1.98 mmol) and benzofuran-2-sulfonyl chloride (854 mg, 3.96 mmol) in pyridine (10 ml).

$^1$H NMR (600 MHz, CDCL$_3$) δ 8.33 (s, 1H), 7.94-7.97 (m, 1H), 7.60-7.64 (m, 1H), 7.45-7.48 (m, 2H), 7.38-7.42 (m, 1H), 7.38 (d, J=0.9 Hz, 1H), 7.24-7.32 (m, 3H), 7.07 (d, J=7.63 Hz, 1H), 6.78-6.83 (m, 1H), 6.70-6.76 (m, 1H), 4.20 (s, 2H), 3.93 (s, 3H), 2.31 (s, 3H).

Compound 325

2-[({2-[(1-benzofuran-2-ylsulfonyl)amino]-4-methylphenyl}sulfanyl)methyl]benzoic acid

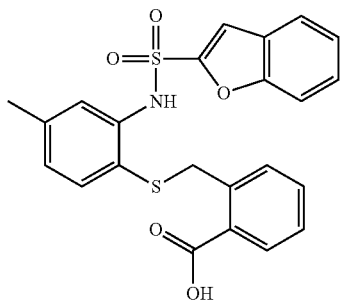 [SMILES: Cc1ccc(SCc2ccccc2C(=O)O)c(NS(=O)(=O)c2cc3ccccc3o2)c1]

Following General Procedure Q, the title compound (250 mg, 98%) was prepared from methyl 2-[({2-[(1-benzofuran-2-ylsulfonyl)amino]-4-methylphenyl}sulfanyl)methyl]benzoate (262 mg, 0.56 mmol).

$^1$H NMR (600 MHz, CDCL$_3$) δ 8.09-8.12 (m, 1H), 7.61-7.63 (m, 1H), 7.50 (d, J=0.88 Hz, 1H), 7.46 (dq, J=0.88, 8.51 Hz, 1H), 7.33-7.42 (m, 4H), 7.25-7.30 (m, 1H), 7.17 (d, J=7.92 Hz, 1H), 6.94 (dd, J=1.76, 7.34 Hz, 1H), 6.78 (ddd, J=0.88, 1.91, 7.78 Hz, 1H), 4.24 (s, 2H), 2.32 (s, 3H).

Compound 326

Methyl 2-[({2-[(1-benzofuran-2-ylsulfonyl)amino]-4-methylphenyl}sulfinyl)methyl]benzoate

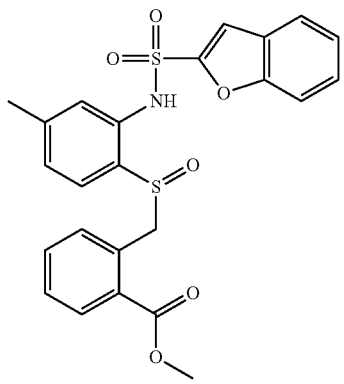 [SMILES: COC(=O)c1ccccc1CS(=O)c1ccc(C)cc1NS(=O)(=O)c1cc2ccccc2o1]

Following General Procedure C, the title compound (162 mg, 94%) was prepared from methyl 2-[({2-[(1-benzofuran-2-ylsulfonyl)amino]-4-methylphenyl}sulfanyl)methyl]benzoate (167 mg, 0.36 mmol).

$^1$H NMR (600 MHz, CDCL$_3$) δ 10.62 (br. s., 1H), 8.07 (dd, J=1.61, 7.48 Hz, 1H), 7.65 (d, J=7.92 Hz, 1H), 7.59 (s, 1H), 7.49 (d, J=0.88 Hz, 1H), 7.37-7.47 (m, 4H), 7.27-7.31 (m, 1H), 7.15 (dd, J=1.61, 7.19 Hz, 1H), 7.07 (d, J=7.92 Hz, 1H), 6.88 (dd, J=0.73, 7.78 Hz, 1H), 4.81 (d, J=11.74 Hz, 1H), 4.55 (d, J=12.03 Hz, 1H), 3.93 (s, 3H), 2.37 (s, 3H).

Compound 327

2-[({2-[(1-benzofuran-2-ylsulfonyl)amino]-4-methylphenyl}sulfinyl)methyl]benzoic acid

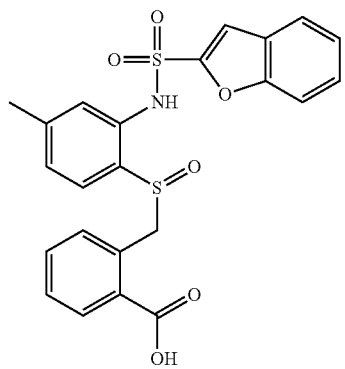 [SMILES: Cc1ccc(S(=O)Cc2ccccc2C(=O)O)c(NS(=O)(=O)c2cc3ccccc3o2)c1]

Following General Procedure Q, the title compound (120 mg, 88%) was prepared from methyl 2-[({2-[(1-benzofuran-2-ylsulfonyl)amino]-4-methylphenyl}sulfinyl)methyl]benzoate (140 mg, 0.29 mmol).

$^1$H NMR (600 MHz, CDCL$_3$) δ 10.48 (br. s., 1H), 8.14-8.20 (m, 1H), 7.66 (d, J=7.92 Hz, 1H), 7.58 (s, 1H), 7.50 (d, J=0.88 Hz, 1H), 7.43-7.49 (m, 3H), 7.37-7.42 (m, 1H), 7.28-7.34 (m, 1H), 7.00-7.14 (m, 2H), 6.90 (dd, J=0.88, 7.92 Hz, 1H), 4.82 (d, J=12.03 Hz, 1H), 4.67 (d, J=12.03 Hz, 1H), 2.37 (s, 3H).

Compound 328

Methyl 2-[({2-[(1-benzofuran-2-ylsulfonyl)amino]-4-methylphenyl}sulfonyl)methyl]benzoate

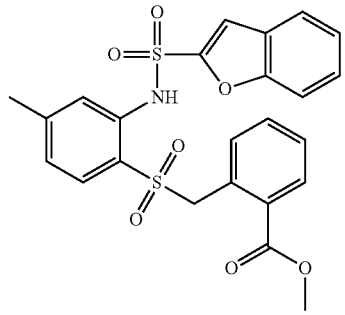 [SMILES: COC(=O)c1ccccc1CS(=O)(=O)c1ccc(C)cc1NS(=O)(=O)c1cc2ccccc2o1]

Following General Procedure D, the title compound (166 mg, 93%) was prepared from methyl 2-[({2-[(1-benzofuran-2-ylsulfonyl)amino]-4-methylphenyl}sulfanyl)methyl]benzoate (168 mg, 0.36 mmol).

$^1$H NMR (600 MHz, CDCL$_3$) δ 7.90-7.93 (m, 1H), 7.66 (d, J=7.63 Hz, 1H), 7.57 (s, 1H), 7.53 (d, J=0.59 Hz, 1H), 7.48 (dd, J=0.59, 8.51 Hz, 1H), 7.38-7.44 (m, 3H), 7.35 (d, J=7.92

Hz, 1H), 7.28-7.32 (m, 1H), 7.11-7.18 (m, 1H), 6.86 (dd, J=0.59, 8.22 Hz, 1H), 5.07 (s, 2H), 3.77 (s, 3H), 2.37 (s, 3H).

Compound 329

2-[({2-[(1-benzofuran-2-ylsulfonyl)amino]-4-methylphenyl}sulfonyl)methyl]benzoic acid

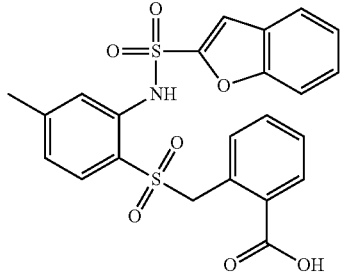 [SMILES: Cc1ccc(S(=O)(=O)Cc2ccccc2C(=O)O)c(NS(=O)(=O)c2cc3ccccc3o2)c1]

Following General Procedure Q, the title compound (117 mg, 86%) was prepared from methyl 2-[({2-[(1-benzofuran-2-ylsulfonyl)amino]-4-methylphenyl}sulfonyl)methyl]benzoate (140 mg, 0.29 mmol).

$^1$H NMR (600 MHz, CDCL$_3$) δ 9.43 (s, 1H), 8.09 (dd, J=1.47, 7.63 Hz, 1H), 7.69 (d, J=7.92 Hz, 1H), 7.40-7.59 (m, 7H), 7.30-7.36 (m, 1H), 7.23-7.29 (m, 1H), 6.91 (d, J=7.92 Hz, 1H), 5.11 (s, 2H), 2.38 (s, 3H).

Compound 330

N-{3-[({2-[(1-benzofuran-2-ylsulfonyl)amino]-4-chlorophenyl}sulfanyl)methyl]phenyl}acetamide

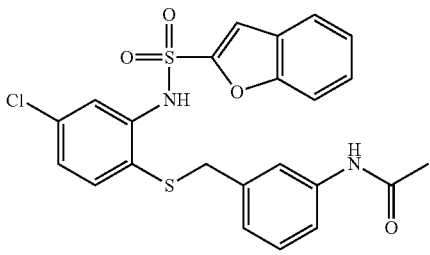 [SMILES: CC(=O)Nc1cccc(CSc2ccc(Cl)cc2NS(=O)(=O)c2cc3ccccc3o2)c1]

To a solution of N-{2-[(3-aminobenzyl)sulfanyl]-5-chlorophenyl}-1-benzofuran-2-sulfonamide (440 mg, 0.90 mmol) in CH$_2$Cl$_2$ (10 ml) was added acetyl chloride (71 μl, 0.99 mmol), pyridine (180 μl, 2.25 mmol), and catalytic amount of DMAP. The reaction was stirred at room temperature for 2 hours, diluted with 1M HCl, and extracted with CH$_2$Cl$_2$. The organic layer was dried over Na$_2$SO$_4$, and concentrated in vacuo. The residue was purified by flash column chromatography on silica gel (5-10% EtOAc in hexane) to yield the title compound (330 mg, 68%).

1H NMR (CHLOROFORM-d) δ 8.10 (s, 1H), 7.67 (d, J=7.6 Hz, 1H), 7.62 (d, J=2.1 Hz, 1H), 7.28-7.53 (m, 6H), 7.25 (s, 1H), 7.07-7.18 (m, 2H), 6.92 (dd, J=8.2, 2.1 Hz, 1H), 6.66 (d, J=7.6 Hz, 1H), 3.75 (s, 2H), 2.15 (s, 3H).

Compound 331

N-(2-{[3-(acetylamino)benzyl]sulfanyl}-5-chlorophenyl)-N-(1-benzofuran-2-ylsulfonyl)acetamide

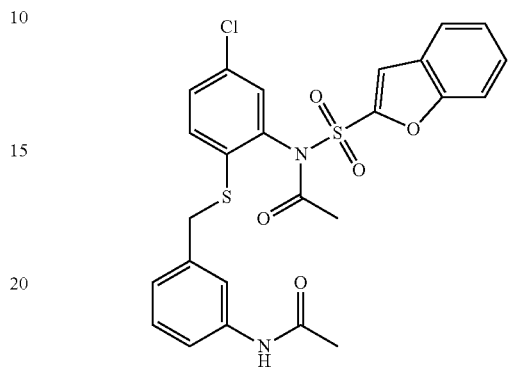

To a solution of N-{2-[(3-aminobenzyl)sulfanyl]-5-chlorophenyl}-1-benzofuran-2-sulfonamide (440 mg, 0.90 mmol) in CH$_2$Cl$_2$ (10 ml) was added acetyl chloride (71 μl, 0.99 mmol), pyridine (180 μl, 2.25 mmol), and catalytic amount of DMAP. The reaction was stirred at room temperature for 2 hours, diluted with 1M HCl, and extracted with CH$_2$Cl$_2$. The organic layer was dried over Na$_2$SO$_4$, and concentrated in vacuo. The residue was purified by flash column chromatography on silica gel (5-10% EtOAc in hexane) to yield the title compound (69 mg, 13%).

1H NMR (CHLOROFORM-d) δ 7.70-7.77 (m, 2H), 7.57-7.64 (m, 1H), 7.32-7.57 (m, 7H), 7.17-7.29 (m, 2H), 7.01 (d, J=7.9 Hz, 1H), 4.10 (s, 2H), 2.14 (s, 3H), 2.01 (s, 3H).

Compound 332

N-[5-chloro-2-({3-[(methylsulfonyl)amino]benzyl}sulfanyl)phenyl]-1-benzofuran-2-sulfonamide

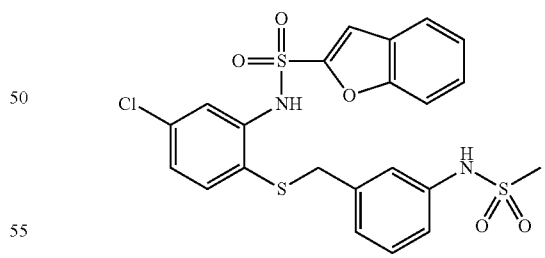

To a solution of N-{2-[(3-aminobenzyl)sulfanyl]-5-chlorophenyl}-1-benzofuran-2-sulfonamide (440 mg, 0.90 mmol) in pyridine (4 ml) was added methanesulfonyl chloride (70 μl, 0.90 mmol). The reaction was stirred at room temperature for 2 hours and was concentrated, diluted with 1M HCl, and extracted with EtOAc. The organic layer was dried over Na$_2$SO$_4$, and concentrated in vacuo. The residue was purified by flash column chromatography on silica gel (4% EtOAc in hexane) to yield the title compound (344 mg, 67%).

1H NMR (CHLOROFORM-d) δ 8.03 (br. s., 1H), 7.68 (d, J=7.9 Hz, 1H), 7.61 (d, J=2.1 Hz, 1H), 7.40-7.55 (m, 3H), 7.30-7.37 (m, 1H), 7.15-7.23 (m, 2H), 7.06-7.13 (m, 1H), 6.94 (dd, J=8.4, 2.2 Hz, 1H), 6.77-6.84 (m, 2H), 6.70 (s, 1H), 3.78 (s, 2H), 2.95 (s, 3H).

Compound 333

N-{3-[({2-[(1-benzofuran-2-ylsulfonyl)amino]-4-chlorophenyl}sulfinyl)methyl]phenyl}acetamide

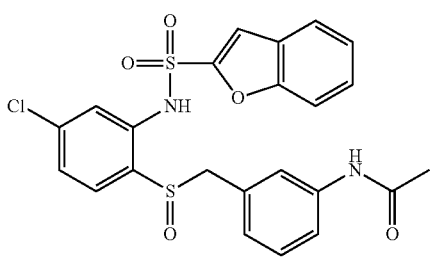 [SMILES: CC(=O)Nc1cccc(CS(=O)c2ccc(Cl)cc2NS(=O)(=O)c2cc3ccccc3o2)c1]

To a solution of N-{3-[({2-[(1-benzofuran-2-ylsulfonyl)amino]-4-chlorophenyl}sulfanyl)methyl]phenyl}acetamide (105 mg, 0.216 mmol) in CH₂Cl₂ (3 ml) was added mCPBA (52 mg, ~0.216 mmol) and the reaction was stirred at room temperature for 1 hour. The reaction mixture was directly loaded onto Celite and purified by flash column chromatography on silica gel (50-100% EtOAc in hexane) to yield the title compound (55 mg, 51%).

1H NMR (METHANOL-d4) δ 7.76 (d, J=7.9 Hz, 1H), 7.57-7.65 (m, 1H), 7.45-7.56 (m, 3H), 7.33-7.41 (m, 1H), 7.23-7.33 (m, 4H), 7.18 (t, J=7.8 Hz, 1H), 6.77 (d, J=7.3 Hz, 1H), 4.32 (d, J=12.9 Hz, 1H), 4.10 (d, J=12.9 Hz, 1H), 2.10 (s, 3H).

Compound 334

N-{3-[({2-[(1-benzofuran-2-ylsulfonyl)amino]-4-chlorophenyl}sulfonyl)methyl]phenyl}acetamide

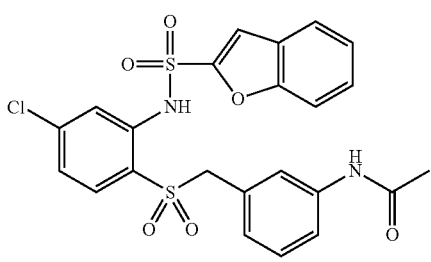 [SMILES: CC(=O)Nc1cccc(CS(=O)(=O)c2ccc(Cl)cc2NS(=O)(=O)c2cc3ccccc3o2)c1]

To a solution of N-{3-[({2-[(1-benzofuran-2-ylsulfonyl)amino]-4-chlorophenyl}sulfanyl)methyl]phenyl}acetamide (145 mg, 0.298 mmol) in CH₂Cl₂ (5 ml) was added mCPBA (179 mg, ~0.744 mmol) and the reaction was stirred at room temperature for 2 hours. The reaction mixture was directly loaded onto Celite and purified by flash column chromatography on silica gel (30-100% EtOAc in hexane) to yield the title compound (154 mg, 100%).

¹H NMR (CHLOROFORM-d) δ 9.34 (br. s., 1H), 7.76 (d, J=1.8 Hz, 1H), 7.70 (d, J=7.6 Hz, 1H), 7.42-7.61 (m, 5H), 7.30-7.39 (m, 2H), 7.22-7.28 (m, 1H), 7.18 (t, J=7.9 Hz, 1H), 7.06 (d, J=8.8 Hz, 1H), 6.68 (d, J=7.6 Hz, 1H), 4.31 (s, 2H), 2.15 (s, 3H).

Compound 335

N-[5-chloro-2-({3-[(methylsulfonyl)amino]benzyl}sulfinyl)phenyl]-1-benzofuran-2-sulfonamide

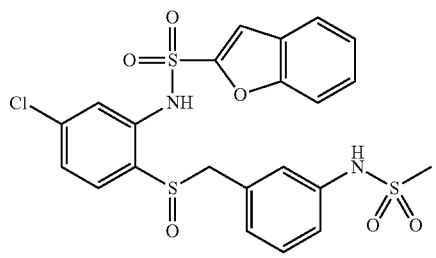 [SMILES: CS(=O)(=O)Nc1cccc(CS(=O)c2ccc(Cl)cc2NS(=O)(=O)c2cc3ccccc3o2)c1]

To a solution of N-[5-chloro-2-({3-[(methylsulfonyl)amino]benzyl}sulfanyl)phenyl]-1-benzofuran-2-sulfonamide (124 mg, 0.237 mmol) in CH₂Cl₂ (5 ml) was added mCPBA (57 mg, ~0.237 mmol) and the reaction was stirred at room temperature for 1 hour. The reaction mixture was directly loaded onto Celite and purified by flash column chromatography on silica gel (50-100% EtOAc in hexane) to yield the title compound (78 mg, 61%).

1H NMR (METHANOL-d4) δ 7.75 (d, J=7.3 Hz, 1H), 7.55-7.62 (m, 1H), 7.45-7.53 (m, 2H), 7.32-7.40 (m, 1H), 7.24-7.29 (m, 1H), 7.14-7.24 (m, 4H), 6.99 (s, 1H), 6.78-6.86 (m, 1H), 4.38 (d, J=13.2 Hz, 1H), 4.15 (d, J=12.9 Hz, 1H), 2.91 (s, 3H).

Compound 336

N-[5-chloro-2-({3-[(methylsulfonyl)amino]benzyl}sulfonyl)phenyl]-1-benzofuran-2-sulfonamide

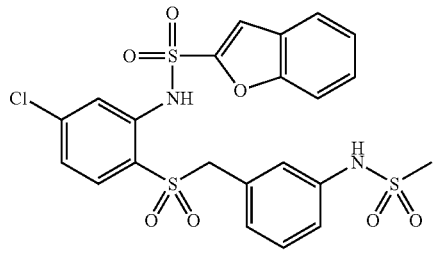 [SMILES: CS(=O)(=O)Nc1cccc(CS(=O)(=O)c2ccc(Cl)cc2NS(=O)(=O)c2cc3ccccc3o2)c1]

To a solution of N-[5-chloro-2-({3-[(methylsulfonyl)amino]benzyl}sulfanyl)phenyl]-1-benzofuran-2-sulfonamide (134 mg, 0.256 mmol) in CH₂Cl₂ (5 ml) was added mCPBA (154 mg, ~0.641 mmol) and the reaction was stirred at room temperature for 2 hours. The reaction mixture was directly loaded onto Celite and purified by flash column chromatography on silica gel (30-100% EtOAc in hexane) to yield the title compound (140 mg, 99%).

1H NMR (METHANOL-d4) δ 7.77 (d, J=7.9 Hz, 1H), 7.68-7.74 (m, 2H), 7.44-7.60 (m, 3H), 7.32-7.40 (m, 1H), 7.18-7.24 (m, 1H), 7.11-7.17 (m, 2H), 6.96 (s, 1H), 6.73-6.81 (m, 1H), 4.51 (s, 2H), 2.88 (s, 3H).

Compound 337

({2-[(1-benzofuran-2-ylsulfonyl)amino]-4-chlorophenyl}sulfanyl)acetic acid

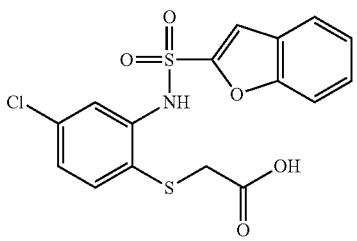 [SMILES: O=C(O)CSc1ccc(Cl)cc1NS(=O)(=O)c1cc2ccccc2o1]

To a solution of N,N'-[dithiobis(5-chloro-2,1-phenylene)]bis(1-benzofuran-2-sulfonamide) (300 mg, 0.44 mmol) in CH$_2$Cl$_2$ (5 ml) and dioxane (5 ml) was added saturated aqueous NaHCO$_3$ (5 ml), polymer-bound triphenylphosphine (~3 mmol/g triphenylphosphine loading, 0.44 g, 1.32 mmol), and 2-bromoacetic acid (65 μl, 0.88 mmol). The reaction was stirred at room temperature for 4 hours and was filtered, extracted with EtOAc (×2). The aqueous layer was acidified with HCl, extracted with EtOAc (×2). The combined organic layer was washed with brine, dried over Na$_2$SO$_4$, and concentrated in vacuo. The residue was purified by column chromatography on silica gel (50-100% EtOAc in hexane) to yield the title compound (144 mg, 41%).

1H NMR (METHANOL-d4) δ 7.70 (dt, J=7.9, 1.0 Hz, 1H), 7.53-7.58 (m, 1H), 7.50 (d, J=2.3 Hz, 1H), 7.47-7.49 (m, 1H), 7.44-7.46 (m, 1H), 7.41 (d, J=0.9 Hz, 1H), 7.30-7.37 (m, 1H), 7.18 (dd, J=8.5, 2.3 Hz, 1H), 3.47 (s, 2H).

Compound 338

({2-[(1-benzofuran-2-ylsulfonyl)amino]-4-chlorophenyl}sulfinyl)acetic acid

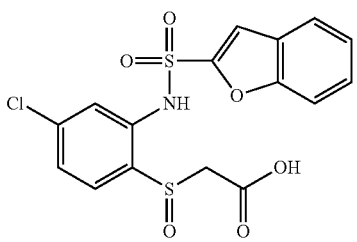 [SMILES: O=C(O)CS(=O)c1ccc(Cl)cc1NS(=O)(=O)c1cc2ccccc2o1]

To a solution of ({2-[(1-benzofuran-2-ylsulfonyl)amino]-4-chlorophenyl}sulfanyl)acetic acid (44 mg, 0.11 mmol) in CH$_2$Cl$_2$ (2 ml) and acetonitrile (2 ml) was added mCPBA (27 mg, ~0.11 mmol). The reaction was stirred at room temperature for 4 hours and was concentrated. The residue was purified by flash column chromatography on silica gel (50-100% EtOAc in hexane, then 20-30% MeOH in EtOAc) followed by PTLC (25% MeOH in EtOAc) to yield the title compound (34 mg, 74%).

1H NMR (CHLOROFORM-d) δ 7.72 (br. s., 1H), 7.66 (d, J=7.9 Hz, 1H), 7.52 (br. s., 2H), 7.45 (t, J=7.5 Hz, 1H), 7.36 (br. s., 1H), 7.32 (t, J=7.3 Hz, 1H), 7.14 (d, J=7.3 Hz, 1H), 4.24 (br. s., 1H), 3.96 (br. s., 1H).

Compound 339

({2-[(1-benzofuran-2-ylsulfonyl)amino]-4-chlorophenyl}sulfonyl)acetic acid

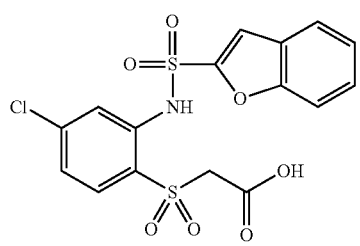 [SMILES: O=C(O)CS(=O)(=O)c1ccc(Cl)cc1NS(=O)(=O)c1cc2ccccc2o1]

To a solution of ({2-[(1-benzofuran-2-ylsulfonyl)amino]-4-chlorophenyl}sulfanyl)acetic acid (38 mg, 0.095 mmol) in CH$_2$Cl$_2$ (2 ml) and acetonitrile (2 ml) was added mCPBA (57 mg, ~0.24 mmol). The reaction was stirred at room temperature for 4 hours and additional mCPBA (34 mg, ~0.14 mmol) was added. The reaction was continued for 2 hours and was concentrated. The residue was purified by flash column chromatography on silica gel (50-100% EtOAc in hexane, then 20% MeOH in EtOAc) followed by PTLC (25% MeOH in EtOAc) to yield the title compound (22 mg, 54%).

1H NMR (CHLOROFORM-d) δ 7.79 (br. s., 2H), 7.66 (d, J=7.3 Hz, 1H), 7.55 (br. s., 1H), 7.47-7.53 (m, 1H), 7.41-7.46 (m, 1H), 7.31 (t, J=6.9 Hz, 1H), 7.11-7.19 (m, 1H), 4.22 (br. s., 2H).

Intermediate 57

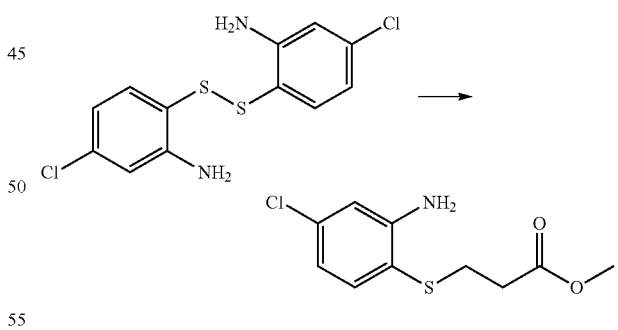

To a solution of 2,2'-dithiobis(5-chloroaniline) (CAS 29124-55-8) (1.27 g, 4.0 mmol) in DMF (20 ml) was added methyl acrylate (0.72 ml, 8.0 mmol), K$_2$CO$_3$ (1.1 g, 8.0 mmol), and sodium hydroxymethanesulfinate dihydrate (Rongalite, CAS 6035-47-8) (2.5 g, 16 mmol). The reaction was stirred at room temperature for 15 minutes, diluted with H$_2$O, extracted with EtOAc. The organic layer was washed with brine, dried over Na$_2$SO$_4$, and concentrated in vacuo. The residue was purified by column chromatography on silica gel (0-20% EtOAc in hexane) to yield methyl 3-((2-amino-4-chlorophenyl)thio)propanoate (1.5 g, 76%).

1H NMR (CHLOROFORM-d) δ 7.29 (d, J=8.2 Hz, 1H), 6.72 (d, J=2.3 Hz, 1H), 6.65 (dd, J=8.2, 2.1 Hz, 1H), 4.49 (br. s., 2H), 3.67 (s, 3H), 2.95 (t, J=7.2 Hz, 2H), 2.54 (t, J=7.2 Hz, 2H).

Compound 340 methyl 3-({2-[(1-benzofuran-2-ylsulfonyl)amino]-4-chlorophenyl}sulfanyl)propanoate

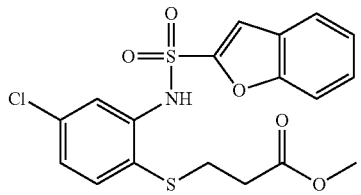 [SMILES: COC(=O)CCSc1ccc(Cl)cc1NS(=O)(=O)c1cc2ccccc2o1]

To a solution of methyl 3-((2-amino-4-chlorophenyl)thio)propanoate (412 mg, 1.67 mmol) in pyridine (2 ml) was added 1-benzofuran-2-sulfonyl chloride (363 mg, 1.67 mmol). The reaction was stirred at room temperature for 72 hours, diluted with EtOAc and extracted with HCl, brine, dried over Na$_2$SO$_4$, and concentrated in vacuo. The residue was purified by column chromatography on silica gel (10-20% EtOAc in hexane) to yield the title compound (373 mg, 52%).

1H NMR (CHLOROFORM-d) δ 8.32 (s, 1H), 7.72 (dd, J=1.9, 1.3 Hz, 1H), 7.67 (dd, J=7.9, 0.6 Hz, 1H), 7.49-7.54 (m, 2H), 7.44-7.48 (m, 1H), 7.39 (dd, J=8.4, 1.3 Hz, 1H), 7.33 (t, J=7.5 Hz, 1H), 7.03 (ddd, J=8.4, 2.2, 1.2 Hz, 1H), 3.69 (s, 3H), 2.91 (t, J=7.0 Hz, 2H), 2.46 (t, J=7.0 Hz, 2H).

Compound 341

3-({2-[(1-benzofuran-2-ylsulfonyl)amino]-4-chlorophenyl}sulfanyl)propanoic acid

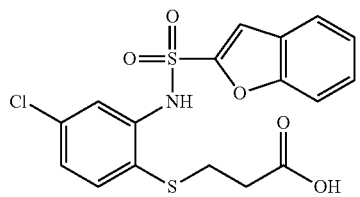 [SMILES: O=C(O)CCSc1ccc(Cl)cc1NS(=O)(=O)c1cc2ccccc2o1]

To a solution of methyl 3-({2-[(1-benzofuran-2-ylsulfonyl)amino]-4-chlorophenyl}sulfanyl)propanoate (125 mg, 0.29 mmol) in THF (3 ml) was added a solution of LiOH.H$_2$O (25 mg, 0.59 mmol) in H$_2$O (1 ml). The reaction was stirred at room temperature for 1 hour, acidified with 1M HCl, and was extracted with EtOAc. The organic layer was washed with brine, dried over Na$_2$SO$_4$, and concentrated in vacuo. The crude product was triturated with MeOH to yield the title compound (102 mg, 84%).

1H NMR (DMSO-d6) δ 10.53 (br. s., 2H), 7.75 (d, J=7.9 Hz, 1H), 7.70 (dd, J=8.5, 0.6 Hz, 1H), 7.48-7.54 (m, 2H), 7.29-7.40 (m, 3H), 7.09 (d, J=2.1 Hz, 1H), 2.88 (t, J=7.3 Hz, 2H), 2.20 (t, J=7.3 Hz, 2H).

Compound 342 methyl 3-({2-[(1-benzofuran-2-ylsulfonyl)amino]-4-chlorophenyl}sulfinyl)propanoate

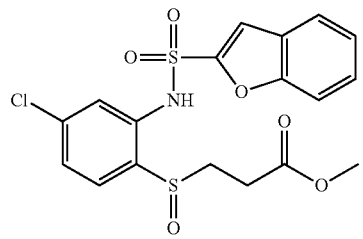 [SMILES: COC(=O)CCS(=O)c1ccc(Cl)cc1NS(=O)(=O)c1cc2ccccc2o1]

To a solution of methyl 3-({2-[(1-benzofuran-2-ylsulfonyl)amino]-4-chlorophenyl}sulfanyl)propanoate (181 mg, 0.43 mmol) in CH$_2$Cl$_2$ (4 ml) was added mCPBA (153 mg, ~0.64 mmol). The reaction was stirred at room temperature for 1 hour, diluted with EtOAc, extracted with saturated aqueous NaHCO$_3$ and brine, dried over Na$_2$SO$_4$, and concentrated in vacuo. The residue was purified by flash column chromatography on silica gel (25-100% EtOAc in hexane, then 10% MeOH in CH$_2$Cl$_2$) to yield the title compound (87 mg, 46%).

1H NMR (METHANOL-d4) δ 7.70-7.73 (m, 1H), 7.56-7.60 (m, 2H), 7.47 (ddd, J=8.5, 7.2, 1.3 Hz, 1H), 7.41 (d, J=0.9 Hz, 1H), 7.32-7.36 (m, 2H), 7.27 (dd, J=8.4, 1.9 Hz, 1H), 3.59 (s, 3H), 3.40 (ddd, J=13.6, 8.1, 7.0 Hz, 1H), 3.25-3.30 (m, 1H), 2.66-2.73 (m, 1H), 2.49-2.56 (m, 1H).

Compound 343 methyl 3-({2-[(1-benzofuran-2-ylsulfonyl)amino]-4-chlorophenyl}sulfonyl)propanoate

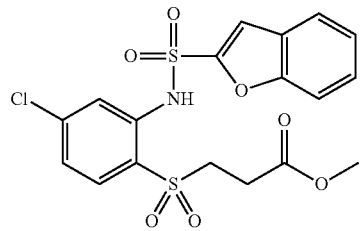 [SMILES: COC(=O)CCS(=O)(=O)c1ccc(Cl)cc1NS(=O)(=O)c1cc2ccccc2o1]

To a solution of methyl 3-({2-[(1-benzofuran-2-ylsulfonyl)amino]-4-chlorophenyl}sulfanyl)propanoate (181 mg, 0.43 mmol) in CH$_2$Cl$_2$ (4 ml) was added mCPBA (153 mg, ~0.64 mmol). The reaction was stirred at room temperature for 1 hour, diluted with EtOAc, extracted with saturated aqueous NaHCO$_3$ and brine, dried over Na$_2$SO$_4$, and concentrated in vacuo. The residue was purified by flash column chromatography on silica gel (25-100% EtOAc in hexane, then 10% MeOH in CH$_2$Cl$_2$) to yield the title compound (75 mg, 38%).

1H NMR (METHANOL-d4) δ 7.76-7.81 (m, 2H), 7.74 (d, J=7.9 Hz, 1H), 7.65 (br. s., 1H), 7.58 (d, J=8.5 Hz, 1H), 7.48

(t, J=7.8 Hz, 1H), 7.35 (t, J=7.5 Hz, 1H), 7.23 (br. s., 1H), 3.66 (br. s., 2H), 3.54 (s, 3H), 2.65 (t, J=7.2 Hz, 2H).

Intermediate 58

N,N'-(disulfanediylbis(3-chloro-6,1-phenylene))bis(4-chloro-2-fluorobenzenesulfonamide)

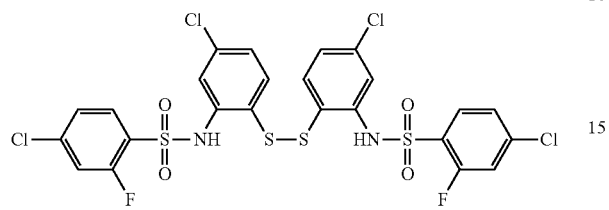

To a solution of 2,2'-dithiobis(5-chloroaniline) (CAS 29124-55-8)(0.83 g, 2.6 mmol) in pyridine (5 ml) was added 4-chloro-2-fluorobenzene-1-sulfonyl chloride (1.20 g, 5.2 mmol) and the reaction was stirred at room temperature for 16 hours. Additional 4-chloro-2-fluorobenzene-1-sulfonyl chloride (1.20 g, 5.2 mmol) was added, and the reaction was stirred for 6 hours. The mixture was concentrated in vacuo and the resulting solid was washed with saturated aqueous $Na_2CO_3$ (×3), $H_2O$ (×3), and dried to give 2.4 g sandy solid, which was taken in methanol (50 ml) and was treated with 4M NaOH (5.5 ml) at 100° C. for 15 min, cooled to room temperature, quenched slowly with 1M HCl with stirring and cooling to pH 7-8. The volume of the resulting suspension was reduced in vacuo, followed by extraction with EtOAc. The organic layer was washed with brine, dried over $Na_2SO_4$, and concentrated in vacuo. The crude product was purified by flash column chromatography on silica gel (5-40% EtOAc in hexane) to yield the title compound (0.81 g, 44%).

Compound 344 methyl 3-[(4-chloro-2-{[(4-chloro-2-fluorophenyl)sulfonyl]amino}phenyl)sulfanyl]propanoate

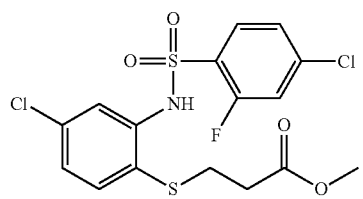 [SMILES: COC(=O)CCSc1ccc(Cl)cc1NS(=O)(=O)c1ccc(Cl)cc1F]

To a solution of N,N'-(disulfanediylbis(3-chloro-6,1-phenylene))bis(4-chloro-2-fluorobenzenesulfonamide) (650 mg, 0.93 mmol) in $CH_2Cl_2$ (10 ml) and dioxane (10 ml) was added saturated aqueous $NaHCO_3$ (10 ml), polymer-bound triphenylphosphine (~3 mmol/g triphenylphosphine loading, 0.93 g, 2.79 mmol), methyl 3-bromopropanoate (0.20 ml, 1.86 mmol). The reaction was stirred at room temperature for 2 hours and was diluted with EtOAc, filtered, and washed with saturated aqueous $NH_4Cl$, brine, dried over $Na_2SO_4$, and concentrated. The residue was purified by column chromatography on silica gel (5-20% ethyl acetate in hexane) to yield the title compound as a pale yellow solid (626 mg, 77%).

1H NMR (CHLOROFORM-d) δ 8.30 (s, 1H), 7.89 (dd, J=8.4, 7.8 Hz, 1H), 7.55 (d, J=2.1 Hz, 1H), 7.41 (d, J=8.2 Hz, 1H), 7.24-7.31 (m, 1H), 7.20 (dd, J=9.7, 2.1 Hz, 1H), 6.98-7.05 (m, 1H), 3.72 (s, 3H), 2.94 (t, J=7.0 Hz, 2H), 2.51 (t, J=7.0 Hz, 2H).

Compound 345

3-[(4-chloro-2-{[(4-chloro-2-fluorophenyl)sulfonyl]amino}phenyl)sulfanyl]propanoic acid

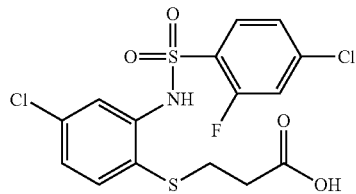 [SMILES: O=C(O)CCSc1ccc(Cl)cc1NS(=O)(=O)c1ccc(Cl)cc1F]

To a solution of methyl 3-[(4-chloro-2-{[(4-chloro-2-fluorophenyl)sulfonyl]amino}phenyl)sulfanyl]propanoate (545 mg, 1.24 mmol) in THF (10 ml) was added a solution of $LiOH.H_2O$ (104 mg, 2.48 mmol) in $H_2O$ (2 ml). The reaction was stirred at room temperature for 1.5 hours, acidified with 1M HCl, and was extracted with EtOAc (×2). The combined organic layer was washed with brine, dried over $Na_2SO_4$, and concentrated. The crude product was triturated with $CH_2Cl_2$, filtered, rinsed with $H_2O$, and dried to yield the title compound as beige solid (500 mg, 95%).

1H NMR (METHANOL-d4) δ 7.78 (t, J=8.2 Hz, 1H), 7.37-7.48 (m, 3H), 7.34 (d, J=8.8 Hz, 1H), 7.18 (dd, J=8.5, 2.3 Hz, 1H), 2.94 (t, J=7.2 Hz, 2H), 2.44 (t, J=7.2 Hz, 2H).

Compound 346 methyl 3-[(4-chloro-2-{[(4-chloro-2-fluorophenyl)sulfonyl]amino}phenyl)sulfonyl]propanoate

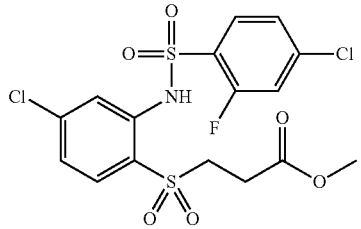 [SMILES: COC(=O)CCS(=O)(=O)c1ccc(Cl)cc1NS(=O)(=O)c1ccc(Cl)cc1F]

To a solution of methyl 3-[(4-chloro-2-{[(4-chloro-2-fluorophenyl)sulfonyl]amino}phenyl)sulfanyl]propanoate (173 mg, 0.39 mmol) in $CH_2Cl_2$ (5 ml) was added mCPBA (142 mg, ~0.59 mmol). The reaction was stirred at room temperature for 1 hour, and was directly loaded on Celite, purified by flash column chromatography on silica gel (30-70% EtOAc in hexane) to yield the title compound (130 mg, 73%).

1H NMR (acetone) δ 8.02 (t, J=8.2 Hz, 1H), 7.68 (d, J=8.5 Hz, 1H), 7.62 (d, J=1.8 Hz, 1H), 7.24-7.45 (m, 2H), 6.83 (br. s., 1H), 3.72 (t, J=7.3 Hz, 2H), 3.61 (s, 3H), 2.64 (t, J=7.3 Hz, 2H).

Compound 347 methyl 3-[(4-chloro-2-{[(4-chloro-2-fluorophenyl)sulfonyl]amino}phenyl)sulfinyl]propanoate

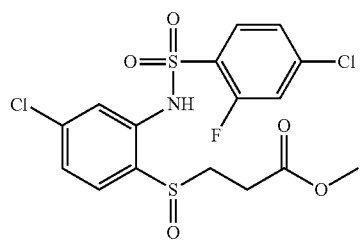 [SMILES: COC(=O)CCS(=O)c1ccc(Cl)cc1NS(=O)(=O)c1ccc(Cl)cc1F]

To a solution of methyl 3-[(4-chloro-2-{[(4-chloro-2-fluorophenyl)sulfonyl]amino}phenyl)sulfanyl]propanoate (173 mg, 0.39 mmol) in CH$_2$Cl$_2$ (5 ml) was added mCPBA (142 mg, ~0.59 mmol). The reaction was stirred at room temperature for 1 hour, and was directly loaded on Celite, purified by flash column chromatography on silica gel (30-70% EtOAc in hexane) to yield the title compound (40 mg, 22%).

1H NMR (METHANOL-d4) δ 7.82 (t, J=8.1 Hz, 1H), 7.70 (d, J=8.5 Hz, 1H), 7.37-7.56 (m, 3H), 7.21 (d, J=1.8 Hz, 1H), 3.65 (s, 3H), 3.33-3.42 (m, 1H), 3.13-3.25 (m, 1H), 2.57-2.86 (m, 2H).

Compound 348

3-[(4-chloro-2-{[(4-chloro-2-fluorophenyl)sulfonyl]amino}phenyl)sulfonyl]propanoic acid

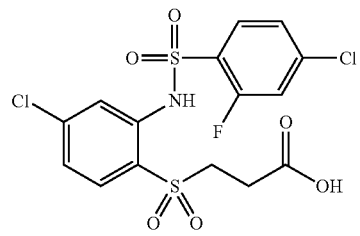 [SMILES: O=C(O)CCS(=O)(=O)c1ccc(Cl)cc1NS(=O)(=O)c1ccc(Cl)cc1F]

To a solution of 3-[(4-chloro-2-{[(4-chloro-2-fluorophenyl)sulfonyl]amino}phenyl)sulfanyl]propanoic acid (160 mg, 0.38 mmol) in CH$_2$Cl$_2$ (5 ml) and acetone (5 ml) was added mCPBA (136 mg, ~0.56 mmol). The reaction was stirred at room temperature for 2 hours, and additional mCPBA (91 mg, ~0.38 mmol) was added. The reaction was continued for 1 hour, and was directly loaded on Celite, purified by flash column chromatography on silica gel (30-100% EtOAc in hexane) to yield the title compound (101 mg, 59%).

1H NMR (DMSO-d6) δ 7.85 (t, J=8.2 Hz, 1H), 7.70 (d, J=8.5 Hz, 1H), 7.55 (d, J=9.1 Hz, 1H), 7.35-7.44 (m, 2H), 7.09 (br. s., 1H), 3.70 (t, J=7.5 Hz, 2H), 2.43 (t, J=7.5 Hz, 2H).

Compound 349

3-[(4-chloro-2-{[(4-chloro-2-fluorophenyl)sulfonyl]amino}phenyl)sulfinyl]propanoic acid

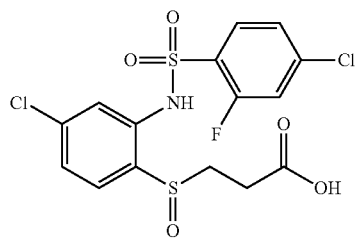 [SMILES: O=C(O)CCS(=O)c1ccc(Cl)cc1NS(=O)(=O)c1ccc(Cl)cc1F]

To a solution of 3-[(4-chloro-2-{[(4-chloro-2-fluorophenyl)sulfonyl]amino}phenyl)sulfanyl]propanoic acid (91 mg, 0.21 mmol) in CH$_2$Cl$_2$ (2 ml) and acetone (2 ml) was added mCPBA (50 mg, ~0.21 mmol). The reaction was stirred at room temperature for 1 hour and was concentrated. The solid residue was rinsed with Et$_2$O to yield the title compound (88 mg, 94%).

1H NMR (DMSO-d6) δ 11.94 (br. s., 1H), 7.71-7.78 (m, 2H), 7.67 (d, J=8.2 Hz, 1H), 7.54 (d, J=7.6 Hz, 1H), 7.46 (dd, J=8.4, 1.9 Hz, 1H), 7.09 (d, J=2.1 Hz, 1H), 3.21 (ddd, J=13.4, 8.9, 6.5 Hz, 1H), 2.94-3.01 (m, 1H), 2.54 (ddd, J=16.8, 8.9, 6.3 Hz, 1H), 2.30-2.39 (m, 1H).

Compound 350

3-[(4-chloro-2-{[(4-chloro-2-fluorophenyl)sulfonyl]amino}phenyl)sulfanyl]-N-ethyl-N-methylpropanamide

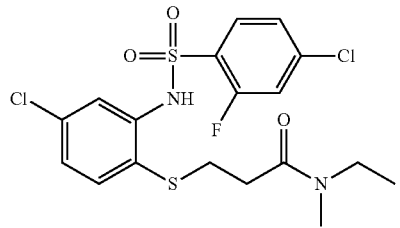 [SMILES: CCN(C)C(=O)CCSc1ccc(Cl)cc1NS(=O)(=O)c1ccc(Cl)cc1F]

To a solution of 3-[(4-chloro-2-{[(4-chloro-2-fluorophenyl)sulfonyl]amino}phenyl)sulfanyl]propanoic acid (297 mg, 0.70 mmol) in DMF (2 ml) was added EDC.HCl (148 mg, 0.77 mmol), HOBT.H$_2$O (104 mg, 0.77 mmol), and N-methylethanamine (0.30 ml, 3.5 mmol). The reaction was stirred at room temperature for 16 hours, diluted with 1M HCl, extracted with EtOAc. The organic layer was washed with brine, dried over Na$_2$SO$_4$, and concentrated in vacuo. The residue was purified by flash column chromatography on silica gel (10-40% EtOAc in hexane) to yield the title compound (269 mg, 83%) as a mixture of amide bond cis-trans isomers.

1H NMR (METHANOL-d4) δ 7.74-7.81 (m, 1H), 7.38-7.45 (m, 3H), 7.34 (ddd, J=8.4, 2.0, 0.7 Hz, 1H), 7.15-7.20

(m, 1H), 3.34-3.46 (m, 2H), 2.89-3.02 (m, 5H), 2.54 (2×t, J=10.3, 7.0 Hz, 2H), 1.11 (2×t, J=8.6, 7.3 Hz, 3H).

Compound 351

3-[(4-chloro-2-{[(4-chloro-2-fluorophenyl)sulfonyl]amino}phenyl)sulfinyl]-N-ethyl-N-methylpropanamide

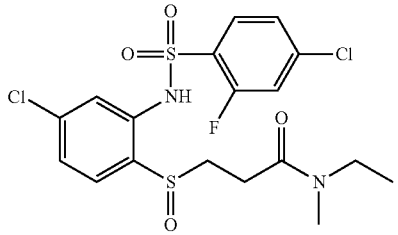 [SMILES: CCN(C)C(=O)CCS(=O)c1ccc(Cl)cc1NS(=O)(=O)c1ccc(Cl)cc1F]

To a solution of 3-[(4-chloro-2-{[(4-chloro-2-fluorophenyl)sulfonyl]amino}phenyl)sulfanyl]-N-ethyl-N-methylpropanamide (119 mg, 0.256 mmol) in $CH_2Cl_2$ (5 ml) was added mCPBA (61 mg, ~0.26 mmol). The reaction was stirred at room temperature for 1 hour and was concentrated. The residue was purified by flash column chromatography on silica gel (50-100% EtOAc in hexane, then 10% MeOH in $CH_2Cl_2$) to yield the title compound (53 mg, 43%) as a mixture of amide bond cis-trans isomers.

1H NMR (METHANOL-d4) δ 7.82 (t, J=8.1 Hz, 1H), 7.69 (d, J=8.5 Hz, 1H), 7.36-7.52 (m, 3H), 7.32 (d, J=2.1 Hz, 1H), 3.34-3.45 (m, 2H), 3.23-3.28 (m, 1H), 3.09-3.21 (m, 1H), 2.90-3.03 (m, 3H), 2.66-2.90 (m, 2H), 1.05-1.22 (m, 3H).

Compound 352

3-[(4-chloro-2-{[(4-chloro-2-fluorophenyl)sulfonyl]amino}phenyl)sulfonyl]-N-ethyl-N-methylpropanamide

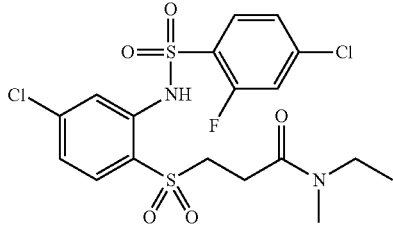 [SMILES: CCN(C)C(=O)CCS(=O)(=O)c1ccc(Cl)cc1NS(=O)(=O)c1ccc(Cl)cc1F]

To a solution of 3-[(4-chloro-2-{[(4-chloro-2-fluorophenyl)sulfonyl]amino}phenyl)sulfanyl]-N-ethyl-N-methylpropanamide (96 mg, 0.21 mmol) in $CH_2Cl_2$ (5 ml) was added mCPBA (124 mg, ~0.52 mmol). The reaction was stirred at room temperature for 1 hour and was concentrated. The residue was purified by flash column chromatography on silica gel (50-100% EtOAc in hexane) to yield the title compound (98 mg, 95%) as a mixture of amide bond cis-trans isomers.

1H NMR (METHANOL-d4) δ 8.00 (t, J=8.2 Hz, 1H), 7.82 (d, J=8.5 Hz, 1H), 7.59 (d, J=1.8 Hz, 1H), 7.39-7.49 (m, 2H), 7.23 (d, J=8.2 Hz, 1H), 3.61 (td, J=6.8, 3.1 Hz, 2H), 3.32-3.42 (m, 2H), 2.74-3.01 (m, 5H), 1.01-1.19 (m, 3H).

Intermediate 59 methyl 2-(((5-chloro-2-nitrophenyl)thio)methyl)benzoate

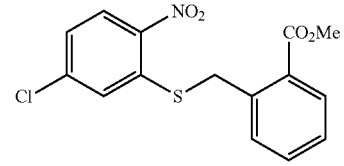 [SMILES: COC(=O)c1ccccc1CSc1cc(Cl)ccc1[N+](=O)[O-]]

To a solution of 4-chloro-2-fluoro-1-nitrobenzene (352 mg, 2.0 mmol) in dioxane (3 ml) was added a solution of $Na_2S \cdot 9H_2O$ (960 mg, 4.0 mmol) in $H_2O$ (3 ml) and the reaction was stirred at room temperature for 30 minutes, then methyl 2-(bromomethyl)benzoate (458 mg, 2.0 mmol) and $K_2CO_3$ (345 mg, 2.5 mmol) was added and the reaction was continued for 2 hours, diluted with water, extracted with EtOAc. The organic layer was washed with brine, dried over $Na_2SO_4$, and concentrated in vacuo. The residue was purified by flash column chromatography on silica gel (0~10% EtOAc in hexane) to yield the title compound (199 mg, 29%).

1H NMR (CHLOROFORM-d) δ 8.16 (d, J=8.8 Hz, 1H), 8.01 (dd, J=7.3, 0.9 Hz, 1H), 7.47-7.52 (m, 3H), 7.39 (ddd, J=8.1, 5.8, 2.8 Hz, 1H), 7.20 (dd, J=8.9, 2.2 Hz, 1H), 4.69 (s, 2H), 3.91 (s, 3H).

Intermediate 60 methyl 2-(((2-amino-5-chlorophenyl)thio)methyl)benzoate

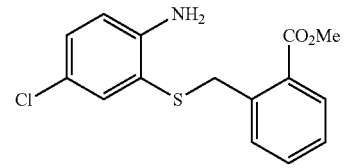 [SMILES: COC(=O)c1ccccc1CSc1cc(Cl)ccc1N]

Following General Procedure L, the title compound (158 mg, crude) was prepared from methyl 2-(((5-chloro-2-nitrophenyl)thio)methyl)benzoate (163 mg, 0.48 mmol), Zn (780 mg, 12.0 mmol) and saturated aqueous $NH_4Cl$ (10 ml) in MeOH (5 ml) and THF (5 ml). The crude product was used in the next reaction without further purification.

Compound 353 methyl 2-(((2-(benzofuran-2-sulfonamido)-5-chlorophenyl)thio)methyl)benzoate

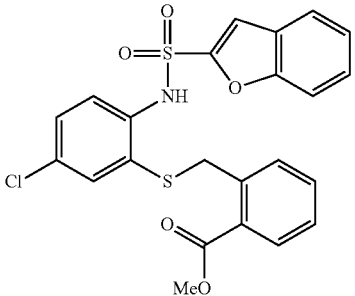 [SMILES: COC(=O)c1ccccc1CSc1cc(Cl)ccc1NS(=O)(=O)c1cc2ccccc2o1]

Following General Procedure B, the title compound (65 mg, 28%) was prepared from methyl 2-(((2-amino-5-chlorophenyl)thio)methyl)benzoate (150 mg, crude) and benzofuran-2-sulfonyl chloride (104 mg, 0.48 mmol) in pyridine (3 ml).

1H NMR (CHLOROFORM-d) δ 8.27 (s, 1H), 7.95-8.03 (m, 1H), 7.56-7.66 (m, 2H), 7.35-7.50 (m, 3H), 7.16-7.35 (m, 5H), 6.80-6.89 (m, 1H), 4.27 (s, 2H), 3.94 (s, 3H).

Compound 354

2-[({2-[(1-benzofuran-2-ylsulfonyl)amino]-5-chlorophenyl}sulfanyl)methyl]benzoic acid

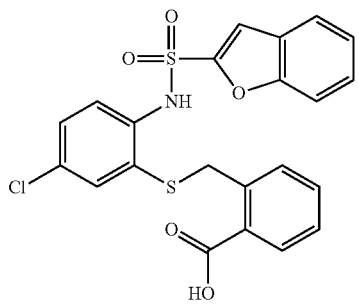 [SMILES: O=C(O)c1ccccc1CSc1cc(Cl)ccc1NS(=O)(=O)c1cc2ccccc2o1]

Following General Procedure Q, the title compound (48 mg, 96%) was prepared from methyl 2-(((2-(benzofuran-2-sulfonamido)-5-chlorophenyl)thio)methyl)benzoate (51 mg, 0.11 mmol).

1H NMR (METHANOL-d4) δ 7.92 (dd, J=7.6, 1.5 Hz, 1H), 7.71 (dt, J=7.9, 1.0 Hz, 1H), 7.51-7.54 (m, 1H), 7.45-7.49 (m, 1H), 7.43 (d, J=8.8 Hz, 1H), 7.38 (d, J=1.2 Hz, 1H), 7.34 (ddd, J=7.9, 7.0, 0.9 Hz, 1H), 7.20-7.30 (m, 3H), 7.12 (d, J=2.6 Hz, 1H), 6.74 (dd, J=7.3, 1.2 Hz, 1H), 4.27 (s, 2H).

Biological Data

HEK-Gqi5 cells stably expressing CCR2 were cultured in DMEM high glucose, 10% FBS, 1% PSA, 400 µg/ml geneticin and 50 µg/ml hygromycin. Appropriate positive control chemokines (MCP-1, MIP1A or RANTES) was used as the positive control agonist for screening compound-induced calcium activity assayed on the FLIPR$^{Tetra}$. The drug plates were prepared in 384-well microplates using the EP3 and the MultiPROBE robotic liquid handling systems. Compounds were synthesized and tested for CCR2 activity.

Table 1 shows activity at CCR2 receptor (IC$_{50}$) nM

TABLE 1

| Compound Name | CCR2 IC50 (nM) | CCR2 % ANTAGONISM |
|---|---|---|
| N-[2-(benzylsulfanyl)-5-chlorophenyl]-4-chloro-3-(trifluoromethyl)benzenesulfonamide | 1284 | 68 |
| N-[2-(benzylsulfinyl)-5-chlorophenyl]-4-chloro-3-(trifluoromethyl)benzenesulfonamide | 493 | 77 |
| N-[2-(benzylsulfonyl)-5-chlorophenyl]-4-chloro-3-(trifluoromethyl)benzenesulfonamide | 538 | 71 |
| N-[2-(benzylsulfanyl)-4-cyanophenyl]-1-benzofuran-2-sulfonamide | 604 | 79 |
| N-[2-(benzylsulfinyl)-4-cyanophenyl]-1-benzofuran-2-sulfonamide | 1030 | 94 |
| N-[2-(benzylsulfonyl)-4-cyanophenyl]-1-benzofuran-2-sulfonamide | 888 | 96 |
| N-[6-(benzylsulfinyl)-1-oxo-2,3-dihydro-1H-inden-5-yl]-1-benzofuran-2-sulfonamide | nd | 73 |
| N-[6-(benzylsulfonyl)-1-oxo-2,3-dihydro-1H-inden-5-yl]-1-benzofuran-2-sulfonamide | 2242 | 45 |
| 4-({[4-chloro-2-({[4-chloro-3-(trifluoromethyl)phenyl]sulfonyl}amino)phenyl]sulfanyl}methyl)benzoic acid | 255 | 102 |
| 4-({[4-chloro-2-({[4-chloro-3-(trifluoromethyl)phenyl]sulfonyl}amino)phenyl]sulfinyl}methyl)benzoic acid | 2105 | 23 |
| tert-butyl ({[4-({[4-chloro-2-({[4-chloro-3-(trifluoromethyl)phenyl]sulfonyl}amino)phenyl]sulfanyl}methyl)phenyl]carbonyl}amino)acetate | 657 | 43 |
| tert-butyl ({[4-({[4-chloro-2-({[4-chloro-3-(trifluoromethyl)phenyl]sulfonyl}amino)phenyl]sulfinyl}methyl)phenyl]carbonyl}amino)acetate | nd | 93 |
| tert-butyl ({[4-({[4-chloro-2-({[4-chloro-3-(trifluoromethyl)phenyl]sulfonyl}amino)phenyl]sulfonyl}methyl)phenyl]carbonyl}amino)acetate | 2662 | 77 |
| ({[4-({[4-chloro-2-({[4-chloro-3-(trifluoromethyl)phenyl]sulfonyl}amino)phenyl]sulfanyl}methyl)phenyl]carbonyl}amino)acetic acid | nd | 75 |
| ({[4-({[4-chloro-2-({[4-chloro-3-(trifluoromethyl)phenyl]sulfonyl}amino)phenyl]sulfinyl}methyl)phenyl]carbonyl}amino)acetic acid | nd | 24 |
| methyl 3-({[4-chloro-2-({[4-chloro-3-(trifluoromethyl)phenyl]sulfonyl}amino)phenyl]sulfanyl}methyl)benzoate | 1359 | 57 |

TABLE 1-continued

| Compound Name | CCR2 IC50 (nM) | CCR2 % ANTAGONISM |
|---|---|---|
| methyl 3-({[4-chloro-2-({[4-chloro-3-(trifluoromethyl)phenyl]sulfonyl}amino)phenyl]sulfinyl}methyl)benzoate | 3108 | 93 |
| methyl 3-({[4-chloro-2-({[4-chloro-3-(trifluoromethyl)phenyl]sulfonyl}amino)phenyl]sulfonyl}methyl)benzoate | 2973 | 55 |
| 3-({[4-chloro-2-({[4-chloro-3-(trifluoromethyl)phenyl]sulfonyl}amino)phenyl]sulfanyl}methyl)benzoic acid | 56 | 102 |
| 3-({[4-chloro-2-({[4-chloro-3-(trifluoromethyl)phenyl]sulfonyl}amino)phenyl]sulfonyl}methyl)benzoic acid | 1578 | 101 |
| 3-({[4-chloro-2-({[4-chloro-3-(trifluoromethyl)phenyl]sulfonyl}amino)phenyl]sulfinyl}methyl)benzoic acid | nd | 89 |
| 3-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide | 2170 | 97 |
| 3-({[4-chloro-2-({[4-chloro-3-(trifluoromethyl)phenyl]sulfonyl}amino)phenyl]sulfinyl}methyl)-N-[2-(pyrrolidin-1-yl)ethyl]benzamide | 910 | 105 |
| 3-({[4-chloro-2-({[4-chloro-3-(trifluoromethyl)phenyl]sulfonyl}amino)phenyl]sulfonyl}methyl)-N-[2-(1-oxidopyrrolidin-1-yl)ethyl]benzamide | nd | 51 |
| 3-({[4-chloro-2-({[4-chloro-3-(trifluoromethyl)phenyl]sulfonyl}amino)phenyl]sulfonyl}methyl)-N-[2-(pyrrolidin-1-yl)ethyl]benzamide | 817 | 110 |
| 4-({[4-chloro-2-({[4-chloro-3-(trifluoromethyl)phenyl]sulfonyl}amino)phenyl]sulfanyl}methyl)-N-[2-(pyrrolidin-1-yl)ethyl]benzamide | 2316 | 75 |
| 4-({[4-chloro-2-({[4-chloro-3-(trifluoromethyl)phenyl]sulfonyl}amino)phenyl]sulfanyl}methyl)-N-[2-(1-oxidopyrrolidin-1-yl)ethyl]benzamide | nd | 31 |
| 4-({[4-chloro-2-({[4-chloro-3-(trifluoromethyl)phenyl]sulfonyl}amino)phenyl]sulfinyl}methyl)-N-[2-(pyrrolidin-1-yl)ethyl]benzamide | 1426 | 85 |
| methyl 2-({[4-chloro-2-({[4-chloro-3-(trifluoromethyl)phenyl]sulfonyl}amino)phenyl]sulfanyl}methyl)benzoate | 2383 | 88 |
| 2-({[4-chloro-2-({[4-chloro-3-(trifluoromethyl)phenyl]sulfonyl}amino)phenyl]sulfanyl}methyl)benzoic acid | 79 | 99 |
| methyl 2-({[4-chloro-2-({[4-chloro-3-(trifluoromethyl)phenyl]sulfonyl}amino)phenyl]sulfinyl}methyl)benzoate | 274 | 101 |
| 2-({[4-chloro-2-({[4-chloro-3-(trifluoromethyl)phenyl]sulfonyl}amino)phenyl]sulfinyl}methyl)benzoic acid | 853 | 99 |
| methyl 2-({[4-chloro-2-({[4-chloro-3-(trifluoromethyl)phenyl]sulfonyl}amino)phenyl]sulfonyl}methyl)benzoate | 515 | 82 |
| 2-({[4-chloro-2-({[4-chloro-3-(trifluoromethyl)phenyl]sulfonyl}amino)phenyl]sulfonyl}methyl)benzoic acid | nd | 105 |
| 2-({[4-chloro-2-({[4-chloro-3-(trifluoromethyl)phenyl]sulfonyl}amino)phenyl]sulfanyl}methyl)benzamide | 167 | 88 |
| 2-({[4-chloro-2-({[4-chloro-3-(trifluoromethyl)phenyl]sulfonyl}amino)phenyl]sulfanyl}methyl)-N,N-dimethylbenzamide | 171 | 71 |
| 2-({[4-chloro-2-({[4-chloro-3-(trifluoromethyl)phenyl]sulfonyl}amino)phenyl]sulfanyl}methyl)-N-ethylbenzamide | 149 | 92 |
| 3-{[4-chloro-2-({[4-chloro-3-(trifluoromethyl)phenyl]sulfonyl}amino)phenyl]sulfinyl}-N,N-diethylpropanamide | 1687 | 56 |
| 3-{[4-chloro-2-({[4-chloro-3-(trifluoromethyl)phenyl]sulfonyl}amino)phenyl]sulfonyl}-N,N-diethylpropanamide | 1861 | 61 |
| 4-chloro-N-(5-chloro-2-{[3-oxo-3-(pyrrolidin-1-yl)propyl]sulfanyl}phenyl)-3-(trifluoromethyl)benzenesulfonamide | 2287 | 60 |
| 4-chloro-N-(5-chloro-2-{[3-oxo-3-(pyrrolidin-1-yl)propyl]sulfinyl}phenyl)-3-(trifluoromethyl)benzenesulfonamide | 1663 | 72 |

TABLE 1-continued

| Compound Name | CCR2 IC50 (nM) | CCR2 % ANTAGONISM |
|---|---|---|
| 4-chloro-N-(5-chloro-2-{[3-oxo-3-(pyrrolidin-1-yl)propyl]sulfonyl}phenyl)-3-(trifluoromethyl)benzenesulfonamide | nd | 58 |
| 2-[({2-[(1-benzofuran-2-ylsulfonyl)amino]-4-chlorophenyl}sulfanyl)methyl]benzoic acid | 7 | 101 |
| 2-[({2-[(1-benzofuran-2-ylsulfonyl)amino]-4-chlorophenyl}sulfinyl)methyl]benzoic acid | 806 | 98 |
| 2-[({2-[(1-benzofuran-2-ylsulfonyl)amino]-4-chlorophenyl}sulfonyl)methyl]benzoic acid | nd | 96 |
| methyl 2-[({2-[(1-benzofuran-2-ylsulfonyl)amino]-4-fluorophenyl}sulfanyl)methyl]benzoate | 272 | 93 |
| 2-[({2-[(1-benzofuran-2-ylsulfonyl)amino]-4-fluorophenyl}sulfanyl)methyl]benzoic acid | 11 | 99 |
| methyl 2-[({2-[(1-benzofuran-2-ylsulfonyl)amino]-4-fluorophenyl}sulfinyl)methyl]benzoate | 140 | 91 |
| 2-[({2-[(1-benzofuran-2-ylsulfonyl)amino]-4-fluorophenyl}sulfinyl)methyl]benzoic acid | 1849 | 92 |
| methyl 2-[({2-[(1-benzofuran-2-ylsulfonyl)amino]-4-fluorophenyl}sulfonyl)methyl]benzoate | 41 | 90 |
| 2-[({2-[(1-benzofuran-2-ylsulfonyl)amino]-4-fluorophenyl}sulfonyl)methyl]benzoic acid | 2471 | 89 |
| N-{3-[({2-[(1-benzofuran-2-ylsulfonyl)amino]-4-chlorophenyl}sulfanyl)methyl]phenyl}acetamide | 379 | 96 |
| N-(2-{[3-(acetylamino)benzyl]sulfanyl}-5-chlorophenyl)-N-(1-benzofuran-2-ylsulfonyl)acetamide | 1605 | 73 |
| N-[5-chloro-2-({3-[(methylsulfonyl)amino]benzyl}sulfanyl)phenyl]-1-benzofuran-2-sulfonamide | 1277 | 90 |
| N-{3-[({2-[(1-benzofuran-2-ylsulfonyl)amino]-4-chlorophenyl}sulfinyl)methyl]phenyl}acetamide | nd | 95 |
| N-{3-[({2-[(1-benzofuran-2-ylsulfonyl)amino]-4-chlorophenyl}sulfonyl)methyl]phenyl}acetamide | 854 | 100 |
| N-[5-chloro-2-({3-[(methylsulfonyl)amino]benzyl}sulfinyl)phenyl]-1-benzofuran-2-sulfonamide | 2422 | 77 |
| N-[5-chloro-2-({3-[(methylsulfonyl)amino]benzyl}sulfonyl)phenyl]-1-benzofuran-2-sulfonamide | 6570 | 91 |
| ({2-[(1-benzofuran-2-ylsulfonyl)amino]-4-chlorophenyl}sulfanyl)acetic acid | 484 | 95 |
| methyl 3-({2-[(1-benzofuran-2-ylsulfonyl)amino]-4-chlorophenyl}sulfanyl)propanoate | 864 | 91 |
| 3-({2-[(1-benzofuran-2-ylsulfonyl)amino]-4-chlorophenyl}sulfanyl)propanoic acid | 46 | 99 |
| methyl 3-({2-[(1-benzofuran-2-ylsulfonyl)amino]-4-chlorophenyl}sulfinyl)propanoate | 217 | 99 |
| methyl 3-({2-[(1-benzofuran-2-ylsulfonyl)amino]-4-chlorophenyl}sulfonyl)propanoate | 225 | 96 |
| methyl 3-[(4-chloro-2-{[(4-chloro-2-fluorophenyl)sulfonyl]amino}phenyl)sulfanyl]propanoate | 995 | 79 |
| 3-[(4-chloro-2-{[(4-chloro-2-fluorophenyl)sulfonyl]amino}phenyl)sulfanyl]propanoic acid | 129 | 102 |
| methyl 3-[(4-chloro-2-{[(4-chloro-2-fluorophenyl)sulfonyl]amino}phenyl)sulfonyl]propanoate | 212 | 82 |
| methyl 3-[(4-chloro-2-{[(4-chloro-2-fluorophenyl)sulfonyl]amino}phenyl)sulfinyl]propanoate | 98 | 93 |
| 3-[(4-chloro-2-{[(4-chloro-2-fluorophenyl)sulfonyl]amino}phenyl)sulfonyl]propanoic acid | nd | 90 |
| 3-[(4-chloro-2-{[(4-chloro-2-fluorophenyl)sulfonyl]amino}phenyl)sulfinyl]propanoic acid | nd | 83 |
| 3-[(4-chloro-2-{[(4-chloro-2-fluorophenyl)sulfonyl]amino}phenyl)sulfanyl]-N-ethyl-N-methylpropanamide | nd | 49 |

TABLE 1-continued

| Compound Name | CCR2 IC50 (nM) | CCR2 % ANTAGONISM |
|---|---|---|
| 3-[(4-chloro-2-{[(4-chloro-2-fluorophenyl)sulfonyl]amino}phenyl)sulfinyl]-N-ethyl-N-methylpropanamide | 7523 | 89 |
| 3-[(4-chloro-2-{[(4-chloro-2-fluorophenyl)sulfonyl]amino}phenyl)sulfonyl]-N-ethyl-N-methylpropanamide | 2262 | 87 | nd: Not determined.

What is claimed is:

1. A compound having Formula I, its enantiomers, diastereoisomers, hydrates, solvates, tautomers or a pharmaceutically acceptable salt thereof:

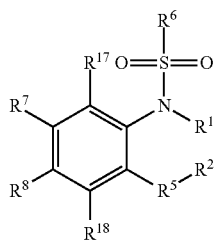

Formula I wherein:
$R^1$ is H or —C(O)(CH$_3$);
$R^2$ is substituted or unsubstituted C$_{1-6}$ alkyl;
$R^5$ is —S—, —S(O)—, or —S(O)$_2$—;
$R^6$ is optionally substituted 1-benzofuran;
$R^{17}$ is H, substituted or unsubstituted C$_{1-6}$ alkyl, halogen, substituted or unsubstituted —OC$_{1-6}$ alkyl, CN, C(O)R$^{19}$, NR$^{20}$R$^{21}$ or hydroxyl;
$R^{18}$ is H, substituted or unsubstituted C$_{1-6}$ alkyl, halogen, substituted or unsubstituted —OC$_{1-6}$ alkyl, CN, C(O)R$^{22}$, NR$^{23}$R$^{24}$ or hydroxyl;
$R^7$ is H, halogen, CN, substituted or unsubstituted —OC$_{1-6}$ alkyl, substituted or unsubstituted C$_{1-6}$ alkyl or is substituted or unsubstituted C$_{3-8}$ cycloalkyl;
$R^8$ is H, substituted or unsubstituted C$_{1-6}$ alkyl, halogen, substituted or unsubstituted —OC$_{1-6}$ alkyl, CN or hydroxyl;
$R^{19}$ is H, OH or substituted or unsubstituted C$_{1-6}$ alkyl
$R^{20}$ is H or substituted or unsubstituted C$_{1-6}$ alkyl;
$R^{21}$ is H or substituted or unsubstituted C$_{1-6}$ alkyl;
$R^{22}$ is H, OH or substituted or unsubstituted C$_{1-6}$ alkyl;
$R^{23}$ is H or substituted or unsubstituted C$_{1-6}$ alkyl;
$R^{24}$ is H or substituted or unsubstituted C$_{1-6}$ alkyl;
with the proviso that the compound of Formula I is not of structure:

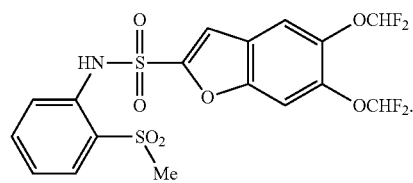 [SMILES: CS(=O)(=O)c1ccccc1NS(=O)(=O)c1cc2cc(OC(F)F)c(OC(F)F)cc2o1]

2. A compound according to claim 1, wherein:
$R^5$ is —S—.
3. A compound according to claim 1, wherein:
$R^5$ is —S(O)—.
4. A compound according to claim 1, wherein:
$R^5$ is —S(O)$_2$—.
5. A compound according to claim 1, wherein:
$R^1$ is H;
$R^2$ is substituted or unsubstituted C$_{1-6}$ alkyl,
$R^5$ is —S—, —S(O)—, or —S(O)$_2$—;
$R^6$ is optionally substituted 1-benzofuran;
$R^{17}$ is H, substituted or unsubstituted C$_{1-6}$ alkyl or halogen;
$R^{18}$ is H, substituted or unsubstituted C$_{1-6}$ alkyl or halogen;
$R^7$ is H, halogen, CN, —OC$_{1-6}$ alkyl, substituted or unsubstituted C$_{1-6}$ alkyl or substituted or unsubstituted C$_{3-8}$ cycloalkyl; and
$R^8$ is H, substituted or unsubstituted C$_{1-6}$ alkyl, CN or halogen.
6. A compound according to claim 5, wherein:
$R^1$ is H;
$R^2$ is substituted or unsubstituted C$_{1-6}$ alkyl;
$R^5$ is —S—, —S(O)—, or —S(O)$_2$—;
$R^6$ is optionally substituted 1-benzofuran;
$R^{17}$ is H;
$R^{18}$ is H;
$R^7$ is H, halogen or C$_{1-6}$ alkyl; and
$R^8$ is H or CN.
7. A compound according to claim 6, wherein:
$R^1$ is H,
$R^2$ is methylpropionate, methyl-2-benzoic acid, methyl-2-methylbenzoate, methyl-3-methylphenylacetamide, methyl-3-methylphenylsulfonamide, methyl acetic acid, methyl-2-methylphenylcarboxylate or propionic acid;
$R^5$ is —S(O)$_2$—, —S— or —S(O)—;
$R^6$ is optionally substituted 1-benzofuran;
$R^7$ is chlorine, methyl or fluorine;
$R^{17}$ is H;
$R^{18}$ is H; and
$R^8$ is H or CN.
8. A compound according to claim 7, wherein:
$R^5$ is —S—.
9. A compound according to claim 7, wherein:
$R^5$ is —S(O)—.
10. A compound according to claim 7, wherein:
$R^5$ is —S(O)$_2$—.
11. A compound according to claim 1, selected from:
3-[({2-[(1-benzofuran-2-ylsulfonyl)amino]-4-fluorophenyl}sulfinyl)methyl]benzoic acid;
4-[({2-[(1-benzofuran-2-ylsulfonyl)amino]-4-fluorophenyl}sulfonyl)methyl]benzoic acid;
methyl 4-[({2-[(1-benzofuran-2-ylsulfonyl)amino]-4-fluorophenyl}sulfonyl)methyl]benzoate;

4-[({2-[(1-benzofuran-2-ylsulfonyl)amino]-4-fluorophenyl}sulfinyl)methyl]benzoic acid;
methyl 4-[({2-[(1-benzofuran-2-ylsulfonyl)amino]-4-fluorophenyl}sulfinyl)methyl]benzoate;
4-[({2-[(1-benzofuran-2-ylsulfonyl)amino]-4-fluorophenyl}sulfanyl)methyl]benzoic acid;
methyl 4-[({2-[(1-benzofuran-2-ylsulfonyl)amino]-4-fluorophenyl}sulfanyl)methyl]benzoate;
3-[({2-[(1-benzofuran-2-ylsulfonyl)amino]-4-fluorophenyl}sulfonyl)methyl]benzoic acid;
methyl 3-[({2-[(1-benzofuran-2-ylsulfonyl)amino]-4-fluorophenyl}sulfonyl)methyl]benzoate;
methyl 3-[({2-[(1-benzofuran-2-ylsulfonyl)amino]-4-fluorophenyl}sulfinyl)methyl]benzoate;
3-[({2-[(1-benzofuran-2-ylsulfonyl)amino]-4-fluorophenyl}sulfanyl)methyl]benzoic acid;
methyl 3-[({2-[(1-benzofuran-2-ylsulfonyl)amino]-4-fluorophenyl}sulfanyl)methyl]benzoate;
2-[({2-[(1-benzofuran-2-ylsulfonyl)amino]-5-chlorophenyl}sulfanyl)methyl]benzoic acid;
2-[({2-[(1-benzofuran-2-ylsulfonyl)amino]-4-methylphenyl}sulfonyl)methyl]benzoic acid;
2-[({2-[(1-benzofuran-2-ylsulfonyl)amino]-4-methylphenyl}sulfinyl)methyl]benzoic acid;
methyl 2-[({2-[(1-benzofuran-2-ylsulfonyl)amino]-4-methylphenyl}sulfonyl)methyl]benzoate;
methyl 2-[({2-[(1-benzofuran-2-ylsulfonyl)amino]-4-methylphenyl}sulfinyl)methyl]benzoate;
2-[({2-[(1-benzofuran-2-ylsulfonyl)amino]-4-methylphenyl}sulfanyl)methyl]benzoic acid;
methyl 2-[({2-[(1-benzofuran-2-ylsulfonyl)amino]-4-methylphenyl}sulfanyl)methyl]benzoate;
methyl 3-({2-[(1-benzofuran-2-ylsulfonyl)amino]-4-chlorophenyl}sulfonyl)propanoate;
methyl 3-({2-[(1-benzofuran-2-ylsulfonyl)amino]-4-chlorophenyl}sulfinyl)propanoate;
3-({2-[(1-benzofuran-2-ylsulfonyl)amino]-4-chlorophenyl}sulfanyl)propanoic acid;
methyl 3-({2-[(1-benzofuran-2-ylsulfonyl)amino]-4-chlorophenyl}sulfanyl)propanoate;
({2-[(1-benzofuran-2-ylsulfonyl)amino]-4-chlorophenyl}sulfonyl)acetic acid;
({2-[(1-benzofuran-2-ylsulfonyl)amino]-4-chlorophenyl}sulfinyl)acetic acid;
2-[({2-[(1-benzofuran-2-ylsulfonyl)amino]phenyl}sulfonyl)methyl]benzoic acid;
methyl 2-[({2-[(1-benzofuran-2-ylsulfonyl)amino]phenyl}sulfonyl)methyl]benzoate;
2-[({2-[(1-benzofuran-2-ylsulfonyl)amino]phenyl}sulfinyl)methyl]benzoic acid;
methyl 2-[({2-[(1-benzofuran-2-ylsulfonyl)amino]phenyl}sulfinyl)methyl]benzoate;
2-[({2-[(1-benzofuran-2-ylsulfonyl)amino]phenyl}sulfanyl)methyl]benzoic acid;
methyl 2-[({2-[(1-benzofuran-2-ylsulfonyl)amino]phenyl}sulfanyl)methyl]benzoate;
({2-[(1-benzofuran-2-ylsulfonyl)amino]-4-chlorophenyl}sulfanyl)acetic acid;
2-[({2-[(1-benzofuran-2-ylsulfonyl)amino]-4-fluorophenyl}sulfonyl)methyl]benzoic acid;
methyl 2-[({2-[(1-benzofuran-2-ylsulfonyl)amino]-4-fluorophenyl}sulfonyl)methyl]benzoate;
2-[({2-[(1-benzofuran-2-ylsulfonyl)amino]-4-fluorophenyl}sulfinyl)methyl]benzoic acid;
methyl 2-[({2-[(1-benzofuran-2-ylsulfonyl)amino]-4-fluorophenyl}sulfinyl)methyl]benzoate;
N-[5-chloro-2-({3-[(methylsulfonyl)amino]benzyl}sulfonyl)phenyl]-1-benzofuran-2-sulfonamide;
N-[5-chloro-2-({3-[(methylsulfonyl)amino]benzyl}sulfinyl)phenyl]-1-benzofuran-2-sulfonamide;
N-{3-[({2-[(1-benzofuran-2-ylsulfonyl)amino]-4-chlorophenyl}sulfonyl)methyl]phenyl}acetamide;
N-{3-[({2-[(1-benzofuran-2-ylsulfonyl)amino]-4-chlorophenyl}sulfinyl)methyl]phenyl}acetamide;
2-[({2-[(1-benzofuran-2-ylsulfonyl)amino]-4-fluorophenyl}sulfanyl)methyl]benzoic acid;
methyl 2-[({2-[(1-benzofuran-2-ylsulfonyl)amino]-4-fluorophenyl}sulfanyl)methyl]benzoate;
N-[5-chloro-2-({3-[(methylsulfonyl)amino]benzyl}sulfanyl)phenyl]-1-benzofuran-2-sulfonamide;
N-(2-{[3-(acetylamino)benzyl]sulfanyl}-5-chlorophenyl)-N-(1-benzofuran-2-ylsulfonyl)acetamide;
N-{3-[({2-[(1-benzofuran-2-ylsulfonyl)amino]-4-chlorophenyl}sulfanyl)methyl]phenyl}acetamide;
2-[({2-[(1-benzofuran-2-ylsulfonyl)amino]-4-chlorophenyl}sulfonyl)methyl]benzoic acid;
2-[({2-[(1-benzofuran-2-ylsulfonyl)amino]-4-chlorophenyl}sulfinyl)methyl]benzoic acid;
2-[({2-[(1-benzofuran-2-ylsulfonyl)amino]-4-chlorophenyl}sulfanyl)methyl]benzoic acid;
N-[6-(benzylsulfonyl)-1-oxo-2,3-dihydro-1H-inden-5-yl]-1-benzofuran-2-sulfonamide;
N-[6-(benzylsulfinyl)-1-oxo-2,3-dihydro-1H-inden-5-yl]-1-benzofuran-2-sulfonamide;
N-[6-(benzylsulfanyl)-1-oxo-2,3-dihydro-1H-inden-5-yl]-1-benzofuran-2-sulfonamide;
N-[2-(benzylsulfonyl)-4-cyanophenyl]-1-benzofuran-2-sulfonamide;
N-[2-(benzylsulfinyl)-4-cyanophenyl]-1-benzofuran-2-sulfonamide;
N-[2-(benzylsulfanyl)-4-cyanophenyl]-1-benzofuran-2-sulfonamide;
methyl 2-(((2-(benzofuran-2-sulfonamido)-4-chlorophenyl)thio)methyl)benzoate; and
methyl 2-(((2-(benzofuran-2-sulfonamido)-5-chlorophenyl)thio)methyl)benzoate.

12. A pharmaceutical composition comprising as active ingredient a therapeutically effective amount of a compound according to claim 1 and a pharmaceutically acceptable adjuvant, diluent or carrier.

13. A pharmaceutical composition according to claim 12 wherein the compound is selected from:
3-[({2-[(1-benzofuran-2-ylsulfonyl)amino]-4-fluorophenyl}sulfinyl)methyl]benzoic acid;
4-[({2-[(1-benzofuran-2-ylsulfonyl)amino]-4-fluorophenyl}sulfonyl)methyl]benzoic acid;
methyl 4-[({2-[(1-benzofuran-2-ylsulfonyl)amino]-4-fluorophenyl}sulfonyl)methyl]benzoate;
4-[({2-[(1-benzofuran-2-ylsulfonyl)amino]-4-fluorophenyl}sulfinyl)methyl]benzoic acid;
methyl 4-[({2-[(1-benzofuran-2-ylsulfonyl)amino]-4-fluorophenyl}sulfinyl)methyl]benzoate;
4-[({2-[(1-benzofuran-2-ylsulfonyl)amino]-4-fluorophenyl}sulfanyl)methyl]benzoic acid;
methyl 4-[({2-[(1-benzofuran-2-ylsulfonyl)amino]-4-fluorophenyl}sulfanyl)methyl]benzoate;
3-[({2-[(1-benzofuran-2-ylsulfonyl)amino]-4-fluorophenyl}sulfonyl)methyl]benzoic acid;
methyl 3-[({2-[(1-benzofuran-2-ylsulfonyl)amino]-4-fluorophenyl}sulfonyl)methyl]benzoate;
methyl 3-[({2-[(1-benzofuran-2-ylsulfonyl)amino]-4-fluorophenyl}sulfinyl)methyl]benzoate;

3-[({2-[(1-benzofuran-2-ylsulfonyl)amino]-4-fluorophenyl}sulfanyl)methyl]benzoic acid;
methyl 3-[({2-[(1-benzofuran-2-ylsulfonyl)amino]-4-fluorophenyl}sulfanyl)methyl]benzoate;
2-[({2-[(1-benzofuran-2-ylsulfonyl)amino]-5-chlorophenyl}sulfanyl)methyl]benzoic acid;
2-[({2-[(1-benzofuran-2-ylsulfonyl)amino]-4-methylphenyl}sulfonyl)methyl]benzoic acid;
2-[({2-[(1-benzofuran-2-ylsulfonyl)amino]-4-methylphenyl}sulfinyl)methyl]benzoic acid;
methyl 2-[({2-[(1-benzofuran-2-ylsulfonyl)amino]-4-methylphenyl}sulfonyl)methyl]benzoate;
methyl 2-[({2-[(1-benzofuran-2-ylsulfonyl)amino]-4-methylphenyl}sulfinyl)methyl]benzoate;
2-[({2-[(1-benzofuran-2-ylsulfonyl)amino]-4-methylphenyl}sulfanyl)methyl]benzoic acid;
methyl 2-[({2-[(1-benzofuran-2-ylsulfonyl)amino]-4-methylphenyl}sulfanyl)methyl]benzoate;
methyl 3-({2-[(1-benzofuran-2-ylsulfonyl)amino]-4-chlorophenyl}sulfonyl)propanoate;
methyl 3-({2-[(1-benzofuran-2-ylsulfonyl)amino]-4-chlorophenyl}sulfinyl)propanoate;
3-({2-[(1-benzofuran-2-ylsulfonyl)amino]-4-chlorophenyl}sulfanyl)propanoic acid;
methyl 3-({2-[(1-benzofuran-2-ylsulfonyl)amino]-4-chlorophenyl}sulfanyl)propanoate;
({2-[(1-benzofuran-2-ylsulfonyl)amino]-4-chlorophenyl}sulfonyl)acetic acid;
({2-[(1-benzofuran-2-ylsulfonyl)amino]-4-chlorophenyl}sulfinyl)acetic acid;
2-[({2-[(1-benzofuran-2-ylsulfonyl)amino]phenyl}sulfonyl)methyl]benzoic acid;
methyl 2-[({2-[(1-benzofuran-2-ylsulfonyl)amino]phenyl}sulfonyl)methyl]benzoate;
2-[({2-[(1-benzofuran-2-ylsulfonyl)amino]phenyl}sulfinyl)methyl]benzoic acid;
methyl 2-[({2-[(1-benzofuran-2-ylsulfonyl)amino]phenyl}sulfinyl)methyl]benzoate;
2-[({2-[(1-benzofuran-2-ylsulfonyl)amino]phenyl}sulfanyl)methyl]benzoic acid;
methyl 2-[({2-[(1-benzofuran-2-ylsulfonyl)amino]phenyl}sulfanyl)methyl]benzoate;
({2-[(1-benzofuran-2-ylsulfonyl)amino]-4-chlorophenyl}sulfanyl)acetic acid;
2-[({2-[(1-benzofuran-2-ylsulfonyl)amino]-4-fluorophenyl}sulfonyl)methyl]benzoic acid;
methyl 2-[({2-[(1-benzofuran-2-ylsulfonyl)amino]-4-fluorophenyl}sulfonyl)methyl]benzoate;
2-[({2-[(1-benzofuran-2-ylsulfonyl)amino]-4-fluorophenyl}sulfinyl)methyl]benzoic acid;
methyl 2-[({2-[(1-benzofuran-2-ylsulfonyl)amino]-4-fluorophenyl}sulfinyl)methyl]benzoate;
N-[5-chloro-2-({3-[(methylsulfonyl)amino]benzyl}sulfonyl)phenyl]-1-benzofuran-2-sulfonamide;
N-[5-chloro-2-({3-[(methylsulfonyl)amino]benzyl}sulfinyl)phenyl]-1-benzofuran-2-sulfonamide;
N-{3-[({2-[(1-benzofuran-2-ylsulfonyl)amino]-4-chlorophenyl}sulfonyl)methyl]phenyl}acetamide;
N-{3-[({2-[(1-benzofuran-2-ylsulfonyl)amino]-4-chlorophenyl}sulfinyl)methyl]phenyl}acetamide;
2-[({2-[(1-benzofuran-2-ylsulfonyl)amino]-4-fluorophenyl}sulfanyl)methyl]benzoic acid;
methyl 2-[({2-[(1-benzofuran-2-ylsulfonyl)amino]-4-fluorophenyl}sulfanyl)methyl]benzoate;
N-[5-chloro-2-({3-[(methylsulfonyl)amino]benzyl}sulfanyl)phenyl]-1-benzofuran-2-sulfonamide;
N-(2-{[3-(acetylamino)benzyl]sulfanyl}-5-chlorophenyl)-N-(1-benzofuran-2-ylsulfonyl)acetamide;
N-{3-[({2-[(1-benzofuran-2-ylsulfonyl)amino]-4-chlorophenyl}sulfanyl)methyl]phenyl}acetamide;
2-[({2-[(1-benzofuran-2-ylsulfonyl)amino]-4-chlorophenyl}sulfonyl)methyl]benzoic acid;
2-[({2-[(1-benzofuran-2-ylsulfonyl)amino]-4-chlorophenyl}sulfinyl)methyl]benzoic acid;
2-[({2-[(1-benzofuran-2-ylsulfonyl)amino]-4-chlorophenyl}sulfanyl)methyl]benzoic acid;
N-[6-(benzylsulfonyl)-1-oxo-2,3-dihydro-1H-inden-5-yl]-1-benzofuran-2-sulfonamide;
N-[6-(benzylsulfinyl)-1-oxo-2,3-dihydro-1H-inden-5-yl]-1-benzofuran-2-sulfonamide;
N-[6-(benzylsulfanyl)-1-oxo-2,3-dihydro-1H-inden-5-yl]-1-benzofuran-2-sulfonamide;
N-[2-(benzylsulfonyl)-4-cyanophenyl]-1-benzofuran-2-sulfonamide;
N-[2-(benzylsulfinyl)-4-cyanophenyl]-1-benzofuran-2-sulfonamide;
N-[2-(benzylsulfanyl)-4-cyanophenyl]-1-benzofuran-2-sulfonamide;
methyl 2-(((2-(benzofuran-2-sulfonamido)-4-chlorophenyl)thio)methyl)benzoate; and
methyl 2-(((2-(benzofuran-2-sulfonamido)-5-chlorophenyl)thio)methyl)benzoate.

14. A compound selected from:
N-[6-(benzylsulfanyl)-1-oxo-2,3-dihydro-1H-inden-5-yl]-1-benzofuran-2-sulfonamide;
N-[6-(benzylsulfinyl)-1-oxo-2,3-dihydro-1H-inden-5-yl]-1-benzofuran-2-sulfonamide; and
N-[6-(benzylsulfonyl)-1-oxo-2,3-dihydro-1H-inden-5-yl]-1-benzofuran-2-sulfonamide.

* * * * *